US008481317B2

(12) United States Patent
Yu et al.

(10) Patent No.: US 8,481,317 B2
(45) Date of Patent: Jul. 9, 2013

(54) HEPATOCYTE PRODUCTION BY FORWARD PROGRAMMING

(75) Inventors: Junying Yu, Madison, WI (US); Fongching Kevin Chau, Madison, WI (US); Jinlan Jiang, Madison, WI (US); Yong Jiang, Madison, WI (US); Maksym A. Vodyanyk, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 65 days.

(21) Appl. No.: 13/086,159

(22) Filed: Apr. 13, 2011

(65) Prior Publication Data

US 2011/0280844 A1 Nov. 17, 2011

Related U.S. Application Data

(60) Provisional application No. 61/323,689, filed on Apr. 13, 2010.

(51) Int. Cl.
*A61K 48/00* (2006.01)
*A61P 1/16* (2006.01)

(52) U.S. Cl.
USPC ........................ 435/377; 424/93.21

(58) Field of Classification Search
USPC ........................ 424/93.21; 435/377
See application file for complete search history.

(56) References Cited

U.S. PATENT DOCUMENTS

| | | | |
|---|---|---|---|
| 5,486,359 A | 1/1996 | Caplan et al. | 424/93.7 |
| 5,736,396 A | 4/1998 | Bruder et al. | 435/366 |
| 5,811,094 A | 9/1998 | Caplan et al. | 424/93.7 |
| 5,827,735 A | 10/1998 | Young et al. | 435/325 |
| 5,827,740 A | 10/1998 | Pittenger | 435/372 |
| 5,837,539 A | 11/1998 | Caplan et al. | 435/332 |
| 5,837,670 A | 11/1998 | Hartshorn | 510/490 |
| 6,833,269 B2 | 12/2004 | Carpenter | 435/377 |
| 7,015,036 B2 * | 3/2006 | Prachumsri et al. | 435/370 |
| 7,473,555 B2 | 1/2009 | Mandalam et al. | 435/377 |
| 7,781,214 B2 | 8/2010 | Smith et al. | 435/377 |
| 2009/0130064 A1 | 5/2009 | Rogiers et al. | 424/93.7 |
| 2009/0317365 A1 | 12/2009 | Lee et al. | 424/93.7 |

FOREIGN PATENT DOCUMENTS

| | | |
|---|---|---|
| EP | 0412700 | 2/1991 |
| WO | WO 03/042405 | 5/2003 |
| WO | WO 2010/014949 | 2/2010 |

OTHER PUBLICATIONS

Harding and Dibson. J Inherit Metab Dis 33:681-687, 2010.*
"ERG v-ets erythroblastosis virus E26 oncogene homolog (avian) [*Homo sapiens*]" Gene ID: 2078. Entrez Gene. Updated May 29, 2010.
Amit et al., "Clonally derived human embryonic stem cell lines maintain pluripotency and proliferative potential for prolonged periods of culture," *Dev. Bio.*, 227:271-278, 2000.
Bailey et al., "Transplanted adult hematopoietic stem cells differentiate into functional endothelial cells," *Blood*, 103(1):13-19, 2004.
Bhatia et al., "Bone morphogenetic proteins regulate the developmental program of human hematopoietic stem cells," *J. Exp. Med.*, 189:1139-1148, 1999.
Boyer et al., "Core transcriptional regulatory circuitry in human embryonic stem cells," *Cell*, 122(6):947-56, 2005.
Chadwick et al., "Cytokines and BMP-4 promote hematopoietic differentiation of human embryonic stem cells," *Blood*, 102(3):906-915, 2003.
Chambers et al., "Functional expression cloning of Nanog, a pluripotency sustaining factor in embryonic stem cells," *Cell*, 113(5):643-55, 2003.
David et al., "Forward programming of pluripotent stem cells towards distinct cardiovascular cell typs," *Cardiovascular Research*, 84:263-272, 2009.
De Val and Black, "Transcriptional control of endothelial cell development," *Developmental Cell*, 16:180-195, 2009.
Dzau et al., "Therapeutic potential of endothelial progenitor cells in cardiovascular diseases," *Hypertension*, 46-7-18, 2005.
Genbank Accession No. NM 000545.4 "*Homo sapiens* HNF-1A homeobox A (HNF1A), mRNA", 1990.
Genbank Accession No. NM_000457.3 "*Homo sapiens* hepatocyte nuclear factor 4, alpha (HNF4A), transcript variant 2, mRNA," 1994.
Genbank Accession No. NM_005996.3, "*Homo sapiens* T-box 3 (TBX3), transcript variant 1, mRNA," 1997.
Genbank Accession No. NM_153675.2, "*Homo sapiens* forkhead box A2 (FOXA2), transcript variant 2, mRNA," 1997.
Genbank Accession No. NM_178849.1, "*Homo sapiens* hepatocyte nuclear factor 4, alpha (HNF4A), transcript variant 1, mRNA" 1994.
Genbank Accession No. NM_178850.1, "*Homo sapiens* hepatocyte nuclear factor 4, alpha (HNF4A), transcript variant 3, mRNA," 1994.
Genbank Accession No. NM_001030003.1, "*Homo sapiens* hepatocyte nuclear factor 4, alpha (HNF4A), transcript variant 5, mRNA," 1994.
Genbank Accession No. NM_001030004.1 "*Homo sapiens* hepatocyte nuclear factor 4, alpha (HNF4A), transcript variant 6, mRNA," 1994.
Genbank Accession No. NM_153675.2, "*Homo sapiens* forkhead box A2 (FOXA2), transcript variant, mRNA," 1997.
Hayhurst et al., "Hepatocyte nuclear factor 4alpha (nuclear receptor 2A1) is essential for maintenance of hepatic gene expression and lipid homeostasis," *Mol. Cell Biol.*, 21(4):1393-403, 2001.
Huang et al., "Induction of functional hepatocyte-like cells from mouse fibroblasts by defined factors," *Nature*, 475(7356):386-389, 2011.
Huber et al., "Cooperative effects of growth factors involved in the induction of hematopoietic mesoderm," *Blood*, 92: 4128-4137, 1998.
Ishizaka et al., "Development of hepatocytes from embryonic stem cells after transfection with the HNF-3β gene," *The FASEB Journal* express article, doi:10.1096/fj.01-0806fje. Published online Jul. 1, 2002.
Kheolamai and Dickson, "Liver-enriched transcription factors are critical for the expression of hepatocyte marker genes in mES-derived hepatocyte-lineage cells," *BMC Molecular Biology*, 10:35. doi:10.11861/1471-2199-10-35, 2009.
Kuzuya et al., "VEGF protects against oxidized LDL toxicity to endothelial cells by an intracellular glutathione-dependent mechanism through the KDR receptor," *Arterioscl., Thromb. Vascular Biol.*, 21:765-70, 2001.

(Continued)

*Primary Examiner* — Marcia S Noble
(74) *Attorney, Agent, or Firm* — Parker Highlander PLLC

(57) ABSTRACT

The invention generally features methods for providing hepatocytes from a variety of cell sources, particularly pluripotent stem cells, therapeutic compositions featuring such cells, and methods of using them for the treatment of subjects.

16 Claims, 9 Drawing Sheets

OTHER PUBLICATIONS

Li et al., "Mammalian hepatocyte differentiation requires the transcription factor HNF-4alpha," *Genes Dev.*, 14(4):464-74, 2000.

Li et al., "Transplantation of human embryonic stem cell-derived endothelial cells for vascular diseases," *J. Cell Biochem.*, 106:194-199, 2009.

Marshall et al., "Polarized expression of bone morphogenetic protein-4 in the human aorta-gonad-mesonephros region," *Blood*, 96:1591-1593, 2000.

Nagaki and Moriwaki, "Transcription factor HNF and hepatocyte differentiation," *Hepatology Research*, 38:961-969, 2008.

Sekiya and Suzuki, "Direct conversion of mouse fibroblasts to hepatocyte-like cells by defined factors," *Nature*, 475(7356):390-393, 2011.

Sullivan et al., "Generationo f functional human hepatic endoderm from human induced pluripotent stem cells," *Hepatology*, 51(1):329-335, 2010.

Takahashi and Yamanaka, "Induction of pluripotent stem cells mouse embryonic and adult fibroblast cultures by defined factors," *Cell*, 126(4):663-676, 2006.

Takahashi et al., "Induction of pluripotent stem cells from adult human fibroblasts by defined factors," *Cell*, 131:861-872, 2007.

Thomson et al. "Isolation of primate embryonic stem cell line," *Proc. Natl. Acad. Scie. USA*, 92:7844-7848, 1995.

Thomson et al., "Embryonic stem cell lines derived from human blastocysts," *Science*, 282:1145, 1998.

U.S. Appl. No. 61/058,858 entitled Methods for the Production of iPS Cells Using Non Viral Approach, by Amanda Mack, filed Jun. 4, 2008.

U.S. Appl. No. 61/184,546 entitled "Reprogramming T Cells," by Matthew Brown et al., filed Jun. 5, 2009.

Watt et al., "HNF4: A central regulator of hepatocyte differentiation and function," *Hepatology*, 37(6): 1249-1253, 2003.

Yu and Thompson, "Pluripotent stem cell lines," *Gene Dev.*, 22(15):1987-97, 2008.

Yu et al., "Human induced pluripotent stem cells free of vector and transgene sequences," *Science*, 324(5928):797-801, 2009.

Yu et al., *Science*, "Induced pluripotent stem cell lines derived from human somatic cells" 318(5858):1917-1920, 2007.

PCT International Search Report and Written Opinion issued in International application No. PCT/US2011/032309, dated Dec. 9, 2011.

Lavon et al., "Study of hepatocyte differentiation using embryonic stem cells," *Journal of Cellular Biochemistry*, 96:1193-1202, 2005.

Levison-Dushnik et al., "Involvement of hepatocyte nuclear factor 3 in endoderm differentiation of embryonic stem cells," *Molecular and Cellular Biology*, 17(7):3817-3822, 1997.

Si-Tayeb et al., "Highly efficient generation of human hepatocyte-like cells from induced pluripotent stem cells," *Hepatology*, 51(1):297-305, 2010.

Zhao et al., "Derivation and Characterization of hepatic progintor cells from human embryonic stem cells," *PLoSONE*, 4(7):e6468, pp. 1010, 2009.

Nikolova-Krstevski et al., "ERG is required for the differentiation of embryonic stem cells along the endothelial lineage," *BMC Developmental Biology*, 9:72, 2009.

PCT International Search Report and Written Opinion issued in International application No. PCT/US2001/043218, dated Feb. 17, 2012.

Ria et al., "Endothelial differentiation of hematopoietic stem and progenitor cells from patients with multiple myeloma," *Clinical Cancer Research*, 14:1678-1685, 2008.

Wong et al., "Identification of vasculature-specific genes by microarray analysis of Etsrp/Etv2 overexpressing zebrafish embryos," *Developmental Dynamics*, 238(7):1836-1850, 2009.

* cited by examiner

HEPATOCYTE PRODUCTION BY FORWARD PROGRAMMING

The present application claims the priority benefit of U.S. provisional application No. 61/323,689, filed Apr. 13, 2010, the entire contents of which are incorporated herein by reference.

BACKGROUND OF THE INVENTION

1. Field of the Invention

The present invention relates generally to the field of molecular biology, stem cells and differentiated cells. More particularly, it concerns programming of somatic cells and undifferentiated cells toward specific cell lineages, particularly hepatic lineage cells.

2. Description of Related Art

In addition to their use in the transplantation therapies to treat various liver diseases, human hepatocytes are in high demand for drug toxicity screening and development due to their critical functions in the detoxification of drugs or other xenobiotics as well as endogenous substrates. Human primary hepatocytes, however, quickly lose their functions when cultured in vitro. Moreover, the drug metabolic ability of human primary hepatocytes exhibits significant difference between different individuals. The availability of an unlimited supply of patient-specific functional hepatocytes would greatly facilitate both the drug development and the eventual clinical application of hepatocyte transplantation.

Therefore, there is a need for production of hepatic lineage cells in therapeutic and research use, especially, human hepatocytes.

SUMMARY OF THE INVENTION

The present invention overcomes a major deficiency in the art in providing hepatocytes by forward programming to provide an unlimited supply of patient-specific hepatocytes. In a first embodiment there is provided a method of providing hepatocytes by forward programming of a variety of cell types, including somatic cells or stem cells. Forward programming into hepatocytes may comprise increasing the expression level of a sufficient number of hepatocyte programming factor genes capable of causing forward programming of non-hepatocytes to hepatocytes.

In another embodiment, there may also be provided a method of directly programming non-hepatocytes, such as differentiation of pluripotent stem cells, into hepatocytes, comprising increasing expression of a sufficient number of hepatocyte programming factor genes (e.g., genes in Table 1 and variants and isoforms thereof) capable of causing forward programming to a hepatic lineage or to hepatocyte cells, therefore directly programming the cells into hepatocytes.

"Forward programming," as used herein, refers to a process having essentially no requirement to culture cells through intermediate cellular stages using culture conditions that are adapted for each such stage and/or, optionally, having no need to add different growth factors during different time points between the starting cell source and the desired end cell product, e.g., hepatocytes, as exemplified in the upper part of FIG. 1. The terms "direct programming" or "direct differentiation," as used in the priority application provisional application 61/323,689, are intended to be commensurate with the term "forward programming," as used in the present application. "Forward programming" may include programming of a multipotent or pluripotent cell, as opposed to a differentiated somatic cell that has lost multipotency or pluripotency, by artificially increasing the expression of one or more specific lineage-determining genes in a multipotent or pluripotent cell. For example, forward programming may describe the process of programming embryonic stem cells (ESCs) or induced pluripotent stem cells (iPSCs) to hepatocyte-like cells or other differentiated precursor or somatic cells. In certain other aspects, "forward programming" may refer to "trans-differentiation," in which differentiated cells are programmed directly into another differentiated cell type without passing through an intermediate pluripotency stage.

On the other hand, the bottom part of FIG. 1 demonstrates various developmental stages present in a step-wise differentiation process and the need to add different growth factors at different times during the process, which costs more labor, time and expenses than methods described in certain aspects of the current invention. Therefore, the methods of forward programming in certain aspects of the present invention are advantageous by avoiding the need to add different growth factors at different stages of programming or differentiation to improve efficiency. For example, the medium for culturing the cells to be programmed or progeny cells thereof may be essentially free of one or more of fibroblast growth factors (FGFs), epidermal growth factors (EGFs), and nicotinamides, which are normally required for progressive programming (i.e., directed differentiation as defined below) along different developmental stages.

Forward programming as used in certain aspects of the present invention may be different from directed differentiation. In directed differentiation, growth factors or small molecules are added to the culture medium, thereby indirectly causing an increased expression of the endogenous genes. In directed differentiation, the added growth factors or small molecules signal though cell surface proteins and surface protein-mediated signaling to activate endogenous pathways toward the lineage desired. To the contrary, in forward programming, the programming factors that normally are only intra-cellular (e.g., transcription factors) are forced to have an increased expression by introducing or inducing the gene expression cassette or by being added directly (e.g., in the form of polypeptides or RNAs), thereby directly activating the programming factor genes for differentiation directly and by-passing the cell surface proteins and surface protein-mediated signaling pathways. These means for increasing the expression of programming factors may be defined as "artificial," and may be different from the directed differentiation which comprises adding growth factors or small molecules to the medium thereby indirectly causing increased expression of endogenous programming factor genes.

Sources of cells suitable for hepatic forward programming may include any stem cells or non-hepatocyte somatic cells. For example, the stem cells may be pluripotent stem cells or any non-pluripotent stem cells. The pluripotent stem cells may be induced pluripotent stem cells, embryonic stem cells, or pluripotent stem cells derived by nuclear transfer or cell fusion. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, skin stem cells. In certain aspects, the stem cells may be isolated from umbilical, placenta, amniotic fluid, chorion villi, blastocysts, bone marrow, adipose tissue, brain, peripheral blood, cord blood, menstrual blood, blood vessels, skeletal muscle, skin and liver.

In other aspects, hepatocytes may be produced by transdifferentiation of non-hepatocyte somatic cells. The somatic cells for hepatic lineage programming can be any cells forming the body of an organism other than hepatocytes. In some embodiments, the somatic cells are human somatic cells such as skin fibroblasts, adipose tissue-derived cells and human umbilical vein endothelial cells (HUVEC). In a particular aspect, the somatic cells may be immortalized to provide an unlimited supply of cells, for example, by increasing the level of telomerase reverse transcriptase (TERT). This can be effected by increasing the transcription of TERT from the endogenous gene, or by introducing a transgene through any gene delivery method or system.

Hepatocyte programming factor genes include any genes that, alone or in combination, directly impose hepatic fate upon non-hepatocytes, especially transcription factor genes or genes that are important in hepatic differentiation or hepatic function when expressed in cells. For example, one, two, three, four, five, six, seven, eight, nine, ten, or more of the exemplary genes and isoforms or variants thereof as listed in Table 1 may be used in certain aspects of the invention. Many of these genes have different isoforms, which might have similar functions and therefore are contemplated for use in certain aspects of the invention.

In a particular embodiment, the hepatocyte programming factor genes used herein may comprise one, two, three, four, five, or six of Forkhead box protein A1 (FOXA1), forkhead box A2 (FOXA2) (e.g., FOXA2-2; NM__153675.2), hematopoietically-expressed homeobox protein (HHEX), hepatocyte nuclear factor 1 homeobox A (HNF1A), hepatocyte nuclear factor 4 alpha (HNF4A) (e.g., HNF4A-2; NM__000457.3), GATA binding protein 4 (GATA4), NR0B2 (nuclear receptor subfamily 0, group B, member 2), sex comb on midleg-like 1 (SCML1), and T-box transcription factor (TBX3) (e.g., TBX3-1; NM__005996.3). In a more particular aspect, the hepatocyte programming factor genes include FOXA2, HHEX, HNF1A, and HNF4A. For example, the hepatocyte programming factor genes may be a combination of FOXA1, FOXA2, HHEX, HNF1A, HNF4A and TBX3. In another example, the hepatocyte programming factor genes may be a combination of FOXA2, HHEX, HNF4A, GATA4, NR0B2 and SCML1.

In certain aspects, there is provided a method of providing hepatocytes by forward programming of pluripotent stem cells, comprising: providing the hepatocytes by culturing the pluripotent stem cells under conditions to increasing the expression level of a sufficient number of hepatocyte programming factor genes capable of causing forward programming of the stem cells (e.g., pluripotent stem cells) to hepatocytes, thereby causing the pluripotent stem cells to directly differentiate into hepatocytes.

The skilled artisan will understand that methods for increasing the expression of the hepatocyte programming factor genes in the cells to be programmed into hepatocytes may include any method known in the art, for example, by induction of expression of one or more expression cassettes previously introduced into the cells, or by introduction of nucleic acids such as DNA or RNA, polypeptides, or small molecules to the cells. Increasing the expression of certain endogenous but transcriptionally repressed programming factor genes may also reverse the silencing or inhibitory effect on the expression of these programming factor genes by regulating the upstream transcription factor expression or epigenetic modulation.

In one aspect, the cells for hepatic lineage programming may comprise at least one exogenous expression cassette, wherein the expression cassette comprises the hepatocyte programming factor genes in a sufficient number to cause forward programming or transdifferentiation of non-hepatocytes to hepatocytes. The exogenous expression cassette may comprise an externally inducible transcriptional regulatory element for inducible expression of the hepatocyte programming factor genes, such as an inducible promoter comprising a tetracycline response element.

In a further aspect, one or more of the exogenous expression cassette for hepatocyte programming may be comprised in a gene delivery system. Non-limiting examples of a gene delivery system may include a transposon system, a viral gene delivery system, or an episomal gene delivery system. The viral gene delivery system may be an RNA-based or DNA-based viral vector. The episomal gene delivery system may be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or the like.

In another aspect, the cells for hepatic lineage programming may be contacted with hepatocyte programming factors in an amount sufficient to cause forward programming of the stem cells to hepatocytes. The hepatocyte programming factors may comprise gene products of the hepatocyte programming factor genes. The gene products may be polypeptides or RNA transcripts of the hepatocyte programming factor genes. In a further aspect, the hepatocyte programming factors may comprise one or more protein transduction domains to facilitate their intracellular entry and/or nuclear entry. Such protein transduction domains are well known in the art, such as an HIV TAT protein transduction domain, HSV VP22 protein transduction domain, *Drosophila* Antennapedia homeodomain or variants thereof.

The method may further comprise a selection or enrichment step for the hepatocytes provided from forward programming or transdifferentiation. To aid selection or enrichment, the cells for programming, such as the pluripotent stem cells or progeny cells thereof, may comprise a selectable or screenable reporter expression cassette comprising a reporter gene. The reporter expression cassette may comprise a hepatocyte-specific transcriptional regulatory element operably linked to a reporter gene. Non-limiting examples of hepatocyte-specific transcriptional regulatory element include a promoter of albumin, α-1-antitrypsin (AAT), cytochrome p450 3A4 (CYP3A4), apolipoprotein A-I, or apoE. Mature hepatocyte-specific transcriptional regulatory element may comprise a promoter of albumin, α1-antitrypsin, asialoglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase.

Characteristics of the hepatocytes provided in certain aspects of the invention include, but are not limited to one or more of: (i) expression of one or more hepatocyte markers including glucose-6-phosphatase, albumin, α-1-antitrypsin (AAT), cytokeratin 8 (CK8), cytokeratin 18 (CK18), asialoglycoprotein receptor (ASGR), alcohol dehydrogenase 1, arginase Type I, cytochrome p450 3A4 (CYP3A4), liver-specific organic anion transporter (LST-1), or a combination thereof; (ii) activity of liver-specific enzymes such as glucose-6-phosphatase or CYP3A4, production of by-products such as bile and urea or bile secretion, or xenobiotic detoxification; (iii) hepatocyte morphological features; or (iv) in vivo liver engraftment in an immunodeficient subject.

For selection or enrichment of the hepatocytes, there may be further provided a step by identifying hepatocytes comprising expression of a hepatic reporter gene or one or more hepatocyte characteristics as described herein.

In particular aspects, the hepatocytes provided herein may be mature hepatocytes. The mature hepatocytes may be selected or enriched by using a screenable or selectable reporter expression cassette comprising a mature hepatocyte-specific transcriptional regulatory element operably linked to a reporter gene, or magnetic cell sorting using antibody against hepatocyte-specific cell surface antigens such as ASGR, or by assessing characteristic specific for mature hepatocytes as known in the art. For example, mature hepatocytes can be identified by one or more of: the presence of hepatocyte growth factor receptor, albumin, α1-antitrypsin, asialoglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase, and the absence of intracellular pancreas-associated insulin or proinsulin production. In further aspects, hepatocyte-like cells provided herein may be further forward programmed into mature hepatocytes by the artificially increased expression of genes detailed in Table 1.

For production of more mature hepatocytes, the starting cell population may be cultured in a medium comprising one or more growth factors such as Oncostain M (OSM), or further comprising hepatocyte growth factor (HGF). The culturing may be prior to, during, or after the effected expression of hepatocyte programming factors. Hepatocytes may be provided at least, about or up to 3, 4, 5, 6, 7, 8, 9, 10, 11, 12, 13, 14, 15, 16, 17, 18, 19, 20 days (or any range derivable therein) after the increased expression or culturing in the presence or absence of growth factors.

In a further embodiment, a hepatocyte may be produced by any of the methods set forth herein. In certain aspects, there may also be provided a tissue engineered liver comprising the hepatocytes provided by the methods described herein. In another aspect, there may be provided a hepatocyte-based bio-artificial liver (BAL) comprising the hepatocytes.

In certain aspects, the invention provides a cell comprising one or more exogenous expression cassettes comprising one or more hepatocyte programming factor genes (e.g., genes in Table 1 and isoforms or variants thereof). The exogenous expression cassettes may comprise two, three, four, five or six of the hepatocyte programming factor gene. For example, the exogenous expression cassettes may comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391. In a particular example, the exogenous expression cassettes comprise FOXA1, FOXA2, HHEX, HNF1A, HNF4A, and TBX3. In another example, the hepatocyte programming factor genes may be a combination of FOXA2, HHEX, HNF4A, GATA4, NR0B2 and SCML1.

For inducible expression of the hepatocyte programming factor genes, at least one of the exogenous expression cassettes may comprise an externally inducible transcriptional regulatory element. In particular aspects, there may be provided a cell comprising one or more exogenous expression cassettes, wherein the one or more exogenous expression cassettes comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391, and at least one of the exogenous expression cassettes is operably linked to an externally inducible transcriptional regulatory element.

The exogenous expression cassettes may be comprised in one or more gene delivery systems. The gene delivery system may be a transposon system; a viral gene delivery system; an episomal gene delivery system; or a homologous recombination system such as utilizing a zinc finger nuclease, a transcription activator-like effector (TALE) nuclease, or a meganuclease, or the like. The cell may further comprise a screenable or selectable reporter expression cassette comprising a hepatocyte-specific promoter operably linked to a reporter gene. The hepatocyte-specific transcriptional regulatory element may be a promoter of albumin, α-1-antitrypsin (AAT), cytochrome p450 3A4 (CYP3A4), apolipoprotein A-I, apoE, or any other hepatocyte-specific promoter or enhancer in the art.

In one aspect, the cell may be a stem cell or a progeny cell thereof. The stem cell may be a pluripotent stem cell or any non-pluripotent stem cell. The pluripotent stem cell may be an induced pluripotent stem cell, an embryonic stem cell, or a pluripotent stem cell derived by nuclear transfer or cell fusion. The stem cell may also be a multipotent stem cell, oligopotent stem cell, or unipotent stem cell. The stem cell may also be a fetal stem cell or an adult stem cell, for example, a hematopoietic stem cell, a mesenchymal stem cell, a neural stem cell, an epithelial stem cell or a skin stem cell. In another aspect, the cell may be a somatic cell, either immortalized or not. The cell may also be a hepatocyte, more particularly, a mature hepatocyte or an immature hepatocyte (e.g., hepatocyte-like cell).

There may also be provided a composition comprising a cell population comprising two cell types, i.e., the cells to be programmed to hepatocytes and hepatocytes, and essentially free of other intermediate cell types. For example, such a cell population may have two cell types including the stem cells and hepatocytes but essentially free of other cells types in the intermediate developmental stages along the hepatic differentiation process. In particular, a composition comprising a cell population consisting of stem cells and hepatocytes may be provided. The stem cells may be particularly pluripotent stem cells, e.g., induced pluripotent stem cells. Hepatocytes may be at least, about, or up to 1, 5, 10, 15, 20, 25, 30, 35, 40, 45, 50, 60, 70, 80, 85, 90, 91, 92, 93, 94, 95, 96, 97, 98, 99, 99.9% (or any intermediate ranges) of the cell population, or any range derivable therein.

There may be also provided a cell population comprising hepatocytes, wherein at least 20, 25, 30, 35, 40, 45, 50, 60, 70, 80, 85, 90, 91, 92, 93, 94, 95, 96, 97, 98, 99, 99.9% (or any intermediate ranges) of the hematopoietic precursor cells comprise one or more expression cassettes that comprise FOXA2, HNF4A and one or more additional hepatocyte programming factor genes selected from the group consisting of HHEX, HNF1A, FOXA1, TBX3-1, GATA4, NR0B2, SCML1, CEBPB, HLF, HLX, NR1H3, NR1H4, NR1I2, NR1I3, NR5A2, SEBOX, ZNF391.

The hepatocytes provided herein may be used in any methods and applications currently known in the art for hepatocytes. For example, a method of assessing a compound may be provided, comprising assaying a pharmacological or toxicological property of the compound on the hepatocyte or tissue engineered liver provided herein. There may also be provided a method of assessing a compound for an effect on a hepatocyte, comprising: a) contacting the hepatocyte provided herein with the compound; and b) assaying an effect of the compound on the hepatocyte.

In a further aspect, there may also be provided a method for treating a subject having or at risk of a liver dysfunction comprising administering to the subject with a therapeutically effective amount of hepatocytes or hepatocyte-containing cell population provided herein.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 4A) Cellular morphological changes during hepatic differentiation of human ESC R/I lines, and restricted expression of mOrange in maturing hepatocytes. (FIG. 4B) Flow cytometric analysis of hepatic marker Albumin and ASGPR1 (marker for mature hepatocytes) in d20 differentiated culture.

(FIG. 5A) A two-vector PiggyBac stable gene expression system. Ptight: an rtTET-responsive inducible promoter; pEF: the eukaryotic elongation factor 1α promoter; hPBase: the coding region for the PiggyBac transposase with codons optimized for expression in human cells. (FIG. 5B) EGFP induction in human ESC R/I lines. The EGFP driven by the Ptight promoter was introduced into human ESC R/I lines using Fugene HD-mediated transfection of both vectors in (FIG. 5A). Human ESCs with stable PiggyBac transposon integration were selected with geneticin (100 µg/ml). Images are shown with human ESC R/I lines after 2 days induction with or without Doxycycline (1 µg/ml). (FIG. 5C) Flow cytometric analysis of EGFP expression in human ESC R/I lines after 4 days induction with or without Doxycycline (1 µg/ml). Gray lines: Human ESC R/I lines without the transfection of the EGFP vector (negative control). Black lines: Human ESC R/I lines with stable PiggyBac transposon integration after 4 days induction with or without Doxycycline.

DESCRIPTION OF ILLUSTRATIVE EMBODIMENTS

Figure 1:
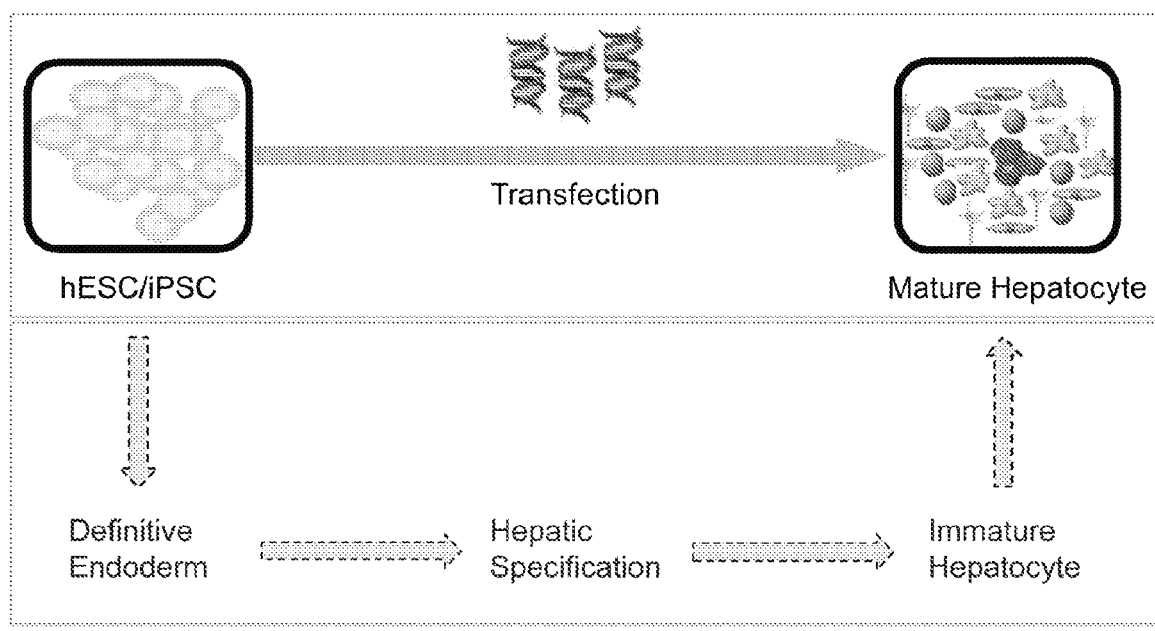
FIG. 1. Alternative approaches for hepatocyte differentiation from human ESC/iPSCs.

The instant invention overcomes several major problems with current technologies by providing methods and compositions for hepatocyte production by programming. In contrast to previous methods using step-wise differentiation protocols, certain aspects of these methods increase the level of hepatocyte programming transcription factors in non-hepatocytes to provide hepatocytes by forward programming. The extra steps including adding different growth factors during various intermediate developmental stages may be unnecessary in certain aspects the present methods. Therefore, certain aspects of the present methods may be more time- and cost-efficient and may enable manufacture of hepatocytes for therapeutics from a renewable source, for example, stem cells. Further embodiments and advantages of the invention are described below.

I. DEFINITIONS

"Programming" is a process that changes a cell to form progeny of at least one new cell type, either in culture or in vivo, than it would have under the same conditions without programming. This means that after sufficient proliferation, a measurable proportion of progeny having phenotypic characteristics of the new cell type if essentially no such progeny could form before programming; alternatively, the proportion having characteristics of the new cell type is measurably more than before programming. This process includes differentiation, dedifferentiation and transdifferentiation. "Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Under certain conditions, the proportion of progeny with characteristics of the new cell type may be at least about 1%, 5%, 25% or more in the in order of increasing preference.

The term "exogenous," when used in relation to a protein, gene, nucleic acid, or polynucleotide in a cell or organism refers to a protein, gene, nucleic acid, or polynucleotide which has been introduced into the cell or organism by artificial means, or in relation a cell refers to a cell which was isolated and subsequently introduced to other cells or to an organism by artificial means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

By "expression construct" or "expression cassette" is meant a nucleic acid molecule that is capable of directing transcription. An expression construct includes, at the least, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as gene delivery system or gene transfer "vehicle") refers to a macromolecule or complex of molecules comprising a polynucleotide to be delivered to a host cell, either in vitro or in vivo.

A "plasmid", a common type of a vector, is an extra-chromosomal DNA molecule separate from the chromosomal DNA which is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid, and/or a site at or near where DNA synthesis initiates. An on for EBV includes FR sequences (20 imperfect copies of a 30 bp repeat), and preferably DS sequences, however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of giving rising to at least one type of a more specialized cell. A stem cells has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent stem cells or induced pluripotent stem cells.

As used herein "totipotent stem cells" refers to cells has the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

In contrast, many progenitor cells are multipotent stem cells, i.e., they are capable of differentiating into a limited number of cell fates. Multipotent progenitor cells can give rise to several other cell types, but those types are limited in number. An example of a multipotent stem cell is a hematopoietic cell—a blood stem cell that can develop into several types of blood cells, but cannot develop into brain cells or other types of cells. At the end of the long series of cell divisions that form the embryo are cells that are terminally differentiated, or that are considered to be permanently committed to a specific function.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

Cells are "substantially free" of certain undesired cell types, as used herein, when they have less that 10% of the undesired cell types, and are "essentially free" of certain cell types when they have less than 1% of the undesired cell types. However, even more desirable are cell populations wherein less than 0.5% or less than 0.1% of the total cell population comprise the undesired cell types. Thus, cell populations wherein less than 0.1% to 1% (including all intermediate percentages) of the cells of the population comprise undesirable cell types are essentially free of these cell types. A medium may be "essentially free" of certain reagents, as used herein, when there is no externally addition of such agents. More preferably, these agents are absent or present at a undetectable amount.

The term "hepatocyte" as used herein is meant to include hepatocyte-like cells that exhibit some but not all characteristics of mature hepatocytes, as well as mature and fully functional hepatocytes. The cells produced by this method may be as at least as functional as the hepatocytes produced by directed differentiation to date. This technique may, as it is further improved, enable the production of completely fully functional hepatocytes, which have all characteristics of hepatocytes as determined by morphology, marker expression, in vitro and in vivo functional assays.

II. CELLS INVOLVED IN HEPATOCYTE PROGRAMMING

In certain embodiments of the invention, there are disclosed methods and compositions for producing hepatocytes by forward programming of cells which are not hepatocytes. There may be also provided cells that comprise exogenous expression cassettes including one or more hepatocyte programming factor genes and/or reporter expression cassettes specific for hepatocyte identification. In some embodiments, the cells may be stem cells, including but are not limited to, embryonic stem cells, fetal stem cells, or adult stem cells. In further embodiments, the cells may be any somatic cells.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

Human embryonic stem cells (ESCs) and induced pluripotent stem cells (iPSC) are capable of long-term proliferation in vitro, while retaining the potential to differentiate into all cell types of the body, including hepatocytes. Thus these cells could potentially provide an unlimited supply of patient-specific functional hepatocytes for both drug development and transplantation therapies. The differentiation of human ESC/iPSCs to hepatocytes in vitro recapitulates normal in vivo development, i.e. they undergo the following sequential developmental stages: definitive endoderm, hepatic specification, immature hepatocyte and mature hepatocyte (FIG. 1). This requires the addition of different growth factors at different stages of differentiation, and generally requires over 20 days of differentiation (FIG. 4). More importantly, the human ESC/iPSC-derived hepatocytes generally are yet to exhibit the full functional spectrum of human primary adult hepatocytes. Certain aspects of the invention provided that hepatocytes such as hepatocyte-like cells or fully functional hepatocytes could be induced directly from human ESC/iPSCs via expression of a combination of transcription factors important for hepatocyte differentiation/function, similar to the generation of iPSCs, bypassing most, if not all, normal developmental stages (FIG. 1). This approach could be more time- and cost-efficient, and generate hepatocytes with functions highly similar, if not identical, to human primary adult hepatocytes. In addition, human ESC/iPSCs, with their unlimited proliferation ability, have a unique advantage over somatic cells as the starting cell population for hepatocyte differentiation.

1. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as described above. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, e.g., an EBV element-based system (see U.S. Application No. 61/058,858, incorporated herein by reference; Yu et al., 2009). In a further aspect, reprogramming proteins or RNA (such as mRNA or miRNA) could be introduced directly into somatic cells by protein transduction or RNA transfection (see U.S. Application No. 61/172,079, incorporated herein by reference; Yakubov et al., 2010).

3. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

4. Other Stem Cells

Fetal stem cells are cells with self-renewal capability and pluripotent differentiation potential. They can be isolated and expanded from fetal cytotrophoblast cells (European Patent EP0412700) and chorionic villi, amniotic fluid and the placenta (WO/2003/042405). These are hereby incorporated by reference in their entirety. Cell surface markers of fetal stem cells include $CD117/c\text{-}kit^+$, $SSEA3^+$, $SSEA4^+$ and $SSEA1^-$.

Somatic stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see U.S. Pat. Nos. 5,635,387; 5,460,964; 5,677,136; 5,750,397; 5,759,793; 5,681,599; 5,716,827; Hill et al., 1996). These are hereby incorporated by reference in their entirety. When transplanted into lethally irradiated animals or humans, hematopoietic stem cells can repopulate the erythroid, neutrophil-macrophage, megakaryocyte and lymphoid hematopoieticcell pool. In vitro, hematopoieticstem cells can be induced to undergo at least some self-renewing cell divisions and can be induced to differentiate to the same lineages as is seen in vivo. Therefore, this cell fulfills the criteria of a stem cell.

The next best characterized is the mesenchymal stem cells (MSC), originally derived from the embryonic mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A number of mesenchymal stem cells have been isolated (see, for example, U.S. Pat. Nos. 5,486,359; 5,827,735; 5,811,094; 5,736,396; U.S. Pat. Nos. 5,837,539; 5,837,670; 5,827,740; Jaiswal et al., 1997; Cassiede et al., 1996; Johnstone et al., 1998; Yoo et al., 1998; Gronthos, 1994; Makino et al., 1999). These are hereby incorporated by reference in their entirety. Of the many mesenchymal stem cells that have been described, all have demonstrated limited differentiation to form only those differentiated cells generally considered to be of mesenchymal origin. To date, the most multipotent mesenchymal stem cell expresses the $SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD45^-$ phenotype.

Other stem cells have been identified, including gastrointestinal stem cells, epidermal stem cells, neural and hepatic stem cells, also termed oval cells (Potten, 1998; Watt, 1997; Alison et al, 1998).

In some embodiments, the stem cells useful for the method described herein include but not limited to embryonic stem cells, induced pluripotent stem cells, mesenchymal stem cells, bone-marrow derived stem cells, hematopoietic stem cells, chondrocyte progenitor cells, epidermal stem cells, gastrointestinal stem cells, neural stem cells, hepatic stem cells adipose-derived mesenchymal stem cells, pancreatic progenitor cells, hair follicular stem cells, endothelial progenitor cells and smooth muscle progenitor cells.

In some embodiments, the stem cells used for the method described herein is isolated from umbilical cord, placenta, amniotic fluid, chorion villi, blastocysts, bone marrow, adipose tissue, brain, peripheral blood, the gastrointestinal tract, cord blood, blood vessels, skeletal muscle, skin, liver and menstrual blood. Stem cells prepared in the menstrual blood are called endometrial regenerative cells (Medistem Inc.).

One ordinary skilled artisan in the art can locate, isolate and expand such stem cells. The detailed procedures for the isolation of human stem cells from various sources are described in Current Protocols in Stem Cell Biology (2007) and it is hereby incorporated by reference in its entirety. Alternatively, commercial kits and isolation systems can be used. For example, the BD FACS Aria cell sorting system, BD IMag magnetic cell separation system, and BD IMag mouse hematopoietic progenitor cell enrichment set from BD Biosciences. Methods of isolating and culturing stem cells from various sources are also described in U.S. Pat. Nos. 5,486, 359, 6,991,897, 7,015,037, 7,422,736, 7,410,798, 7,410,773, 7,399,632 and these are hereby incorporated by reference in their entirety.

B. Somatic Cells

In certain aspects of the invention, there may also be provided methods of transdifferentiation, i.e., the direct conversion of one somatic cell type into another, e.g., deriving hepatocytes from other somatic cells. Transdifferentiation may involve the use of hepatocyte programming factor genes or gene products to increase expression levels of such genes in somatic cells for production of hepatocytes.

However, the human somatic cells may be limited in supply, especially those from living donors. In certain aspects to provide a unlimited supply of staring cells for programming, somatic cells may be immortalized by introduction of immortalizing genes or proteins, such as hTERT or oncogenes. The immortalization of cells may be reversible (e.g., using removable expression cassettes) or inducible (e.g., using inducible promoters).

Somatic cells in certain aspects of the invention may be primary cells (non-immortalized cells), such as those freshly isolated from an animal, or may be derived from a cell line (immortalized cells). The cells may be maintained in cell culture following their isolation from a subject. In certain embodiments the cells are passaged once or more than once (e.g., between 2-5, 5-10, 10-20, 20-50, 50-100 times, or more) prior to their use in a method of the invention. In some embodiments the cells will have been passaged no more than 1, 2, 5, 10, 20, or 50 times prior to their use in a method of the invention. They may be frozen, thawed, etc.

The somatic cells used or described herein may be native somatic cells, or engineered somatic cells, i.e., somatic cells which have been genetically altered. Somatic cells of the present invention are typically mammalian cells, such as, for example, human cells, primate cells or mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc.

Mammalian somatic cells useful in the present invention include, but are not limited to, Sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, and other muscle cells, etc.

In some embodiments cells are selected based on their expression of an endogenous marker known to be expressed only or primarily in a desired cell type. For example, vimentin is a fibroblast marker. Other useful markers include various keratins, cell adhesion molecules such as cadherins, fibronectin, CD molecules, etc. The population of somatic cells may have an average cell cycle time of between 18 and 96 hours, e.g., between 24-48 hours, between 48-72 hours, etc. In some embodiments, at least 90%, 95%, 98%, 99%, or more of the cells would be expected to divide within a predetermined time such as 24, 48, 72, or 96 hours.

Methods described herein may be used to program one or more somatic cells, e.g., colonies or populations of somatic cells into hepatocytes. In some embodiments a population of cells of the present invention is substantially uniform in that at least 90% of the cells display a phenotype or characteristic of interest. In some embodiments at least 95%, 96%, 97%, 98%, 99%, 99.5%, 99.8%, 99.9, 99.95% or more of the cells display a phenotype or characteristic of interest. In certain embodiments of the invention the somatic cells have the capacity to divide, i.e., the somatic cells are not post-mitotic.

Somatic cells may be partially or completely differentiated. Differentiation is the process by which a less specialized cell becomes a more specialized cell type. Cell differentiation can involve changes in the size, shape, polarity, metabolic activity, gene expression and/or responsiveness to signals of the cell. For example, hematopoietic stem cells differentiate to give rise to all the blood cell types including myeloid (monocytes and macrophages, neutrophils, basophils, eosinophils, erythrocytes, megakaryocytes/platelets, dendritic cells) and lymphoid lineages (T-cells, B-cells, NK-cells). During progression along the path of differentiation, the ultimate fate of a cell becomes more fixed. As described herein, both partially differentiated somatic cells and fully differentiated somatic cells can be programmed as described herein to produce desired cell types such as hepatocytes.

III. HEPATOCYTE PROGRAMMING FACTORS

Certain aspects of the invention provide hepatocyte programming factors for hepatocyte forward programming. The hepatocytes could be produced directly from other cell sources by increasing the level of hepatocyte programming factors in cells. The numerous functions of hepatocytes could be controlled at the transcriptional level by the concerted actions of a limited number of hepatocyte-enriched transcription factors. Any transcription factors important for hepatocyte differentiation or function may be used herein, like hepatocyte-enriched transcription factors, particularly the genes thereof listed in Table 1. All the isoforms and variants of the genes listed in Table 1 may be included in this invention, and non-limiting examples of accession numbers for certain isoforms or variants are provided.

For example, by effecting expression of a combination of transcription factors in Table 1, forward programming into hepatocytes from pluripotent stem cells may bypass most, if not all, normal developmental stages. Examples shown are a combination of the following transcription factors: FOXA1, FOXA2, HHEX, HNF1A, HNF4A and TBX3, or a combination of FOXA2, HHEX, HNF4A, GATA4, NR0B2 and SCML1.

TABLE 1

A list of genes for forward programming to hepatocytes.

| # | Symbol | Entrez Gene ID | Exemplary Accession No. | SEQ ID NO: | Name |
|---|---|---|---|---|---|
| 1 | SOX17 | 64321 | NM_022454.3 | 9 | SRY (sex determining region Y)-box 17 [Homo sapiens] |
| 2 | FOXA1 | 3169 | NM_004496.2 | 10 | forkhead box A1 [Homo sapiens] |
| 3 | FOXA2 | 3170 | NM_021784.4 | 11 | forkhead box A2 [Homo sapiens] |
|   |   |   | NM_153675.2 | 12 |   |
| 4 | HHEX | 3087 | NM_002729.4 | 13 | hematopoietically expressed homeobox [Homo sapiens] |
| 5 | GATA4 | 2626 | NM_002052.3 | 14 | GATA binding protein 4 [Homo sapiens] |
| 6 | GATA6 | 2627 | NM_005257.3 | 15 | GATA binding protein 6 [Homo sapiens] |
| 7 | PROX1 | 5629 | NM_002763.3 | 16 | prospero homeobox 1 [Homo sapiens] |
| 8 | TBX3 | 6926 | NM_005996.3 | 17 | T-box 3 [Homo sapiens] |
|   |   |   | NM_016569.3 | 18 |   |
| 9 | HLX | 3142 | NM_021958.3 | 19 | H2.0-like homeobox [Homo sapiens] |
| 10 | ONECUT1 | 3175 | NM_004498.1 | 20 | one cut homeobox 1 [Homo sapiens] |
| 11 | ONECUT2 | 9480 | NM_004852.2 | 21 | one cut homeobox 2 [Homo sapiens] |
| 12 | MYC | 4609 | NM_002467.4 | 22 | v-myc myelocytomatosis viral oncogene homolog (avian) [Homo sapiens] |
| 13 | FOXA3 | 3171 | NM_004497.2 | 23 | forkhead box A3 [Homo sapiens] |
| 14 | HNF4A | 3172 | NM_000457.3 | 24 | hepatocyte nuclear factor 4, alpha [Homo sapiens] |
| 15 | HNF1A | 6927 | NM_000545.5 | 25 | HNF1 homeobox A [Homo sapiens] |
| 16 | HNF1B | 6928 | NM_000458.2 | 26 | HNF1 homeobox B [Homo sapiens] |
| 17 | CEBPA | 1050 | NM_004364.3 | 27 | CCAAT/enhancer binding protein (C/EBP), alpha [Homo sapiens] |
| 18 | CEBPB | 1051 | NM_005194.2 | 28 | CCAAT/enhancer binding protein (C/EBP), beta [Homo sapiens] |
| 19 | DBP | 1628 | NM_001352.3 | 29 | D site of albumin promoter (albumin D-box) binding protein [Homo sapiens] |
| 20 | ZBTB20 | 26137 | NM_001164342.1 | 30 | zinc finger and BTB domain containing 20 |
|   |   |   | NM_001164343.1 | 31 | [Homo sapiens] |
| 21 | NR1I3 | 9970 |   |   | nuclear receptor subfamily 1, group I, member 3 [Homo sapiens] |
| 22 | NR1I2 | 8856 | NM_003889.3 | 32 | nuclear receptor subfamily 1, group I, member |
|   |   |   | NM_022002.2 | 33 | 2 [Homo sapiens] |
| 23 | NR1H4 | 9971 | NM_005123.2 | 34 | nuclear receptor subfamily 1, group H, member 4 [Homo sapiens] |
| 24 | ATF5 | 22809 | NM_012068.5 | 35 | activating transcription factor 5 [Homo sapiens] |
| 25 | NR5A2 | 2494 | NM_003822.3 | 36 | nuclear receptor subfamily 5, group A, member 2 [Homo sapiens] |
| 26 | NR1H3 | 10062 | NM_005693.2 | 37 | nuclear receptor subfamily 1, group H, member 3 [Homo sapiens] |
| 27 | CREB3L3 | 84699 | NM_032607.1 | 38 | cAMP responsive element binding protein 3-like 3 [Homo sapiens] |
| 28 | NKX2-8 | 26257 | NM_014360.2 | 39 | NK2 homeobox 8 [Homo sapiens] |
| 29 | CEBPD | 1052 | NM_005195.3 | 40 | CCAAT/enhancer binding protein (C/EBP), delta [Homo sapiens] |
| 30 | HLF | 3131 | NM_002126.4 | 41 | hepatic leukemia factor [Homo sapiens] |
| 31 | NR0B2 | 8431 | NM_021969.2 | 42 | nuclear receptor subfamily 0, group B, member 2 [Homo sapiens] |
| 32 | ABLIM3 | 22885 | NM_014945.2 | 43 | actin binding LIM protein family, member 3 [Homo sapiens] |
| 33 | ATOH8 | 84913 | NM_032827.6 | 44 | atonal homolog 8 (Drosophila) [Homo sapiens] |
| 34 | C14orf39 | 317761 | NM_174978.2 | 45 | chromosome 14 open reading frame 39 [Homo sapiens] |
| 35 | SCML1 | 6322 | NM_001037540.1 | 46 | sex comb on midleg-like 1 (Drosophila) |
|   |   |   | NM_006746.4 | 47 | [Homo sapiens] |
| 36 | SEBOX | 645832 | NM_001083896.1 | 48 | SEBOX homeobox [Homo sapiens] |

TABLE 1-continued

A list of genes for forward programming to hepatocytes.

| # | Symbol | Entrez Gene ID | Exemplary Accession No. | SEQ ID NO: | Name |
|---|---|---|---|---|---|
| 37 | ZBED3 | 84327 | NM_032527.3 | 49 | zinc finger, BED-type containing 3 [*Homo sapiens*] |
| 38 | ZGPAT | 84619 | NM_032527.3 NM_181485.2 | 49 50 | zinc finger, CCCH-type with G patch domain [*Homo sapiens*] |
| 39 | ZNF391 | 346157 | NM_001076781.1 | 51 | zinc finger protein 391 [*Homo sapiens*] |
| 40 | ZNF426 | 79088 | NM_024106.1 | 52 | zinc finger protein 426 [*Homo sapiens*] |
| 41 | ZNF517 | 340385 | NM_213605.2 | 53 | zinc finger protein 517 [*Homo sapiens*] |

The hepatocyte-enriched transcription factors include, but are not limited to, hepatocyte nuclear factor 1-α (HNF-1α), -1β, -3α, -3β, -3γ, -4α, and -6 and members of the c/ebp family). Hepatocyte nuclear factors (HNFs) are a group of phylogenetically unrelated transcription factors that regulate the transcription of a diverse group of genes into proteins. These proteins include blood clotting factors and in addition, enzymes and transporters involved with glucose, cholesterol, and fatty acid transport and metabolism. Of these, HNF4A (also known as HNF4α or nuclear receptor 2A1 or (NR2A1)) and HNF1A (i.e., HNF1α) appear to be correlated with the differentiated phenotype of cultured hepatoma cells. HNF1A-null mice are viable, indicating that this factor is not an absolute requirement for the formation of an active hepatic parenchyma. In contrast, HNF4A-null mice die during embryogenesis. HNF4A is expressed early in development, visible by in situ hybridization in the mouse visceral endoderm at embryonic day 4.5, long before liver development. Whereas HNF4A appears to be essential in the visceral endoderm it may not be necessary for the earliest steps in the development of the fetal liver (Li et al., 2000). HNF-4A is both essential for hepatocyte differentiation during mammalian liver development and also crucial for metabolic regulation and proper liver function (Hayhurst et al., 2001). HNF-4A is also known as TCF; HNF4; MODY; MODY1; NR2A1; TCF14; HNF4a7; HNF4a8; HNF4a9; NR2A21; and FLJ39654. Six transcriptional variants or isoforms are produced from the genomic gene, isoforms a, b c, d, d, e, and f (Genbank Accession NOs: NM_000457.3, NM_001030003.1, NM_001030004.1, NMJ75914.3, NM_178849.1, and NM_178850.1). All isoforms contain a zinc finger, C4 type DNA binding domain and ligand-binding domain. The encoded protein is a nuclear transcription factor which binds DNA as a homodimer and controls the expression of several genes, including HNF1A, a transcription factor which in turns regulates the expression of several hepatic genes. Over 55 distinct target genes have been identified for HNF4A. Since many of those genes contain more than one HNF4A binding site, the total number of distinct, non species redundant HNF4A binding sites is now 74. These genes can be grouped into several different categories, according to function, such as nutrient transport and metabolism, blood maintenance, immune function, liver differentiation and growth factors. The best characterized HNF-4A target genes are those involved in lipid transport (e.g., apolipoprotein genes) and glucose metabolism (e.g., L-PK and PEPCK). Nearly all of the target genes identified thus far are expressed primarily in the liver; several are expressed in other organs as well, such as the pancreas.

HNF1A is also known as HNF1, LFB1, TCF1, and M0DY3. HNF1A is a transcription factor that is highly expressed in the liver and is involved in the regulation of the expression of several liver specific genes such as the human class I alcohol dehydrogenase. HNF-1A (Genbank Accession No: NM 000545.4) belongs to the homeobox gene family for it contains a homeobox DNA binding domain. A homeobox is a DNA sequence that binds DNA. The translated homeobox is a highly conserved stretch of 60 amino acid residues.

Forkhead box A2 (FOXA2), is also known as HNF-3β, HNF3B, TCF3B and MGC19807. FOXA2 is a member of the forkhead class of DNA-binding proteins. The forkhead box is a sequence of 80 to 100 amino acids that form a motif that binds to DNA. This forkhead motif is also known as the winged helix due to the butterfly-like appearance of the loops in the protein structure of the domain. These hepatocyte nuclear factors are transcriptional activators for liver-specific genes such as albumin and transthyretin, and they also interact with chromatin. Similar family members in mice have roles in the regulation of metabolism and in the differentiation of the pancreas and liver. This gene has been linked to sporadic cases of maturity-onset diabetes of the young. Transcript variants encoding different isoforms, isoform 1 and 2, have been identified for this gene (Genbank Accession Nos: NM 021784.4; FOXA2-1) and NM_153675.2; FOXA2-2).

CCAAT/enhancer binding protein (C/EBP) alpha is a CCAAT/enhancer-binding protein. C/EBPs are a family of transcription factors that are critical for cellular differentiation, terminal functions and inflammatory response. Six members of the family have been characterized (C/EBP alpha, C/EBP beta, C/EBP delta, C/EBP epsilon, C/EBP gamma and C/EBP zeta) and are distributed in a variety of tissues.

Hematopoietically-expressed homeobox protein HHEX is a protein that in humans is encoded by the HHEX gene. This gene encodes a member of the homeobox family of transcription factors, many of which are involved in developmental processes. HHEX is required for early development of the liver. A null mutation of HHEX results in a failure to form the liver bud and embryonic lethality.

T-box transcription factor TBX3 is a protein that in humans is encoded by the TBX3 gene. This gene is a member of a phylogenetically conserved family of genes that share a common DNA-binding domain, the T-box. T-box genes encode transcription factors involved in the regulation of developmental processes. This protein is a transcriptional repressor and is thought to play a role in the anterior/posterior axis of the tetrapod forelimb. Mutations in this gene cause ulnar-mammary syndrome, affecting limb, apocrine gland, tooth, hair, and genital development. Alternative splicing of this gene results in three transcript variants encoding different isoforms.

GATA4 gene encodes a member of the GATA family of zinc finger transcription factors. Members of this family recognize the GATA motif which is present in the promoters of many genes. GATA4 protein is thought to regulate genes involved in embryogenesis and in myocardial differentiation and function. Mutations in this gene have been associated with cardiac septal defects as well as reproductive defects.

NR0B2 gene (nuclear receptor subfamily 0, group B, member 1; previous name is dosage-sensitive sex reversal (DAX1)) encodes a protein that contains a DNA-binding domain. The encoded protein acts as a dominant-negative regulator of transcription which is mediated by the retinoic acid receptor. This protein also functions as an anti-testis gene by acting antagonistically to Sry. Mutations in this gene result in both X-linked congenital adrenal hypoplasia and hypogonadotropic hypogonadism. The encoded protein plays an important role in the normal development of several hormone-producing tissues. These tissues include the adrenal glands), the pituitary gland and hypothalamus which are located in the brain and the male and female reproductive structures (the testes and ovaries). The encoded protein controls the activity of certain genes in the cells that form these tissues during embryonic development. Proteins that control the activity of other genes are known as transcription factors. The encoded protein also plays a role in regulating hormone production in these tissues after they have been formed.

SCML1 (Sex comb on midleg-like protein 1) encodes a putative Polycomb group (PcG) protein. PcG proteins act by forming multiprotein complexes, which are required to maintain the transcriptionally repressive state of homeotic genes throughout development. The encoded protein may be involved in spermatogenesis during sexual maturation

IV. DELIVERY OF GENE OR GENE PRODUCTS

In certain embodiments, vectors for delivery of nucleic acids encoding hepatic lineage programming or differentiation factors could be constructed to express these factors in cells. Details of components of these vectors and delivery methods are disclosed below. In addition, protein transduction compositions or methods may be also used to effect expression of the hepatocyte programming factors.

In a further aspect, the following systems and methods may also be used in delivery of reporter expression cassette for identification of desired cell types, such as hepatocytes. In particular, a hepatocyte-specific regulatory element may be used to drive expression of a reporter gene, therefore hepatocytes derived from forward programming may be characterized, selected or enriched.

A. Nucleic Acid Delivery Systems

One of skill in the art would be well equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV, etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

1. Viral Vectors

In generating recombinant viral vectors, non-essential genes are typically replaced with a gene or coding sequence for a heterologous (or non-native) protein. Viral vectors are a kind of expression construct that utilizes viral sequences to introduce nucleic acid and possibly proteins into a cell. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

2. Episomal Vectors

The use of plasmid- or liposome-based extra-chromosomal (i.e., episomal) vectors may be also provided in certain aspects of the invention. Such episomal vectors may include, e.g., oriP-based vectors, and/or vectors encoding a derivative of EBNA-1. These vectors may permit large fragments of DNA to be introduced to a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-Based System

According to a particular embodiment the introduction of nucleic acids may use a transposon-transposase system. The used transposon-transposase system could be the well known Sleeping Beauty, the Frog Prince transposon-transposase system (for the description of the latter see e.g. EP1507865), or the TTAA-specific transposon piggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

4. Homologous Recombination Nuclease-Based Systems

Homologous recombination (HR) is a targeted genome modification technique that has been the standard method for genome engineering in mammalian cells since the mid 1980s. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154).

B. Regulatory Elements:

Eukaryotic expression cassettes included in the vectors preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988; Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

Tissue-specific transgene expression, especially for reporter gene expression (such as antibiotic resistant gene expression) in hepatocytes produced from forward programming, is desirable as a way to identify produced hepatocytes. To increase both specificity and activity, the use of cis-acting regulatory elements has been contemplated. For example, a hepatocyte-specific promoter may be used, such as a promoter of albumin, α-1-antitrypsin (AAT), cytochrome p450 3A4 (CYP3A4), apolipoprotein A-I, or APOE.

In certain aspects, this also concerns enhancer sequences, i.e. nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter. For the liver, numerous approaches to incorporate such organ-specific regulatory sequences into retroviral, lentiviral, adenoviral and adeno-associated viral vectors or non-viral vectors (often in addition to house-keeping hepatocyte-specific cellular promoters) have been reported so far (Ferry et al., 1998; Ghosh et al., 2000; Miao et al., 2000; Follenzi et al., 2002).

Several enhancer sequences for liver-specific genes have been documented. WO2009130208 describes several liver-specific regulatory enhancer sequences. WO95/011308 describes a gene therapy vector comprising a hepatocyte-specific control region (HCR) enhancer linked to a promoter and a transgene. The human apolipoprotein E-Hepatocyte Control Region (ApoE-HCR) is a locus control region (LCR) for liver-specific expression of the apolipoprotein E (ApoE) gene. The ApoE-HCR is located in the ApoE/CI/CII locus, has a total length of 771 bp and is important in expression of the genes ApoE and ApoC-1 in the liver (Simonet et al., 1993). In WO01/098482, the combination of this specific ApoE enhancer sequence or a truncated version thereof with hepatic promoters is suggested. It was shown that vector constructs combining the (non-truncated) ApoE-HCR enhancer with a human alpha-antitrypsin (AAT) promoter were able to produce the highest level of therapeutic protein in vivo (Miao et al., 2000) and may confer sustained expression when used in conjunction with a heterologous transgene (Miao et al., 2001).

This ApoE-HCR-AAT expression cassette as used, e.g., in the pAAV-ApoHCR-AAT-FIXIA construct (Vanden-Driessche et al., 2007) is one of the most potent liver-specific FIX expression constructs known, and has been successfully applied in a phase ½ dose-escalation clinical study in humans with severe hemophilia B (Manno et al., 2006). The expression of this hFIX minigene is driven from an ApoE-HCR joined to the human AAT promoter. The 5'-flanking sequence of the human AAT gene contains multiple cis-regulatory elements, including a distal enhancer and proximal sequences, with a total length of around 1.2 kb. It was shown to be sufficient to confer tissue specificity in vivo by driving gene expression primarily in the liver and also, to a lesser extent, in other tissues known to express AAT (Shen et al., 1989). A 347 bp fragment of this 1.2 kb region in combination with the ApoE enhancer is capable of achieving long-term liver-specific gene expression in vivo (Le et al., 1997). Interestingly, this shorter promoter targets expression to the liver with a greater specificity than that reported for larger AAT promoter fragments (Yull et al., 1995).

Other chimeric liver-specific constructs have also been proposed in the literature, e.g., with the AAT promoter and the albumin or hepatitis B enhancers (Kramer et al., 2003), or the alcohol dehydrogenase 6 (ADH6) basal promoter linked to two tandem copies of the apolipoprotein E enhancer element (Gehrke et al., 2003). The authors of the latter publication stress the importance of the relatively small size (1068 bp) of this enhancer-promoter combination.

2. Initiation Signals and Internal Ribosome Binding Sites

A specific initiation signal also may be used for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select for hepatocytes after the programming factors have effected a desired programming change in those cells.

C. Nucleic Acid Delivery

Introduction of a nucleic acid, such as DNA or RNA, into cells to be programmed with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780, 448, 5,736,524, 5,702,932, 5,656,610, 5,589,466 and 5,580, 859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L (A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

6. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

B. Protein Transduction

In certain aspects of the present invention, the cells to be programmed into hepatocytes may be contacted with hepatocyte programming factors comprising polypeptides of hepatocyte transcription factor genes at a sufficient amount for forward programming. Protein transduction has been used as a method for enhancing the delivery of macromolecules into cells. Protein transduction domains may be used to introduce hepatocyte programming polypeptides or functional fragments thereof directly into cells. Research by many groups has shown that a region of the TAT protein which is derived from the HIV Tat protein can be fused to a target protein allowing the entry of the target protein into the cell. A particular exemplary protein sequence of this domain is RKKRRQRRR (SEQ ID NO:1) where R encodes Arginine, K encodes Lysine and Q encodes Glutamine. This sequence has been shown to enable the entry of a protein fusion both as an N-terminal or C-terminal fusion. The mechanism of TAT mediated entry is thought to be by macropinocytosis (Gump and Dowdy).

A "protein transduction domain" or "PTD" is an amino acid sequence that can cross a biological membrane, particularly a cell membrane. When attached to a heterologous polypeptide, a PTD can enhance the translocation of the heterologous polypeptide across a biological membrane. The PTD is typically covalently attached (e.g., by a peptide bond) to the heterologous DNA binding domain. For example, the PTD and the heterologous DNA binding domain can be encoded by a single nucleic acid, e.g., in a common open reading frame or in one or more exons of a common gene. An exemplary PTD can include between 10-30 amino acids and may form an amphipathic helix. Many PTD's are basic in character. For example, a basic PTD can include at least 4, 5, 6 or 8 basic residues (e.g., arginine or lysine). A PTD may be able to enhance the translocation of a polypeptide into a cell that lacks a cell wall or a cell from a particular species, e.g., a mammalian cell, such as a human, simian, murine, bovine, equine, feline, or ovine cell.

A PTD can be linked to an artificial transcription factor, for example, using a flexible linker. Flexible linkers can include one or more glycine residues to allow for free rotation. For example, the PTD can be spaced from a DNA binding domain of the transcription factor by at least 10, 20, or 50 amino acids. A PTD can be located N- or C-terminal relative to a DNA binding domain. Being located N- or C-terminal to a particular domain does not require being adjacent to that particular domain. For example, a PTD N-terminal to a DNA binding domain can be separated from the DNA binding domain by a spacer and/or other types of domains. A PTD can be chemically synthesized then conjugated chemically to separately prepared DNA binding domain with or without linker peptide. An artificial transcription factor can also include a plurality of PTD's, e.g., a plurality of different PTD's or at least two copies of one PTD.

Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the *Drosophila* Antennapedia (Antp) homeotic transcription factor. The small protein transduction domains (PTDs) from these proteins can be fused to other macromolecules, peptides or proteins to successfully transport them into a cell. Sequence alignments of the transduction domains from these proteins show a high basic amino acid content (Lys and Arg) which may facilitate interaction of these regions with negatively charged lipids in the membrane. Secondary structure analyses show no consistent structure between all three domains.

The advantages of using fusions of these transduction domains is that protein entry is rapid, concentration-dependent and appears to work with difficult cell types.

The Tat protein from human immunodeficiency virus type I (HIV-1) has the remarkable capacity to enter cells when added exogenously (Frankel and Pabo, 1988; Mann and Frankel, 1991; Fawell et al., 1994). A particular example of Tat PTD may include residues 47-57 of the human immunodeficiency virus Tat protein: YGRKKRRQRRR (SEQ ID NO:2). This peptide sequence is referred to as "TAT" herein. This peptide has been shown to successfully mediate the introduction of heterologous peptides and proteins in excess of 100 kDa into mammalian cells in vitro and in vivo (Ho et al., 2001). Schwarze et al. showed that when the 120 kDa β-galactosidase protein fused with TAT was injected into mouse intraperitoneally, the fusion proteins were found in all types of cells and tissues even including brain, which has been thought to be difficult because of the blood-brain-barrier (Schwarze et al., 1999).

The antennapedia homeodomain also includes a peptide that is a PTD (Derossi et al., 1994). This peptide, also referred to as "Penetratin", includes the amino acid sequence: AKIW-FQNRRMKWKKENN (SEQ ID NO:3).

The HSV VP22 protein also includes a PTD. This PTD is located at the VP22 C-terminal 34 amino acid residues: DAATATRGRSAASRPTERPRAPARSASRPRRPVE (SEQ ID NO:4). See, e.g., Elliott and O'Hare (1997) and U.S. Pat. No. 6,184,038.

In one embodiment, the PTD is obtained from a human or other mammalian protein. Exemplary mammalian PTD's are described in WO 03/059940 (human SIM-2) and WO 03/059941 (Mph). In certain embodiments, the PTD could be a synthetic PTD. The minimal Tat PTD (aa 47-57) was modified to optimize protein transduction potential (Ho et al., 2001). A FITC coupled with series of synthetic PTD's was tested with cultured T lymphocytes. Some synthetic PTD's showed enhanced protein transduction compared to Tat PTD. These PTD include: YARKARRQARR (SEQ ID NO:5); YARAARRAARR (SEQ ID NO:6); YARAARRAARA (SEQ ID NO:7); YARAAARQARA (SEQ ID NO:8). Especially, the FITC conjugated with synthetic PTD YARAAAR-QARA (SEQ ID NO:8); showed enhanced uptake by whole blood cells when the mice were i.p. injected.

The poly-arginine peptides composed of about 6-12 arginine residues also can mediate protein transduction in some cases. For additional information about poly-arginine, see, e.g., Rothbard et al. (2000); Wender et al. (2000).

For additional information about PTD's, see also U.S. 2003/0082561; U.S. 2002/0102265; U.S. 2003/0040038; Schwarze et al. (1999); Derossi et al. (1996); Hancock et al. (1991); Buss et al. (1988); Derossi et al. (1998); Lindgren et al. (2000); Kilic et al. (2003); Asoh et al. (2002); and Tanaka et al. (2003).

In addition to PTD's, cellular uptake signals can be used. Such signals include amino acid sequences which are specifically recognized by cellular receptors or other surface proteins. Interaction between the cellular uptake signal and the cell cause internalization of the artificial transcription factor that includes the cellular uptake signal. Some PTD's may also function by interaction with cellular receptors or other surface proteins.

A number of assays are available to determine if an amino acid sequence can function as a PTD. For example, the amino acid sequence can be fused to a reporter protein such as β-galactosidase to form a fusion protein. This fusion protein is contacted with culture cells. The cells are washed and then assayed for reporter activity. Another assay detects the presence of a fusion protein that includes the amino acid sequence in question and another detectable sequence, e.g., an epitope tag. This fusion protein is contacted with culture cells. The cells are washed and then analyzed by Western or immunofluorescence to detect presence of the detectable sequence in cells. Still other assays can be used to detect transcriptional regulatory activity of a fusion protein that includes the putative PTD, a DNA binding domain, and optionally an effector domain. For example, cells contacted with such fusion proteins can be assayed for the presence or level of mRNA or protein, e.g., using microarrays, mass spectroscopy, and high-throughput techniques.

V. CELL CULTURING

Generally, cells of the present invention are cultured in a culture medium, which is a nutrient-rich buffered solution capable of sustaining cell growth.

Culture media suitable for isolating, expanding and differentiating stem cells into hepatocytes according to the method described herein include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transfernin, insulin, vitamins, essential and non essential amino acids, sodium pyruvate, glutamine and a mitogen is also suitable. As used herein, a mitogen refers to an agent that stimulates cell division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2 U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

Pluripotent stem cells to be differentiated into hepatocytes may be cultured in a medium sufficient to maintain the pluripotency. Culturing of induced pluripotent stem (iPS) cells generated in certain aspects of this invention can use various medium and techniques developed to culture primate pluripotent stem cells, more specially, embryonic stem cells, as described in U.S. Pat. App. 20070238170 and U.S. Pat. App. 20030211603. For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM .beta.-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM .beta.-mercaptoethanol. Just before use, human bFGF may be added to a final concentration of about 4 ng/mL (WO 99/20741).

Hepatocytes of this invention can be made by culturing pluripotent stem cells or other non-hepatocytes in a medium under conditions that increase the intracellular level of hepatocyte programming factors to be sufficient to promote programming of the cells into hepatocytes. The medium may also contain one or more hepatocyte differentiation and maturation agents, like various kinds of growth factors. However, by increasing the intracellular level of hepatocyte programming transcription factors, aspects of the present invention bypass most stages toward mature hepatocytes without the need to change the medium for each of the stages. Therefore, in view of the advantages provided by the present invention, in particular aspects, the medium for culturing cells under hepatocyte programming may be essentially free of one or more of the hepatocyte differentiation and maturation agents, or may not undergo serial change with media containing different combination of such agents.

These agents may either help induce cells to commit to a more mature phenotype—or preferentially promote survival of the mature cells—or have a combination of both these effects. Hepatocyte differentiation and maturation agents illustrated in this disclosure may include soluble growth factors (peptide hormones, cytokines, ligand-receptor complexes, and other compounds) that are capable of promoting the growth of cells of the hepatocyte lineage. Non-limiting examples of such agents include but are not limited to epidermal growth factor (EGF), insulin, TGF-$\alpha$, TGF-$\beta$, fibroblast growth factor (FGF), heparin, hepatocyte growth factor (HGF), Oncostatin M (OSM), IL-1, IL-6, insulin-like growth factors I and II (IGF-I, IGF-2), heparin binding growth factor 1 (HBGF-1), and glucagon. The skilled reader will already appreciate that Oncostatin M is structurally related to Leukemia inhibitory factor (LIF), Interleukin-6 (IL-6), and ciliary neurotrophic factor (CNTF).

An additional examples is n-butyrate, as described in previous patent disclosures (U.S. Pat. No. 6,458,589, U.S. Pat. No. 6,506,574; WO 01/81549). Homologs of n-butyrate can readily be identified that have a similar effect, and can be used as substitutes in the practice of this invention. Some homologs have similar structural and physicochemical properties to those of n-butyrate: acidic hydrocarbons comprising 3-10 carbon atoms, and a conjugate base selected from the group consisting of a carboxylate, a sulfonate, a phosphonate, and other proton donors. Examples include isobutyric acid, butenoic acid, propanoic acid, other short-chain fatty acids, and dimethylbutyrate. Also included are isoteric hydrocarbon sulfonates or phosphonates, such as propanesulfonic acid and propanephosphonic acid, and conjugates such as amides, saccharides, piperazine and cyclic derivatives. A further class of butyrate homologs is inhibitors of histone deacetylase. Non-limiting examples include trichostatin A, 5-azacytidine, trapoxin A, oxamflatin, FR901228, cisplatin, and MS-27-275. Another class of agents is organic solvents like DMSO. Alternatives with similar properties include but are not limited to dimethylacetamide (DMA), hexmethylene bisacetamide, and other polymethylene bisacetamides. Solvents in this class are related, in part, by the property of increasing membrane permeability of cells. Also of interest are solutes such as nicotinamide.

VI. HEPATOCYTES CHARACTERISTICS

Cells can be characterized according to a number of phenotypic criteria. The criteria include but are not limited to the detection or quantitation of expressed cell markers, enzymatic activity, and the characterization of morphological features and intercellular signaling. In other aspects, cells to be programmed may comprise reporter gene expression cassette comprising tissue- or cell-specific transcriptional regulatory element, like hepatocyte-specific promoters for hepatocyte identification.

Hepatocytes embodied in certain aspects of this invention have morphological features characteristic of hepatocytes in the nature, such as primary hepatocytes from organ sources. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. A number of these features present in a single cell are consistent with the cell being a member of the hepatocyte lineage. Unbiased determination of whether cells have morphologic features characteristic of hepatocytes can be made by coding micrographs of programming progeny cells, adult or fetal hepatocytes, and one or more negative control cells, such as a fibroblast, or RPE (Retinal pigment epithelial) cells—then evaluating the micrographs in a blinded fashion, and breaking the code to determine if the cells produced from forward programming are accurately identified.

Cells of this invention can also be characterized according to whether they express phenotypic markers characteristic of cells of the hepatocyte lineage. Non-limiting examples of cell markers useful in distinguishing hepatocytes include albumin, asialoglycoprotein receptor, $\alpha$1-antitrypsin, $\alpha$-fetoprotein, apoE, arginase I, apoAI, apoAII, apoB, apoCIII, apoCII, aldolase B, alcohol dehydrogenase 1, catalase, CYP3A4, glucokinase, glucose-6-phosphatase, insulin growth factors 1 and 2, IGF-1 receptor, insulin receptor, leptin, liver-specific organic anion transporter (LST-1), L-type fatty acid binding protein, phenylalanine hydroxylase, transferrin, retinol binding protein, and erythropoietin (EPO). Mature hepatocyte markers include, but are limited to, albumin, $\alpha$1-antitrypsin, asialoglycoprotein receptor, cytokeratin 8 (CK8), cytokeratin 18 (CK18), CYP3A4, fumaryl acetoacetate hydrolase (FAH), glucose-6-phosphates, tyrosine aminotransferase, phosphoenolpyruvate carboxykinase, and tryptophan 2,3-dioxygenase.

Assessment of the level of expression of such markers can be determined in comparison with other cells. Positive controls for the markers of mature hepatocytes include adult hepatocytes of the species of interest, and established hepatocyte cell lines. The reader is cautioned that permanent cell lines or long-term liver cell cultures may be metabolically altered, and fail to express certain characteristics of primary hepatocytes. Negative controls include cells of a separate lineage, such as an adult fibroblast cell line, or retinal pigment epithelial (RPE) cells. Undifferentiated stem cells are positive for some of the markers listed above, but negative for markers of mature hepatocytes, as illustrated in the examples below.

Tissue-specific (e.g., hepatocyte-specific) protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific (e.g., hepatocyte-specific) markers can also be detected at the mRNA level by Northern blot analysis, dot-blot hybridization analysis, or by real time polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of tissue-specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display enzymatic activity that is characteristic of cells of the hepatocyte lineage. For example, assays for glucose-6-phosphatase activity are described by Bublitz (1991); Yasmineh et al. (1992); and Ockerman (1968). Assays for alkaline phosphatase (ALP) and 5-nucleotidase (5'-Nase) in liver cells are described by Shiojiri (1981). A number of laboratories that serve the research and health care sectors provide assays for liver enzymes as a commercial service.

In other embodiments, cells of the invention are assayed for activity indicative of xenobiotic detoxification. Cytochrome p450 is a key catalytic component of the mono-oxygenase system. It constitutes a family of hemoproteins responsible for the oxidative metabolism of xenobiotics (administered drugs), and many endogenous compounds. Different cytochromes present characteristic and overlapping substrate specificity. Most of the biotransforming ability is attributable by the cytochromes designated 1A2, 2A6, 2B6, 3A4, 2C 9-11, 2D6, and 2E1 (Gomes-Lechon et al., 1997).

A number of assays are known in the art for measuring xenobiotic detoxification by cytochrome p450 enzyme activity. Detoxification by CYP3 A4 is demonstrated using the P450-Glo™ CYP3A4 DMSO-tolerance assay (Luciferin-PPXE) and the P450-Glo™ CYP3A4 cell-based/biochemical assay (Luciferin-PFBE) (Promega Inc, # V8911 and # V8901). Detoxification by CYP1A1 and or CYP1B1 is demonstrated using the P450-Glo™ assay (Luciferin-CEE) (Promega Inc., # V8762). Detoxification by CYP1A2 and or CYP4A is demonstrated using the P450-Glo™ assay (Luciferin-ME) (Promega Inc., # V8772) Detoxification by CYP2C9 is demonstrated using the P450-Glo™ CYP2C9 assay (Luciferin-H) (Promega Inc., # V8791).

In another aspect, the biological function of a hepatocyte cell provided by programming is evaluated, for example, by analysing glycogen storage. Glycogen storage is characterized by assaying Periodic Acid Schiff (PAS) functional staining for glycogen granules. The hepatocyte-like cells are first oxidized by periodic acid. The oxidative process results in the formation of aldehyde groupings through carbon-to-carbon bond cleavage. Free hydroxyl groups should be present for oxidation to take place. Oxidation is completed when it reaches the aldehyde stage. The aldehyde groups are detected by the Schiff reagent. A colorless, unstable dialdehyde compound is formed and then transformed to the colored final product by restoration of the quinoid chromophoric grouping (Thompson, 1966; Sheehan and Hrapchak, 1987). PAS staining can be performed according the protocol described at world wide web at jhu.edu/~iic/PDFjrotocols/LM/Glycogen-Staining.pdf and library.med.utah.edu/WebPath/HISTHTML/MANUALS/PAS.PDF with some modifications for an in vitro culture of hepatocyte-like cells. One of ordinary skill in the art should be able to make the appropriate modifications.

In another aspect, a hepatocyte cell produced by forward programming in certain aspects of the invention is characterized for urea production. Urea production can be assayed colorimetrically using kits from Sigma Diagnostic (Miyoshi et al, 1998) based on the biochemical reaction of urease reduction to urea and ammonia and the subsequent reaction with 2-oxoglutarate to form glutamate and NAD.

In another aspect, bile secretion is analyzed. Biliary secretion can be determined by fluorescein diacetate time lapse assay. Briefly, monolayer cultures of hepatocyte-like cells are rinsed with phosphate buffered saline (PBS) three times and incubated with serum-free hepatocyte growth media supplemented with doxycycline and fluorescein diacetate (20 µg/ml) (Sigma-Aldrich) at 37° C. for 35 minutes. The cells are washed with PBS three times and fluorescence imaging is carried out. Fluorescein diacetate is a non fluorescent precursor of fluorescein. The image is evaluated to determine that the compound had been taken up and metabolized in the hepatocyte-like cell to fluorescein. In some embodiments, the compound is secreted into intercellular clefts of the monolayer of cells. Alternatively, bile secretion is determined by a method using sodium fluorescein described by Gebhart and Wang (1982).

In yet another aspect, lipid synthesis is analyzed. Lipid synthesis in the hepatocyte-like cell can be determined by oil red 0 staining Oil Red 0 (Solvent Red 27, Sudan Red 5B, C.I. 26125, $C_{26}H_{24}N_4O$) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red 0 is one of the dyes used for Sudan staining Similar dyes include Sudan III, Sudan IV, and Sudan Black B. The staining has to be performed on fresh samples and/or formalin fixed samples. Hepatocyte-like cells are cultured on microscope slides, rinsed in PBS three times, the slides are air dried for 30-60 minutes at room temperature, fixed in ice cold 10% formalin for 5-10 minutes, and then rinse immediately in 3 changes of distilled water. The slide is then placed in absolute propylene glycol for 2-5 minutes to avoid carrying water into Oil Red O and stained in prewarmed Oil Red O solution for 8 minutes in 600° C. oven. The slide is then placed in 85% propylene glycol solution for 2-5 minutes and rinsed in 2 changes of distilled water. Oil red 0 staining can also be performed according the protocol described at library.med.utah.edu/WebPath/HISTHTML/MANUALS/OILRED.PDF with some modifications for an in vitro culture of hepatocyte-like cell by one of ordinary skill in the art.

In still another aspect, the cells are assayed for glycogen synthesis. Glycogen assays are well known to one of ordinary skill in the art, for example, in Passonneau and Lauderdale (1974). Alternatively, commercial glycogen assays can be used, for example, from BioVision, Inc. catalog #K646-100.

Cells of the hepatocyte lineage can also be evaluated by their ability to store glycogen. A suitable assay uses Periodic Acid Schiff (PAS) stain, which does not react with mono- and disaccharides, but stains long-chain polymers such as glycogen and dextran. PAS reaction provides quantitative estimations of complex carbohydrates as well as soluble and membrane-bound carbohydrate compounds. Kirkeby et al. (1992) describe a quantitative PAS assay of carbohydrate compounds and detergents. van der Laarse et al. (1992) describe a microdensitometric histochemical assay for glycogen using the PAS reaction. Evidence of glycogen storage is determined if the cells are PAS-positive at a level that is at least 2-fold, and preferably more than 10-fold above that of a control cell, such as a fibroblast The cells can also be characterized by karyotyping according to standard methods.

Assays are also available for enzymes involved in the conjugation, metabolism, or detoxification of small molecule drugs. For example, cells can be characterized by an ability to conjugate bilirubin, bile acids, and small molecule drugs, for excretion through the urinary or biliary tract. Cells are contacted with a suitable substrate, incubated for a suitable period, and then the medium is analyzed (by GCMS or other suitable technique) to determine whether a conjugation product has been formed. Drug metabolizing enzyme activities include de-ethylation, dealkylation, hydroxylation, demethylation, oxidation, glucuroconjugation, sulfoconjugation, glutathione conjugation, and N-acetyl transferase activity (A. Guillouzo, pp 411-431 in In vitro Methods in Pharmaceutical Research, Academic Press, 1997). Assays include peenacetin de-ethylation, procainamide N-acetylation, paracetamol sulfoconjugation, and paracetamol glucuronidation (Chesne et al., 1988).

A further feature of certain cell populations of this invention is that they are susceptible under appropriate circumstances to pathogenic agents that are tropic for primate liver cells. Such agents include hepatitis A, B, C, and delta, Epstein-Barr virus (EBV), cytomegalovirus (CMV), tuberculosis, and malaria. For example, infectivity by hepatitis B can be determined by combining cultured forward programming-derived hepatocytes with a source of infectious hepatitis B particles (such as serum from a human HBV carrier). The liver cells can then be tested for synthesis of viral core antigen (HBcAg) by immunohistochemistry or RT-PCR.

The skilled reader will readily appreciate that an advantage of forward programming-derived hepatocytes is that they will be essentially free of other cell types that typically contaminate primary hepatocyte cultures isolated from adult or fetal liver tissue. Markers characteristic of sinusoidal endothelial cells include Von Willebrand factor, CD4, CD14, and CD32. Markers characteristic of bile duct epithelial cells include cytokeratin-7, cytokeratin-19, and γ-glutamyl transpeptidase. Markers characteristic of stellate cells include α-smooth muscle actin (α-SMA), vimentin, synaptophysin, glial fibrillary acidic protein (GFAP), neural-cell adhesion molecule (N-CAM), and presence of lipid droplets (detectable by autofluorescence or staining by oil red O). Markers characteristic of Kupffer cells include CD68, certain lectins, and markers for cells of the macrophage lineage (such as HLA Class II, and mediators of phagocytosis). Forward programming-derived hepatocytes can be characterized as essentially free of some or all of these cell types if less than 0.1% (preferably less than 100 or 10 ppm) bear markers or other features of the undesired cell type, as determined by immunostaining and fluorescence-activated quantitation, or other appropriate technique.

Hepatocytes provided by forward programming according to certain aspects of this invention can have a number of the features of the stage of cell they are intended to represent. The more of these features that are present in a particular cell, the more it can be characterized as a cell of the hepatocyte lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

Other desirable features of hepatocytes provided in certain aspects of this invention are an ability to act as target cells in drug screening assays, and an ability to reconstitute liver function, both in vivo, and as part of an extracorporeal device. These features are described further in sections that follow.

VII. USE OF HEPATOCYTES

The hepatocytes provided by methods and compositions of certain aspects of the invention can be used in a variety of applications. These include but not limited to transplantation or implantation of the hepatocytes in vivo; screening cytotoxic compounds, carcinogens, mutagens growth/regulatory factors, pharmaceutical compounds, etc., in vitro; elucidating the mechanism of liver diseases and infections; studying the mechanism by which drugs and/or growth factors operate; diagnosing and monitoring cancer in a patient; gene therapy; and the production of biologically active products, to name but a few.

A. Test Compound Screening

Forward programming-derived hepatocytes of this invention can be used to screen for factors (such as solvents, small molecule drugs, peptides, and polynucleotides) or environmental conditions (such as culture conditions or manipulation) that affect the characteristics of hepatocytes provided herein.

In some applications, stem cells (differentiated or undifferentiated) are used to screen factors that promote maturation of cells along the hepatocyte lineage, or promote proliferation and maintenance of such cells in long-term culture. For example, candidate hepatocyte maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cell programmed to the hepatocyte lineage play the role of test cells for standard drug screening and toxicity assays, as have been previously performed on hepatocyte cell lines or primary hepatocytes in short-term culture. Assessment of the activity of candidate pharmaceutical compounds generally involves combining the hepatocytes provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on liver cells, or because a compound designed to have effects elsewhere may have unintended hepatic side effects. Two or more drugs can be tested in combination (by combining with the cells either simultaneously or sequentially), to detect possible drug-drug interaction effects.

In some applications, compounds are screened initially for potential hepatotoxicity (Castell et al., 1997). Cytotoxicity can be determined in the first instance by the effect on cell viability, survival, morphology, and leakage of enzymes into the culture medium. More detailed analysis is conducted to determine whether compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al. (1996) describes a microassay for measuring glycogen, which can be used to measure the effect of pharmaceutical compounds on hepatocyte gluconeogenesis.

Other current methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of α-glutathione s-transferase; ATP, ADP, and AMP metabolism; intracellular $K^+$ and $Ca^{2+}$ concentrations; the release of nuclear matrix proteins or oligonucleosomes; and induction of apoptosis (indicated by cell rounding, condensation of chromatin, and nuclear fragmentation). DNA synthesis can be measured as [$^3$H]-thymidine or BrdU incorporation. Effects of a drug on DNA synthesis or structure can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers (1997) for further elaboration.

B. Liver Therapy and Transplantation

This invention also provides for the use of hepatocytes provided herein to restore a degree of liver function to a subject needing such therapy, perhaps due to an acute, chronic, or inherited impairment of liver function.

To determine the suitability of hepatocytes provided herein for therapeutic applications, the cells can first be tested in a suitable animal model. At one level, cells are assessed for their ability to survive and maintain their phenotype in vivo. Hepatocytes provided herein are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether starting cell types such as pluripotent stem cells are still present. This can be performed by providing the administered cells with a detectable label (such as green fluorescent protein, or β-galactosidase); or by measuring a constitutive marker specific for the administered cells. Where hepatocytes provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure. General descriptions for determining the fate of hepatocyte-like cells in animal models is provided in Grompe et al. (1999); Peeters et al., (1997); and Ohashi et al. (2000).

At another level, hepatocytes provided herein are assessed for their ability to restore liver function in an animal lacking full liver function. Braun et al. (2000) outline a model for toxin-induced liver disease in mice transgenic for the HSV-tk gene. Rhim et al. (1995) and Lieber et al. (1995) outline models for liver disease by expression of urokinase. Mignon et al. (1998) outline liver disease induced by antibody to the cell-surface marker Fas. Overturf et al. (1998) have developed a model for Hereditary Tyrosinemia Type I in mice by targeted disruption of the Fah gene. The animals can be rescued from the deficiency by providing a supply of 2-(2-nitro-4-fluoro-methyl-benzyol)-1,3-cyclohexanedione (NTBC), but they develop liver disease when NTBC is withdrawn. Acute liver disease can be modeled by 90% hepatectomy (Kobayashi et al., 2000). Acute liver disease can also be modeled by treating animals with a hepatotoxin such as galactosamine, $CCl_4$, or thioacetamide.

Chronic liver diseases such as cirrhosis can be modeled by treating animals with a sub-lethal dose of a hepatotoxin long enough to induce fibrosis (Rudolph et al., 2000). Assessing the ability of hepatocytes provided herein to reconstitute liver function involves administering the cells to such animals, and then determining survival over a 1 to 8 week period or more, while monitoring the animals for progress of the condition. Effects on hepatic function can be determined by evaluating markers expressed in liver tissue, cytochrome p450 activity, and blood indicators, such as alkaline phosphatase activity, bilirubin conjugation, and prothrombin time), and survival of the host Any improvement in survival, disease progression, or maintenance of hepatic function according to any of these criteria relates to effectiveness of the therapy, and can lead to further optimization.

Hepatocytes provided in certain aspects of this invention that demonstrate desirable functional characteristics according to their profile of metabolic enzymes, or efficacy in animal models, may also be suitable for direct administration to human subjects with impaired liver function. For purposes of hemostasis, the cells can be administered at any site that has adequate access to the circulation, typically within the abdominal cavity. For some metabolic and detoxification functions, it is advantageous for the cells to have access to the biliary tract. Accordingly, the cells are administered near the liver (e.g., in the treatment of chronic liver disease) or the spleen (e.g., in the treatment of fulminant hepatic failure). In one method, the cells administered into the hepatic circulation either through the hepatic artery, or through the portal vein, by infusion through an in-dwelling catheter. A catheter in the portal vein can be manipulated so that the cells flow principally into the spleen, or the liver, or a combination of both. In another method, the cells are administered by placing a bolus in a cavity near the target organ, typically in an excipient or matrix that will keep the bolus in place. In another method, the cells are injected directly into a lobe of the liver or the spleen.

The hepatocytes provided in certain aspects of this invention can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or $\alpha_1$-antitrypsin deficiency), hepatobiliary carcinoma, autoimmune liver disease (such as autoimmune chronic hepatitis or primary biliary cirrhosis), and any other condition that results in impaired hepatic function. For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Use in a Liver Assist Device

Certain aspects of this invention include hepatocytes provided herein that are encapsulated or part of a bioartificial liver device. Various forms of encapsulation are described in *Cell Encapsulation Technology and Therapeutics*, 1999. Hepatocytes provided in certain aspects of this invention can be encapsulated according to such methods for use either in vitro or in vivo.

Bioartificial organs for clinical use are designed to support an individual with impaired liver function—either as a part of long-term therapy, or to bridge the time between a fulminant hepatic failure and hepatic reconstitution or liver transplant. Bioartificial liver devices are reviewed by Macdonald et al., pp. 252-286 of "Cell Encapsulation Technology and Therapeutics", op cit., and exemplified in U.S. Pat. Nos. 5,290,684, 5,624,840, 5,837,234, 5,853,717, and 5,935,849. Suspension-type bioartificial livers comprise cells suspended in plate dialysers, microencapsulated in a suitable substrate, or attached to microcarrier beads coated with extracellular matrix. Alternatively, hepatocytes can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

Hepatocytes are prepared according to the methods described earlier, and then plated into the device on a suitable substrate, such as a matrix of Matrigel® or collagen. The efficacy of the device can be assessed by comparing the composition of blood in the afferent channel with that in the efferent channel—in terms of metabolites removed from the afferent flow, and newly synthesized proteins in the efferent flow.

Devices of this kind can be used to detoxify a fluid such as blood, wherein the fluid comes into contact with the hepatocytes provided in certain aspects of this invention under conditions that permit the cell to remove or modify a toxin in the fluid. The detoxification will involve removing or altering at least one ligand, metabolite, or other compound (either natural and synthetic) that is usually processed by the liver. Such compounds include but are not limited to bilirubin, bile acids, urea, heme, lipoprotein, carbohydrates, transferrin, hemopexin, asialoglycoproteins, hormones like insulin and glucagon, and a variety of small molecule drugs. The device can also be used to enrich the efferent fluid with synthesized proteins such as albumin, acute phase reactants, and unloaded carrier proteins. The device can be optimized so that a variety of these functions is performed, thereby restoring as many hepatic functions as are needed. In the context of therapeutic care, the device processes blood flowing from a patient in hepatocyte failure, and then the blood is returned to the patient.

D. Distribution for Commercial, Therapeutic, and Research Purposes

For purposes of manufacture, distribution, and use, the hepatocyte lineage cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to programming-derived cells (hepatocyte lineage cells, their precursors and subtypes), in combination with undifferentiated stem cells, somatic cell-derived hepatocytes, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. CELLS AND METHODS FOR TESTING CANDIDATE GENE IN PROGRAMMING

The ability of a particular candidate gene or a combination of candidate genes to act as forward programming factors for a specific cell type, such as hepatocytes, can be tested using the methods and cells provided in this disclosure. Efficacy of particular candidate genes or combinations of candidate genes in forward programming can be assessed by their effect on cell morphology, marker expression, enzymatic activity, proliferative capacity, or other features of interest, which is then determined in comparison with parallel cultures that did not include the candidate genes or combinations. Candidate genes may be transcription factors important for differentiation into desired cell types or for function of the desired cell types.

In certain embodiments, starting cells, such as pluripotent stem cells, comprising at least one expression cassette for expression of a candidate gene or a combination of candidate genes may be provided. The expression cassette may comprise an externally controllable transcriptional regulatory element, such as an inducible promoter. The activity of these promoters may be induced by the presence or absence of biotic or abiotic factors. Inducible promoters are a very powerful tool in genetic engineering because the expression of genes operably linked to them can be turned on or off at certain stages of development of an organism or in a particular tissue. Tet-On and Tet-Off inducible gene expression systems based on the essential regulatory components of the *E. coli* tetracycline-resistance operon may be used. Once established in the starting cells, the inducer doxycycline (Dox, a tetracycline derivative) could controls the expression system in a dose-dependent manner, allowing to precisely modulate the expression levels of candidate genes.

To aid identification of desired cell types, the starting cells may further comprise a cell-specific or tissue-specific reporter expression cassette. The reporter expression cassette may comprise a reporter gene operably linked to a transcriptional regulatory element specific for the desired cell types. For example, the reporter expression cassette may comprise a hepatocyte-specific promoter for hepatocyte production, isolation, selection, or enrichment. The reporter gene may be any selectable or screenable marker gene known in the art and exemplified in the preceding disclosure.

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Forward Programming into Hepatocytes

Alternative approaches for hepatocyte differentiation from human ESC/iPSCs are shown in FIG. 1. Hepatic lineage cells such as mature hepatocytes can likely be efficiently induced from human ESC/iPSCs via expression of appropriate transgene combination (top box), bypassing most, if not all, developmental stages required during normal differentiation (bottom box).

Figure 2:
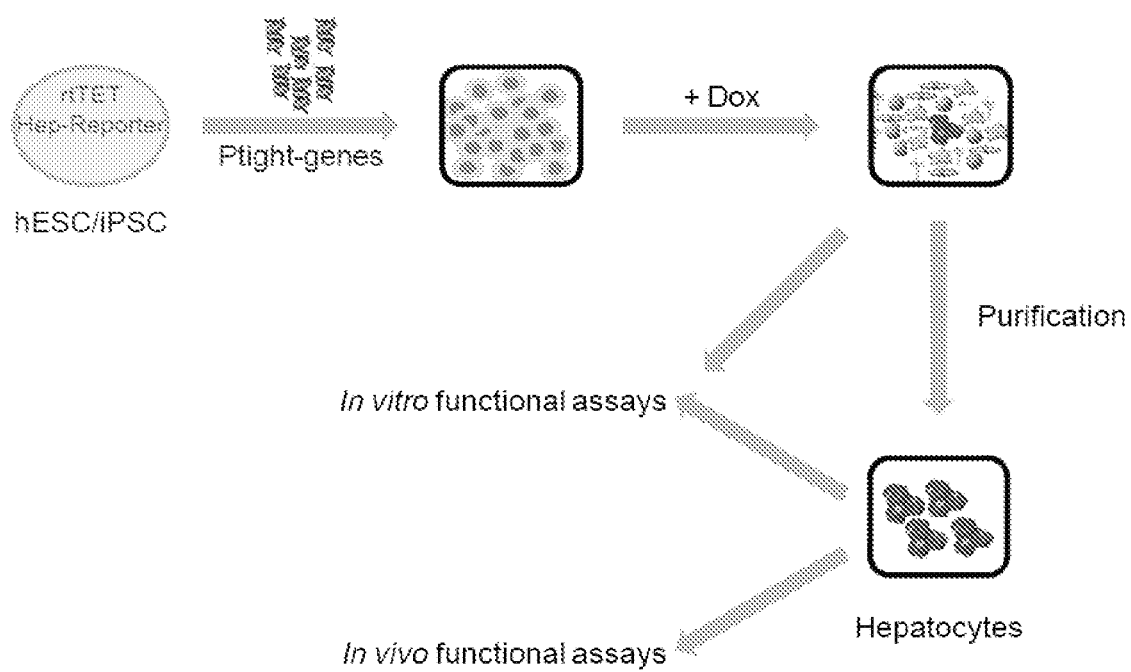
FIG. 2. The strategy employed for identifying transgenes that could forward program human ESC/iPSCs to mature hepatocytes.

The strategy employed for identifying transgenes that could directly convert human ESC/iPSCs to hepatic lineage cells including mature hepatocytes is shown in FIG. 2. Human ESC/iPSCs were engineered to carry reporters under the control of a hepatocyte-specific promoter, and to constitutively express rtTET protein for inducible gene expression. Transgenes under the control of the inducible promoter Ptight will be introduced into the engineered hESC/iPSCs either by lipid-mediated transfection or electroporation. Upon doxycycline (Dox) addition, transgene expression will be induced, and hepatocyte differentiation will be monitored by the expression of reporters and hepatocyte-specific marker genes, and additional hepatocyte-specific function analyses. Once the right transgene combination is identified, the hepatocytes will be purified for both in vitro and in vivo functional assays.

Figure 3:
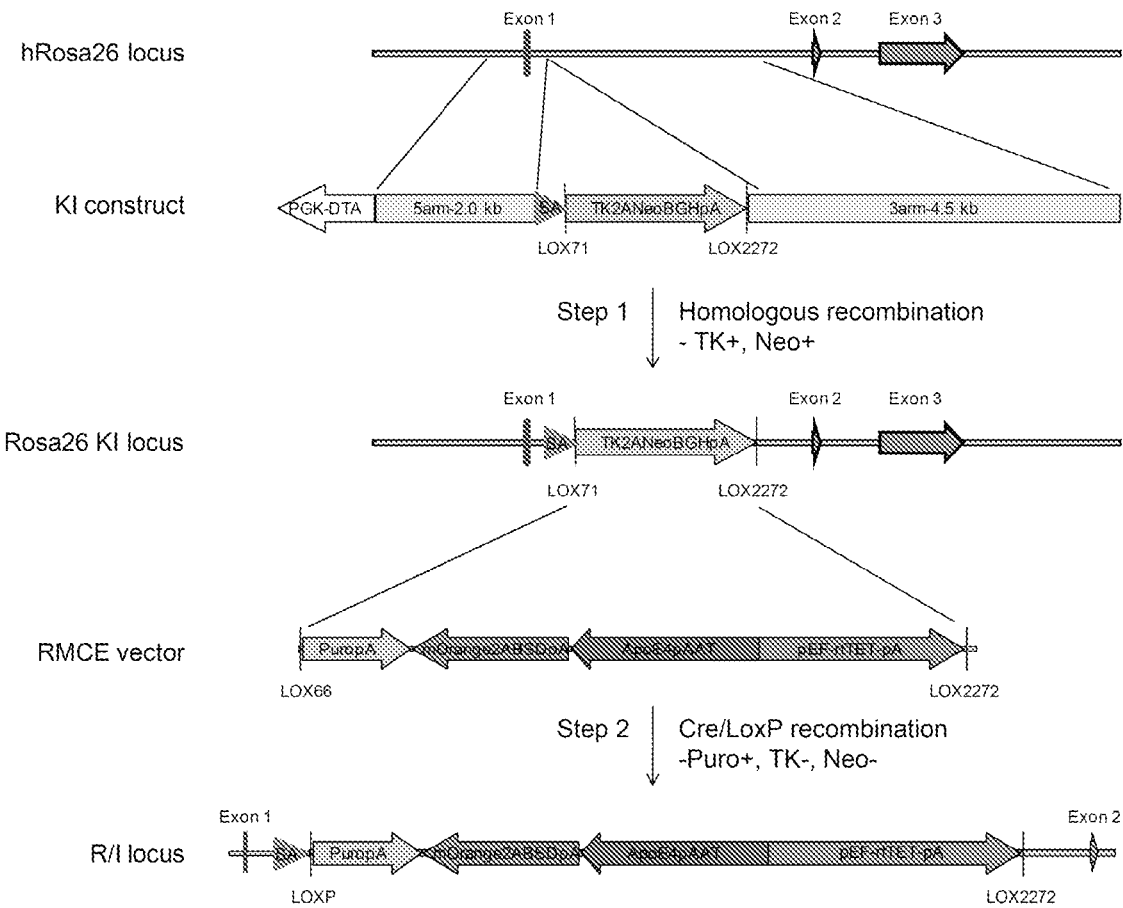
FIG. 3. The establishment of human ESC/iPSC reporter/inducible (R/I) lines for hepatocyte differentiation.

Human ESC/iPSC reporter/inducible (R/I) lines were established for hepatocyte differentiation (FIG. 3). The human Rosa26 locus on chromosome 3 was selected to allow the expression of both hepatocyte-specific reporter and rtTET, while minimizing the chromosome location-dependent silencing effect. First, the LoxP recombination sites (LOX71 and LOX2272) were introduced into a site between exon 1 and exon 2 of human ROSA 26 gene via homologous recombination. The targeting construct (KI construct) used the phosphoglycerate kinase promoter (PGK)-driven expression of diphtheria toxin A fragment gene (DTA) for negative selection, and contains a ~2.0 kb 5' arm and a 4.5 kb 3' arm. A splicing acceptor signal from human BCL2 gene (SA) was placed in front of LOX71 site to allow the expression of selection markers from the endogenous human ROSA26 promoter. The coding region for thymidine kinase (TK) was included to enable negative selection against incorrect Cre/LoxP recombination events at step 2 using ganciclovir. The neomycin phosphotransferase (Neo) was used for positive selection during homologous recombination (step 1). The foot-and-mouth disease virus peptide (F2A) was used to co-express the TK and Neo genes from the endogenous human ROSA26 promotor. BGHpA is polyadenylation signal derived from bovine growth hormone gene. The homologous recombination yielded parental human ESC/iPSC lines for efficient cassette exchange via Cre/LoxP recombination. To establish reporter/inducible cell lines for hepatocyte differentiation, F2A peptide linked marker gene mOrange and Blasticidin S deaminase (BSD) (driven by a hepatocyte-specific promoter ApoE4pAAT) and rtTET (driven by the constitutively active eukaryotic elongation factor 1α promoter—pEF) was introduced into the Rosa 26 locus by lipid-mediated cotransfection of the recombination mediated cassette exchange (RMCE) vector and a Cre-expressing plasmid. The puromycin N-acetyl-transferase (Puro) was used to select for recombination events. The correctly recombined R/I cells are resistant to puromycin (Puro$^+$) and ganciclovir (TK$^-$), and sensitive to geneticin selection (Neo$^-$).

Figure 4A:
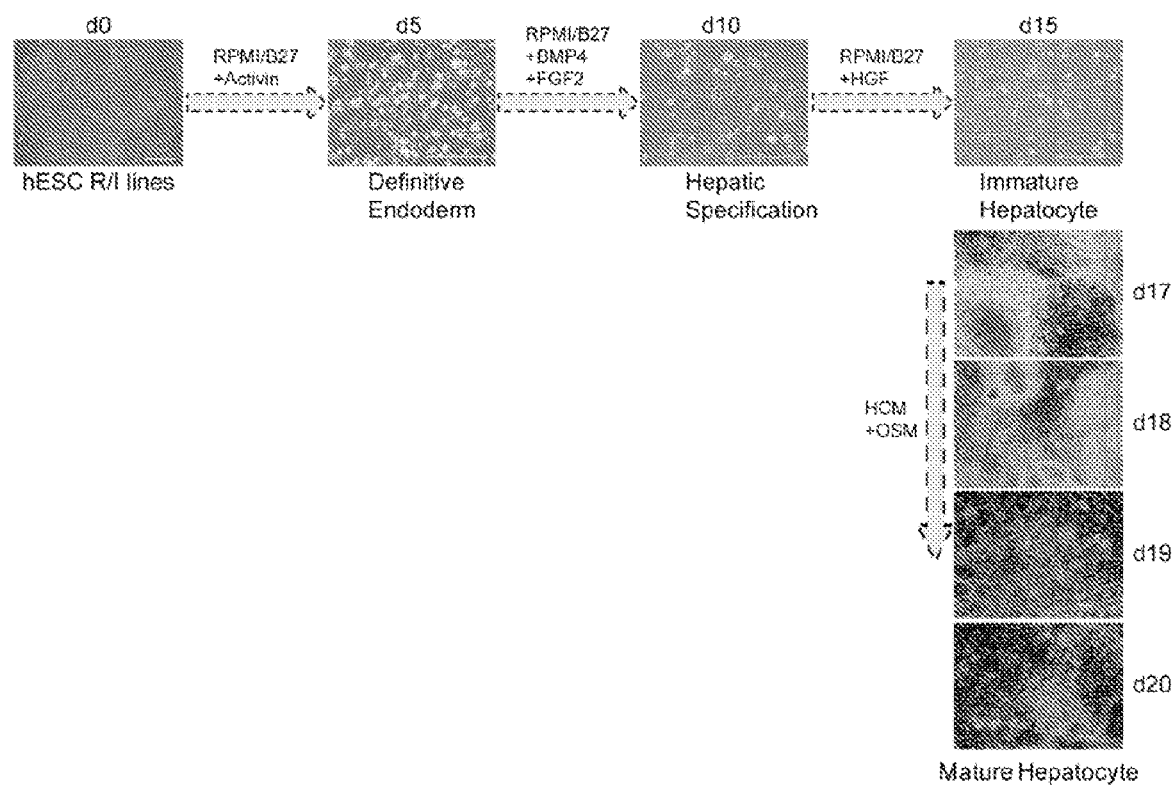
FIGS. 4A-4B. Confirmation of restricted marker gene (mOrange) expression in hepatocytes during normal human ESC differentiation.
Figure 4B:
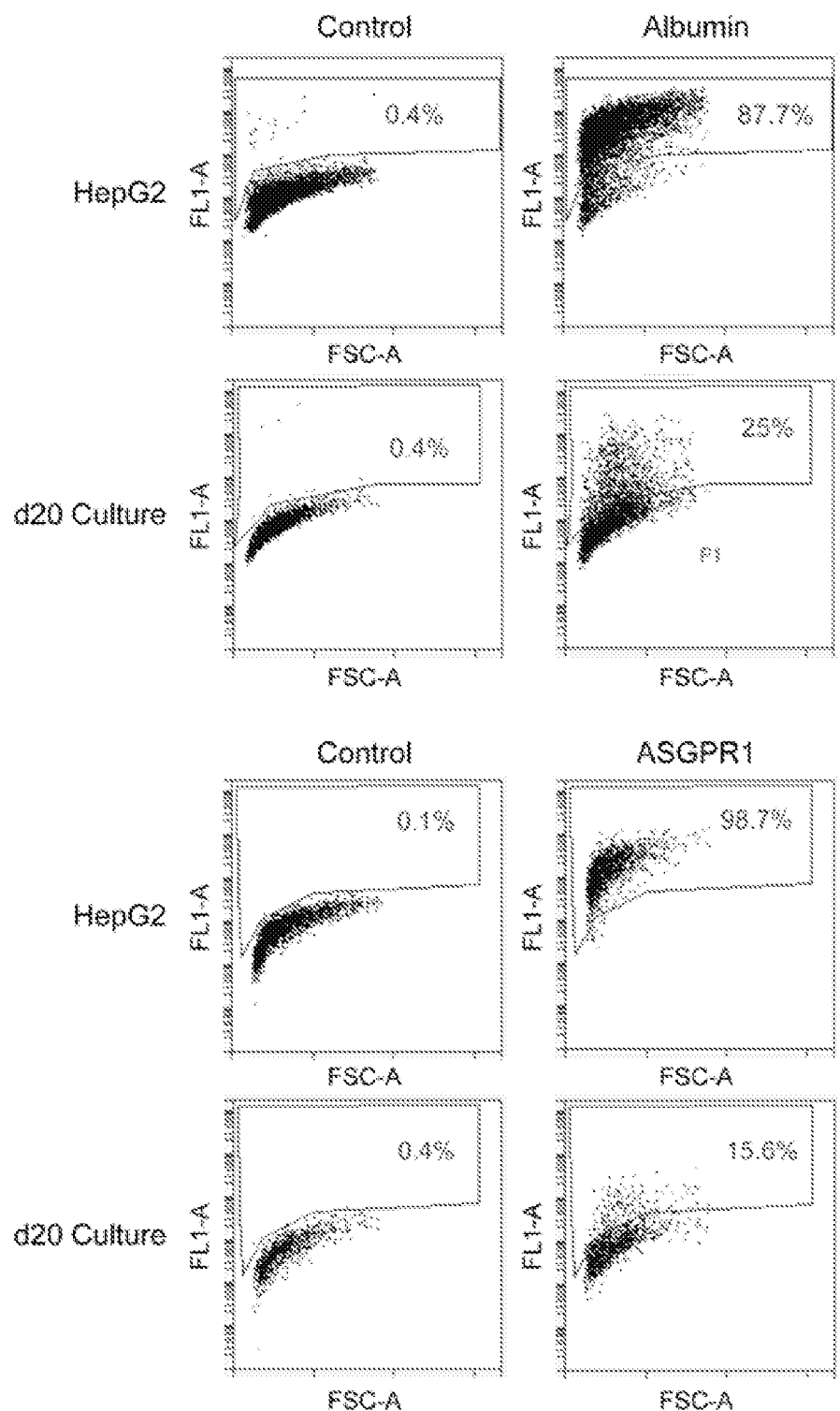

Restricted marker gene (mOrange) expression in hepatocytes during normal human ESC differentiation were confirmed (FIGS. 4A-4B). Human H1 ESC R/I lines were routinely maintained in MEF-conditioned human ES cell medium supplemented with 100 ng/ml bFGF (CM100) on matrigel (Growth Factor Reduced; BD Bioscience). For differentiation, human ESCs were harvested using Accutase (Invitrogen), and plated on matrigel-coated 10-cm dishes at a density of 0.5×10$^5$ cells/cm$^2$ in CM100 for 3 days. Hepatocyte differentiation was initiated by culture for 5 days with 100 ng/ml Activin A (R&D Systems) in RPMI/B27 medium (Invitrogen) (definitive endoderm differentiation), followed by 5 days with 20 ng/ml BMP4 (Peprotech) and 10 ng/ml FGF-2 (Invitrogen) in RPMI/B27 (hepatic specification), then 5 days with 20 ng/ml HGF (Peprotech) in RPMI/B27 (immature hepatocyte differentiation) and finally for 5 days with 20 ng/ml Oncostatin-M (R&D Systems) in Hepatocyte Culture Media (Lonza) supplemented with SingleQuots (hepatocyte maturation).

Figure 5A:
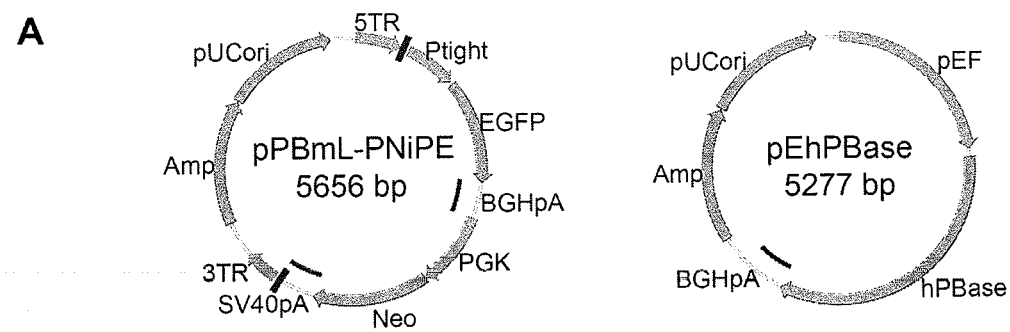
FIGS. 5A-5C. Confirmation of the Tet-On inducible gene expression in human H1 ESC R/I lines.
Figure 5B:
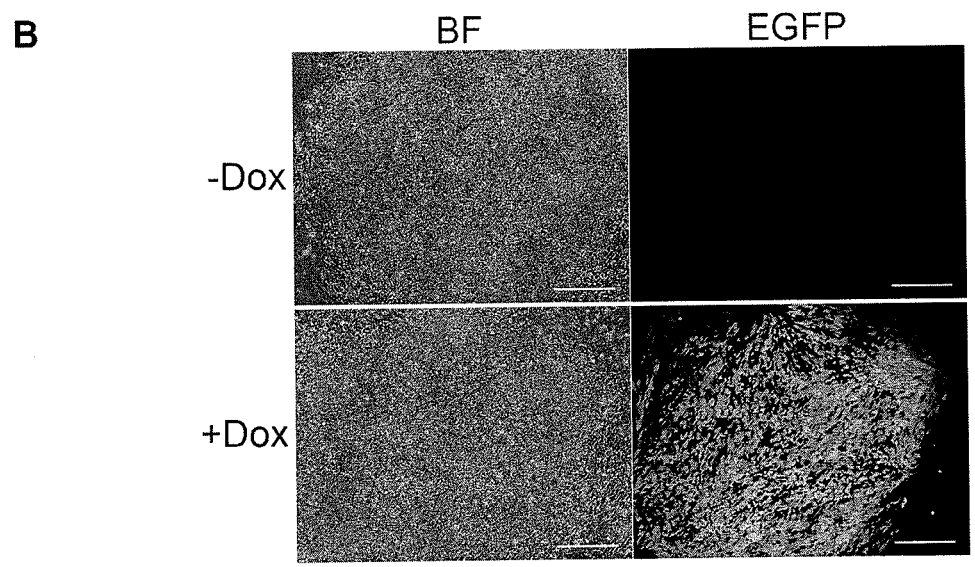
Figure 5C:
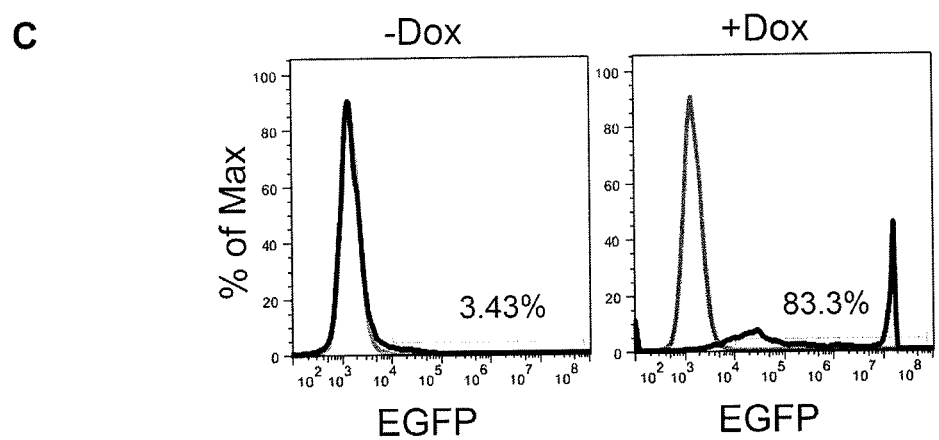

The Tet-On inducible gene expression was confirmed in human H1 ESC R/I lines (FIGS. 5A-5C). The EGFP driven by the Ptight promoter (an rtTET-responsive inducible promoter) was introduced into human ESC R/I lines using Fugene HD-mediated transfection of both vectors in FIG. 5A. Human ESCs with stable PiggyBac transposon integration were selected with geneticin (100 μg/ml). Images are shown in FIG. 5B with human ESC R/I lines after 2 days induction with or without Doxycycline (1 μg/ml). EGFP expression was analyzed by flow cytometry in human ESC R/I lines after 4 days induction with or without Doxycycline (1 μg/ml) (FIG. 5C). After 4 days of Doxycycline induction, 83.3% human ESC R/I lines showed stable PiggyBac transposon integration by EGFP expression.

Figure 6:
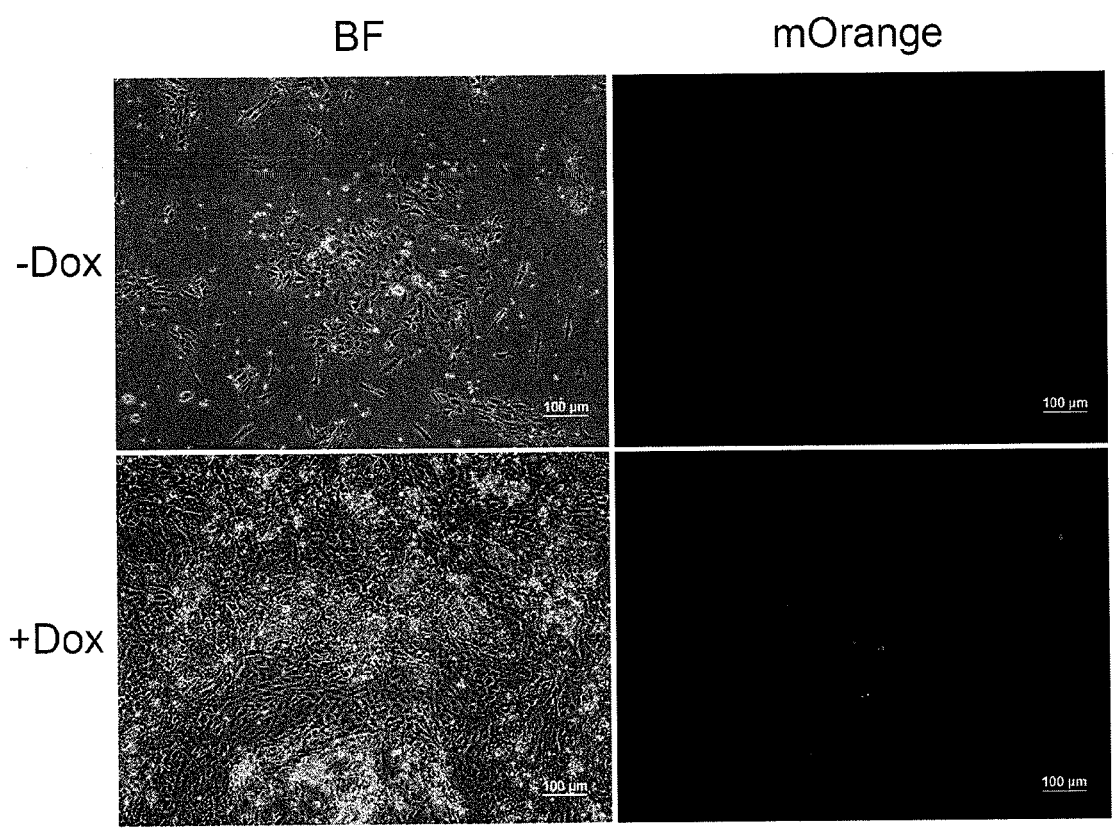
FIG. 6. Direct induction of hepatocytes from human ESC R/I lines through transgene expression.

Hepatocytes were directly induced from human ESC R/I lines through transgene expression (FIG. 6). Genes that are either implicated in hepatic differentiation during normal mammalian development or enriched in adult hepatocytes were cloned into the PiggyBac vector (FIG. 5A) under the control of the Ptight promoter (Table 1). These genes were further prioritized based on their known functional importance during normal hepatic differentiation or hepatic functions. To screen for transcription factors that are able to directly impose hepatic fate upon human ESCs, various combinations of transgene-expressing PiggyBac vectors along with the hPBase-expressing vector were introduced into the human ESC R/I lines cultured in CM100 on matrigel via Fugene HD-mediated transfection or electroporation. Following Geneticin (100 µg/ml) selection for stable genomic transgene integration, Doxycycline (1 µg/ml) was added to induce transgene expression, and the CM100 was replaced with Hepatocyte Culture Media (Lonza) supplemented with SingleQuots, 20 ng/ml HGF and 50 ng/ml Oncostatin-M (HCM). Hepatic lineage induction was monitored with mOrange marker gene expression between day 3-5 post induction. In the absence of Doxycycline induction, significant cell death was observed after 3-day culture in HCM medium in contrast to those with Doxycycline induction. The combination of transcription factors used herein are from the following: FOXA1, FOXA2-2, HHEX, HNF1A, HNF4A-2 and TBX3-1 (Table 1). Significant number of hepatocyte-specific promoter-driven mOrange-expressing cells were observed after five days of Doxycycline induction in HCM.

Figures 7A, 7B, 7C:
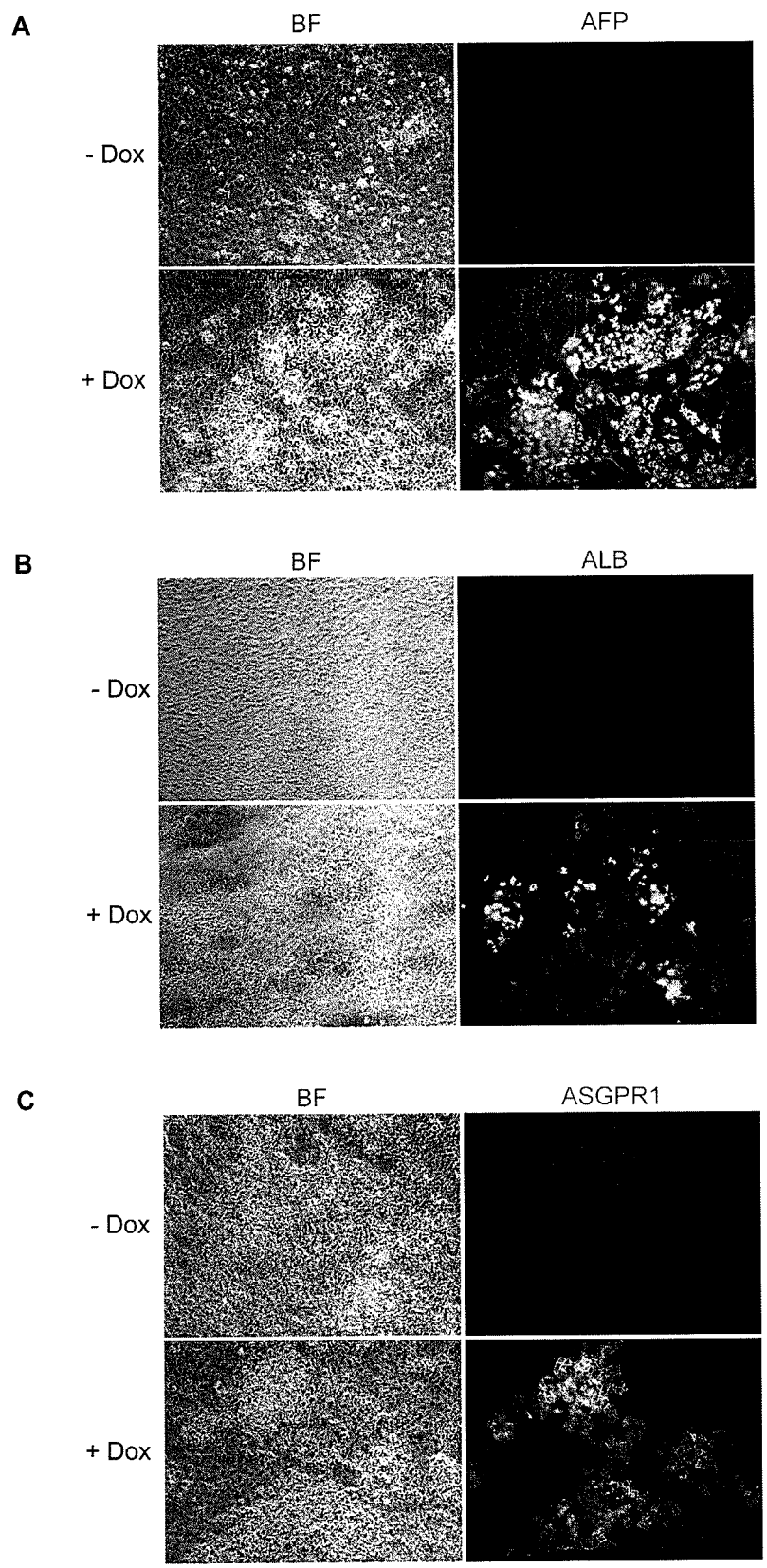
FIGS. 7A-7C. Forward programming of human ESC RA lines to hepatocyte-like cells by transgene expression. Among genes that are either implicated in hepatic differentiation during normal mammalian development or enriched in adult hepatocytes (Table 1), a combination of genes (FOXA2, HHEX, HNF4A, GATA4, NR0B2 and SCML1) were identified that are sufficient to convert human ESCs directly into hepatocyte-like cells.

Another combination of genes (FOXA2, HHEX, HNF4A, GATA4, NROB2 and SCML1) were identified that are sufficient to convert human ESCs directly into hepatocyte-like cells (FIGS. 7A-7C). Briefly, the transgene-expressing PiggyBac vectors (2 µg each) along with the hPBase-expressing vector (4 µg) were introduced into the human ESC R/I lines cultured in mTeSR1 on matrigel via nucleofection. About $2-3 \times 10^6$ ESCs were used for each nucleofection (nucleofection solution: 100 µA of Ingenio® Electroporation solution from Minis, Madison, Wis.; program: Amaxa B-016). Following Geneticin (100 µg/ml) selection for stable genomic transgene integration, cells were plated into 12-well matrigel plates for forward programming. The next day following plating, Doxycycline (1 µg/ml) was added to induce transgene expression, initially in mTeSR1 for 1 day followed by Hepatocyte Maintenance Medium supplemented with SingleQuot (HMM, Lonza), 20 ng/ml HGF and 20 ng/ml Oncostatin-M (OSM) for 5 days. After 6-day transgene induction, cells were further cultured in HMM supplemented with OSM for an additional 10-11 days prior to analysis. Hepatic induction was examined by immunological staining with antibodies for hepatocyte-specific markers alpha-fetoprotein (AFP) (FIG. 7A), albumin (ALB) (FIG. 7B), and asiologlycoprotein receptor 1 (ASGPR1) (FIG. 7C). Expression of additional genes (Table 1) may improve either the efficiency of hepatic lineage programming from human ESCs or hepatic functions.

Additional combinations that could induce hepatocyte-like cells from human ESC R/I lines via forward programming are presented in Table 2.

TABLE 2

Additional transgene combinations for hepatocyte forward programming

| # | | | | |
|---|---|---|---|---|
| C1 | FOXA2 | HNF1A | HNF4A | CEBPB |
| C2 | FOXA2 | HNF1A | HNF4A | FOXA1 |
| C3 | FOXA2 | HNF1A | HNF4A | GATA4 |
| C4 | FOXA2 | HNF1A | HNF4A | HHEX |
| C5 | FOXA2 | HNF1A | HNF4A | HLF |
| C6 | FOXA2 | HNF1A | HNF4A | HLX |
| C7 | FOXA2 | HNF1A | HNF4A | NR0B2 |
| C8 | FOXA2 | HNF1A | HNF4A | NR1H3 |
| C9 | FOXA2 | HNF1A | HNF4A | NR1H4 |
| C10 | FOXA2 | HNF1A | HNF4A | NR1I2 |
| C11 | FOXA2 | HNF1A | HNF4A | NR1I3 |
| C12 | FOXA2 | HNF1A | HNF4A | NR5A2 |
| C13 | FOXA2 | HNF1A | HNF4A | SCML1 |
| C14 | FOXA2 | HNF1A | HNF4A | SEBOX |
| C15 | FOXA2 | HNF1A | HNF4A | ZNF391 |
| C16 | FOXA2 | HNF1A | HNF4A | ZNF517 |

Figure 8:
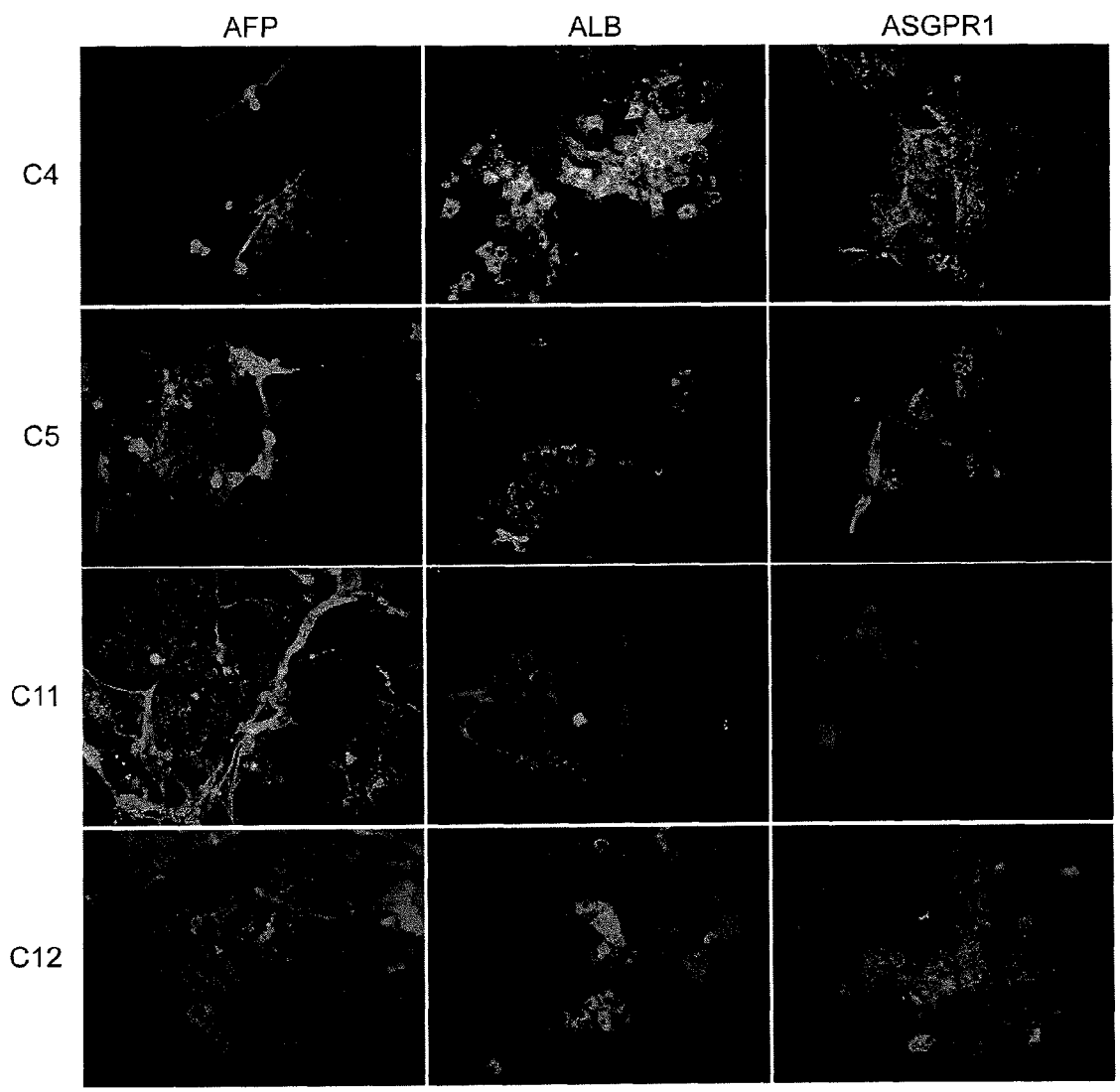
FIG. 8. Examples of additional combinations (Table 2) that could induce hepatocyte-like cells from human ESC RA lines via forward programming. AFP, ALB, ASGPR1 expression of cells by forward programming using combinations 4, 5, 11, 12 (C4, C5, C11, C12) in Table 2 were shown.

Examples of additional combinations for forward programming are shown in FIG. 8. The transgene-expressing PiggyBac vectors (2 µg each) along with the hPBase-expressing vector (4 µg) were introduced into the human ESC R/I lines cultured in mTeSR1 on matrigel via nucleofection. About $2-3 \times 10^6$ ESCs were used for each nucleofection (nucleofection solution: 100 µl of Ingenio® Electroporation solution from Minis, Madison, Wis.; program: Amaxa B-016). Following Geneticin (100 µg/ml) selection for stable genomic transgene integration, cells were plated into 12-well matrigel plates for forward programming. The next day following plating, Doxycycline (1 µg/ml) was added to induce transgene expression, in Hepatocyte Maintenance Medium supplemented with SingleQuot (HMM, Lonza), 20 ng/ml HGF and 20 ng/ml Oncostatin-M (OSM) for 4 days. After 4-day transgene induction, cells were further cultured in HMM supplemented with OSM for an additional 12 days prior to analysis. Hepatic induction was examined by immunostaining with antibodies for hepatocyte-specific markers alpha-fetoprotein (AFP), albumin (ALB), and asiologlycoprotein receptor 1 (ASGPR1).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,030,015
U.S. Pat. No. 5,290,684
U.S. Pat. No. 5,302,523
U.S. Pat. No. 5,322,783
U.S. Pat. No. 5,384,253
U.S. Pat. No. 5,460,964
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,624,840
U.S. Pat. No. 5,635,387
U.S. Pat. No. 5,656,610
U.S. Pat. No. 5,677,136
U.S. Pat. No. 5,681,599
U.S. Pat. No. 5,702,932
U.S. Pat. No. 5,716,827

U.S. Pat. No. 5,736,396
U.S. Pat. No. 5,736,524
U.S. Pat. No. 5,750,397
U.S. Pat. No. 5,759,793
U.S. Pat. No. 5,780,448
U.S. Pat. No. 5,789,215
U.S. Pat. No. 5,811,094
U.S. Pat. No. 5,827,735
U.S. Pat. No. 5,827,740
U.S. Pat. No. 5,837,234
U.S. Pat. No. 5,837,539
U.S. Pat. No. 5,837,670
U.S. Pat. No. 5,843,780
U.S. Pat. No. 5,853,717
U.S. Pat. No. 5,925,565
U.S. Pat. No. 5,928,906
U.S. Pat. No. 5,935,819
U.S. Pat. No. 5,935,849
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,184,038
U.S. Pat. No. 6,458,589
U.S. Pat. No. 6,506,574
U.S. Pat. No. 6,833,269
U.S. Pat. No. 6,991,897
U.S. Pat. No. 7,015,037
U.S. Pat. No. 7,399,632
U.S. Pat. No. 7,410,773
U.S. Pat. No. 7,410,798
U.S. Pat. No. 7,422,736
U.S. Patent Publn. 2002/0102265
U.S. Patent Publn. 2003/0040038
U.S. Patent Publn. 2003/0082561
U.S. Patent Publn. 20030211603
U.S. Patent Publn. 20070238170
U.S. application Ser. No. 08/464,599
U.S. Appln. Ser. 61/058,858
U.S. Appln. Ser. 61/172,079
U.S. Appln. Ser. 61/184,546
Alexander et al., *Proc. Nat. Acad. Sci. USA*, 85:5092-5096, 1988.
Alison et al, *Hepatol.*, 29:678-83, 1998.
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Asoh et al., *Proc. Natl. Acad. Sci. USA*, 99(26):17107-12, 2002.
Ausubel et al., *Current Protocols in Molecular Biology*, Greene Publ. Assoc. Inc. & John Wiley & Sons, Inc., MA, 1996.
Ausubel et al., In: *Current Protocols in Molecular Biology*, John, Wiley & Sons, Inc, New York, 1994.
Blomer et al., *J. Virol.*, 71(9):6641-6649, 1997.
Boyer et al., *Cell*, 122(6):947-56, 2005.
Braun et al., *Nature Med.*, 6:320, 2000.
Bublitz, *Mol. Cell. Biochem.*, 108:141, 1991.
Buss et al., *Mol. Cell. Biol.*, 8:3960-3963, 1988.
Byrne et al., *Nature*, 450(7169):497-502, 2007.
Capecchi, *Nature*, 348:109, 1990.
Cassiede et al., *J. Bone Miner. Res.*, 11(9):1264-1273, 1996.
Castell et al., In: *In vitro Methods in Pharmaceutical Research*, Academic Press, 375-410, 1997. *Cell Encapsulation Technology and Therapeutics*, Kuhtreiber et al. eds., Birkhauser, Boston Mass., 1999.
Chambers et al., *Cell*, 113(5):643-55, 2003.
Chen and Okayama, *Mol. Cell. Biol.*, 7(8):2745-2752, 1987.
Chesne et al., In: *Liver Cells and Drugs*, Guillouzo (Ed.), John Libbey Eurotext, London, 343-350, 1988.
Chevalier et al., *Mol. Cell.*, 10:895-905, 2002.
*Current Protocols in Stem Cell Biology*, Bhatia et. al. (Ed.), John Wiley and Sons, Inc., 2007.
Derossi et al., *J. Bio. Chem.*, 269:10444-10450, 1994.
Derossi et al., *J. Biol. Chem.*, 271:18188, 1996.
Derossi et al., *Trends in Cell Biol.*, 8:84-87, 1998.
Durai et al., *Nucleic Acids Res.*, 33:5978-5990, 2005.
Elliott and O'Hare, *Cell*, 88:223-234, 1997.
EP 1507865
EP0412700
Ercolani et al., *J. Biol. Chem.*, 263:15335-15341, 1988.
Evans, et al., In: *Cancer Principles and Practice of Oncology*, Devita et al. (Eds.), Lippincot-Raven, N.Y., 1054-1087, 1997.
Fawell et al., *Proc. Natl. Acad. Sci. USA*, 91:664-668, 1994.
Fechheimer et al., *Proc Natl. Acad. Sci. USA*, 84:8463-8467, 1987.
Ferry et al., *Hum. Gene Ther.*, 9(14):1975-81, 1998.
Follenzi et al., *Hum. Gene Ther.*, 13(2):243-60, 2002.
Fraley et al., *Proc. Natl. Acad. Sci. USA*, 76:3348-3352, 1979.
Frankel and Pabo, *Cell*, 55(6):1189-1193, 1988.
Gebhart and Wang, *J. Cell Sci.*, 56233-244, 1982.
Gehrke et al., *Gene*, 322:137-43, 2003.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh et al., *J. Hepatol.*, 32(1Suppl):238-52, 2000.
Gomes-Lechon et al., In: *In vitro Methods in Pharmaceutical Research*, Academic Press, 129-153, 1997
Gomez-Lechon et al., *Anal. Biochem.*, 236:296, 1996.
Gopal, *Mol. Cell. Biol.*, 5:1188-1190, 1985.
Graham and Van Der Eb, *Virology*, 52:456-467, 1973.
Grompe et al., *Sem. Liver Dis.*, 19:7, 1999.
Gronthos, *Blood*, 84(12):41644173, 1994.
Hancock et al., *EMBO J.*, 10:4033-4039, 1991.
Harland and Weintraub, *J. Cell Biol.*, 101(3):1094-1099, 1985.
Hayhurst et al., *Mol. Cell. Biol.*, 21(4):1393-403, 2001.
Hill et al., *Exp. Hematol.*, 24(8):936-943, 1996.
Ho et al., *Cancer Res.*, 61(2):474-7, 2001.
*In vitro Methods in Pharmaceutical Research*, Academic Press, 1997.
Jaiswal et al., *J. Cell Biochem.*, 64(2):295-312, 1997.
Johnstone et al., 238(1):265-272, 1998.
Kaeppler et al., *Plant Cell Rep.*, 8:415-418, 1990.
Kaneda et al., *Science*, 243:375-378, 1989.
Karin et al. *Cell*, 36: 371-379, 1989.
Kato et al, *J. Biol. Chem.*, 266:3361-3364, 1991.
Kilic et al., *Stroke*, 34:1304-10, 2003.
Kirchmaier and Sugden, *J. Virol.*, 72(6):4657-4666, 1998.
Kirkeby et al., *Biochem. Biophys. Meth.*, 24:225, 1992.
Klein et al., *Nature*, 327:70-73, 1987.
Kobayashi et al., *Science*, 287:1258, 2000.
Kramer et al., *Mol. Ther.*, 7(3):375-85, 2003.
Laarse et al., *Biotech Histochem.*, 67:303, 1992.
Langle-Rouault et al., *J. Virol.*, 72(7):6181-6185, 1998.
Le et al., *Blood*, 89(4):1254-9, 1997.
Levitskaya et al., *Proc. Natl. Acad. Sci. USA*, 94(23):12616-12621, 1997.
Li et al., *Genes Dev.*, 14:464-74, 2000.
Lieber et al., *Proc. Natl. Acad. Sci. USA*, 92:6210, 1995.
Lindgren et al., *Trends in Pharmacol. Sci.*, 21:99-103, 2000.
Lindner et. al., *J. Virol.*, 82(12):5693-702, 2008.

Macdonald et al., pp. 252-286, *Cell Encapsulation Technology and Therapeutics*
Macejak and Sarnow, *Nature*, 353:90-94, 1991.
Makino et al., *J. Clin. Invest.*, 103(5):697-705, 1999.
Maniatis, et al., *Molecular Cloning, A Laboratory Manual*, Cold Spring Harbor Press, Cold Spring Harbor, N.Y., 1988.
Mann and Frankel, *EMBO J.*, 10:1733-1739, 1991. Mann et al., *Cell*, 33:153-159, 1983.
Manno et al., *Nat. Med.*, 12(3):342-7, 2006.
Miao et al., *Mol. Ther.*, 1(6):522-32, 2000.
Mignon et al., *Nature Med.*, 4:1185, 1998.
Miller et al., *Am. J. Clin. Oncol.*, 15(3):216-221, 1992.
Miller et al., *Nat. Biotechnol.*, 29:143-148, 2011.
Miyoshi et al, *J. Biomater. Sci. Polym. Ed.*, 9:227-237, 1998.
Nabel et al., *Science*, 244(4910):1342-1344, 1989.
Naldini et al., *Science*, 272(5259):263-267, 1996.
Ng, *Nuc. Acid Res.*, 17:601-615, 1989.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Ockerman, *Clin. Chim. Acta*, 17:201, 1968.
Ohashi et al., *Nature Med.*, 6:327, 2000.
Overturf et al., *Human Gene Ther.*, 9:295, 1998.
Paskind et al., *Virology*, 67:242-248, 1975.
Passonneau and Lauderdale, *Anal. Biochem.*, 60:405-415, 1974.
Pingoud and Silva, *Nat. Biotechnol.*, 25:743-744, 2007.
PCT Appln. WO 01/81549
PCT Appln. WO 03/059940
PCT Appln. WO 03/059941
PCT Appln. WO 94/09699
PCT Appln. WO 94/09699
PCT Appln. WO 95/06128
PCT Appln. WO 99/20741
PCT Appln. WO/2003/042405
PCT Appln. WO 01/098482
PCT Appln. WO 95/011308
PCT Appln. WO 96/39487
PCT/US2004/030606
PCT/IB2010/000154
Peeters et al., *Hepatology*, 25:884, 1997.
Pelletier and Sonenberg, *Nature*, 334:320-325, 1988.
Potrykus et al., *Mol. Gen. Genet.*, 199(2):169-177, 1985.
Potten, *Philos. Trans. R Soc. Lond. B Biol. Sci.*, 353:821-30, 1998.
Potter et al., *Proc. Natl. Acad. Sci. USA*, 81:7161-7165, 1984.
Quitsche et al., *J. Biol. Chem.*, 264:9539-9545, 1989.
Reubinoff et al., *Nat. Biotechnol.*, 18:399 B404, 2000.
Rhim et al., *Proc. Natl. Acad. Sci. USA*, 92:4942, 1995.
Richards et al., *Cell*, 37: 263-272, 1984.
Rippe, et al., *Mol. Cell. Biol.*, 10:689-695, 1990.
Rothbard et al., *Nat. Med.*, 6(11):1253-7, 2000.
Rudolph et al., *Science*, 287:1253, 2000.
Sambrook and Russell, *Molecular Cloning: A Laboratory Manual*, 3rd Ed. Cold Spring Harbor Lab. Press, 2001.
Sambrook et al., In: *Molecular Cloning: A Laboratory Manual*, Vol. 1, Cold Spring Harbor Laboratory Press, Cold Spring Harbor, N.Y., (7)7:19-17.29, 1989.
Schwarze et al., *Science*, 285(5433):1466-7, 1999.
Schwarze et al., *Science*, 285:1569-1572, 1999.
Sheehan and Hrapchak, In: *Theory and Practise of Histotechnology*, 2nd Ed., Battelle Memorial Institute, Columbus, Ohio, 1987.
Shen et al., *DNA*, 8(2):101-8, 1989.
Shiojiri, *J. Embryol. Exp. Morph.*, 62:139, 1981.
Simonet et al., *J. Biol. Chem.*, 268(11):8221-9, 1993.
Smith, In: *Origins and Properties of Mouse Embryonic Stem Cells*, Annu Rev. Cell. Dev. Biol., 2000.
Takahashi and Yamanaka, *Cell*, 126:663-676, 2006.
Takahashi et al., *Cell*, 126(4):663-76, 2007.
Takahashi et al., *Cell*, 131:861-872, 2007.
Tanaka et al., *J. Immunol.*, 170(3):1291-8, 2003.
Temin, In: *Gene Transfer*, Kucherlapati (Ed.), NY, Plenum Press, 149-188, 1986.
Thompson, In: *Selected Histochemical and Histopathological Methods*, Tomas (Ed.), Sprungfield, Ill., 1966.
Thomson and Marshall, *Curr. Top. Dev. Biol.*, 38:133-165, 1998.
Thomson and Odorico, *J. Trends. Biotechnol.*, 18:53 B57, 2000.
Thomson et al. *Proc. Natl. Acad. Scie. USA*, 92:7844-7848, 1995.
Thomson et al., *Science*, 282:1145, 1998.
Tur-Kaspa et al., *Mol. Cell. Biol.*, 6:716-718, 1986.
VandenDriessche et al., *J. Thromb. Haemost.*, 5(1):16-24, 2007.
Vickers In: *In vitro Methods in Pharmaceutical Research*, Academic Press, 375-410, 1997
Watt, *Philos. Trans. R. Soc. Lond. B. Biol. Sci.*, 353:831, 1997.
Wender et al., *Proc. Natl. Acad. Sci. USA*, 97(24):13003-8, 2000.
Wilson et al., *Science*, 244:1344-1346, 1989.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Xu et al., *Nat. Biotechnol.*, 19:971-974, 2001.
Yakubov et al., *Biochemical and Biophysical Research Communications* 394: 189-193, 2010.
Yang and Russell, *Proc. Natl. Acad. Sci. USA*, 87:4144-4148, 1990.
Yasmineh et al., *Clin. Biochem.*, 25:109, 1992.
Ying et al., *Cell*, 115:281-292, 2003.
Yoo et al., *J. Bone Joint Sure. Am.*, 80(12):1745-1757, 1998.
Yu and Thompson, *Genes Dev.*, 22(15):1987-97, 2008.
Yu et al., *Science*, 318:1917-1920, 2007.
Yu et al., *Science*, 324(5928):797-801, 2009.
Yull et al., *Transgenic Res.*, 4(1):70-4, 1995.
Zufferey et al., *Nat. Biotechnol.*, 15(9):871-875, 1997.

What is claimed is:

1. A method of producing hepatocytes by forward programming of stem cells, comprising transfecting the stem cells with at least one exogenous expression cassette comprising at least the hepatocyte programming factor genes FOXA2, HHEX, HNF1A and GATA4, thereby producing hepatocytes by forward programming of the stem cells.

2. The method of claim 1, wherein the stem cells are mesenchymal stem cells, hematopoietic stem cells, or induced pluripotent stem cells.

3. The method of claim 1, wherein the number of the hepatocyte programming factor genes are five or six.

4. The method of claim 3, wherein the stem cells are further transfected with T-box transcription factor (TBX3).

5. The method of claim 1, wherein the stem cells or progeny cells thereof further comprise a reporter expression cassette comprising a hepatocyte-specific transcriptional regulatory element operably linked to a reporter gene.

6. The method of claim 5, wherein the hepatocyte-specific transcriptional regulatory element is a promoter of albumin, α-1-antitrypsin (AAT), cytochrome p450 3A4 (CYP3A4), apolipoprotein A-I, or APOE.

7. The method of claim 1, wherein the hepatocytes comprise the following hepatocyte characteristics:

(i) expression of one or more hepatocyte markers including glucose-6-phosphatase, albumin, α-1-antitrypsin (AAT), cytokeratin 8 (CK8), cytokeratin 18 (CK18), asialoglycoprotein receptor (ASGR), alcohol dehydrogenase 1, arginase type I, cytochrome p450 3A4 (CYP3A4), liver-specific organic anion transporter (LST-1), or a combination thereof;

(ii) activity of glucose-6-phosphatase, CYP3A4, bile production or secretion, urea production, or xenobiotic detoxification;

(iii) hepatocyte morphological features; and (iv) in vivo liver engraftment in an immunodeficient subject.

8. The method of claim 1, further comprising selecting or enriching for hepatocytes.

9. The method of claim 1, wherein the stem cells or progeny cells thereof are cultured in a medium comprising one or more growth factors including Oncostain M (OSM).

10. The method of claim 9, wherein the medium further comprises hepatocyte growth factor (HGF).

11. The method of claim 1, wherein the stem cells and progeny cells thereof are cultured in a medium essentially free of fibroblast growth factor (FGF).

12. The method of claim 1, wherein the stem cells and progeny cells thereof are cultured in a medium essentially free of epidermal growth factor (EGF).

13. The method of claim 1, wherein the stem cells and progeny cells thereof are cultured in a medium essentially free of nicotinamide.

14. The method of claim 1, comprising obtaining the hepatocytes less than or about 10 days after culturing in said conditions.

15. The method of claim 14, comprising obtaining the hepatocytes less than or about 5 days after culturing in said conditions.

16. A method of assessing a compound for a pharmacological or toxicological effect on a hepatocyte, comprising:
   a) contacting the hepatocyte provided by the method in accordance with claim 1 with the compound; and
   b) assaying a pharmacological or toxicological effect of the compound on the hepatocyte.

\* \* \* \* \*

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 1

Arg Lys Lys Arg Arg Gln Arg Arg Arg
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Arg
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Ala Lys Ile Trp Phe Gln Asn Arg Arg Met Lys Trp Lys Lys Glu Asn
1               5                   10                  15

Asn

<210> SEQ ID NO 4
<211> LENGTH: 34
<212> TYPE: PRT
<213> ORGANISM: Artificial Sequence
<220> FEATURE:
<223> OTHER INFORMATION: Synthetic peptide

<400> SEQUENCE: 4

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Tyr Ala Arg Lys Ala Arg Arg Gln Ala Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Tyr Ala Arg Ala Ala Arg Arg Ala Ala Arg Arg
1               5                   10
```

-continued

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Ala Arg Ala Ala Arg Arg Ala Ala Arg Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Tyr Ala Arg Ala Ala Ala Arg Gln Ala Arg Ala
1               5                   10

<210> SEQ ID NO 9
<211> LENGTH: 2350
<212> TYPE: DNA
<213> ORGANISM: Homo sapiens

<400> SEQUENCE: 9

| | | | | | |
|---|---|---|---|---|---|
| gcagtgtcac | taggccggct | ggggccctg | ggtacgctgt | agaccagacc | gcgacaggcc | 60 |
| agaacacggg | cggcggcttc | gggccgggag | acccgcgcag | ccctcggggc | atctcagtgc | 120 |
| ctcactcccc | acccctccc | ccgggtcggg | ggaggcggcg | cgtccggcgg | agggttgagg | 180 |
| ggagcggggc | aggcctggag | cgccatgagc | agcccggatg | cgggatacgc | cagtgacgac | 240 |
| cagagccaga | cccagagcgc | gctgcccgcg | gtgatggccg | ggctgggccc | ctgccccctgg | 300 |
| gccgagtcgc | tgagccccat | cggggacatg | aaggtgaagg | gcgaggcgcc | ggcgaacagc | 360 |
| ggagcaccgg | ccggggccgc | gggccgagcc | aagggcgagt | cccgtatccg | gcggccgatg | 420 |
| aacgctttca | tggtgtgggc | taaggacgag | cgcaagcggc | tggcgcagca | gaatccagac | 480 |
| ctgcacaacg | ccgagttgag | caagatgctg | ggcaagtcgt | ggaaggcgct | gacgctggcg | 540 |
| gagaagcggc | ccttcgtgga | ggaggcagag | cggctgcgcg | tgcagcacat | gcaggaccac | 600 |
| cccaactaca | agtaccggcc | gcggcggcgc | aagcaggtga | agcggctgaa | gcgggtggag | 660 |
| ggcggcttcc | tgcacggcct | ggctgagccg | caggcggccg | cgctgggccc | cgagggcggc | 720 |
| cgcgtggcca | tggacggcct | gggcctccag | ttccccgagc | agggcttccc | cgccggcccg | 780 |
| ccgctgctgc | ctccgcacat | gggcggccac | taccgcgact | gccagagtct | gggcgcgcct | 840 |
| ccgctcgacg | gctacccgtt | gccacgcccc | gacacgtccc | cgctggacgg | cgtggacccc | 900 |
| gacccggctt | tcttcgccgc | ccgatgccc | gggactgcc | cggcggccgg | cacctacagc | 960 |
| tacgcgcagg | tctcggacta | cgctggcccc | ccggagcctc | ccgccggtcc | catgcacccc | 1020 |
| cgactcggcc | cagagcccgc | gggtcctctcg | attccgggcc | tcctggcgcc | acccagcgcc | 1080 |
| cttcacgtgt | actacggcgc | gatgggctcg | cccgggggcgg | gcggcgggcg | cggcttccag | 1140 |
| atgcagccgc | aacaccagca | ccagcaccag | caccagcacc | accccccggg | ccccggacag | 1200 |
| ccgtcgcccc | ctccggaggc | actgccctgc | cgggacggca | cggaccccag | tcagcccgcc | 1260 |
| gagctcctcg | gggaggtgga | ccgcacggaa | tttgaacagt | atctgcactt | cgtgtgcaag | 1320 |
| cctgagatgg | gcctccccta | ccaggggcat | gactccggtg | tgaatctccc | cgacagccac | 1380 |

```
ggggccattt cctcggtggt gtccgacgcc agctccgcgg tatattactg caactatcct    1440
gacgtgtgac aggtccctga tccgccccag cctgcaggcc agaagcagtg ttacacactt    1500
cctggaggag ctaaggaaat cctcagactc ctgggttttt gttgttgctg ttgttgtttt    1560
ttaaaaggtg tgttggcata taatttatgg taatttattt tgtctgccac ttgaacagtt    1620 tggggggtg aggtttcatt taaaatttgt tcagagattt gtttcccata gttggattgt    1680
caaaacccta tttccaagtt caagttaact agctttgaat gtgtcccaaa acagcttcct    1740
ccatttcctg aaagtttatt gatcaaagaa atgttgtcct gggtgtgttt tttcaatctt    1800
ctaaaaaata aaatctggaa tcctgctttt tgctctact agtacctctg tcacactagt     1860
cttatcaaaa accagttctt aagatcaatg ttaagtttat tagttaatgt aaatttctca    1920
tcctcgaaaa gggtgaacat aaatgccttt aaggagtata tctaaaaata aacattagga    1980
tatctaagtt tgatgtaatt gtttcaggaa ggaaaaaaga aaagcattct ggaatgagcc    2040
tacttcaagt aatcttagtt tctaaaacta acagttaata ttttcaattc cagtatatca    2100
ctttaagtag aaggggatgt ccaagtaatt ttggttttct aactgttgaa tcataagctt    2160
gacctgcccc cagaggcttt ttggatgttt ttatctgtgt tttgccatct ctttacactc    2220
ctcgacattc agtttacctt aatcttcaca tttttacacc ttgggaagtg gcaagcatcg    2280
ctgggtttaa gataaaggag tcacaaaaac taatcaaaat aaaatttgca ttatgacaac    2340
ttttaataca                                                           2350

<210> SEQ ID NO 10
<211> LENGTH: 3124
<212> TYPE: DNA
<213> ORGANISM: Homo sapiens

<400> SEQUENCE: 10
taagatccac atcagctcaa ctgcacttgc ctcgcagagg cagcccgctc acttcccgcg      60
gaggcgctcc ccggcgccgc gctccgcggc agccgcctgc ccccgcgct gccccgcc       120 gccgcgccgc cgccgccgcc gcgcacgccg cgccccgcag ctctgggctt cctcttcgcc    180
cgggtggcgt tgggcccgcg cgggcgctcg ggtgactgca gctgctcagc tcccctcccc    240
cgccccgcgc cgcgcggccg cccgtcgctt cgcacagggc tggatggttg tattgggcag    300
ggtggctcca ggatgttagg aactgtgaag atggaagggc atgaaaccag cgactggaac    360
agctactacg cagacacgca ggaggcctac tcctccgtcc cggtcagcaa catgaactca    420
ggcctgggct ccatgaactc catgaacacc tacatgacca tgaacaccat gactacgagc    480
ggcaacatga cccgggcgtc cttcaacatg tcctatgcca acccgggcct aggggccggc    540
ctgagtcccg gcgcagtagc cggcatgccg gggggctcgg cgggcgccat gaacagcatg    600
actgcggccg gcgtgacggc catgggtacg gcgctgagcc cgagcggcat gggcgccatg    660
ggtgcgcagc aggcggcctc catgaatggc ctgggccct acgcggccgc catgaacccg    720
tgcatgagcc ccatggcgta cgcgccgtcc aacctgggcc gcagccgcgc gggcggcggc    780
ggcgacgcca agacgttcaa gcgcagctac ccgcacgcca agccgcccta ctcgtacatc    840
tcgctcatca ccatggccat ccagcaggcg cccagcaaga tgctcacgct gagcgagatc    900
taccagtgga tcatggacct cttcccctat accggcagaa accagcagcg ctggcagaac    960
tccatccgcc actcgctgtc cttcaatgac tgcttcgtca aggtggcacg ctccccggac   1020
aagccgggca agggctccta ctggacgctg caccgggact ccggcaacat gttcgagaac   1080
ggctgctact tgcgccgcca gaagcgcttc aagtgcgaga agcagccggg ggccggcggc   1140
```

```
ggggcggga gcggaagcgg gggcagcggc gccaagggcg gccctgagag ccgcaaggac    1200
ccctctggcg cctctaaccc cagcgccgac tcgcccctcc atcggggtgt gcacgggaag    1260
accggccagc tagagggcgc gccggccccc gggcccgccg ccagccccca gactctggac    1320
cacagtgggg cgacgcgac aggggggcgcc tcggagttga agactccagc ctcctcaact    1380
gcgcccccca taagctccgg gccggggcg ctggcctctg tgcccgcctc tcacccggca    1440
cacggcttgg caccccacga gtcccagctg cacctgaaag gggaccccca ctactccttc    1500
aaccacccgt tctccatcaa caacctcatg tcctcctcgg agcagcagca taagctggac    1560
ttcaaggcat acgaacaggc actgcaatac tcgccttacg gctctacgtt gcccgccagc    1620
ctgcctctag gcagcgccctc ggtgaccacc aggagcccca tcgagccctc agccctggag    1680
ccggcgtact accaaggtgt gtattccaga cccgtcctaa acacttccta gctcccggga    1740 ctgggggtt tgtctggcat agccatgctg gtagcaagag agaaaaaatc aacagcaaac    1800
aaaaccacac aaaccaaacc gtcaacagca taataaaatc ccaacaacta tttttatttc    1860 attttcatg cacaaccttt cccccagtgc aaaagactgt tactttatta ttgtattcaa    1920
aattcattgt gtatattact acaaagacaa ccccaaacca atttttttcc tgcgaagttt    1980
aatgatccac aagtgtatat atgaaattct cctccttcct tgcccccctc tctttcttcc    2040
ctctttcccc tccagacatt ctagtttgtg gagggttatt taaaaaaaca aaaaaggaag    2100
atggtcaagt ttgtaaaata tttgtttgtg cttttctccc ctccttacct gacccctac    2160 gagtttacag gtctgtggca atactcttaa ccataagaat tgaaatggtg aagaaacaag    2220
tatacactag aggctcttaa aagtattgaa agacaatact gctgttatat agcaagacat    2280
aaacagatta taaacatcag agccatttgc ttctcagttt acatttctga tacatgcaga    2340
tagcagatgt ctttaaatga aatacatgta tattgtgtat ggacttaatt atgcacatgc    2400
tcagatgtgt agacatcctc cgtatattta cataacatat agaggtaata gataggtgat    2460
atacatgata cattctcaag agttgcttga ccgaaagtta caaggacccc aacccctttg    2520
tcctctctac ccacagatgg ccctgggaat caattcctca ggaattgccc tcaagaactc    2580
tgcttcttgc tttgcagagt gccatggtca tgtcattctg aggtcacata acacataaaa    2640
ttagttccta tgagtgtata ccatttaaag aatttttttt tcagtaaaag ggaatattac    2700
aatgttggag gagagataag ttatagggag ctggatttca aaacgtggtc caagattcaa    2760
aaatcctatt gatagtggcc atttaatca ttgccatcgt gtgcttgttt catccagtgt    2820
tatgcacttt ccacagttgg acatggtgtt agtatagcca gacgggtttc attattattt    2880
ctctttgctt tctcaatgtt aatttattgc atggtttatt cttttctttt acagctgaaa    2940
ttgctttaaa tgatggttaa aattacaaat taaattgtta atttttatca atgtgattgt    3000
aattaaaaat attttgattt aaataacaaa aataatacca gattttaagc cgtggaaaat    3060
gttcttgatc atttgcagtt aaggacttta aataaatcaa atgttaacaa aaaaaaaaaa    3120
aaaa                                                                3124
```

```
<210> SEQ ID NO 11
<211> LENGTH: 2428
<212> TYPE: DNA
<213> ORGANISM: Homo sapiens

<400> SEQUENCE: 11
cccgcccact tccaactacc gcctccggcc tgcccaggga gagagaggga gtggagccca      60
gggagaggga gcgcgagaga gggagggagg aggggacggt gctttggctg acttttttt     120
```

```
aaaagagggt gggggtgggg ggtgattgct ggtcgtttgt tgtggctgtt aaattttaaa    180
ctgccatgca ctcggcttcc agtatgctgg gagcggtgaa gatggaaggg cacgagccgt    240
ccgactggag cagctactat gcagagcccg agggctactc ctccgtgagc aacatgaacg    300
ccggcctggg gatgaacggc atgaacacgt acatgagcat gtcggcggcc gccatgggca    360
gcggctcggg caacatgagc gcgggctcca tgaacatgtc gtcgtacgtg ggcgctggca    420
tgagcccgtc cctggcgggg atgtccccgg gcgcgggcgc catggcgggc atgggcggct    480
cggccggggc ggccggcgtg gcgggcatgg ggccgcactt gagtcccagc ctgagcccgc    540
tcgggggggca ggcggccggg gccatggggcg gcctggcccc ctacgccaac atgaactcca    600
tgagccccat gtacgggcag gcgggcctga ccgcgcccg cgaccccaag acctacaggc    660
gcagctacac gcacgcaaag ccgccctact cgtacatctc gctcatcacc atggccatcc    720
agcagagccc caacaagatg ctgacgctga gcgagatcta ccagtggatc atggacctct    780
tccccttcta ccggcagaac cagcagcgct ggcagaactc catccgccac tcgctctcct    840
tcaacgactg tttcctgaag gtgccccgct cgcccgacaa gccggcaag ggctcccttct    900
ggaccctgca ccctgactcg ggcaacatgt tcgagaacgg ctgctacctg cgccgccaga    960
agcgcttcaa gtgcgagaag cagctggcgc tgaaggaggc cgcaggcgcc gccggcagcg   1020
gcaagaaggc ggccgccgga gcccaggcct cacaggctca actcggggag gccgccgggc   1080
cggcctccga gactccggcg ggcaccgagt cgcctcactc gagcgcctcc ccgtgccagg   1140
agcacaagcg aggggggcctg ggagagctga aggggacgcc ggctgcggcg ctgagccccc   1200
cagagccggc gccctctccc gggcagcagc agcaggccgc ggcccacctg ctgggcccgc   1260
cccaccaccc gggcctgccg cctgaggcc acctgaagcc ggaacaccac tacgccttca   1320
accacccgtt ctccatcaac aacctcatgt cctcggagca gcagcaccac cacagccacc   1380
accaccacca cccccacaaa atggacctca aggcctacga acaggtgatg cactacccccg   1440
gctacggttc cccatgcct ggcagcttgg ccatgggccc ggtcacgaac aaaacgggcc   1500
tggacgcctc gccctggcc gcagataacct cctactacca gggggtgtac tcccggccca   1560
ttatgaactc ctcttaagaa gacgacggct tcaggcccgg ctaactctgg cacccccggat   1620
cgaggacaag tgagagagca agtgggggtc gagactttgg ggagacggtg ttgcagagac   1680
gcaagggaga agaaatccat aacacccca ccccaacacc cccaagacag cagtcttctt   1740
cacccgctgc agccgttccg tcccaaacag agggccacac agatacccca cgttctatat   1800
aaggaggaaa acgggaaaga atataaagtt aaaaaaaagc ctccggtttc cactactgtg   1860
tagactcctg cttcttcaag cacctgcaga ttctgatttt tttgttgttg ttgttctcct   1920
ccattgctgt tgttgcaggg aagtcttact taaaaaaaaa aaaaattttt gtgagtgact   1980
cggtgtaaaa ccatgtagtt ttaacagaac cagagggttg tactattgtt taaaaacagg   2040
aaaaaaaata atgtaagggt ctgttgtaaa tgaccaagaa aaagaaaaaa aaagcattcc   2100
caatcttgac acggtgaaat ccaggtctcg ggtccgatta atttatggtt tctgcgtgct   2160
ttatttatgg cttataaatg tgtattctgg ctgcaagggc cagagttcca caaatctata   2220
ttaaagtgtt ataccccggtt ttatccccttg aatcttttct tccagatttt tcttttcttt   2280
acttggctta caaatatac aggcttgaa attatttcaa gaaggaggga gggatacccct   2340
gtctggttgc aggttgtatt ttattttggc ccagggagtg ttgctgtttt cccaacattt   2400
tattaataaa attttcagac ataaaaaa                                      2428
```

<210> SEQ ID NO 12

<211> LENGTH: 2415
<212> TYPE: DNA
<213> ORGANISM: Homo sapiens

<400> SEQUENCE: 12

| | | | | | |
|---|---|---|---|---|---|
| cggccgctgc | tagaggggct | gcttgcgcca | ggcgccggcc | gccccactgc | gggtccctgg | 60 |
| cggccggtgt | ctgaggagtc | ggagagccga | ggcggccaga | ccgtgcgccc | cgcgcttctc | 120 |
| ccgaggccgt | tccgggtctg | aactgtaaca | gggaggggcc | tcgcaggagc | agcagcgggc | 180 |
| gagttaaagt | atgctgggag | cggtgaagat | ggaagggcac | gagccgtccg | actggagcag | 240 |
| ctactatgca | gagcccgagg | ctactcctc | cgtgagcaac | atgaacgccg | gcctggggat | 300 |
| gaacggcatg | aacacgtaca | tgagcatgtc | ggcggccgcc | atgggcagcg | gctcgggcaa | 360 |
| catgagcgcg | ggctccatga | acatgtcgtc | gtacgtgggc | gctggcatga | gcccgtccct | 420 |
| ggcggggatg | tccccggcg | cgggcgccat | ggcgggcatg | ggcggctcgg | ccggggcggc | 480 |
| cggcgtggcg | ggcatggggc | cgcacttgag | tcccagcctg | agcccgctcg | ggggcaggc | 540 |
| ggccggggcc | atgggcggcc | tggcccccta | cgccaacatg | aactccatga | gccccatgta | 600 |
| cgggcaggcg | ggcctgagcc | gcgccgcga | ccccaagacc | tacaggcgca | gctacacgca | 660 |
| cgcaaagccg | ccctactcgt | acatctcgct | catcaccatg | gccatccagc | agagccccaa | 720 |
| caagatgctg | acgctgagcg | agatctacca | gtggatcatg | gacctcttcc | ccttctaccg | 780 |
| gcagaaccag | cagcgctggc | agaactccat | ccgccactcg | ctctccttca | acgactgttt | 840 |
| cctgaaggtg | ccccgctcgc | cgacaagcc | cggcaagggc | tccttctgga | ccctgcaccc | 900 |
| tgactcgggc | aacatgttcg | agaacggctg | ctacctgcgc | cgccagaagc | gcttcaagtg | 960 |
| cgagaagcag | ctggcgctga | aggaggccgc | aggcgccgcc | ggcagcggca | agaaggcggc | 1020 |
| cgccggagcc | caggcctcac | aggctcaact | cggggaggcc | gccgggccgg | cctccgagac | 1080 |
| tccggcgggc | accgagtcgc | ctcactcgag | cgcctcccg | tgccaggagc | acaagcgagg | 1140 |
| gggcctggga | gagctgaagg | ggacgccggc | tgcggcgctg | agcccccag | agccggcgcc | 1200 |
| ctctcccggg | cagcagcagc | aggccgcggc | ccacctgctg | ggcccgcccc | accccggg | 1260 |
| cctgccgcct | gaggcccacc | tgaagccgga | acaccactac | gccttcaacc | acccgttctc | 1320 |
| catcaacaac | ctcatgtcct | cggagcagca | gcaccaccac | agccaccacc | accaccaacc | 1380 |
| ccacaaaatg | gacctcaagg | cctacgaaca | ggtgatgcac | taccccggct | acggttcccc | 1440 |
| catgcctggc | agcttggcca | tgggcccggt | cacgaacaaa | acgggcctgg | acgcctcgcc | 1500 |
| cctggccgca | gatacctcct | actaccaggg | ggtgtactcc | cggcccatta | tgaactcctc | 1560 |
| ttaagaagac | gacggcttca | ggcccggcta | actctggcac | cccggatcga | ggacaagtga | 1620 |
| gagagcaagt | ggggtcgag | actttgggga | acggtgttg | cagagacgca | agggagaaga | 1680 |
| aatccataac | accccaccc | caacaccccc | aagacagcag | tcttcttcac | ccgctgcagc | 1740 |
| cgttccgtcc | caaacagagg | gccacacaga | taccccacgt | tctatataag | gaggaaaacg | 1800 |
| ggaaagaata | taaagttaaa | aaaaagcctc | cggtttccac | tactgtgtag | actcctgctt | 1860 |
| cttcaagcac | ctgcagattc | tgatttttt | gttgttgttg | ttctcctcca | ttgctgttgt | 1920 |
| tgcagggaag | tcttacttaa | aaaaaaaaaa | aaattttgtg | agtgactcgg | tgtaaaacca | 1980 |
| tgtagtttta | acagaaccag | agggttgtac | tattgtttaa | aaacaggaaa | aaaaataatg | 2040 |
| taagggtctg | ttgtaaatga | ccaagaaaaa | gaaaaaaaaa | gcattcccaa | tcttgacacg | 2100 |
| gtgaaatcca | ggtctcgggt | ccgattaatt | tatggtttct | gcgtgcttta | tttatggctt | 2160 |
| ataaatgtgt | attctggctg | caagggccag | agttccacaa | atctatatta | aagtgttata | 2220 |

-continued

| | |
|---|---|
| cccggttttta tcccttgaat cttttcttcc agatttttct tttctttact tggcttacaa | 2280 |
| aatatacagg cttggaaatt atttcaagaa ggagggaggg atacccctgtc tggttgcagg | 2340 |
| ttgtattttta ttttggccca gggagtgttg ctgttttccc aacatttat taataaaatt | 2400 |
| ttcagacata aaaaa | 2415 |

<210> SEQ ID NO 13
<211> LENGTH: 1772
<212> TYPE: DNA
<213> ORGANISM: Homo sapiens

<400> SEQUENCE: 13

| | |
|---|---|
| ggataaatgt agcgccgcgg cgcgggccag cagctctgcg aggggccgga gcgcggcgga | 60 |
| gccatgcagt acccgcaccc cgggccggcg gcgggcgccg tggggtgcc gctgtacgcg | 120 |
| cccacgccgc tgctgcaacc cgcacacccg acgccttttt acatcgagga catcctgggc | 180 |
| cgcgggcccg ccgcgccac gcccgccccc acgctgccgt cccccaactc ctccttcacc | 240 |
| agcctcgtgt cccctaccg gaccccggtg tacgagccca cgccgatcca tccagccttc | 300 |
| tcgcaccact ccgccgccgc gctggccgct gcctacggac ccggcggctt cgggggcccct | 360 |
| ctgtaccct tcccgcggac ggtgaacgac tacacgcacg ccctgctccg ccacgacccc | 420 |
| ctgggcaaac ctctactctg gagcccccttc ttgcagaggc ctctgcataa aaggaaaggc | 480 |
| ggccaggtga gattctccaa cgaccagacc atcgagctgg agaagaaatt cgagacgcag | 540 |
| aaatatctct ctccgcccga gaggaagcgt ctggccaaga tgctgcagct cagcgagaga | 600 |
| caggtcaaaa cctggtttca gaatcgacgc gctaaatgga ggagactaaa acaggagaac | 660 |
| cctcaaagca ataaaaaaga gaactggaa agtttggaca gttcctgtga tcagaggcaa | 720 |
| gatttgccca gtgaacagaa taaggtgct tctttggata gctctcaatg ttcgccctcc | 780 |
| cctgcctccc aggaagacct tgaatcagag atttcagagg attctgatca ggaagtggac | 840 |
| attgagggcg ataaaagcta ttttaatgct ggatgatgac cactggcatt ggcatgttca | 900 |
| gaaaactgga tttaggaata atgttttgct acagaaaatc ttcatagaag aactggaagg | 960 |
| ctatataaga aagggaatca attctctggt attctggaaa cctaaaaata tttggtgcac | 1020 |
| tgctcaatta acaaacctac atggagacct aatttgac ttaacaaata gtttatgtac | 1080 |
| tgctcttagg ttgttttgat aaagtgacat tatagtgatt aaattcttcc ccctttaaaa | 1140 |
| aaacagttag tggttttcac tatttataaa aaattaattt tgaactttt gttaaatttt | 1200 |
| taagttatag ctttaaaggt tttaatagga ccttcttgaa cgacttttct gtaatctgtt | 1260 |
| tatctcccac ttaatggaaa ggcaaggggg taccccaaat ccagaggtgc ctacatttca | 1320 |
| ggcagccttg gagtatttta aaggaaaaac attctttact tttatatgac attcttatac | 1380 |
| tgctgtctca aatccaaaaa catttcagag ctcttgtctc agagatgtgt gttctttttg | 1440 |
| tcagagatat ggttgatgag aatcttaaat gcttgttttg cactatcact tagtacctgt | 1500 |
| ttgaccaagg tgttaagggg atagtacctc ccaattcaag cagagaaact gacctgacta | 1560 |
| aagttaatcg cagatgaact agaagtcaca ggttaattaa atgtaagtag attgtagata | 1620 |
| ctgtttata tcaaacaatg tttataatgt gtatatagaa ttgttcactg taaaaaaaat | 1680 |
| ggccaaaatg tgtttttttt ttaataagta acttgactat aaaataaagc cgtccgtggg | 1740 |
| acgactgacc tcgttgcaaa aaaaaaaaaa aa | 1772 |

<210> SEQ ID NO 14
<211> LENGTH: 3419
<212> TYPE: DNA

<213> ORGANISM: Homo sapiens

<400> SEQUENCE: 14

```
ttggaggcgg ccggcgcagg ggccgcgaga ggcttcgtcg ccgctgcagc tccggggct      60
cccaggggag cgtgcgcgga acctccaggc ccagcaggac cccggctgcg gcgaggagga    120
aggagccagc ctagcagctt ctgcgcctgt ggccgcgggt gtcctggagg cctctcggtg    180
tgacgagtgg gggaccccgaa ggctcgtgcg ccacctccag gcctgacgc tgccctccgt    240
cttctgcccc caataggtgc gccggacctt caggccctgg ggtgaattca gctgctccta    300
catcagcttc cggaaccacc aaaaattcaa attgggattt ccggagtaa caagagcct     360
agagcccttt gctcaatgct ggatttaata cgtatatatt tttaagcgag ttggttttt     420
cccctttgat ttttgatctt cgcgacagtt cctcccacgc atattatcgt tgttgccgtc    480
gttttctctc cccgcgtggc tccttgacct gcgagggaga gagaggacac cgaagccggg    540
agctcgcagg gaccatgtat cagagcttgg ccatggccgc caaccacggg ccgcccccg     600
gtgcctacga ggcgggcggc cccggcgcct tcatgcacgg cgcgggcgcc gcgtcctcgc    660
cagtctacgt gcccacaccg cggggtgccc tctccgtgct gggcctgtcc tacctccagg    720
gcggaggcgc gggctctgcg tccggaggcg cctcgggcgg cagctccggt ggggccgcgt    780
ctggtgcggg gccgggacc cagcagggca gcccgggatg gagccaggcg ggagccgacg     840
gagccgctta caccccgccg ccggtgtcgc cgcgcttctc cttcccgggg accaccgggt    900
ccctggcggc cgccgccgcc gctgccgcgg cccgggaagc tgcggcctac agcagtggcg    960
gcggagcggc gggtgcgggc ctggcgggcc gcgagcagta cggcgcgcc ggcttcgcgg    1020
gctcctactc cagcccctac ccggcttaca tggccgacgt gggcgcgtcc tgggccgcag    1080
ccgccgccgc ctccgccggc cccttcgaca gcccggtcct gcacagcctg cccggccggg    1140
ccaacccggc cgcccgacac cccaatctcg atatgtttga cgacttctca gaaggcagag    1200
agtgtgtcaa ctgtggggct atgtccaccc cgctctggag gcgagatggg acgggtcact    1260
atctgtgcaa cgcctgcggc ctctaccaca gatgaacgg catcaaccgg ccgctcatca    1320
agcctcagcg ccggctgtcc gcctcccgcc gagtgggcct ctcctgtgcc aactgccaga    1380
ccaccaccac cacgctgtgg cgccgcaatg cggagggcga gcctgtgtgc aatgcctgcg    1440
gcctctacat gaagctccac ggggtcccca ggctcttgc aatgcggaaa gaggggatcc     1500
aaaccagaaa acggaagccc aagaacctga ataaatctaa gacaccagca gctccttcag    1560
gcagtgagag ccttcctccc gccagcggtg cttccagcaa ctccagcaac gccaccacca    1620
gcagcagcga ggagatgcgt cccatcaaga cggagcctgg cctgtcatct cactacgggc    1680
acagcagctc cgtgtcccag acgttctcag tcagtgcgat gtctggccat gggccctcca    1740
tccaccctgt cctctcggcc ctgaagctct ccccacaagg ctatgcgtct cccgtcagcc    1800
agtctccaca gaccagctcc aagcaggact cttggaacag cctggtcttg gccgacagtc    1860
acgggggacat aatcactgcg taatcttccc tcttccctcc tcaaattcct gcacggacct    1920
gggacttgga ggatagcaaa gaaggaggcc ctgggctccc aggggccggc ctcctctgcc    1980
tggtaatgac tccagaacaa caactgggaa gaaacttgaa gtcgacaatc tggttagggg    2040
aagcgggtgt tggatttctct cagatgcctt tacacgctga tgggactgga gggagcccac    2100
ccttcagcac gagcacactg catctctcct gtgagttgga gacttctttc caagatgtc    2160
cttgtcccct gcgttcccca ctgtggccta ccgtgggt tttgcattgt gtttctagca    2220
ccgaggatct gagaacaagc ggagggccgg gccctgggac ccctgctcca gcccgaatga    2280
```

| | |
|---|---|
| cggcatctgt ttgccatgta cctggatgcg acgggcccct ggggacaggc ccttgcccca | 2340 |
| tccatccgct tgaggcatgg caccgccctg catccctaat accaaatctg actccaaaat | 2400 |
| tgtggggtgt gacatacaag tgactgaaca cttcctgggg agctacaggg gcacttaacc | 2460 |
| caccacagca cagcctcatc aaaatgcagc tggcaacttc tcccccaggt gccttccccc | 2520 |
| tgctgccggc ctttgctcct tcacttccaa catctctcaa aataaaaatc cctcttcccg | 2580 |
| ctctgagcga ttcagctctg cccgcagctt gtacatgtct ctcccctggc aaaacaagag | 2640 |
| ctgggtagtt tagccaaacg gcacccctc gagttcactg cagacccttc gttcaccgtg | 2700 |
| tcacacatag aggggttctg agtaagaaca aaacgttctg ctgctcaagc cagtctggca | 2760 |
| agcactcagc ccagcctcga ggtccttctg gggagagtgt aagtggacag agtcctggtc | 2820 |
| aggggggcagg agtgtcccaa gggctggccc acctgctgtc tgtctgctcc tcctagccct | 2880 |
| tggtcagatg gcagccagag tccctcagga cctgcagcct cgccccggca gaagtctttt | 2940 |
| gtccaggagg caaaaagcca gagattctgc aacacgaatt cgaagcaaac aaacacaaca | 3000 |
| caacagaatt cctggaaaga gacgactgc taagacacgg caggggggcc tggagggagc | 3060 |
| ctccgactct gagctgctcc gggatctgcc gcgttctcct ctgcacattg ctgtttctgc | 3120 |
| ccctgatgct ggagctcaag gagactcctt cctctttctc agcagagctg tagctgactg | 3180 |
| tggcattact acgcctcccc acacgccag acccctcact ccaaaatcct actggctgta | 3240 |
| gcagagaata cctttgaacc aagattctgt tttaatcatc atttacattg ttttcttcca | 3300 |
| aaggccccct cgtatacct ccctaaccca caaacctgtt aacattgtct taaggtgaaa | 3360 |
| tggctggaaa atcagtattt aactaataaa tttatctgta ttcctcttaa aaaaaaaa | 3419 |

<210> SEQ ID NO 15
<211> LENGTH: 3494
<212> TYPE: DNA
<213> ORGANISM: Homo sapiens

<400> SEQUENCE: 15

| | |
|---|---|
| ggcacccttc ggcgagcgct gtttgtttag ggctcggtga gtccaatcag gagcccaggc | 60 |
| tgcagttttc cggcagagca gtaagaggcg cctcctctct ccttttatt caccagcagc | 120 |
| gcggcgcaga ccccggactc gcgctcgccc gctggcgccc tcggcttctc tccgcgcctg | 180 |
| ggagcaccct ccgccgcggc cgttctccat gcgcagcgcc cgcccgagga gctagacgtc | 240 |
| agcttggagc ggcgccggac cgtggatggc cttgactgac ggcggctggt gcttgccgaa | 300 |
| gcgcttcggg gccgcgggtg cggacgccag cgactccaga gcctttccag cgcgggagcc | 360 |
| ctccacgccg ccttcccca tctcttcctc gtcctcctcc tgctcccggg gcggagagcg | 420 |
| gggcccggc ggcgccagca actgcgggac gcctcagctc gacacggagg cggcggccgg | 480 |
| acccccggcc cgctcgctgc tgctcagttc ctacgcttcg catcccttcg ggctccccca | 540 |
| cggaccttcg gcgcctgggg tcgcgggccc cgggggcaac ctgtcgagct gggaggactt | 600 |
| gctgctgttc actgaccctcg accaagccgc gaccgccagc aagctgctgt ggtccagccg | 660 |
| cggcgccaag ctgagcccct tcgcaccgga cagccggag gagatgtacc agaccctcgc | 720 |
| cgctctctcc agccagggtc cggccgccta cgacggcgcg cccggcggct tcgtgcactc | 780 |
| tgcggccgcg gcggcagcag ccggcggcgg ggccagctcc ccggtctacg tgcccaccac | 840 |
| ccgcgtgggt tccatgctgc ccggcctacc gtaccacctg caggggtcgg gcagtgggcc | 900 |
| agccaaccac gcgggcggcg cgggcgcgca ccccggctgg cctcaggcct cggccgacag | 960 |
| ccctccatac ggcagcggag gcggcgcggc tggcggcggg gccgcgggc ctggcggcgc | 1020 |

```
tggctcagcc gcggcgcacg tctcggcgcg cttccsctac tctcccagcc cgcccatggc    1080
caacggcgcc gcgcgggagc cgggaggcta cgcggcggcg ggcagtgggg gcgcgggagg    1140
cgtgagcggc ggcggcagta gcctggcggc catgggcggc cgcgagcccc agtacagctc    1200
gctgtcggcc gcgcggccgc tgaacgggac gtaccaccac caccaccacc accaccacca    1260
ccatccgagc ccctactcgc cctacgtggg ggcgccactg acgcctgcct ggcccgccgg    1320
acccttcgag accccggtgc tgcacagcct gcagagccgc gccggagccc cgctcccggt    1380
gccccggggt cccagtgcag acctgctgga ggacctgtcc gagagccgcg agtgcgtgaa    1440
ctgcggctcc atccagacgc cgctgtggcg gcgggacggc accggccact acctgtgcaa    1500
cgcctgcggg ctctacagca agatgaacgg cctcagccgg cccctcatca gccgcagaa    1560
gcgcgtgcct tcatcacggc ggcttggatt gtcctgtgcc aactgtcaca ccacaactac    1620
caccttatgg cgcagaaacg ccgagggtga acccgtgtgc aatgcttgtg gactctacat    1680
gaaactccat ggggtgccca gaccacttgc tatgaaaaaa gagggaattc aaaccaggaa    1740
acgaaaacct aagaacataa ataaatcaaa gacttgctct ggtaatagca ataattccat    1800
tcccatgact ccaacttcca cctcttctaa ctcagatgat gcagcaaaa atacttcccc    1860
cacaacacaa cctacagcct caggggcggg tgccccggtg atgactggtg cgggagagag    1920
caccaatccc gagaacagcg agctcaagta ttcgggtcaa gatgggctct acataggcgt    1980
cagtctcgcc tcgccggccg aagtcacgtc ctccgtgcga ccggattcct ggtgcgccct    2040
ggccctggcc tgagcccacg ccgccaggag gcagggaggg ctccgccgcg ggcctcactc    2100
cactcgtgtc tgcttttgtg cagcggtcca gacagtggcg actgcgctga cagaacgtga    2160
ttctcgtgcc tttatttttga aagagatgtt tttcccaaga ggcttgctga aagagtgaga    2220
gaagatggaa gggaagggcc agtgcaactg ggcgcttggg ccactccagc cagcccgcct    2280
ccggggcgga ccctgctcca cttccagaag ccaggactag gacctgggcc ttgcctgcta    2340
tggaatattg agagagattt tttaaaaaag attttgcatt ttgtccaaaa tcatgtgctt    2400
cttctgatca atttttggttg ttccagaatt tcttcatacc ttttccacat ccagatttca    2460
tgtgcgttca tggagaagat cacttgaggc catttggtac acatctctgg aggctgagtc    2520
ggttcatgag gtctcttatc aaaaatatta ctcagtttgc aagactgcat tgtaacttta    2580
acatacactg tgactgacgt ttctcaaagt tcatattgtg tggctgatct gaagtcagtc    2640
ggaatttgta aacagggtag caaacaagat attttcttc catgtataca ataatttttt    2700
taaaaagtgc aatttgcgtt gcagcaatca gtgttaaatc atttgcataa gatttaacag    2760
cattttttat aatgaatgta aacattttaa cttaatggta cttaaaataa tttaaaagaa    2820
aaatgttaac ttagacattc ttatgcttct tttacaacta catcccattt tatatttcca    2880
attgttaaag aaaaatattt caagaacaaa tcttctctca ggaaaattgc ctttctctat    2940
ttgttaagaa ttttttataca agaacaccaa tataccccct ttattttact gtggaatatg    3000
tgctggaaaa attgcaacaa cactttacta cctaacggat agcatttgta aatactctag    3060
gtatctgtaa acactctgat gaagtctgta tagtgtgact aacccacagg caggttggtt    3120
tacattaatt tttttttttg aatgggatgt cctatggaaa cctatttcac cagagtttta    3180
aaaataaaaa gggtattgtt ttgtcttctg tacagtgagt tccttccctt ttcaaagctt    3240
tcttttatg ctgtatgtga ctatagatat tcatataaaa caagtgcacg tgaagtttgc    3300
aaaatgcttt aaggccttcc tttcaaagca tagtcctttt ggagccgttt tgtacccttt    3360
ataccttggc ttatttgaag ttgacacatg gggttagtta ctactctcca tgtgcattgg    3420
```

```
ggacagtttt tataagtggg aaggactcag tattattata tttgagatga taagcatttt    3480
gtttgggaac aatg                                                      3494

<210> SEQ ID NO 16
<211> LENGTH: 3088
<212> TYPE: DNA
<213> ORGANISM: Homo sapiens

<400> SEQUENCE: 16 cccctttttcc agaatcactt gcactgtctt gttcttgaat gagaaaggaa gaaaagagcc     60
tcccattact cagacccgtg taaacattat tcccccagg agaaaatggt gttattcaaa      120
tgaatcataa taaaatagcc tctaaacagt ttctaagcgg gagcctccgt ggaactcagc     180
gctccgctcc tcccagttcc taagaggtcc cgggattctt gagctgtgcc cagctgacga     240
gcttttgaag atggcacaat aaccgtccag tgatgcctga ccatgacagc acagccctct     300
taagccggca aaccaagagg agaagagttg acattggagt gaaaaggacg gtagggacag     360
catctgcatt ttttgctaag gcaagagcaa cgttttttag tgccatgaat ccccaaggtt     420
ctgagcagga tgttgagtat tcagtggtgc agcatgcaga tggggaaaag tcaaatgtac     480
tccgcaagct gctgaagagg gcgaactcgt atgaagatgc catgatgcct tttccaggag     540
caaccataat ttcccagctg ttgaaaaata acatgaacaa aaatggtggc acggagccca     600
gtttccaagc cagcggtctc tctagtacag gctccgaagt acatcaggag gatatatgca     660
gcaactcttc aagagacagc ccccagagt gtctttcccc ttttggcagg cctactatga     720
gccagtttga tatggatcgc ttatgtgatg agcacctgag agcaaagcgc gcccgggttg     780
agaatataat tcgggtatg agccattccc ccagtgtggc attaaggggc aatgaaaatg     840
aaagagagat ggccccgcag tctgtgagtc cccgagaaag ttacagagaa aacaaacgca     900
agcaaaagct tccccagcag cagcaacaga gtttccagca gctggtttca gcccgaaaag     960
aacagaagcg agaggagcgc cgacagctga acagcagct ggaggacatg cagaaacagc    1020
tgcgccagct gcaggaaaag ttctaccaaa tctatgacag cactgattcg gaaaatgatg    1080
aagatggtaa cctgtctgaa gacagcatgc gctcggagat cctggatgcc agggcccagg    1140
actctgtcgg aaggtcagat aatgagatgt gcgagctaga cccaggacag tttattgacc    1200
gagctcgagc cctgatcaga gagcaggaaa tggctgaaaa caagccgaag cgagaaggca    1260
acaacaaaga aagagaccat gggccaaact ccttacaacc ggaaggcaaa catttggctg    1320
agaccttgaa acaggaactg aacactgcca tgtcgcaagt tgtggacact gtggtcaaag    1380
tcttttcggc caagcctccc cgccaggttc ctcaggtctt cccacctctc cagatccccc    1440
aggccagatt tgcagtcaat ggggaaaacc acaatttcca caccgccaac cagcgcctgc    1500
agtgctttgg cgacgtcatc attccgaacc ccctggacac cttttggcaat gtgcagatgg    1560 ccagttccac tgaccagaca gaagcactgc ccctggttgt ccgcaaaaac tcctctgacc    1620
agtctgcctc cggccctgcc gctggcggcc accaccagcc cctgcaccag tcgcctctct    1680
ctgccaccac gggcttcacc acgtccacct tccgccaccc cttccccctt ccctttgatgg   1740 cctatccatt tcagagccca ttaggtgctc cctccggctc cttctctgga aaagacagag    1800
cctctcctga atccttagac ttaactaggg ataccacgag tctgaggacc aagatgtcat    1860
ctcaccacct gagccaccac ccttgttcac cagcacaccc gcccagcacc gccgaagggc    1920
tctccttgtc gctcataaag tccgagtgcg gcgatcttca agatatgtct gaaatatcac    1980
cttattcggg aagtgcaatg caggaaggat tgtcacccaa tcacttgaaa aaagcaaagc    2040
```

| | | | | |
|---|---|---|---|---|
| tcatgttttt | ttatacccgt | tatcccagct | ccaatatgct | gaagacctac ttctccgacg | 2100 |
| taaagttcaa | cagatgcatt | acctctcagc | tcatcaagtg | gtttagcaat ttccgtgagt | 2160 |
| tttactacat | tcagatggag | aagtacgcac | gtcaagccat | caacgatggg gtcaccagta | 2220 |
| ctgaagagct | gtctataacc | agagactgtg | agctgtacag | ggctctgaac atgcactaca | 2280 |
| ataaagcaaa | tgactttgag | gttccagaga | gattcctgga | agttgctcag atcacattac | 2340 |
| gggagttttt | caatgccatt | atcgcaggca | agatgttga | tccttcctgg aagaaggcca | 2400 |
| tatacaaggt | catctgcaag | ctggatagtg | aagtccctga | gattttcaaa tccccgaact | 2460 |
| gcctacaaga | gctgcttcat | gagtagaaat | ttcaacaact | cttttttgaat gtatgaagag | 2520 |
| tagcagtccc | ctttggatgt | ccaagttata | tgtgtctaga | ttttgatttc atatatatgt | 2580 |
| gtatgggagg | catggatatg | ttatgaaatc | agctggtaat | tcctcctcat cacgtttctc | 2640 |
| tcatttttctt | ttgttttcca | ttgcaagggg | atggttgttt | tctttctgcc tttagtttgc | 2700 |
| ttttgcccaa | ggcccttaac | atttggacac | ttaaaatagg | gttaattttc agggaaaaag | 2760 |
| aatgttggcg | tgtgtaaagt | ctctattagc | aatgaaggga | atttgttaac gatgcatcca | 2820 |
| cttgattgat | gacttattgc | aaatggcggt | tggctgagga | aaacccatga cacagcacaa | 2880 |
| ctctacagac | agtgatgtgt | ctcttgtttc | tactgctaag | aaggtctgaa aatttaatga | 2940 |
| aaccacttca | tacatttaag | tattttgttt | ggtttgaact | caatcagtag cttttcctta | 3000 |
| catgtttaaa | aataattcca | atgacagatg | agcagctcac | ttttccaaag taccccaaaa | 3060 |
| ggccaaatta | aaaaaaaaaa | aaaaaaaa | | | 3088 |

<210> SEQ ID NO 17
<211> LENGTH: 4754
<212> TYPE: DNA
<213> ORGANISM: Homo sapiens

<400> SEQUENCE: 17

| | | | | |
|---|---|---|---|---|
| gaattctaga | ggcggcggag | ggtggcgagg | agctctcgct | ttctctcgct ccctccctct | 60 |
| ccgactccgt | ctctctctct | ctctctctct | ctccccctccc | tctctttccc tctgttccat | 120 |
| tttttccccc | tctaaatcct | ccctgccctg | cgcgcctgga | cacagattta ggaagcgaat | 180 |
| tcgctcacgt | tttaggacaa | ggaagagaga | gaggcacggg | agaagagccc agcaagattt | 240 |
| ggattgaaac | cgagacaccc | tccggaggct | cggagcagag | gaaggaggag gagggcggcg | 300 |
| aacggaagcc | agtttgcaat | tcaagttttg | atagcgctgg | tagaaggggg tttaaatcag | 360 |
| attttttttt | tttaaagga | gagagacttt | ttccgctctc | tcgctcccctg ttaaagccgg | 420 |
| gtctagcaca | gctgcagacg | ccaccagcga | gaaagaggga | gaggaagaca gatagggggc | 480 |
| ggggggaagaa | gaaaaagaaa | ggtaaaaagt | cttctaggag | aacctttcac atttgcaaca | 540 |
| aaagacctag | gggctggaga | gagattcctg | ggacgcaggg | ctggagtgtc tatttcgagc | 600 |
| tcagcggcag | ggctcgggcg | cgagtcgaga | ccctgctcgc | tcctctcgct tctgaaaccg | 660 |
| acgttcagga | gcggcttttt | aaaaacgcaa | ggcacaagga | cggtcacccg cgcgactatg | 720 |
| tttgctgatt | tttcgccttg | ccctctttaa | aagcggcctc | ccattctcca aaagacactt | 780 |
| cccctcctcc | ctttgaagtg | cattagttgt | gatttctgcc | tccttttctt ttttctttct | 840 |
| tttttgtttt | gcttttttccc | cccttttgaa | ttatgtgctg | ctgttaaaca acaacaaaaa | 900 |
| aacaacaaaa | cacagcagct | gcggacttgt | ccccggctgg | agcccagcgc cccgcctgga | 960 |
| gtggatgagc | ctctccatga | gagatccggt | cattcctggg | acaagcatgg cctaccatcc | 1020 |
| gttcctacct | caccgggcgc | cggacttcgc | catgagcgcg | gtgctgggtc accagccgcc | 1080 |

```
gttcttcccc gcgctgacgc tgcctcccaa cggcgcggcg gcgctctcgc tgccgggcgc    1140
cctggccaag ccgatcatgg atcaattggt gggggcggcc gagaccggca tcccgttctc    1200
ctccctgggg ccccaggcgc atctgaggcc tttgaagacc atggagcccg aagaagaggt    1260
ggaggacgac cccaaggtgc acctggaggc taaagaactt tgggatcagt tcacaagcg    1320 gggcaccgag atggtcatta ccaagtcggg aaggcgaatg tttcctccat ttaaagtgag    1380
atgttctggg ctggataaaa aagccaaata cattttattg atggacatta tagctgctga    1440
tgactgtcgt tataaatttc acaattctcg gtggatggtg gctggtaagg ccgaccccga    1500
aatgccaaag aggatgtaca ttcacccgga cagccccgct actggggaac agtggatgtc    1560
caaagtcgtc actttccaca aactgaaact caccaacaac atttcagaca acatggatt    1620 tactatattg aactccatgc acaaatacca gccccggttc cacattgtaa gagccaatga    1680
catcttgaaa ctcccttata gtacatttcg gacatacttg ttccccgaaa ctgaattcat    1740
cgctgtgact gcataccaga atgataagat aacccagtta aaaatagaca caacccttt    1800 tgcaaaaggt ttccgggaca ctggaaatgg ccgaagagaa aaagaaaac agctcaccct    1860 gcagtccatg agggtgtttg atgaaagaca caaaaggag aatgggacct ctgatgagtc    1920
ctccagtgaa caagcagctt tcaactgctt cgcccaggct tcttctccag ccgcctccac    1980
tgtagggaca tcgaacctca agatttatg tcccagcgag ggtgagagcg acgccgaggc    2040
cgagagcaaa gaggagcatg ccccgaggc ctgcgacgcg ccaagatct ccaccaccac    2100 gtcggaggag ccctgccgtg acaagggcag ccccgcggtc aaggctcacc ttttcgctgc    2160
tgagcggccc cgggacagcg gcggctgga caaagcgtcg cccgactcac gccatagccc    2220
cgccaccatc tcgtccagca ctcgcggcct gggcgcggag gagcgcagga gcccggttcg    2280
cgagggcaca gcgccggcca aggtggaaga ggcgcgcgcg ctcccgggca aggaggcctt    2340
cgcgccgctc acggtgcaga cggacgcggc cgccgcgcac ctggcccagg gcccctgcc    2400 tggcctcggc ttcgccccgg gcctggcggg ccaacagttc ttcaacgggc accgctctt    2460 cctgcacccc agccagtttg ccatggggggg cgccttctcc agcatggcgg ccgctggcat    2520
gggtcccctc ctggccacgg tttctggggc ctccaccggt gtctcgggcc tggattccac    2580
ggccatggcc tctgccgctg cggcgcaggg actgtccggg gcgtccgcgg ccaccctgcc    2640
cttccacctc cagcagcacg tcctggcctc tcagggcctg gccatgtccc ctttcggaag    2700
cctgttccct tacccctaca cgtacatggc cgcagcggcg ccgcctcct ctgcggcagc    2760 ctccagctcg gtgcaccgcc acccttcct caatctgaac accatgcgcc gcggctgcg    2820 ctacagcccc tactccatcc cggtgccggt cccggacggc agcagtctgc tcaccaccgc    2880
cctgccctcc atggcggcgg ccgcgggcc cctggacggc aaagtcgccg ccctggccgc    2940
cagcccggcc tcggtggcag tggactcggg ctctgaactc aacagccgct cctccacgct    3000
ctcctccagc tccatgtcct tgtcgcccaa actctgcgcg gagaaagagg cggccaccag    3060
cgaactgcag agcatccagc ggttggttag cggcttggaa gccaagccgg acaggtcccg    3120
cagcgcgtcc ccgtagaccc gtcccagaca cgtcttttca ttccagtcca gttcaggctg    3180
ccgtgcactt tgtcggatat aaaataaacc acgggcccgc catggcgtta gcccttcctt    3240
ttgcagttgc gtctgggaag ggccccggga ctccctcgag agaatgtgct agagacagcc    3300
cctgtcttct tggcgtggtt tatatgtccg ggatctggat cagattctgg gggctcagaa    3360
acgtcggttg cattgagcta ctgggggtag gagttccaac atttatgtcc agagcaactt    3420
ccagcaaggc tggtctgggt ctctgcccac caggcgggga ggtgttcaaa gacatctccc    3480
```

```
tcagtgcgga tttatatata tattttttcct tcactgtgtc aagtggaaac aaaaacaaaa    3540
tctttcaaaa aaaaaatcgg gacaagtgaa cacattaaca tgattctgtt tgtgcagatt    3600
aaaaacttta tagggacttg cattatcggt tctcaataaa ttactgagca gctttgtttg    3660
gggagggaag tccctaccat ccttgtttag tctatattaa gaaaatctgt gtcttttttaa   3720
tattcttgtg atgttttcag agccgctgta ggtctcttct tgcatgtcca cagtaatgta    3780
tttgtggttt ttattttgaa cgcttgcttt tagagagaaa acaatatagc cccctacccct   3840
tttcccaatc ctttgccctc aaatcagtga cccaagggag gggggatttt aaagggaagg    3900
agtgggcaaa acacataaaa tgaatttatt atatctaagc tctgtagcag gattcatgtc    3960
gttctttgac agttctttct ctttcctgta tatgcaataa caaggttttta aaaaaataat   4020
aaagaagtga gactattaga caaagtattt atgtaattat ttgataactc ttgtaaatag    4080
gtggaatatg aatgcttgga aaattaaact ttaatttatt gacattgtac atagctctgt    4140
gtaaatagaa ttgcaactgt caggttttgt gttcttgttt cctttagtt gggtttattt     4200
ccaggtcaca gaattgctgt taacactaga aaacacactt cctgcaccaa caccaatacc    4260
cttttcaaaag agttgtctgc aacatttttt ttttctttttt taatgtccaa aagtgggga   4320
aagtgctatt tcctattttc accaaaattg gggaaggagt gccactttcc agctccactt    4380
caaattcctt aaaatataac tgagattgct gtggggaggg aggagggcag aggctgcggt    4440
ttgactttttt aatttttctt ttgttatttg tatttgctag tctctgattt cctcaaaacg   4500
aagtggaatt tactactgtt gtcagtatcg gtgttttgaa ttggtgcctg cctatagaga    4560
tatattcaca gttcaaaagt caggtgctga gagatggttt aaagacaaat tcatgaaggt    4620
atattttgtg ttatagttgt tgatgagttc tttggttttc tgtattttttc ccctctctt    4680
taaaacatca ctgaaatttc aataaatttt tattgaaatg tctaaaaaaa aaaaaaaaaa    4740
aaaaaaaaaa aaaa                                                      4754
```

<210> SEQ ID NO 18
<211> LENGTH: 4814
<212> TYPE: DNA
<213> ORGANISM: Homo sapiens

<400> SEQUENCE: 18

```
gaattctaga ggcggcggag ggtggcgagg agctctcgct ttctctcgct ccctccctct     60
ccgactccgt ctctctctct ctctctctct ctccctccc tctctttccc tctgttccat    120
ttttccccc tctaaatcct ccctgccctg cgcgcctgga cacagattta ggaagcgaat    180
tcgctcacgt tttaggacaa ggaagagaga gaggcacggg agaagagccc agcaagattt    240
ggattgaaac cgagacaccc tccgaggct cggagcagag gaaggaggag gagggcggcg     300
aacggaagcc agtttgcaat tcaagttttg atagcgctgg tagaagggggg tttaaatcag   360
attttttttt ttttaaagga gagagacttt ttccgctctc tcgctccctg ttaaagccgg   420
gtctagcaca gctgcagacg ccaccagcga gaaagaggga gaggaagaca gataggggggc  480
gggggaagaa gaaaagaaa ggtaaaaagt cttctaggag aacctttcac atttgcaaca    540
aaagacctag gggctggaga gagattcctg ggacgcaggg ctggagtgtc tatttcgagc    600
tcagcggcag ggctcgggcg cgagtcgaga ccctgctcgc cctctctgct tctgaaaccg    660
acgttcagga gcggctttttt aaaaacgcaa ggcacaagga cggtcacccg cgcgactatg   720
tttgctgatt tttcgcccttg ccctctttaa aagcggcctc ccattctcca aaagacactt   780
cccctcctcc ctttgaagtg cattagttgt gatttctgcc tcctttttctt ttttctttct   840
```

```
tttttgtttt gcttttcccc ccctttgaa ttatgtgctg ctgttaaaca acaacaaaaa    900
aacaacaaaa cacagcagct gcggacttgt ccccggctgg agcccagcgc cccgcctgga    960
gtggatgagc ctctccatga gagatccggt cattcctggg acaagcatgg cctaccatcc   1020
gttcctacct caccgggcgc cggacttcgc catgagcgcg tgctgggtc accagccgcc    1080
gttcttcccc gcgctgacgc tgcctcccaa cggcgcggcg cgctctcgc tgccgggcgc    1140
cctggccaag ccgatcatgg atcaattggt ggggcggcc gagaccggca tcccgttctc    1200
ctccctgggg ccccaggcgc atctgaggcc tttgaagacc atggagcccg aagaagaggt   1260
ggaggacgac cccaaggtgc acctggaggc taaagaactt tgggatcagt ttcacaagcg   1320
gggcaccgag atggtcatta ccaagtcggg aaggcgaatg tttcctccat ttaaagtgag   1380
atgttctggg ctggataaaa aagccaaata cattttattg atggacatta tagctgctga   1440
tgactgtcgt tataaatttc acaattctcg gtggatggtg gctggtaagg ccgaccccga   1500
aatgccaaag aggatgtaca ttcacccgga cagccccgct actggggaac agtggatgtc   1560
caaagtcgtc actttccaca aactgaaact caccaacaac atttcagaca aacatggatt   1620
tactttggcc ttcccaagtg atcacgctac gtggcagggg aattatagtt ttggtactca   1680
gactatattg aactccatgc acaaatacca gccccggttc cacattgtaa gagccaatga   1740
catcttgaaa ctcccttata gtacatttcg gacatacttg ttccccgaaa ctgaattcat   1800
cgctgtgact gcataccaga atgataagat aacccagtta aaaatagaca acaaccctttt  1860
tgcaaaggt ttccgggaca ctggaaatgg ccgaagagaa aaaagaaaac agctcaccct    1920
gcagtccatg agggtgtttg atgaaagaca caaaaggag aatgggacct ctgatgagtc    1980
ctccagtgaa caagcagctt tcaactgctt cgcccaggct tcttctccag ccgcctccac   2040
tgtagggaca tcgaacctca agatttatg tcccagcgag ggtgagagcg acgccgaggc   2100
cgagagcaaa gaggagcatg gccccgaggc ctgcgacgcg gccaagatct ccaccaccac   2160
gtcggaggag ccctgccgtg acaagggcag ccccgcggtc aaggctcacc ttttcgctgc   2220
tgagcggccc cgggacagcg ggcggctgga caaagcgtcg cccgactcac gccatagccc   2280
cgccaccatc tcgtccagca ctcgcggcct gggcgcggag gagcgcagga gcccggttcg   2340
cgagggcaca gcgccggcca aggtggaaga ggcgcgcgcg ctcccgggca aggaggcctt   2400
cgcgccgctc acggtgcaga cggacgcggc cgccgcgcac ctggcccagg gccccctgcc   2460
tggcctcggc ttcgccccgg gcctggcggg ccaacagttc ttcaacgggc acccgctctt   2520
cctgcacccc agccagtttg ccatgggggg cgccttctcc agcatggcgg ccgctggcat   2580
gggtcccctc ctggccacgg tttctggggc ctccaccggt gtctcgggcc tggattccac   2640
ggccatggcc tctgccgctg cggcgcaggg actgtccggg gcgtccgcgg ccaccctgcc   2700
cttccacctc cagcagcacg tcctggcctc tcagggcctg gccatgtccc ctttcggaag   2760
cctgttccct taccccctaca cgtacatggc cgcagcggcg gccgcctcct ctgcggcagc   2820
ctccagctcg gtgcaccgcc accccttcct caatctgaac accatgcgcc gcggctgcg   2880
ctacagcccc tactccatcc cggtgccggt cccggacggc agcagtctgc tcaccaccgc   2940
cctgccctcc atggcggcgg ccgcggggcc cctggacggc aaagtcgccg ccctggccgc   3000
cagcccggcc tcggtggcag tggactcggg ctctgaactc aacagccgct cctcacacgct   3060
ctcctccagc tccatgtcct tgtcgcccaa actctgcgcg gagaaagagg cggccaccag   3120
cgaactgcag agcatccagc ggttggttag cggcttggaa gccaagccgg acaggtcccg   3180
cagcgcgtcc ccgtagaccc gtcccagaca cgtcttttca ttccagtcca gttcaggctg   3240
```

-continued

```
ccgtgcactt tgtcggatat aaaataaacc acgggcccgc catggcgtta gcccttcctt      3300
ttgcagttgc gtctgggaag gggccccgga ctccctcgag agaatgtgct agagacagcc      3360
cctgtcttct tggcgtggtt tatatgtccg ggatctggat cagattctgg gggctcagaa      3420
acgtcggttg cattgagcta ctgggggtag gagttccaac atttatgtcc agagcaactt      3480
ccagcaaggc tggtctgggt ctctgcccac caggcgggga ggtgttcaaa gacatctccc      3540
tcagtgcgga tttatatata tatttttcct tcactgtgtc aagtggaaac aaaaacaaaa      3600
tctttcaaaa aaaaaatcgg gacaagtgaa cacattaaca tgattctgtt tgtgcagatt      3660
aaaaacttta tagggacttg cattatcggt tctcaataaa ttactgagca gctttgtttg      3720
gggagggaag tccctaccat ccttgtttag tctatattaa gaaaatctgt gtcttttaa       3780 tattcttgtg atgttttcag agccgctgta ggtctcttct tgcatgtcca cagtaatgta      3840
tttgtggttt ttattttgaa cgcttgcttt tagagagaaa acaatatagc cccctaccct      3900
tttcccaatc ctttgccctc aaatcagtga cccaagggag gggggattt aaagggaagg       3960 agtgggcaaa acacataaaa tgaatttatt atatctaagc tctgtagcag gattcatgtc      4020
gttctttgac agttctttct ctttcctgta tatgcaataa caaggtttta aaaaataat       4080 aaagaagtga gactattaga caaagtattt atgtaattat ttgataactc ttgtaaatag      4140
gtggaatatg aatgcttgga aaattaaact ttaatttatt gacattgtac atagctctgt      4200
gtaaatagaa ttgcaactgt caggttttgt gttcttgttt cctttagtt gggtttattt       4260 ccaggtcaca gaattgctgt taacactaga aaacacactt cctgcaccaa caccaatacc      4320 cttttcaaaag agttgtctgc aacattttg ttttcttttt taatgtccaa aagtggggga     4380
aagtgctatt tcctattttc accaaaattg gggaaggagt gccactttcc agctccactt     4440
caaattcctt aaaatataac tgagattgct gtggggaggg aggagggcag aggctgcggt      4500
ttgacttttt aatttttctt ttgttatttg tatttgctag tctctgattt cctcaaaacg      4560
aagtggaatt tactactgtt gtcagtatcg gtgttttgaa ttggtgcctg cctatagaga      4620
tatattcaca gttcaaaagt caggtgctga gagatggttt aaagacaaat tcatgaaggt      4680
atattttgtg ttatagttgt tgatgagttc tttggttttc tgtattttc cccctctctt      4740 taaaacatca ctgaaatttc aataaatttt tattgaaatg tctaaaaaaa aaaaaaaaa      4800 aaaaaaaaaa aaaa                                                       4814
```

<210> SEQ ID NO 19
<211> LENGTH: 2308
<212> TYPE: DNA
<213> ORGANISM: Homo sapiens

<400> SEQUENCE: 19

```
aaaactttgg gagtttttag agacgagttt ttttttttt ctattacttt tccccccccc       60
taactaacgg actattattg ttgttgtttt aaatttagct cttagggctt agctatttgg     120
gttttcttgc ggtgtccggc tccgtctcc ctggctcccc cgcccgccct gcggccccag      180
cgcccctcgc tctcatccag cccgcgagga gtgcgggcgc cgcgccgcct ttaaagcgag     240
gccagggagc gaggcggtga ccggccgaga tccggccctc gcctcctccc tcggtggcgc     300
tagggctccc ggcctctctt cctcagtgcg ggcggagaag cgaaagcgga tcgtcctcgg     360
ctgccgccgc cttctccggg actcgcgcgc ccctccccgc gcgcccaccc acccagtccg     420
gctggactgc ggcagccgcg cggctcaccc cggcaggatg ttcgcagccg ggctggctcc     480
cttctacgcc tccaacttca gcctctggtc ggccgcttac tgctcctcgg ccggcccagg     540
```

-continued

| | |
|---|---|
| cggctgctcc ttccccttgg accccgccgc cgtcaaaaag ccctccttct gcatcgcaga | 600 |
| cattctgcac gccggcgtgg gggatctggg ggcggcccg gagggcctgg caggggcctc | 660 |
| ggccgccgcc ctcaccgcgc acttgggctc ggttcacccg cacgcctctt ccaagcggc | 720 |
| ggccagatcc ccgcttcgac ccaccccagt ggtggcgccc tccgaagtcc cggctggctt | 780 |
| cccgcagcgg ctgtctccgc tctcagccgc ctaccaccac catcacccgc aacaacaaca | 840 |
| gcagcagcaa cagccgcagc agcaacagcc tccgcctccg ccccgggctg gcgccctgca | 900 |
| gcccccggcc tcggggacgc gagtggttcc gaaccccac cacagtggct ctgccccggc | 960 |
| cccctccagc aaagacctca aatttggaat tgaccgcatt ttatctgcag aatttgaccc | 1020 |
| aaaagtcaaa gaaggcaaca cgctgagaga tctcacttcc ctgctaaccg gtgggcggcc | 1080 |
| cgccggggtg cacctctcag gcctgcagcc ctcggccggc cagttcttcg catctctaga | 1140 |
| tcccattaac gaggcttctg caatcctgag tcccttaaac tcgaacccaa gaaattcagt | 1200 |
| tcagcatcag ttccaagaca cgtttccagg tccctatgct gtgctcacga aggacaccat | 1260 |
| gccgcagacg tacaaaagga agcgttcatg gtcgcgcgct gtgttctcca acctgcagag | 1320 |
| gaaaggcctg gagaaaaggt ttgagattca gaagtacgtg accaagccgg accgaaagca | 1380 |
| gctggcggcg atgctgggcc tcacggacgc acaggtgaag gtgtggttcc agaaccggcg | 1440 |
| gatgaagtgg cggcactcca aggaggccca ggcccaaaag gacaaggaca aggaggctgg | 1500 |
| cgagaagcca tcaggtggag ccccggctgc ggatggcgag caggacgaga ggagccccag | 1560 |
| ccgttctgaa ggcgaggctg agagcgagag cagcgactcc gagtccctgg acatggcccc | 1620 |
| cagcgacacg gagcggactg aggggagtga gcgttctctg caccaaacaa cagttattaa | 1680 |
| ggccccggtc actggcgccc tcattaccgc cagcagtgct gggagtggtg ggagcagcgg | 1740 |
| cggcggcggc aatagtttca gcttcagcag cgccagcagt cttagtagca gcagcaccag | 1800 |
| tgcgggttgc gccagcagcc ttggcggcgg cggcgcctcg gagcttctcc ctgcaacaca | 1860 |
| gcccacagcc agcagcgctc ccaaaagccc cgagccagcc caaggcgcgc ttggctgctt | 1920 |
| atagactgta ctagggcgga ggggatccgg gccttgcgtg cagcctccca accatgggct | 1980 |
| gggttttgtg cttactgtat gttggcgact tggtagggca ggagacgcag cgtggagcct | 2040 |
| acctcccgac attcacgctt cgccccacgc tgctccgact ggctgcagcg gacactgccc | 2100 |
| aaagcagagg ggagtctcag tgtcctgcta gccagccgaa cacttctctc cggaagcagg | 2160 |
| ctggttcgac tgtgaggtgt ttgactaaac tgtttctctg actcgcccca gaggtcgtgg | 2220 |
| ctcaaaggca cttaggacgc cttaaatttg taaataaaat gtttactacg gtttgtaaaa | 2280 |
| aaaaaaaaaa aaaaaaaaa aaaaaaaa | 2308 |

```
<210> SEQ ID NO 20
<211> LENGTH: 1925
<212> TYPE: DNA
<213> ORGANISM: Homo sapiens

<400> SEQUENCE: 20
```

| | |
|---|---|
| ccccacagtg agaggaagga aggcaacagt cgccagcagc cgatgtgaag accggactcc | 60 |
| gtgcgcccct cgccgcctct gcctggccac atcgatgttg tgtccgccgc ctgctcgccc | 120 |
| ggatcacgat gaacgcgcag ctgaccatgg aagcgatcgg cgagctgcac ggggtgagcc | 180 |
| atgagccggt gcccgcccct ccgacctgc tgggcggcag ccccacgcg cgcagctccg | 240 |
| tggcgcaccg cggcagccac ctgccccccg cgcaccccgcg ctccatgggc atggcgtccc | 300 |
| tgctggacgg cggcagcggc ggcggagatt accaccacca ccaccgggcc cctgagcaca | 360 |

```
gcctggccgg cccctgcat cccaccatga ccatggcctg cgagactccc ccaggtatga    420
gcatgcccac cacctacacc accttgaccc ctctgcagcc gctgcctccc atctccacag    480
tctcggacaa gttccccac catcaccacc accaccatca ccaccaccac ccgcaccacc    540
accagcgcct ggcgggcaac gtgagcggta gcttcacgct catgcgggat gagcgcgggc    600
tggcctccat gaataacctc tatacccct accacaagga cgtggccggc atgggccaga    660
gcctctcgcc cctctccagc tccggtctgg gcagcatcca caactcccag caagggctcc    720
cccactatgc ccacccgggg gccgccatgc ccaccgacaa gatgctcacc cccaacggct    780
tcgaagccca ccaccggcc atgctcggcc gccacgggga gcagcacctc acgcccacct    840
cggccggcat ggtgcccatc aacggccttc ctccgcacca tccccacgcc cacctgaacg    900
cccagggcca cgggcaactc ctgggcacag cccgggagcc caaccttcg gtgaccggcg    960 cgcaggtcag caatggaagt aattcagggc agatggaaga gatcaatacc aaagaggtgg   1020
cgcagcgtat caccaccgag ctcaagcgct acagcatccc acaggccatc ttcgcgcaga   1080
gggtgctctg ccgctcccag gggaccctct cggacctgct gcgcaaccc aaaccctgga   1140 gcaaactcaa atccggccgg gagaccttcc ggaggatgtg gaagtggctg caggagccgg   1200
agttccagcg catgtccgcg ctccgcttag cagcatgcaa aaggaaagaa caagaacatg   1260
ggaaggatag aggcaacaca cccaaaaagc ccaggttggt cttcacagat gtccagcgtc   1320
gaactctaca tgcaatattc aaggaaaata agcgtccatc caagaattg caaatcacca   1380 tttcccagca gctggggttg gagctgagca ctgtcagcaa cttcttcatg aacgcaagaa   1440
ggaggagtct ggacaagtgg caggacgagg gcagctccaa ttcaggcaac tcatcttctt   1500
catcaagcac ttgtaccaaa gcatgaagga agaaccacaa actaaaacct cggtggaaaa   1560
gctttaaatt aaaaaaaatt tttaaaagac caggacctca agatagcagg tttatactta   1620
gaaatatttg aagaaaaaaa agcgttattt atagtccaaa gaaaccaaag acttagctca   1680
cctgcattct gactttgttt ggagacacac acttcagcag ggcggcgact tggcaagaca   1740
aatgatgagc aggaaaacac cactggatct cacaccttca atccatgacc atcctgctg   1800 tgcttggctg tttagtggtt tggagcatag tgatttgag ccattgagcg gacatctttt   1860
aagatcgaac tttctcatct gttctaccat gccacgaagg tgtatggtgt ctcagtacta   1920
ccacc                                                                1925

<210> SEQ ID NO 21
<211> LENGTH: 16142
<212> TYPE: DNA
<213> ORGANISM: Homo sapiens

<400> SEQUENCE: 21
gcccccgccg ccccgggcc ctgatggact gaatgaaggc tgcctacacc gcctatcgat     60
gcctcaccaa agacctagaa ggctgcgcca tgaacccgga gctgacaatg gaaagtctgg    120
gcactttgca cggccggcc ggcggcggca gtggcggggg cggcggcggg ggcggcgggg    180
gcggcggcgg gggcccgggc catgagcagg agctgctggc cagccccagc ccccaccacg    240
cgggccgcgg cgccgctggc tcgctgcggg ccctccgcc gcctccaacc gcgcaccagg    300
agctgggcac ggcggcagcg gcggcagcgg cggcgtcgcg ctcggccatg gtcaccagca    360
tggcctcgat cctggacggc ggcgactacc ggcccgagct ctccatcccg ctgcaccacg    420
ccatgagcat gtcctgcgac tcgtctccgc ctggcatggg catgagcaac acctacacca    480
cgctgacacc gctccagccg ctgccaccca tctccaccgt gtctgacaag ttccaccacc    540
```

```
ctcacccgca ccaccatccg caccaccacc accaccacca ccaccagcgc ctgtccggca    600
acgtcagcgg cagcttcacc ctcatgcgcg acgagcgcgg gctcccggcc atgaacaacc    660
tctacagtcc ctacaaggag atgcccggca tgagccagag cctgtccccg ctggccgcca    720
cgccgctggg caacgggcta ggcggcctcc acaacgcgca gcagagtctg cccaactacg    780
gtccgccggg ccacgacaaa atgctcagcc ccaacttcga cgcgcaccac actgccatgc    840
tgacccgcgc tgagcaacac ctgtcccgcg gcctgggcac cccacctgcg gccatgatgt    900
cgcacctgaa cggcctgcac cacccgggcc acactcagtc tcacgggccg gtgctggcac    960
ccagtcgcga gcggccaccc tcgtcctcat cgggctcgca ggtggccacg tcgggccagc   1020
tggaagaaat caacaccaaa gaggtggccc agcgcatcac agcggagctg aagcgctaca   1080
gtatccccca ggcgatcttt gcgcagaggg tgctgtgccg gtctcagggg actctctccg   1140
acctgctccg gaatccaaaa ccgtggagta aactcaaatc tggcagggag accttccgca   1200
ggatgtggaa gtggcttcag gagcccgagt tccagcgcat gtccgcctta cgcctggcag   1260
cgtgcaaacg caaagagcaa gaaccaaaca aagacaggaa caattcccag aagaagtccc   1320
gcctggtgtt cactgacctc aacgccgaaa cactcttcgc catcttcaag gagaacaaac   1380
gcccgtcaaa ggagatgcag atcaccattt cccagcagct gggcctggag ctcacaaccg   1440
tcagcaactt cttcatgaac gcccggcgcc gcagcctgga gaagtggcaa gacgatctga   1500 gcacagggg ctcctcgtcc acctccagca cgtgtaccaa agcatgatgg aaggactctc   1560
acttgggcac aagtcacctc caatgagga caacagatac caaaagaaaa caaggaaaa    1620 agacaccgga ttcctagctg gggcccttca ctggtgattt gaaagcacaa ttctcttgca   1680
aagaaactta tattctagct gtaatcatag gccaggtgtt cttctttttgt ttttaatggc   1740 tatggagtcc aagtgcaagc tgaaaaatta atctcttaga accagacact gttctctgag   1800
catgctaagc atcccagaaa cccaaatggg gccttcctgg agcgagttaa ttccagtatg   1860
gtgtcaacca agctcgggat tgcttaaaat atcatccatc ccacttcagg tcctgtcagc   1920
ttcttgcagt cagagttcct atgagtaaca ataggagttt ggcctatgta aggactctga   1980
gtttaggctt ccaagataca acaataagag aagaatctag caacgagaat gacctcattt   2040
gctttccaca tgcttagcct cattatacca tgttatgtcc aagttcacag ccacaacatc   2100
agaatggtaa ttactgagca caagttttaa atatggacgt taaaaaaaaa atccaagga    2160 cctgttttc caacccagac atcttttcat tgaatgattt agaaagcttt aagttgatcc    2220
agcttacaat ttttttttc tttacctcct ggaaatctca tatggtcttg gatccgtcaa    2280
aaaaaccagt cagttcactt gcgctcaaag tatcaagcac aacaaagata aacagaagtg   2340
aggaaggttc tgggttcact acatctggat tttcaagaca cctattgtga agtcattagg   2400
gaattgatga aatatggct tcaagcacat tttgcagttt gctacaaatt ctgttgtaca    2460
taatgcagac gcacactcag gaggccaatt taactgttaa cagtgcatgg agcgaatgca   2520 gcatttaaa agatctaggt ttttttaggt cattaatgtg tccttggttg atcagtcatc    2580
tggtccctcc tactgtgtgt tatgaccacc acgtaatcca ttctcgctct ttctgatttg   2640 gggttttcc tcatccatcc cattagtagg gatgttttct gtgttttcta gcaagaaaaa    2700
aaaatcaatc aatcaaacct gcatacatgt tactcatgac tgtcatctag tcctaaatct   2760
cttctgttgt tgaatcatcc ttgcaaaaca gctgaataca tctggagaaa acacagcaca   2820
ccaaagaagc agaatactgc aaaccaagag catttatgac ttgtcatttt ctagcctaaa   2880
aatactgtga ttacttttag aaatcagaaa acctctgcaa ctccgaatgg cattcagctc   2940
```

```
ttgcatttgg cgcatcatcg ggctgagcgg accagctaca ccaaggacat tagccaagcc    3000
acccagaggg gtggctttgc cacaccagtt gtcaccttcc catagcaagt ggaagagcgc    3060
ccacagaact ctgggagatt gcaaaggtca caatgtgcat atttaccagt gaatggcccc    3120
gggtggggcc acgtgggggt gttcaaagca agccaaacgc tgcaatcatt ctttacagac    3180
acttgagact gactttttta tgaattactt agtcgaaacc aaagaaactt tttctgcacc    3240
tacttctgca acaaacaaaa ctgtcccatt aaaatgaata aataaatccg taaatcaatg    3300
gaaatcacca ccaataagaa ggaagcacgc cagaaaataa acgaaaacaa aaacagggag    3360
acacactgtg ttcaaacaga cctcttggga catttttttgg aagcagattt taaagaaagg    3420
gttgagacaa agatagaaat aaggaagagc ctcagtggct gctgcttcat ttgacaactc    3480
acacggtaat cttaaagctg aagattgtct ttaatttgtg cctatgcagt ttttcaaaag    3540
aacacggaac agagcaacag aaacctcaac agctacaata ccaaagatga ggatttctca    3600 cacctttttgt ttcagttcat tatctcctct tgcctggcta aaatactaat agcgccattg    3660
aactgtataa aggtaatcaa ttatgtttct ctgagcaaca aaaggaaagg gccatttatt    3720 tgatttatt gtttcatttc aattttgtct tatggttttt tgccccaaca tggaatctct    3780
caaaagtttc catggactcc aagtttaaga tgttgggata ttgaacagtt ctctctgctc    3840
agcagagggt agggaataac attatcactt gaatgttctt tgcttaaccc ttagacttgg    3900
ttccttctat gttcagagtc tcatcatcag gggaaggaaa gggagtgagg gtcagggata    3960
ggggtcttgg tgatgcatcc tctcccgagc cacagaacca aagagtttat agaggaattt    4020
acagcctcgt tttcatgtga ttgctacatc ctaacagggc ttcatttggg ggtgggggga    4080
aacatgtaaa aataattgcc agtttctact tttctattag cttttttaaaa atcagctgta    4140 aagttgcatt tctaaagaaa gatatatata atatataaaa tacatatata gatcaacttg    4200
acattggtga taaccaaaat tattgctgtc caaattcatg tcttgttttg gtccagtgct    4260
tcatttgcta agtattcggt tcagaatttt tctcatttct catgccattc cagagttaat    4320
ttgccactgt ggatgatttg aagtattcag atctctatgg aagtttctgg gacaggttta    4380
aagtcaagat caagcatttt agcatttaac ctgttgataa atggatccat ggtgtacatg    4440
agttttattt gtattcggag tcatctctat tctatccctc agcctcgatt aaggtggtga    4500
gtgaagtgca tccaacagac tcggcccaga actgggtcct gacagtgggg tgctcatctt    4560
ctgtaactgt tgggaaggct cggtggtcca ttttcaccag ttaaagaata tgaggccagc    4620
ccagaaatct gttctccagg agctgccctg tcccatctgg gtgtgccaga cccctcagt    4680 gagcaggtcc accaaaggga cttctcacag gggaagccca actcctgttg caatgggttg    4740
atagatttcc tcagggtggt aattaccaat tcgtattttg acaagcctat gtgcaaccac    4800
agctggcact ggggtgggca gtggtgttgg gtgggatggg ggagagtgtc tcaatcctga    4860
agagaaaata taaagcaggt tttggggaga cttctggagt cctgcccta gagagcccca    4920 tgttgttct ttgtgccccc tcctcattcc ccctatgtgg gtctccctat gcaggagctg    4980
tgagagaatg tgactctcca caatttttat aattcatcct tcctaggaga ttgttcattg    5040
gctcttccct tgtgtcccctt tgtcccttgc tcatactcca tgtttccttt gtcaaaggac    5100
taagaaaaga gcatatttca gcagaggagt gttcccatgt gggttgattt caacttgggt    5160
atttctaaaa gagtccttgt gacatgtgtc cagtggaaat ggttgctctt ttccagactg    5220
gattgaggaa tggagcctgt ttgatttggt tagtgattct ttgacatact aatctcagcg    5280
tttgggtctc cagcatcctc tgaagatgtc tagactagta gaggctgcct ttgtgacctg    5340
```

```
acattacaac attggtcaaa ccagtcctct gataatcaga agaacatgtc ataattgttt    5400
aaaaaaaaaa aaaaggcaag aatttctctc caaggagctt taataaatgt ctcattccag    5460
ataatgtcat accagagaaa agtgcttgct tttagaaaat tatttacata catatataaa    5520
tatatatgtg tatctataca gttatgtatc aaaattttaa gccctgcaga atttcaattt    5580
gttagaaatc taacagaaaa aaatttctat attgaaaggt aatagaattt aacccagtga    5640
gtttactcaa ggattttaa atttaagtta ataatttcag agaaaataac catttgggtg     5700
tggttatagt ttagtatcca ttacctcaat ccaaggaaaa ttccaggcat tcctcaacca    5760
tcaggaaaag gtacagtgtg aaggaacagt tctcagccaa atttcacatt cttgaggcaa    5820
cagaaatcaa aacactcaga gccattgagt ggaaaaacaa tttactttat tcctttacac    5880
aaataggctt gcattgtttt tgttttaatg tgattttggt actagggata taattatttc    5940
attccaggaa ataataaaaa aaaacagaca gagccaatac atttcttttt ttaaaggaaa    6000
cagcaacaac aataaaaact cagcaccaat atttaaaagc ttttccaaaa tgtaaaagaa    6060
gtgtttagct tgcaccatgc ataaaggtgc aggctagttg aaccaggaag catggcactt    6120
cctctggaga aatccagaaa gagttgcttc taagctccct tttcccctg caggctcttg     6180 gcaattgtag gctttagcaa atccagaata attttcaatt caagctaaaa taaaatcaac    6240
atttggaatg taaatctgat acacacacac ttttctaagt caaacaacat atttcaaaac    6300 caaaataaa taccttttag ataatcagtt attttctttg tctatactgg gcacccacct     6360
actagtgcca gtaaattcaa gttgaacaga ttttttaaaat cactattatc tgggtatggg   6420
ggaaacttcc ccacttttga aaatgttggt agaattatag gaatgtctgt ttgattatca    6480
ttaccaaagt gtcatgacag tatgcctttg tagtgaactc ggattttcag gagtttgaat    6540
agttggatat tttaaaatct aagaagaaaa ggcctgtttc caatgttgtt gaagaataat    6600
gaactctatt aaaagtggaa gaaaagata atacatgtgg tcaaggttga ccacaaggcc     6660
caggcacaac taccttggcg ataatcttct agattcgtaa caggttagag ctgacttttt    6720 gttttgttg ttgctgatgc tgtgtgattc agacttctca gcctaaccag gaagagtaag     6780
tggaaatggt agatgaagaa ggggtagagc tggtgtatct ataactttct gatatttgtc    6840
tgccaaactt gatatattag taattttttt atctttagct aagatcaagt caccctgaa     6900 acaacaggag attctagttt taaaataagg ccacaaaaat ccttacggaa tgaagaatgg    6960
caccccagtt ggttgtataa gtctcataag ataatgatgt tgattttaaa tatggatgtc    7020
tcaatgcctg ttttctatca atgatttgtt tgtttccaag gtcggggagg gaaagagggg    7080
agggtttatc tgttttagaa agtctcagaa tacttataaa atacagaagt agttattaaa    7140
atatatagga cctcacatag gtagatacag aacttaccat tgaggctgat gggctgttgt    7200
gtgaatcaca caggacctta aatgaggctc attattctca cacaccaaaa tgactctgac    7260
agcctgaagc agttattgct agagcccaag ctttccttgg aggttttgga gttaggttga    7320
ttggaagtaa ccagctaata ccttttctag tggagaaaaa gacattgcta ccagcttgtt    7380
catcccatag aagtcttcca ctctgctcca tttttagcag caagcatttc atgtagcata    7440
aaccttggca gataagtgtg cctaaggttt atacagtctg tccgcttgga tgtatacaaa    7500
tttagataca tattttaaca tgtgttctca tagatgactt tataacaaca cacattacct    7560
ataggtgtct agactgtgta catacaagtg tgtacagaca agcttcatac gtatatactg    7620
taatccgtta caacaaataa attttaaatc atcgtttaac atgtatgtgg tacttctaca    7680
gtgtacattg ttttcattat ttattgtaac attgaaaacc acagtgcagg gaaaacaaaa    7740
```

```
gtatcccagc atcttcatcc tgtacacttg gaattaattt catttgggca tatccaagat    7800
aaactcaact ttcaagaaat cttgtatatt atttaatcat ctgtgttagg atgacaccta    7860
tgattgatga cttcggttga atagctttat tctggatttt tcataactaa agctaaatcc    7920
aaagacctga aaaggacaa aaagaaaaaa aaaaaagaa aaacaaaga aaagaagaa         7980 aaataataa agtcaagcgc aaactgatgg ggagacagtg ggctctggtt tccaggattg      8040
agacaatggt actgcggtct tggggagact gcgttagcta gtggggagtg gtgatttttt    8100
tcatgcttgt cacatctaaa tggtctttaa catgagaaag ttttagaggt tataatttcc    8160
tgctttgttt ttatttagac tatcaaatga agttatacat gttgtcagtc aaaaaatgaa    8220
gacaccctct gccccacccc acagaatgct ttttatcttg tctctttggg ttatgaccca    8280
acaagctaag taccattaat gtaattaact tatttaaatt agttcctagt acataaatgt    8340
ataggatttg ggtaattatt taatcatcct tccttagttt gattctactc cttgtactta    8400
tttatcaaaa cctagaccaa tggtgcatca gagatgcaaa attctacttg gaatactctt    8460
gaagtttagt ttgcttatta aagcagtgaa attctgttac agacagggaa gaaatacagg    8520
ttacaaaaag agaatttggg atattcttcc ctcttaaatt aactttaaa atagtctaag     8580 taacaatttt taaattattt aacttaagtt cgcagcccca cctggtacca ggcgaacttc    8640
acctcttaat tattgtggcc ctcggagcct tcatattgta acttatttat ttaacttatt    8700
cagcatctgt gaaaggtgca ctgtatagtt tatattttta atttaaaaca acagagagca    8760
ctgcagtttg tttgctgtca gaacaacaga gcaaattttg tggacaagca atgactattc    8820
agcctgaacc tgtgcattca gaaaacataa gctgagaccc tgcttcacca gcctggattt    8880
cggggcttct atacagaaac tggaaaaata aattttaaaa aaatcgtaaa caaaagaga     8940 gaaacccta cactagctgc ttccaagaat gaactctgtg tgtatgtaaa gcaacaaaac    9000 aaaaaggaa aaaacaaaa agcagaaaaa agaaaaaaaa aatgaaaaac tttctatttc     9060
tagtgagaac caaagaaggc tacctcactg acttttttcca tttgtaattt taatcgtgtt    9120
gatgacacca aagataccaa agatttcttt ctctgtgcgg tctgcatttt gcttgtgctc    9180
ttttataatt tgaacgattt tctctgacat atggtatgta cagccacagc tcagataccc    9240
caaagaaata attatctatg cgacggcggc tgctaatttg gaaagggata ttttctgtgt    9300
ttctcttata tgttgctgt ctgctcgaca tgttcaagat gcgagttcag atgctgctgt     9360
aattggattc cttaaattct gattacaaat tgaggaagga aactggttgg aaatggcctt    9420
cagtcctagc catggcctct atccccgctg ggacctgtca cagtaaagac tgccaattac    9480
tgaaccacag aagctctgac cattgagtag ttgagctgga agagacctta ggaatcattt    9540
agtccaagcc ccgtggccc agaggaatga aatagttatc caaatcaaat aactcttgag     9600
agtgaaagcc cacacatgcc tcctggttcc tgccccagtg ctccgcttat tgtacagtgc    9660
tacctctgca tgagagcggt cccacattga caaataggat ggtggcaatc ctttagcaat    9720
gagcagggac tggggtttat ctcttaacat tttcagctgt aaaattagtc acaagcattt    9780
tcagtgtccc attagtacat agtcacatat ggtcggttgc ttcgtgaagg tggcctgtct    9840
tgaaatacta gggctcatac gggattttg ccctaggaaa aacatgttga tcccaatgat     9900
gtgatcactt ttgaaccttt ccattacaaa gcattgtata gataacttt taattcagta     9960 ggaggagaaa gttcattctt ggcctgttgg ctttgattat tatgggtact ttaaagtcag   10020
tatttatcaa gaaagggaac ttgaccacca ttggcacatg tgacatttaa gctcttcagc   10080
cttttccttt ttagttgtag gtgtttacat ttcatttcta agccaactct gtatttatga   10140
```

```
gagaagttta agccttacat catttgatac taaagggtta tttgtggtaa atgaaaaatg   10200
accccaaaat tacagaggaa tatgccagtt taagaaatgg ctacttaaag ttgcttctct   10260 cttccttct tactcatgaa attaattggt cttcttcaag tttctttaga ttccattaaa    10320
tgattaaatc actattaaga gccattcatc aacgtgattt gtgtgttagc caatgaatct   10380
gtctcagctt ttgaccaaat gggttttaga caaatgcaaa gatctgcctc tagtccatat   10440
ggctcttttt gagtgctagt attttgcatt tcacataatg tagttatttt gagcttttaa   10500
agagagcatt tagacaaaga agcaaagaga ggaagggacc aatcaactca tcagttccat   10560
gcatcaacaa agcatagcta gtagaggaat ataaatgaca gattgacaaa ctgtaggaaa   10620
cactgttact ctctttctga agttttcaag caccatccta tgtgaaagtt ccctcctgtc   10680
caaacaagct caaggcccat cttctcccta tacaaggcaa acctgtaagg ccttccttcc   10740
aaagagtaca ttgctttggt tttcttccta aattcctatt ggaattagaa ctctcagaat   10800
ccctgggaga cagagcaaag atgacttaat tcattgagca gcagagctcc ctataagtga   10860
acatcacctt ccccatcttt cctactgcca cacccatacg agagaggatc tagaaagagc   10920
gatggcagcc tgaacacaga aaacatcccc acttggcaga cctctcctca gcaatccccc   10980
cagcctcatg cttcacttgc aaagtgtgac ataaccacgg gacgagtgcc ttgcttgaac   11040
caaagcaacg atttagccag tctggacctc tctgtgcttt ttttaattct tcctgtgaat   11100
acctcagctt caactgggcc tccatacagt cagttggtgg gcttattgta ctgtggtgct   11160
ttgcaatgca accctgcaaa gaacaagatt tgtactaata ccaaaggttc tttctctatg   11220
tctcctcctc tgcctccctc gttcttccct tttttctagt tcttcacggt tccaaagctt   11280
tactatgaac ctgggcatgt tggcaatgca gaccgcgcaa ttccttaccg aatttttctca  11340 gatataccto atagacaata gtgtttagag taatgttatt atagcgtatg taataaatta   11400
ttcactgttt cttttggtaa ctgtgattta aaaaagaaa aagaaaaaa aagctttata    11460 cgttttaggt tgtgcttttg taatagatga aaaaggtgc gcttaaaaag aaaatgtatg    11520 ttttttcc ccttttggatt ttatttatgc tggattgggg aaagttgcag aatgagccca   11580
aagtttacag tttcatattt tgctgaagaa acaatctgtg ttcatttgct ctgttgaaaa   11640
gaataattat tttctacatt tgtgccactt ggtctgaaca attaattgtt ccgtgttaac   11700
agtgtagtat tatgattagc aactgccaat cagtgctata attttatgca tgaggctaaa   11760
aatttagcag tgtgatgcat tgtggtctta atagcaacat ttttcatttt gaactagatc   11820
ttcccctttg gttcaatgga ctttatttat gcatgggcgc ctattgtttg ttagcagttg   11880
tggaacagtt gtgtatacat taaactgtga aaatgtacac agttcagcct cagacggtgg   11940
taatattggt tttattggga gatgtgtcac ctcgaaaata ccctttacat ctgttgggat   12000
ctgaaaatga gtcacattga attgggttcc agctttataa tgagaaacgt tattcctaat   12060
ttttgagtta gccaatttgc attccacaaa ttgggatcct cataacccaa atatatcacc   12120
gtatgtgaga gggatttgaa agcgagtatt gaaaaactca cctttgcata tttaatttcc   12180
accaaaagga gttattttgg ctttatgctc atgaacttag acctaactgg ccatgtatat   12240
gtagatgcaa attcatctag ctgtggccct ctttgatctc tgcttgggaa tggctatttt   12300
tgactatgcg tggtttcttc tcgtattttg tgatcaggtc agctcccagt agaaactcaa   12360
atggcatcaa tattactaac tcttctctgc ccacttctct tttgtccact ctcctagaca   12420
ttcccaccaa ctgttccagt gatttgggca aaaatacgca gccatttccc aaaacttcac   12480
atgtgcagct atcatggctg tccctcccta gacttggagg tgactctcac ttaattttta   12540
```

```
cctgcccaac aatgttccat ctaccatcta aaaggtaata taagaagaag ttttgaaacc   12600
cactttagga aaaccatctt ctttaaatcc ttcaattatc tgaggcctct atatgtcaaa   12660 actattttc agttgcaggg gattgggcaa acttgttctt tcttatactt gggttcaaag   12720
acccattctc cagtttcata tttcccaaac caaaatgctt gacataaagc caaatcaact   12780
gccaagcaca ctttattttg cataggagta tgcagcctag gaaccttgg ttgaaaagca    12840 gcagtctgct atgcaaaata ttggaaatca ctgacagtgt agcattcata ttatctgtca   12900
atgagggtat attgggaacg tgctctcgtg aataataaaa agcaacatat ttttatttgg   12960
ccttataaat taggttgtgg taatgtaaac tttgatatat agtcttttta tttttctctt   13020
attaatctgc caaagatggg aacagataca agaatttttc aaattggctt ttgtaagaca   13080
attgatgatt gtaatagtgt ttaatcttcc agaaagcttt atatgttgtt ccacaataaa   13140
attgatattt gtttcagcaa agttttcctg acactcacaa acccacaaac tgttcctctt   13200
aatgcagata ttgtagaatc tacaaagttc aaatccattt ttgatccaaa gaaagtagag   13260
gagtatttga gacatgagtg tacccagccc ttttttttaat cacaggcaat gcatgggtct   13320
ggctggttac actttgccaa gaagacttgt cttatgaaac ccaaggtata ttttgttatg   13380
ccattttatg tcctttctt ttaacattgt ggaaagtggt atgttgaatc aagtgtaagc    13440
tgagttttcc agacaactga agtagctaca tcatgaatgt tattttgtta ttaaagggtt   13500
tttactcagt gctttgtgcc aatggatgtc cttttccttg gagacacata actacaaaat   13560
tacctcagct tggcctggtt ttctctcctg ccctcttggg gaaacatggg cctggcctgg   13620
gaaaaggcag gtcatgggct ggaaggtagg ttttggtact aggaagaaat ctctgtatct   13680
gtcagcttta aagagaactg ggccaaaaat ctctaacctc actctctctg gactccaaca   13740
cttccctgca atcctttggt cttgagcatg tgccagcatg aaggcagact ccagttcata   13800
catgaaaggc aagaaaaaga aaatagtaac cttgaatctt ctgtgggcca ccaggcactc   13860 accttttcccc accttgcaca ctatccagtc aaggctattg cagcccatct ggtggcttta   13920
catgggacat taccaaaggc ttcttcctcc atcctggggt tgcaaaggat ccaggtcccc   13980
tccatccagt ggggctcttc cacatcagaa gtccccctcc caccatcctc tgcatcctgt   14040
ttagctatcc catctatacc ttttggagat gattatttag aaaacaaaga aaggtatgga   14100 atgggggtttc ctattgtttg ctaggttata ttttagcaat tctcaattct ttgatctgga   14160
aaaatacaag agggaaaagg agaccccact atctccctgt gctttgctcc catctcaggg   14220
ggcagggcga gtgcacattg cctatgctgt tgatctgtct tgggcgacag gctgaatcac   14280
agctattgcc ccagccaaaa acatggccca tcaatgccta ctttatctct gcttgaaaat   14340
cctattcaaa aagttgtaga gtttgaggtt tttatccccc catatccttt gctttggtcc   14400
agtttggcct ttagcataag agtcagcttt atctctagga agttttttc agattatgac    14460 aaggaacctg ccacctggga agaaaagagt ccgaagacta gcaatcggat aggtagtcat   14520
accattaaca gatacttcct tgaaggtaga atattatttc ctttctttac agttttgtgt   14580
tacacaagtc caagtggtgc cagcaaactt cttaccgtga aatgttgtaa acacctggc    14640 atactgaaat ttctgaaaca aaaacacaag ctccacattg ataacttgat aaataaccac   14700
taaagtttag atgcagggac tgagatgata caggcaaaat cttggtgttg gtttctcttt   14760
taattcgtat cttcgatcac ctaacctttc tcaatccaag agcagttcag tcttttctcc   14820
ccaagtctag gatgccaaag agcatcatag gaaaagataa ttagggattg accagcattt   14880
caattagttc tcttcttcat ctttgcattt ctcaaaagtg ttctcctgga ccagagggaa   14940
```

```
agagctggtc catttttttt cattcttcct attcaaattt ttccacccag acaatacttt    15000
attaacacag atactgtaga tccttccttg gtcagtgaat tattacaaga ggagctatcc    15060
ttccaccaaa gtgagtgaaa acaagttcca gtatctttc ttccatccag ttttgttctc    15120
agaatccaag tcagtcctgg gtcttttctc actttagacc ctggcctcag atgtgtttat    15180
tcttgctatt taaaaatacc tttaaatttc acatgctggc ctgcagaact tgcatccttt    15240
gttctatact gttgactgct tgatggtatt gaaaggtgac tataatgagg gaagaaagga    15300
ggaggtaaag agagaagaat tgtcccaga tctgtttaaa gtttcaaaat ttaaaaaggg    15360
acccattaaa ttatgggaaa atggctatag agtgtgagcc tccgttgacc atatgctcaa    15420
agaccgtact ctgccacctg ccttccaggt agctattcta gaaactcagt cctttgtgga    15480
aacccaacta ccttttaaaa gtctctttcc agattccaaa aggacaagag atcagagagt    15540
cacatatacg cctcttgttt tatttcttg ctttcacggg tattattgcc aagaaaatcg    15600
tagggaaaaa ctttaaactt ttcttttcag ttgatcccctt tgacatcacc tctcatgttt    15660
aaaatcagga aaacacaccc ctaaaatttg cactctcttc cgttttgaaa aagaaaaccc    15720
acacacaaat gcacactatt accgtctttc accctgcgct atatttccaa agtgtattat    15780
aatccagata ttgccccatc tcaaacatgt taagtcagac tgtgctgaaa gacttccag    15840 ggacggtcaa cagggtatat gttcagtggc tgccctgaaa tcctggtggg gatgaggatc    15900
acgcttcatc atcaagggga tgcccatccc ctgataagct cccagtcctt ttggaagatt    15960
tctttgaatg ttaattgcat tttcagtttt gctcatttcc caccccaatg ttttgtctgc    16020
aacatcgctt acactggatt cttctatttt ttattcctat cattaaatgg tagtgctgta    16080
aattctgcaa ttaatgttaa ataaactgct ttaattcatt gaaaaaaaaa aaaaaaaaa    16140 aa                                                                   16142

<210> SEQ ID NO 22
<211> LENGTH: 2379
<212> TYPE: DNA
<213> ORGANISM: Homo sapiens

<400> SEQUENCE: 22 gaccccccgag ctgtgctgct cgcggccgcc accgccgggc cccggccgtc cctggctccc      60
ctcctgcctc gagaagggca gggcttctca gaggcttggc gggaaaaga acggagggag     120 ggatcgcgct gagtataaaa gccggttttc ggggctttat ctaactcgct gtagtaattc     180
cagcgagagg cagagggagc gagcgggcgg ccggctaggg tggaagagcc gggcgagcag     240
agctgcgctg cgggcgtcct gggaagggag atccggagcg aatagggggc ttcgcctctg     300 gcccagcct cccgctgatc ccccagccag cggtccgcaa cccttgccgc atccacgaaa     360
ctttgcccat agcagcgggc gggcactttg cactggaact acaacacccc gagcaaggac     420
gcgactctcc cgacgcgggg aggctattct gcccatttgg ggacacttcc ccgccgctgc     480
caggacccgc ttctctgaaa ggctctcctt gcagctgctt agacgctgga ttttttttcgg     540 gtagtggaaa accagcagcc tcccgcgacg atgcccctca cgttagctt caccaacagg     600 aactatgacc tcgactacga ctcggtgcag ccgtatttct actgcgacga ggaggagaac     660
ttctaccagc agcagcagca gagcgagctg cagccccgg cgcccagcga ggatatctgg     720
aagaaattcg agctgctgcc cacccccgcc ctgtccccta gccgccgctc cgggctctgc     780 tcgcctcct acgttgcggt cacccctc tccctcggg gagacaacga cggcggtggc     840
gggagcttct ccacggccga ccagctggag atggtgaccg agctgctggg aggagacatg     900
```

| | | | |
|---|---|---|---|
| gtgaaccaga | gtttcatctg | cgacccggac | gacgagacct tcatcaaaaa catcatcatc | 960 |
| caggactgta | tgtggagcgg | cttctcggcc | gccgccaagc tcgtctcaga gaagctggcc | 1020 |
| tcctaccagg | ctgcgcgcaa | agacagcggc | agcccgaacc ccgcccgcgg ccacagcgtc | 1080 |
| tgctccacct | ccagcttgta | cctgcaggat | ctgagcgccg ccgcctcaga gtgcatcgac | 1140 |
| ccctcggtgg | tcttccccta | ccctctcaac | gacagcagct cgcccaagtc ctgcgcctcg | 1200 |
| caagactcca | gcgccttctc | tccgtcctcg | gattctctgc tctcctcgac ggagtcctcc | 1260 |
| ccgcagggca | gccccgagcc | cctggtgctc | catgaggaga caccgcccac caccagcagc | 1320 |
| gactctgagg | aggaacaaga | agatgaggaa | gaaatcgatg ttgtttctgt ggaaaagagg | 1380 |
| caggctcctg | gcaaaaggtc | agagtctgga | tcaccttctg ctggaggcca cagcaaacct | 1440 |
| cctcacagcc | cactggtcct | caagaggtgc | acgtctcca cacatcagca caactacgca | 1500 |
| gcgcctccct | ccactcggaa | ggactatcct | gctgccaaga gggtcaagtt ggacagtgtc | 1560 |
| agagtcctga | cacagatcag | caacaaccga | aaatgcacca gccccaggtc ctcggacacc | 1620 |
| gaggagaatg | tcaagaggcg | aacacacaac | gtcttggagc gccagaggag gaacgagcta | 1680 |
| aaacggagct | tttttgccct | gcgtgaccag | atcccggagt tggaaaacaa tgaaaaggcc | 1740 |
| cccaaggtag | ttatccttaa | aaaagccaca | gcatacatcc tgtccgtcca agcagaggag | 1800 |
| caaaagctca | tttctgaaga | ggacttgttg | cggaaacgac gagaacagtt gaaacacaaa | 1860 |
| cttgaacagc | tacggaactc | ttgtgcgtaa | ggaaagtaa ggaaaacgat tccttctaac | 1920 |
| agaaatgtcc | tgagcaatca | cctatgaact | tgtttcaaat gcatgatcaa atgcaacctc | 1980 |
| acaaccttgg | ctgagtcttg | agactgaaag | atttagccat aatgtaaact gcctcaaatt | 2040 |
| ggactttggg | cataaaagaa | cttttttatg | cttaccatct tttttttttc tttaacagat | 2100 |
| ttgtatttaa | gaattgtttt | taaaaaattt | taagatttac acaatgtttc tctgtaaata | 2160 |
| ttgccattaa | atgtaaataa | ctttaataaa | acgtttatag cagttacaca gaatttcaat | 2220 |
| cctagtatat | agtacctagt | attataggta | ctataaaccc taatttttttt tatttaagta | 2280 |
| cattttgctt | tttaaagttg | attttttttct | attgttttta gaaaaaataa aataactggc | 2340 |
| aaatatatca | ttgagccaaa | tcttaaaaaa | aaaaaaaa | 2379 |

<210> SEQ ID NO 23
<211> LENGTH: 2046
<212> TYPE: DNA
<213> ORGANISM: Homo sapiens

<400> SEQUENCE: 23

| | | | |
|---|---|---|---|
| ggagcccggg | gcgggcgagg | gcggggtgt | cccggctata aagcgtggcc gcctcccgcg | 60 |
| gcgctcggga | cagccgtacc | ccgggcggtc | ggacgggcgg gcgccggtgg gagctcgggc | 120 |
| cgtgcccgct | gagagatcca | gagcgctccg | ttccccgggg gccggagcgg gggcgggtgg | 180 |
| gggcgtaagc | ccggggatg | ctgggctcag | tgaagatgga ggcccatgac ctggccgagt | 240 |
| ggagctacta | cccggaggcg | ggcgaggtct | actcgccggt gaccccagtg cccaccatgg | 300 |
| cccccctcaa | ctcctacatg | accctgaatc | ctctaagctc tccctatccc cctgggggc | 360 |
| tccctgcctc | cccactgccc | tcaggacccc | tggcacccccc agcacctgca gcccccctgg | 420 |
| ggcccacttt | cccaggcctg | ggtgtcagcg | gtggcagcag cagctccggg tacggggccc | 480 |
| cgggtcctgg | gctggtgcac | gggaaggaga | tgccgaaggg gtatcggcgg ccctggcac | 540 |
| acgccaagcc | accgtattcc | tatatctcac | tcatcaccat ggccatccag caggcgccgg | 600 |
| gcaagatgct | gaccttgagt | gaaatctacc | agtggatcat ggacctcttc ccttactacc | 660 |

| | |
|---|---|
| gggagaatca gcagcgctgg cagaactcca ttcgccactc gctgtctttc aacgactgct | 720 |
| tcgtcaaggt ggcgcgttcc ccagacaagc ctggcaaggg ctcctactgg gccctacacc | 780 |
| ccagctcagg gaacatgttt gagaatggct gctacctgcg ccgccagaaa cgcttcaagc | 840 |
| tggaggagaa ggtgaaaaaa gggggcagcg ggctgccac caccaccagg aacgggacag | 900 |
| ggtctgctgc ctcgaccacc accccgcgg ccacagtcac ctccccgccc cagccccgc | 960 |
| ctccagcccc tgagcctgag gcccaggcg gggaagatgt gggggctctg gactgtggct | 1020 |
| cacccgcttc ctccacaccc tatttcactg gcctggagct cccaggggag ctgaagctgg | 1080 |
| acgcgcccta caacttcaac caccctttct ccatcaacaa cctaatgtca gaacagacac | 1140 |
| cagcacctcc caaactggac gtggggtttg ggggctacgg ggctgaaggt ggggagcctg | 1200 |
| gagtctacta ccagggcctc tattcccgct ctttgcttaa tgcatcctag caggggttgg | 1260 |
| gaacatggtg gtgggtatgg ctggagctca caccacgaag ctcttggggc ctgatccttc | 1320 |
| tggtgacact tcacttgtcc cattggttaa catctgggtg ggtctattac ttactgtgat | 1380 |
| gactgctgtc tcagtgggca tggtgttgat ccacggggta ctgtgataac caccatggat | 1440 |
| acatttggt ggcccactgg gtactgtgag gactgctaca ttgatggatg ttattggcta | 1500 |
| atccactgca tggtttgatg gccaccatct cggttggccc tttgggtgtg atggtgatag | 1560 |
| catttcagtg acatcttctt tggccccccc cattaggtgc tgtgcccact tctttttttgg | 1620 |
| tgtacttggc acagtaggtg ccaagttggc caccattctg tgtaacacct tttttggccc | 1680 |
| attgggtgct ttgatggaca tcatactggg taggtgacaa cgtcagtggg ccaccatgtg | 1740 |
| ccatgatggc tgctgcagcc ccgtgttggc catgtcgtca ccattctctc tggcatgggt | 1800 |
| tgggtagggg atggaggtga gaatactcct tggttttctc tgaagcccac cctttccccc | 1860 |
| aactctggtc caggagaaac cagaaaaggc tggttagggt gtggggaatt tctactgaag | 1920 |
| tctgattctt tcccgggaag cggggtactg gctgtgttta atcattaaag gtaccgtgtc | 1980 |
| cgcctcttaa aaaaaaaaa aaaaaaaaa aaaaaaaaa aaaaaaaaa aaaaaaaaa | 2040 |
| aaaaaa | 2046 |

<210> SEQ ID NO 24
<211> LENGTH: 3239
<212> TYPE: DNA
<213> ORGANISM: Homo sapiens

<400> SEQUENCE: 24

| | |
|---|---|
| gggaggaggc agtgggaggg cggagggcgg gggccttcgg ggtgggcgcc cagggtaggg | 60 |
| caggtggccg cggcgtggag gcagggagaa tgcgactctc caaaaccctc gtcgacatgg | 120 |
| acatggccga ctacagtgct gcactggacc cagcctacac caccctggaa tttgagaatg | 180 |
| tgcaggtgtt gacgatgggc aatgacacgt ccccatcaga aggcaccaac ctcaacgcgc | 240 |
| ccaacagcct gggtgtcagc gccctgtgtg ccatctgcgg ggaccgggcc acgggcaaac | 300 |
| actacggtgc ctcgagctgt gacggctgca aggggttctt ccggaggagc gtgcggaaga | 360 |
| accacatgta ctcctgcaga tttagccggc agtgcgtggt ggacaaagac aagaggaacc | 420 |
| agtgccgcta ctgcaggctc aagaaatgct tccgggctgg catgaagaag gaagccgtcc | 480 |
| agaatgagcg ggaccggatc agcactcgaa ggtcaagcta tgaggacagc agcctgccct | 540 |
| ccatcaatgc gctcctgcag gcggaggtcc tgtcccgaca gatcacctcc ccgtctccg | 600 |
| ggatcaacgg cgacattcgg gcgaagaaga ttgccagcat cgcagatgtg tgtgagtcca | 660 |
| tgaaggagca gctgctggtt ctcgttgagt gggccaagta catcccagct ttctgcgagc | 720 |

```
tcccctgga cgaccaggtg gccctgctca gagcccatgc tggcgagcac ctgctgctcg      780
gagccaccaa gagatccatg gtgttcaagg acgtgctgct cctaggcaat gactacattg      840
tccctcggca ctgcccggag ctggcggaga tgagccgggt gtccatacgc atccttgacg      900
agctggtgct gcccttccag gagctgcaga tcgatgacaa tgagtatgcc tacctcaaag      960
ccatcatctt ctttgaccca gatgccaagg ggctgagcga tccagggaag atcaagcggc     1020
tgcgttccca ggtgcaggtg agcttggagg actacatcaa cgaccgccag tatgactcgc     1080
gtggccgctt tggagagctg ctgctgctgc tgcccacctt gcagagcatc acctggcaga     1140
tgatcgagca gatccagttc atcaagctct cggcatggc caagattgac aacctgttgc      1200
aggagatgct gctgggaggg tcccccagcg atgcacccca tgcccaccac cccctgcacc     1260
ctcacctgat gcaggaacat atgggaacca acgtcatcgt tgccaacaca atgcccactc     1320
acctcagcaa cggacagatg tgtgagtggc cccgacccag gggacaggca gccaccctg      1380
agacccaca gccctcaccg ccaggtggct cagggtctga gccctataag ctcctgccgg     1440
gagccgtcgc cacaatcgtc aagcccctct ctgccatccc ccagccgacc atcaccaagc    1500
aggaagttat ctagcaagcc gctggggctt gggggctcca ctggctcccc ccagcccct     1560
aagagagcac ctggtgatca cgtggtcacg gcaaaggaag acgtgatgcc aggaccagtc    1620
ccagagcagg aatgggaagg atgaagggcc cgagaacatg gcctaagggc cacatcccac   1680
tgccacccctt gacgccctgc tctggataac aagactttga cttggggaga cctctactgc   1740
cttgacaac ttttctcatg ttgaagccac tgccttcacc ttcacttca tccatgtcca     1800
accccgact tcatcccaaa ggacagccgc ctggagatga cttgaggcct tacttaaacc     1860
cagctccctt cttccctagc ctggtgcttc tcctctccta gccctgtca tggtgtccag    1920
acagagccct gtgaggctgg gtccaattgt ggcacttggg gcaccttgct cctccttctg    1980
ctgctgcccc cacctctgct gcctccctct gctgtcacct tgctcagcca tcccgtcttc  2040
tccaacacca cctctccaga ggccaaggag gccttggaaa cgattccccc agtcattctg   2100
ggaacatgtt gtaagcactg actgggacca ggcaccaggc agggtctaga aggctgtggt   2160
gagggaagac gccttctcc tccaacccaa cctcatcctc cttcttcagg gacttgggtg    2220
ggtacttggg tgaggatccc tgaaggcctt caacccgaga aaacaaaccc aggttggcga    2280
ctgcaacagg aacttggagt ggagaggaaa agcatcagaa agaggcagac catccaccag   2340
gcctttgaga aagggtagaa ttctggctgg tagagcaggt gagatgggac attccaaaga    2400
acagcctgag ccaaggccta gtggtagtaa gaatctagca agaattgagg aagaatggtg    2460
tgggagaggg atgatgaaga gagagagggc ctgctggaga gcatagggtc tggaacacca   2520
ggctgaggtc ctgatcagct tcaaggagta tgcagggagc tgggcttcca gaaaatgaac    2580
acagcagttc tgcagaggac gggaggctgg aagctgggag gtcaggtggg gtggatgata    2640
taatgcgggt gagagtaatg aggcttgggg ctggagagga caagatgggt aaaccctcac    2700
atcagagtga catccaggag gaataagctc ccagggcctg tctcaagctc ttccttactc    2760
ccaggcactg tcttaaggca tctgacatgc atcatctcat ttaatcctcc cttcctccct   2820
attaacctag agattgtttt tgttttttat tctcctcctc cctcccgcc ctcacccgcc    2880
ccactccctc ctaacctaga gattgttaca gaagctgaaa ttgcgttcta agaggtgaag   2940
tgatttttt tctgaaactc acacaactag gaagtggctg agtcaggact tgaacccagg    3000
tctccctgga tcgaacagg agctcttaac tacagtggct gaatagcttc tccaaaggct    3060
ccctgtgttc tcaccgtgat caagttgagg ggcttccggc tcccttctac agcctcagaa    3120
```

-continued

| | |
|---|---|
| accagactcg ttcttctggg aaccctgccc actcccagga ccaagattgg cctgaggctg | 3180 |
| cactaaaatt cacttagggt cgagcatcct gtttgctgat aaatattaag gagaattca | 3239 |

<210> SEQ ID NO 25
<211> LENGTH: 3241
<212> TYPE: DNA
<213> ORGANISM: Homo sapiens

<400> SEQUENCE: 25

| | |
|---|---|
| cgtggccctg tggcagccga gccatggttt ctaaactgag ccagctgcag acggagctcc | 60 |
| tggcggccct gctcgagtca gggctgagca aagaggcact gatccaggca ctgggtgagc | 120 |
| cggggcccta cctcctggct ggagaaggcc ccctggacaa gggggagtcc tgcggcggcg | 180 |
| gtcgagggga gctggctgag ctgcccaatg ggctggggga gactcggggc tccgaggacg | 240 |
| agacggacga cgatggggaa gacttcacgc cacccatcct caaagagctg gagaacctca | 300 |
| gccctgagga ggcggcccac cagaaagccg tggtggagac ccttctgcag gaggaccgt | 360 |
| ggcgtgtggc gaagatggtc aagtcctacc tgcagcagca acatccca cagcgggagg | 420 |
| tggtcgatac cactggcctc aaccagtccc acctgtccca cacctcaac aagggcactc | 480 |
| ccatgaagac gcagaagcgg gccgccctgt acacctggta cgtccgcaag cagcgagagg | 540 |
| tggcgcagca gttcacccat gcagggcagg gagggctgat tgaagagccc acaggtgatg | 600 |
| agctaccaac caagaagggg cggaggaacc gtttcaagtg gggcccagca tcccagcaga | 660 |
| tcctgttcca ggcctatgag aggcagaaga ccctagcaa ggaggagcga gagacgctag | 720 |
| tggaggagtg caatagggcg gaatgcatcc agagaggggt gtccccatca caggcacagg | 780 |
| ggctgggctc caacctcgtc acggaggtgc gtgtctacaa ctggtttgcc aaccggcgca | 840 |
| aagaagaagc cttccggcac aagctggcca tggacacgta cagcgggccc ccccagggc | 900 |
| caggcccggg acctgcgctg cccgctcaca gctcccctgg cctgcctcca cctgccctct | 960 |
| ccccagtaa ggtccacggt gtgcgctatg gacagcctgc gaccagtgag actgcagaag | 1020 |
| taccctcaag cagcggcggt cccttagtga cagtgtctac accctccac caagtgtccc | 1080 |
| ccacgggcct ggagcccagc cacagcctgc tgagtacaga agccaagctg gtctcagcag | 1140 |
| ctgggggccc cctccccct gtcagcaccc tgacagcact gcacagcttg agcagacat | 1200 |
| ccccaggcct caaccagcag ccccagaacc tcatcatggc ctcacttcct ggggtcatga | 1260 |
| ccatcgggcc tggtgagcct gcctccctgg tcctacgtt caccaacaca ggtgcctcca | 1320 |
| ccctggtcat cggcctggcc tccacgcagg cacagagtgt gccggtcatc aacagcatgg | 1380 |
| gcagcagcct gaccaccctg cagcccgtcc agttctccca gccgctgcac ccctcctacc | 1440 |
| agcagccgct catgccacct gtgcagagcc atgtgaccca gagccccttc atggccacca | 1500 |
| tggctcagct gcagagcccc cacgccctct acagccacaa gcccgaggtg gcccagtaca | 1560 |
| cccacacggg cctgctcccg cagactatgc tcatcaccga caccaccaac ctgagcgccc | 1620 |
| tggccagcct cacgcccacc aagcaggtct tcacctcaga cactgaggcc tccagtgagt | 1680 |
| ccgggcttca cacgccggca tctcaggcca ccacccacca cgtccccagc caggaccctg | 1740 |
| ccggcatcca gcacctgcag cggcccacc ggctcagcgc cagcccaca gtgtcctcca | 1800 |
| gcagcctggt gctgtaccag agctcagact ccagcaatgg ccagagccac ctgctgccat | 1860 |
| ccaaccacag cgtcatcgag accttcatct ccacccagat ggcctcttcc tcccagtaac | 1920 |
| cacggcacct gggccctggg gcctgtactg cctgcttggg gggtgatgag ggcagcagcc | 1980 |
| agccctgcct ggaggacctg agcctgccga gcaaccgtgg ccctccctgg acagctgtgc | 2040 |

```
ctcgctcccc actctgctct gatgcatcag aaagggaggg ctctgaggcg ccccaacccg    2100
tggaggctgc tcggggtgca caggaggggg tcgtggagag ctaggagcaa agcctgttca    2160
tggcagatgt aggagggact gtcgctgctt cgtgggatac agtcttctta cttggaactg    2220 aaggggggcgg cctatgactt gggcaccccc agcctgggcc tatggagagc cctgggaccg    2280
ctacaccact ctggcagcca cacttctcag gacacaggcc tgtgtagctg tgacctgctg    2340
agctctgaga ggccctggat cagcgtggcc ttgttctgtc accaatgtac ccaccgggcc    2400
actccttcct gccccaactc cttccagcta gtgacccaca tgccatttgt actgaccca    2460 tcacctactc acacaggcat ttcctgggtg gctactctgt gccagagcct ggggctctaa    2520
cgcctgagcc cagggaggcc gaagctaaca gggaaggcag gcagggctct cctggcttcc    2580
catccccagc gattccctct cccaggcccc atgacctcca gctttcctgt atttgttccc    2640
aagagcatca tgcctctgag gccagcctgg cctcctgcct ctactgggaa ggctacttcg    2700
gggctgggaa gtcgtcctta ctcctgtggg agcctcgcaa cccgtgccaa gtccaggtcc    2760
tggtggggca gctcctctgt ctcgagcgcc ctgcagaccc tgcccttgtt tggggcagga    2820
gtagctgagc tcacaaggca gcaaggcccg agcagctgag cagggccggg gaactggcca    2880
agctgaggtg cccaggagaa gaaagaggtg accccagggc acaggagcta cctgtgtgga    2940
caggactaac actcagaagc ctgggggcct ggctggctga gggcagttcg cagccaccct    3000
gaggagtctg aggtcctgag cactgccagg agggacaaag gagcctgtga acccaggaca    3060
agcatggtcc cacatccctg ggcctgctgc tgagaacctg gccttcagtg taccgcgtct    3120
accctgggat tcaggaaaag gcctggggtg acccggcacc cctgcagct tgtagccagc    3180 cggggcgagt ggcacgttta tttaactttt agtaaagtca aggagaaatg cggtggaaaa    3240
a                                                                    3241
```

<210> SEQ ID NO 26
<211> LENGTH: 2842
<212> TYPE: DNA
<213> ORGANISM: Homo sapiens

<400> SEQUENCE: 26

```
aatttgcata tcttatatgg cctaatggtg gcgatcatgg caagttagaa gttttctgac     60
tcctttcgga ggagcctccg ggaccccggg gagtaacagg tgtctggagg ctgaagggtg    120
gaggggttcc tggatttggg gtttgcttgt gaaactcccc tccaccctcc tctctcgcac    180
ccacccaccc cctcaccccc ttcttttttcc gtccttggaa aatggtgtcc aagctcacgt    240
cgctccagca agaactcctg agcgccctgc tgagctccgg ggtcaccaag gaggtgctgg    300
ttcaggcctt ggaggagttg ctgccatccc cgaacttcgg ggtgaagctg agacgctgc    360 ccctgtcccc tggcagcggg gccgagcccg acaccaagcc ggtcttccat actctcacca    420
acggccacgc caagggccgc ttgtccggcg acgagggctc cgaggacggc gacgactatg    480
acacacctcc catcctcaag gagctgcagg cgctcaacac cgaggaggcg gcggagcagc    540
gggcggaggt ggaccggatg ctcagtgagg acccttggag ggctgctaaa atgatcaagg    600
gttacatgca gcaacacaac atcccccaga gggaggtggt cgatgtcacc ggcctgaacc    660
agtcgcacct ctcccagcat ctcaacaagg gcacccctat gaagacccag aagcgtgccg    720
ctctgtacac ctggtacgtc agaaagcaac gagagatcct ccgacaattc aaccagacag    780
tccagagttc tggaaatatg acagacaaaa gcagtcagga tcagctgctg tttctctttc    840
cagagttcag tcaacagagc catgggcctg ggcagtccga tgatgcctgc tctgagccca    900
```

```
ccaacaagaa gatgcgccgc aaccggttca aatgggggcc cgcgtcccag caaatcttgt    960
accaggccta cgatcggcaa aagaacccca gcaaggaaga gagagaggcc ttagtggagg   1020
aatgcaacag ggcagaatgt ttgcagcgag gggtgtcccc ctccaaagcc cacggcctgg   1080
gctccaactt ggtcactgag gtccgtgtct acaactggtt tgcaaaccgc aggaaggagg   1140
aggcattccg gcaaaagctg gccatggacg cctatagctc caaccagact cacagcctga   1200
accctctgct ctcccacggc tccccccacc accagcccag ctcctctcct ccaaacaagc   1260
tgtcaggagt gcgctacagc cagcagggaa acaatgagat cacttcctcc tcaacaatca   1320
gtcaccatgg caacgcgcc atggtgacca gccagtcggt tttacagcaa gtctccccag   1380
ccagcctgga cccaggccac aatctcctct cacctgatgg taaaatgatc tcagtctcag   1440
gaggaggttt gccccagtc agcaccttga cgaatatcca cagcctctcc caccataatc   1500
cccagcaatc tcaaaacctc atcatgacac ccctctctgg agtcatggca attgcacaaa   1560
gcctcaacac ctcccaagca cagagtgtcc ctgtcatcaa cagtgtggcc ggcagcctgg   1620
cagccctgca gcccgtccag ttctcccagc agctgcacag ccctcaccag cagcccctca   1680
tgcagcagag cccaggcagc cacatggccc agcagccctt catggcagct gtgactcagc   1740
tgcagaactc acacatgtac gcacacaagc aggaaccccc ccagtattcc cacacctccc   1800
ggtttccatc tgcaatggtg gtcacagata ccagcagcat cagtacactc accaacatgt   1860
cttcaagtaa acagtgtcct ctacaagcct ggtgatgccc acacaccact tacttcgtgc   1920
gcaacaacaa ggaccctgtt ttccacacca tcacctctg gcagctgtc atggaaaagc   1980 ccagtgacct gaccggcacc tgcgagaggt ccctgcttac ctgacggacg tcctgctggc   2040
acctcagaca atccactctc aggaggcgca gcccgaagcc cagtttccct tctatgcagt   2100
attgccacaa tgcctctccc acgatgtcaa ggactcctgt ctgtcctgga ggtgggagac   2160
aaggaaccac cgaagaggaa gcaagaaagc cgtactgtct atgttgtgat ccttcatcga   2220
acaaactgat gcgaaaactt gaatctgtta ctgaaatgag gagagaagga catgtgctat   2280
tgaactgagc caaacacact gtaaatatcc acagactccc tccctgccc ccatcccaca   2340 tgatcttgag atttcttta aagaagtaaa tttgtccaat ggctgtaaac tataaactac   2400
tgtaattaag tgcaatttcc cctctgtgtc ctctcccctc tgccctgtat ataatactaa   2460
agtgtctatt agttttcttt gtaaaggtca gagtcaaaat ttcaaaagtg atctgtcccc   2520
tctcccctca tggagaaaca tcctaagtgg gaagtgaagc cccttgtcct ctcccgcggg   2580
cctggacact tatggggaca gcataccttg gactgactac cagctaactc cagtctcctg   2640
acattaagac acacctctgg atccctggag gggctgaatg tagtgtgtca gagtaacatg   2700
ccagcttcct gtgggccagg agctcagccg tgcactccct aagaaccccc agggcaggga   2760
aactggctgt ttgatagcag aagaaaaagt tgcagtctca gaaagccttc cattaaaaca   2820
atttatttta tcactaaaaa aa                                            2842
```

<210> SEQ ID NO 27  
<211> LENGTH: 2591  
<212> TYPE: DNA  
<213> ORGANISM: Homo sapiens

<400> SEQUENCE: 27

```
cggaggtgcg cgggcgcggg cgagcagggt ctccgggtgg gcggcggcga cgccccgcgc     60
aggctggagg ccgccgaggc tcgccatgcc gggagaactc taactccccc atggagtcgg    120
ccgacttcta cgaggcggag ccgcggcccc cgatgagcag ccacctgcag agccccccgc    180
```

```
acgcgcccag cagcgccgcc ttcggctttc cccggggcgc gggccccgcg cagcctcccg    240
ccccacctgc cgccccggag ccgctgggcg gcatctgcga gcacgagacg tccatcgaca    300
tcagcgccta catcgacccg gccgccttca acgacgagtt cctggccgac ctgttccagc    360
acagccggca gcaggagaag gccaaggcgg ccgtgggccc cacgggcggc ggcggcggcg    420
gcgactttga ctacccgggc gcgcccgcgg gccccggcgg cgccgtcatg cccggggggag   480 cgcacgggcc cccgccggc tacgctgcg cggccgccgg ctacctggac ggcaggctgg      540
agcccctgta cgagcgcgtc ggggcgccgg cgctgcggcc gctggtgatc aagcaggagc    600
cccgcgagga ggatgaagcc aagcagctgg cgctggccgg cctcttccct taccagccgc    660
cgccgccgcc gccgccctcg cacccgcacc cgcacccgcc gccgcgcac ctggccgccc     720 cgcacctgca gttccagatc gcgcactgcg gccagaccac catgcacctg cagcccggtc    780
accccacgcc gccgcccacg cccgtgccca gcccgcaccc cgcgcccgcg ctcggtgccg    840
ccggcctgcc gggccctggc agcgcgctca aggggctggg cgccgcgcac cccgacctcc    900
gcgcgagtgg cggcagcggc gcgggcaagg ccaagaagtc ggtggacaag aacagcaacg    960
agtaccgggt gcgcgcgag cgcaacaaca tcgcggtgcg caagagccgc gacaaggcca    1020
agcagcgcaa cgtggagacg cagcagaagg tgctggagct gaccagtgac aatgaccgcc    1080
tgcgcaagcg ggtggaacag ctgagccgcg aactggacac gctgcgggc atcttccgcc    1140 agctgccaga gagctccttg gtcaaggcca tgggcaactg cgcgtgaggc gcgcggctgt    1200
gggaccgccc tggccagcc tccgcgggg acccagggag tggtttgggg tcgccggatc      1260
tcgaggcttg cccgagccgt gcgagccagg actaggagat tccggtgcct cctgaaagcc    1320
tggcctgctc cgcgtgtccc ctcccttcct ctgcgccgga cttggtgcgt ctaagatgag    1380
ggggccaggc ggtggcttct ccctgcgagg aggggagaat tcttggggct gagctgggag    1440
cccggcaact ctagtattta ggataacctt gtgccttgga aatgcaaact caccgctcca    1500
atgcctactg agtaggggga gcaaatcgtg ccttgtcatt ttatttggag gttcctgcc    1560 tccttcccga ggctacagca gaccccccatg agagaaggag gggagcaggc ccgtggcagg   1620
aggagggctc agggagctga gatcccgaca agcccgccag ccccagccgc tcctccacgc    1680
ctgtccttag aaaggggtgg aaacatagg acttggggct tggaacctaa ggttgttccc    1740
ctagttctac atgaaggtgg agggtctcta gttccacgcc tctcccacct ccctccgcac    1800
acaccccacc ccagcctgct ataggctggg cttccccttg gggcggaact cactgcgatg    1860
ggggtcacca ggtgaccagt gggagccccc acccgagtc acaccagaaa gctaggtcgt     1920
gggtcagctc tgaggatgta tacccctggt gggagaggga gacctagaga tctggctgtg    1980
gggcgggcat gggggtgaa gggccactgg gaccctcagc cttgtttgta ctgtatgcct     2040
tcagcattgc ctaggaacac gaagcacgat cagtccatcc cagagggacc ggagttatga    2100
caagcttccc aaatatttg ctttatcagc cgatatcaac acttgtatct ggcctctgtg     2160
ccccagcagt gccttgtgca atgtgaatgt gcgcgtctct gctaaaccac cattttattt    2220
ggtttttgtt ttgttttggt tttgctcgga tacttgccaa aatgagactc tccgtcggca    2280
gctgggggaa gggtctgaga ctcccttttcc ttttggtttt gggattactt tgatcctgg    2340 gggaccaatg aggtgagggg ggttctcctt tgccctcagc tttccccagc ccctccggcc    2400
tgggctgccc acaaggcttg tccccagag gccctggctc ctggtcggga agggaggtgg     2460
cctcccgcca acgcatcact ggggctggga gcagggaagg acggcttggt tctcttcttt    2520
tggggagaac gtagagtctc actctagatg ttttatgtat tatatctata atataaacat    2580
```

| | |
|---|---|
| atcaaagtca a | 2591 |

<210> SEQ ID NO 28
<211> LENGTH: 1837
<212> TYPE: DNA
<213> ORGANISM: Homo sapiens

<400> SEQUENCE: 28

| | | | | | |
|---|---|---|---|---|---|
| gagccgcgca | cgggactggg | aagggggaccc | acccgagggt | ccagccacca | gcccctcac | 60 |
| taatagcggc | caccccggca | gcggcggcag | cagcagcagc | gacgcagcgg | cgacagctca | 120 |
| gagcagggag | gccgcgccac | ctgcgggccg | gccgagcgg | gcagcccag | gcccctccc | 180 |
| cgggcacccg | cgttcatgca | acgcctggtg | gcctgggacc | cagcatgtct | ccccctgccg | 240 |
| ccgccgccgc | ctgcctttaa | atccatggaa | gtgccaact | tctactacga | ggcggactgc | 300 |
| ttggctgctg | cgtacggcgg | caaggcggcc | cccgcggcgc | ccccgcggc | cagacccggg | 360 |
| ccgcgcccc | ccgccggcga | gctgggcagc | atcggcgacc | acgagcgcgc | catcgacttc | 420 |
| agcccgtacc | tggagccgct | gggcgcgccg | caggcccgg | cgcccgccac | ggccacggac | 480 |
| accttcgagg | cggctccgcc | cgcgcccgcc | cccgcgcccg | cctcctccgg | gcagcaccac | 540 |
| gacttcctct | ccgacctctt | ctccgacgac | tacggggggca | agaactgcaa | gaagccggcc | 600 |
| gagtacggct | acgtgagcct | ggggcgcctg | ggggccgcca | agggcgcgct | gcaccccggc | 660 |
| tgcttcgcgc | ccctgcaccc | accgccccg | ccgccgccgc | cgcccgccga | gctcaaggcg | 720 |
| gagccgggct | tcgagcccgc | ggactgcaag | cggaaggagg | aggccggggc | gccgggcggc | 780 |
| ggcgcaggca | tggcggcggg | cttcccgtac | gcgctgcgcg | cttacctcgg | ctaccaggcg | 840 |
| gtgccgagcg | gcagcagcgg | gagcctctcc | acgtcctcct | cgtccagccc | gcccggcacg | 900 |
| ccgagccccg | ctgacgccaa | ggcgccccg | accgcctgct | acgcggggggc | cgcgccggcg | 960 |
| ccctcgcagg | tcaagagcaa | ggccaagaag | accgtggaca | gcacagcga | cgagtacaag | 1020 |
| atccggcgcg | agcgcaacaa | catcgccgtg | cgcaagagcc | gcgacaaggc | caagatgcgc | 1080 |
| aacctggaga | cgcagcacaa | ggtcctggag | ctcacggccg | agaacgagcg | gctgcagaag | 1140 |
| aaggtggagc | agctgtcgcg | cgagctcagc | accctgcgga | acttgttcaa | gcagctgccc | 1200 |
| gagcccctgc | tcgcctcctc | cggccactgc | tagcgcggcc | cccgcgcgcg | tcccctgcc | 1260 |
| ggccggggct | gagactccgg | ggagcccccg | cgcccgcgcg | ctcgcccccg | ccccggcgg | 1320 |
| cgccggcaaa | actttggcac | tggggcactt | ggcagcgcgg | ggagcccgtc | ggtaattta | 1380 |
| atattttatt | atatatatat | atctatattt | ttgtccaaac | caaccgcaca | tgcagatggg | 1440 |
| gctcccgccc | gtggtgttat | ttaaagaaga | aacgtctatg | tgtacagatg | aatgataaac | 1500 |
| tctctgcttc | tccctctgcc | cctctccagg | cgccggcggg | cgggccggtt | tcgaagttga | 1560 |
| tgcaatcggt | ttaaacatgg | ctgaacgcgt | gtgtacacgg | gactgacgca | acccacgtgt | 1620 |
| aactgtcagc | cggccctga | gtaatcgctt | aaagatgttc | ctacgggctt | gttgctgttg | 1680 |
| atgttttgtt | ttgttttgtt | ttttggtctt | ttttgtatt | ataaaaaata | atctatttct | 1740 |
| atgagaaaag | aggcgtctgt | atattttggg | aatcttttcc | gtttcaagca | ttaagaacac | 1800 |
| ttttaataaa | cttttttttg | agaatggtta | caaagcc | | | 1837 |

<210> SEQ ID NO 29
<211> LENGTH: 1658
<212> TYPE: DNA
<213> ORGANISM: Homo sapiens

<400> SEQUENCE: 29

-continued

```
cgcgcacacc tctcggtgca gattgcaaag cgccttccgt tgcgagagct gcagattttg      60
caagagccag gctcgcccac cttgtagaag gagcgccttg agtcccctct caccctcggt     120
tgcaaagagc cgaccgcttg atctggacac ccctcgccc agattgcatg atctcccggg     180
accctcttga gttgcacgtt tctgcaccga ggacctcaaa tccccgtcgc tcctaggatt     240
tgcagcgttc tggatactgg agggttgcag gctacactcg cccgcccctg ggcagacact     300
cgtccaaacc actggagtgt gctggtgact ggcaggccag cccttcgcct ctccatgaac     360
ccgtgagcct gggggcaggt gccaggcgat ggcgcggcct gtgagcgaca ggaccccggc     420
ccctctgctg ctgggcggcc cggccgggac accccctggc gggggagcgc tgcttgggtt     480
gcggagcctt ctgcagggga ccagcaagcc caaagagccg gccagctgtc tcctgaagga     540
aaaggagcgc aaggcggccc tgcctgcagc acaacccct gggccaggcc tggagactgc      600
gggcccggcg gatgccccgg ctggggcagt ggtgggcgga gggtccccgc ggggggcgccc    660
ggggccggtg cccgccccgg gtctgttggc gccactgctg tgggagcgca cgctgccgtt     720
cggcgatgtg gagtacgtag acctggacgc cttcctgctg gagcacgggc tcccgcccag     780
ccccgccgcc cccggtggcc cgtcgccgga gccgtcgccc gcgcggacgc ccgcaccctc     840
cccagggccg ggttcgtgcg gctcggcttc ccccgctcc tctcctgggc acgccccgc       900
ccgggctgcc ctcgggaccg ccagcggcca ccgcgcaggc ctgacctctc gggacacacc     960
cagccctgtg gacccagaca ccgtggaggt gttgatgacc tttgaacccg acccagctga    1020
tcttgcccta tcaagcattc ctggccacga gacctttgac cctcgaagac atcgcttctc    1080
agaagaggaa cttaagcccc agccaatcat gaagaaggca agaaaaatcc aggtgccgga    1140
ggagcagaag gatgagaaat actggagccg gcggtacaag aacaacgagg cagccaagcg    1200
gtcccgtgac gcccggcggc tcaaggagaa ccagatatcg gtgcgggcgg ccttcctgga    1260
gaaggagaac gccctgctgc ggcaggaagt tgtggccgtg cgccaggagc tgtcccacta    1320
ccgcgccgtg ctgtcccgat accaggccca gcacggggcc ctgtgaggct gccccacatc    1380
cccacctggc ggagctctcc tccgccttgc tgagacttac gccctgttcc cttcctgccc    1440
tgtggcccac gggccggcca gctgggtgcc ccagggacgt gataatgcag ataaatacat    1500
ttatattttt aagaaaaagc gagcctcccc cctcccttgc gggggcgggg agggttctct    1560
gtgtgtgtcc ccggcacgtc agggaccctca tcctcccacc gcctccgtta acacgatcct   1620
gaataaatct tgagaacccc agaaaaaaaa aaaaaaaa                            1658
```

<210> SEQ ID NO 30
<211> LENGTH: 3317
<212> TYPE: DNA
<213> ORGANISM: Homo sapiens

<400> SEQUENCE: 30

```
gttgggaaac agcccagtgg tataaggatg aggaaactga agcccagaga ggtgaagtga      60
ggtgcccaag gccacacagc aagttagagg cacagctagt acggtagctc aagtctcctg     120
actcccagtc cagtgctcct cccattactc cacgagtcct gtctctaagc ttcctgacaa     180
atgctagaac ggaagaaacc caagacagct gaaaaccaga aggcatctga ggagaatgag     240
attactcagc cgggtggatc cagcgccaag ccgggccttc cctgcctgaa ctttgaagct     300
gttttgtctc cagacccagc cctcatccac tcaacacatt cactgacaaa ctctcacgct     360
cacaccgggt catctgattg tgacatcagt tgcaagggga tgaccgagcg cattcacagc     420
atcaaccttc acaacttcag caattccgtg ctcgagaccc tcaacgagca gcgcaaccgt     480
```

```
ggccacttct gtgacgtaac ggtgcgcatc cacgggagca tgctgcgcgc acaccgctgc    540
gtgctggcag ccggcagccc cttcttccag gacaaactgc tgcttggcta cagcgacatc    600
gagatcccgt cggtggtgtc agtgcagtca gtgcaaaagc tcattgactt catgtacagc    660
ggcgtgctac gggtctcgca gtcggaagct ctgcagatcc tcacggccgc cagcatcctg    720
cagatcaaaa cagtcatcga cgagtgcacg cgcatcgtgt cacagaacgt gggcgatgtg    780
ttcccgggga tccaggactc gggccaggac acgccgcggg cactcccga gtcaggcacg    840 tcaggccaga gcagcgacac ggagtcgggc tacctgcaga gccacccaca gcacagcgtg    900
gacaggatct actcggcact ctacgcgtgc tccatgcaga tggcagcgg cgagcgctct    960 ttttacagcg gcgcagtggt cagccaccac gagactgcgc tcggcctgcc ccgcgaccac   1020
cacatggaag accccagctg gatcacacgc atccatgagc gctcgcagca gatggagcgc   1080
tacctgtcca ccaccccga ccacgcac tgccgcaagc agccccggcc tgtgcgcatc   1140
cagaccctag tgggcaacat ccacatcaag caggagatgg aggacgatta cgactactac   1200
gggcagcaaa gggtgcagat cctggaacgc aacgaatccg aggagtgcac ggaagacaca   1260
gaccaggccg agggcaccga gagtgagccc aaaggtgaaa gcttcgactc gggcgtcagc   1320
tcctccatag gcaccgagcc tgactcggtg gagcagcagt ttgggcctgg ggcggcgcgg   1380
gacagccagg ctgaacccac ccaacccgag caggctgcag aagccccgc tgagggtggt   1440 ccgcagacaa accagctaga aacaggtgct tcctctccgg agagaagcaa tgaagtggag   1500
atggacagca ctgttatcac tgtcagcaac agctccgaca gagcgtcct acaacagcct   1560 tcggtcaaca cgtccatcgg gcagccattg ccaagtaccc agctctactt acgccagaca   1620
gaaaccctca ccagcaacct gaggatgcct ctgaccttga ccagcaacac gcaggtcatt   1680
ggcacagctg gcaacaccta cctgccagcc ctcttcacta cccagcccgc gggcagtggc   1740
cccaagcctt tcctcttcag cctgccacag cccctggcag ccagcagac ccagtttgtg   1800 acagtgtccc agcccggtct gtcgaccttt actgcacagc tgccagcgcc acagcccctg   1860
gcctcatccg caggccacag cacagccagt gggcaaggcg aaaaaaagcc ttatgagtgc   1920
actctctgca caagactttt caccgccaaa cagaactacg tcaagcacat gttcgtacac   1980
acaggtgaga agccccacca atgcagcatc tgttggcgct ccttctcctt aaaggattac   2040
cttatcaagc acatggtgac acacacagga gtgagggcat accagtgtag tatctgcaac   2100
aagcgcttca cccagaagag ctccctcaac gtgcacatgc gcctccaccg gggagagaag   2160
tcctacgagt gctacatctg caaaaagaag ttctctcaca gaccctcct ggagcgacac   2220 gtggccctgc acagtgccag caatgggacc cccctgcag gcacacccc aggtgcccgc   2280 gctggccccc caggcgtggt ggcctgcacg gaggggacca cttacgtctg ctccgtctgc   2340
ccagcaaagt ttgaccaaat cgagcagttc aacgaccaca tgaggatgca tgtgtctgac   2400
ggataagtag tatctttctc tctttcttat gaacaaaaca aaacaacaac aaaaaacaaa   2460
caaacaaaaa agctatggca ctagaattta agaaatgttt tggtttcatt tttacttttct   2520 gttttttgttt ttgtttcgtt tcattttgta ctacatgaag aactgttttt tgcctgctgg   2580
tacattacat ttccggaggc ttgggtgaat aatagttttc ccagtctccc tcggatggtg   2640
gccttaaggc ctggtagtgc ttcaagaggt ccactggttg gatctctagc tactggcctc   2700
taaatacaac ccttctttac aaaaaaatct tttaaaaaaa agtaaaaaaa aaaaaaaat   2760 ttccacttgt gaagagcact acaaaaaata tataacaaaa tctaaaggc ctactgtctt   2820 taagtacacc gcttgcagtg tttcagtgga cattttcaca attctggccg cttggacttc   2880
```

| | |
|---|---|
| acagtaaccagttaaaactgtggaatatcacttctggttgaaaacccagaggaaaggccc | 2940 |
| tgctgttttccacctaccacgttgtctgatttcataaaagggctgtggggtgtgggaaggg | 3000 |
| cagtgggttcggtggtgtggaaagaaagacgaatggcaggcttcttcccagattctgc | 3060 |
| ccgggtccacacaccctggcccaccttctccatatccccctcttgcagcagaagccagga | 3120 |
| agacttggacaagcaacaagcaacagtggctatcgtatttattcagtgtcttcgctgagc | 3180 |
| cacagcctcagcacaatcaagagggactttcatgaaaggcaggaatgcagataaaacaaa | 3240 |
| gatatcagaaatttgcacctatgtttctaggtacaagagaaggattatttccaacaatct | 3300 |
| ttgcaaaaaaaaaaaaa | 3317 |

<210> SEQ ID NO 31
<211> LENGTH: 3779
<212> TYPE: DNA
<213> ORGANISM: Homo sapiens

<400> SEQUENCE: 31

| | |
|---|---|
| gcactgccaggacttaccgtacaacactccttggcttctgaattttatctctgctcaca | 60 |
| gtctacattacaacattagttcattctgggcactttagcttccttgaatctccagttgat | 120 |
| ctcacacccatgcctatgatattcttctcctggttaatcaagaattctctatttctgctc | 180 |
| cgtcatccatgccactacaaataaaaagaagtgttaagaattgcctttgggactctgaag | 240 |
| gctgaagaattgatgaattgcaagtttgtgccccatagctgcacagcctatgtctaagca | 300 |
| cagctcatcttcacaaactgaagtggatcttgatttctggaaatgtccaaataatgacaa | 360 |
| caaccccatggaggtggatacatcagagtcagctggaggtggtcagaattatttgcaatg | 420 |
| tttgggaaagcacctaccaaggcttcctatacctatttcacagaatgttcatcattac | 480 |
| taacaggatattcctcatgacattgctgtctgatctttgaccatcagtctgtgacctgcc | 540 |
| ccttctctttacatgcagccgctctctgctccctgccccaatgaacatctgcactaggcc | 600 |
| caagccttggagtaatttactgaagagtgacaccattgatttttgaaactactgaagaaa | 660 |
| cccaagacagctgaaaaccagaaggcatctgaggagaatgagattactcagccgggtgga | 720 |
| tccagcgccaagccgggcctcccctgcctgaactttgaagctgttttgtctccagaccca | 780 |
| gccctcatccactcaacacattcactgacaaactctcacgctcacaccggtcatctgat | 840 |
| tgtgacatcagttgcaagggatgaccgagcgcattcacagcatcaacctcacaacttc | 900 |
| agcaattccgtgctcgagaccctcaacgagcagcgcaaccgtggccacttctgtgacgta | 960 |
| acggtgcgcatccacggagcatgctgcgcgcacaccgctgcgtgctggcagccggcagc | 1020 |
| cccttcttccaggacaaaactgctgcttggctacagcgacatcgagatcccgtcggtggtg | 1080 |
| tcagtgcagtcagtgcaaaagctcattgacttcatgtacagcggcgtgctacgggtctcg | 1140 |
| cagtcggaagctctgcagatcctcacggccgccagcatcctgcagatcaaacagtcatc | 1200 |
| gacgagtgcacgcgcatcgtgtcacagaacgtgggcgatgtgttcccgggatccaggac | 1260 |
| tcgggccaggacacgccgcgggcactcccgagtcaggcacgtcaggccagagcagcgac | 1320 |
| acggagtcggctacctgcagagccacccacagcacagcgtggacaggatctactcggca | 1380 |
| ctctacgcgtgctccatgcagaatggcagcggcgagcgcttttttacagcggcgcagtg | 1440 |
| gtcagccaccacgagactgcgctcggcctgccccgcgaccaccacatggaagaccccagc | 1500 |
| tggatcacacgcatccatgagcgctcgcagcagatggagcgctacctgtccaccaccccc | 1560 |
| gagaccacgcactgccgcaagcagcccggcctgtgcgcatccagaccctagtgggcaac | 1620 |
| atccacatcaagcaggagatggaggacgattacgactactacgggcagcaaagggtgcag | 1680 |

| | | | | |
|---|---|---|---|---|
| atcctggaac | gcaacgaatc | cgaggagtgc | acggaagaca | cagaccaggc cgagggcacc | 1740 |
| gagagtgagc | ccaaaggtga | aagcttcgac | tcgggcgtca | gctcctccat aggcaccgag | 1800 |
| cctgactcgg | tggagcagca | gtttgggcct | ggggcggcgc | gggacagcca ggctgaaccc | 1860 |
| acccaacccg | agcaggctgc | agaagccccc | gctgagggtg | gtccgcagac aaaccagcta | 1920 |
| gaaacaggtg | cttcctctcc | ggagagaagc | aatgaagtgg | agatggacag cactgttatc | 1980 |
| actgtcagca | acagctccga | caagagcgtc | ctacaacagc | cttcggtcaa cacgtccatc | 2040 |
| gggcagccat | tgccaagtac | ccagctctac | ttacgccaga | cagaaaccct caccagcaac | 2100 |
| ctgaggatgc | ctctgacctt | gaccagcaac | acgcaggtca | ttggcacagc tgcaacacc | 2160 |
| tacctgccag | ccctcttcac | tacccagccc | gcgggcagtg | gccccaagcc tttcctcttc | 2220 |
| agcctgccac | agcccctggc | aggccagcag | acccagtttg | tgacagtgtc ccagcccggt | 2280 |
| ctgtcgacct | ttactgcaca | gctgccagcg | ccacagcccc | tggcctcatc cgcaggccac | 2340 |
| agcacagcca | gtgggcaagg | cgaaaaaaag | ccttatgagt | gcactctctg caacaagact | 2400 |
| ttcaccgcca | aacagaacta | cgtcaagcac | atgttcgtac | acacaggtga aagcccccac | 2460 |
| caatgcagca | tctgttggcg | ctccttctcc | ttaaaggatt | accttatcaa gcacatggtg | 2520 |
| acacacacag | gagtgagggc | ataccagtgt | agtatctgca | caagcgctt cacccagaag | 2580 |
| agctccctca | acgtgcacat | gcgcctccac | cggggagaga | agtcctacga gtgctacatc | 2640 |
| tgcaaaaaga | agttctctca | caagaccctc | ctggagcgac | acgtggccct gcacagtgcc | 2700 |
| agcaatggga | ccccccctgc | aggcacaccc | ccaggtgccc | cgcgctggccc cccaggcgtg | 2760 |
| gtggcctgca | cggaggggac | cacttacgtc | tgctccgtct | gcccagcaaa gtttgaccaa | 2820 |
| atcgagcagt | tcaacgacca | catgaggatg | catgtgtctg | acggataagt agtatctttc | 2880 |
| tctctttctt | atgaacaaaa | caaaacaaca | acaaaaaaca | aacaaacaaa aaagctatgg | 2940 |
| cactagaatt | taagaaatgt | tttggtttca | tttttacttt | ctgttttgt ttttgtttcg | 3000 |
| tttcattttg | tactacatga | agaactgttt | tttgcctgct | ggtacattac atttccggag | 3060 |
| gcttgggtga | ataatagttt | tcccagtctc | cctcggatgg | tggccttaag gcctggtagt | 3120 |
| gcttcaagag | gtccactggt | tggatctcta | gctactggcc | tctaaataca acccttcttt | 3180 |
| acaaaaaaat | cttttaaaaa | aaagtaaaaa | aaaaaaaaaa | atttccactt gtgaagagca | 3240 |
| ctacaaaaaa | tatataacaa | aatctaaaag | gcctactgtc | tttaagtaca ccgcttgcag | 3300 |
| tgtttcagtg | gacattttca | caattctggc | cgcttggact | tcacagtaac cagttaaaac | 3360 |
| tgtggaatat | cacttctggt | tgaaaaccca | gaggaaaggc | cctgctgttt tccacctacc | 3420 |
| acgttgtctg | atttcataaa | agggctgtgg | gggtgggaag | ggcagtgggt tcggtggtgt | 3480 |
| gggaaagaaa | gacgaatggc | aggcttcttc | cccagattct | gcccgggtcc acacaccctg | 3540 |
| gcccaccttc | tccatatccc | cctcttgcag | cagaagccag | gaagacttgg acaagcaaca | 3600 |
| agcaacagtg | gctatcgtat | ttattcagtg | tcttcgctga | gccacagcct cagcacaatc | 3660 |
| aagagggact | tcatgaaaag | gcaggaatgc | agataaaaca | aagatatcag aaatttgcac | 3720 |
| ctatgtttct | aggtacaaga | gaaggattat | ttccaacaat | cttgcaaaa aaaaaaaaa | 3779 |

<210> SEQ ID NO 32
<211> LENGTH: 4446
<212> TYPE: DNA
<213> ORGANISM: Homo sapiens

<400> SEQUENCE: 32

| | | | | |
|---|---|---|---|---|
| ttcttaaccc | tttccagctt | tcccaccctc | tttggcttta | gccatggcct tctgatctgt | 60 |

```
gtttctcagg ggacctgcag gccccagata tagccccatg ctgtcctcct accccagagc    120
acactgttca ggctacttcc actggtactg aaatccagta tttcacttac tcttttcctt    180
tccaatatcc tcatgacatt caatatttca cttactctag gtcctccctg cctaaggccc    240
aagtcaactt tctgtccagt gggatttgta atccaatacc tcctagccct agcagaatcc    300
catgtggata atcagaaatg tgactggaaa aaggacagag ctctatggct gtgggtccca    360
gtccccactg ctggcagtaa gtccccagca gtgagctgtg taagcacctt acattctgcg    420
cttggttgaa aacagcaagg caagcatcca cttgagaaat gtcaacccct aggaaatccc    480
agcctcaagt ctttctcatc ccttgggaag tgcaaattgg atagagaaga aaccaattaa    540
aaacaaaaca aacaaatcat acttagatat tctggctttt ctcaccaggg ctggattaaa    600
gcatgtactt caaataata acaacttaag tcaataaata aatgtaagga agtccaaatg    660
ttcacctgaa gacaactgtg gtcatttttt ggcaatccca ggttctcttt tctacctgtt    720
tgctcaatcg tggtctccct ctccctctct tgttggggcc catgcccctg ctttactgtt    780
gccagaggct tgtacttgtt tgcctttag gtaggagcag ttacttccac tcccctcacc    840
tgccataaag catctttata aacaaagcaa gtagaagaaa cacatcctgg tatccaccac    900
attcggcttt tgttgattct gttcacttgg gagcacctgc tgctagggaa taagaaggtt    960
gaggctgaag agtgaggact cttcagctcc cctctggcag gacccgggag aggaaagagc   1020
cctcagctgg tccatcctcc ccactcctgg tcagccttct gttctgagat caaagtggtg   1080
gggtcacatt ctcgagaact gtgctcagcc ccctcatctc acacccttc cctctccctg   1140 tgtgcctgcc cccctcttac ataaccatgc tggtgattgg caccgtcata aatcaatact   1200
ttgctcactt tcacatcaag taacactatc cagggaggtg gtttcaacaa aggaggaagt   1260
ataaggagat ctaggttcaa attaatgttg ccctagtgg taaaggacag agaccctcag   1320
actgatgaaa tgcactcaga attacttaga caaagcggat atttgccact ctcttcccct   1380
tttcctgtgt ttttgtagtg aagagacctg aaagaaaaaa gtaggagaa cataatgaga   1440 acaaatacgg taatctcttc atttgctagt tcaagtgctg gacttgggac ttaggagggg   1500
caatggagcc gcttagtgcc tacatctgac ttggactgaa atataggtga gagacaagat   1560
tgtctcatat ccggggaaat cataacctat gactaggacg ggaagaggaa gcactgcctt   1620
tacttcagtg ggaatctcgg cctcagcctg caagccaagt gttcacagtg agaaaagcaa   1680
gagaataagc taatactcct gtcctgaaca aggcagcggc tccttggtaa agctactcct   1740
tgatcgatcc tttgcaccgg attgttcaaa gtggacccca ggggagaagt cggagcaaag   1800
aacttaccac caagcagtcc aagaggccca gaagcaaacc tggaggtgag acccaaagaa   1860
agctggaacc atgctgactt tgtacactgt gaggacacag agtctgttcc tggaaagccc   1920
agtgtcaacg cagatgagga agtcggaggt ccccaaatct gccgtgtatg tggggacaag   1980
gccactggct atcacttcaa tgtcatgaca tgtgaaggat gcaagggctt tttcaggagg   2040
gccatgaaac gcaacgcccg gctgaggtgc ccttccgga agggcgcctg cgagatcacc   2100
cggaagaccc ggcgacagtg ccaggcctgc cgcctgcgca gtgcctgga gagcggcatg   2160 aagaaggaga tgatcatgtc cgacgaggcc gtggaggaga ggcgggcctt gatcaagcgg   2220 aagaaagtg aacggacagg gactcagcca ctggagtgc aggggctgac agaggagcag   2280
cggatgatga tcagggagct gatggacgct cagatgaaaa cctttgacac taccttctcc   2340
catttcaaga atttccggct gccaggggtg cttagcagtg gctgcgagtt gccagagtct   2400
ctgcaggccc catcgaggga agaagctgcc aagtggagcc aggtccggaa agatctgtgc   2460
```

```
tctttgaagg tctctctgca gctgcggggg gaggatggca gtgtctggaa ctacaaaccc    2520
ccagccgaca gtggcgggaa agagatcttc tccctgctgc cccacatggc tgacatgtca    2580
acctacatgt tcaaaggcat catcagcttt gccaaagtca tctcctactt cagggacttg    2640
cccatcgagg accagatctc cctgctgaag ggggccgctt cgagctgtg tcaactgaga     2700 ttcaacacag tgttcaacgc ggagactgga acctgggagt gtggccggct gtcctactgc    2760
ttggaagaca ctgcaggtgg cttccagcaa cttctactgg agcccatgct gaaattccac    2820
tacatgctga agaagctgca gctgcatgag gaggagtatg tgctgatgca ggccatctcc    2880
ctcttctccc cagaccgccc aggtgtgctg cagcaccgcg tggtggacca gctgcaggag    2940
caattcgcca ttactctgaa gtcctacatt gaatgcaatc ggccccagcc tgctcatagg    3000
ttcttgttcc tgaagatcat ggctatgctc accgagctcc gcagcatcaa tgctcagcac    3060
acccagcggc tgctgcgcat ccaggacata caccccttg ctacgcccct catgcaggag     3120
ttgttcggca tcacaggtag ctgagcggct gcccttgggt gacacctccg agaggcagcc    3180
agacccagag ccctctgagc cgccactccc gggccaagac agatggacac tgccaagagc    3240
cgacaatgcc ctgctggcct gtctccctag ggaattcctg ctatgacagc tggctagcat    3300
tcctcaggaa ggacatgggt gcccccacc cccagttcag tctgtaggga gtgaagccac     3360
agactcttac gtggagagtg cactgacctg taggtcagga ccatcagaga ggcaaggttg    3420
cccttccctt ttaaaaggcc ctgtggtctg gggagaaatc cctcagatcc cactaaagtg    3480
tcaaggtgtg gaagggacca agcgaccaag gatgggccat ctgggggtcta tgcccacata   3540 cccacgtttg ttcgcttcct gagtcttttc attgctacct ctaatagtcc tgtctcccac    3600
ttcccactcg ttccctcct cttccgagct gctttgtggg ctccaggcct gtactcatcg     3660
gcaggcgcat gagtatctgt gggagtcctc tagagagatg agaagccagg aggcctgcac    3720
caaatgtcag aagcttggca tgacctcatt ccggccacat cattctgtgt ctctgcatcc    3780
atttgaacac attattaagc accgataata ggtagcctgc tgtggggtat acagcattga    3840
ctcagatata gatcctgagc tcacagagtt tatagttaaa aaaacaaaca gaaacacaaa    3900
caatttggat caaaaggaga aatgataagt gacaaaagca gcacaaggaa tttccctgtg    3960
tggatgctga gctgtgatgg cgggcactgg gtacccaagt gaaggttccc gaggacatga    4020
gtctgtagga gcaagggcac aaactgcagc tgtgagtgcg tgtgtgtgat ttggtgtagg    4080
taggtctgtt tgccacttga tggggcctgg gtttgttcct ggggctggaa tgctgggtat    4140
gctctgtgac aaggctacgc tgacaatcag ttaaacacac cggagaagaa ccatttacat    4200
gcaccttata tttctgtgta cacatctatt ctcaaagcta aagggtatga aagtgcctgc    4260
cttgtttata gccacttgtg agtaaaaatt tttttgcatt ttcacaaatt atactttata   4320
taaggcattc cacacctaag aactagtttt gggaaatgta gccctgggtt taatgtcaaa    4380
tcaaggcaaa aggaattaaa taatgtactt ttggctaaaa aaaaaaaaaa aaaaaaaaaa    4440
aaaaaa                                                               4446

<210> SEQ ID NO 33
<211> LENGTH: 2772
<212> TYPE: DNA
<213> ORGANISM: Homo sapiens

<400> SEQUENCE: 33
ggcctgctgg gttagtgctg gcagcccct gaggccaagg acagcagcat gacagtcacc       60
aggactcacc acttcaagga ggggtccctc agagcacctg ccatacccct gcacagtgct    120
```

-continued

| | |
|---|---|
| gcggctgagt tggcttcaaa ccatccaaga ggcccagaag caaacctgga ggtgagaccc | 180 |
| aaagaaagct ggaaccatgc tgactttgta cactgtgagg acacagagtc tgttcctgga | 240 |
| aagcccagtg tcaacgcaga tgaggaagtc ggaggtcccc aaatctgccg tgtatgtggg | 300 |
| gacaaggcca ctggctatca cttcaatgtc atgacatgtg aaggatgcaa gggctttttc | 360 |
| aggagggcca tgaaacgcaa cgcccggctg aggtgcccct tccggaaggg cgcctgcgag | 420 |
| atcacccgga gacccggcg acagtgccag gcctgccgcc tgcgcaagtg cctggagagc | 480 |
| ggcatgaaga aggagatgat catgtccgac gaggccgtgg aggagaggcg ggccttgatc | 540 |
| aagcggaaga aaagtgaacg gacagggact cagccactgg gagtgcaggg gctgacagag | 600 |
| gagcagcgga tgatgatcag ggagctgatg gacgctcaga tgaaaacctt tgacactacc | 660 |
| ttctcccatt tcaagaattt ccggctgcca ggggtgctta gcagtggctg cgagttgcca | 720 |
| gagtctctgc aggccccatc gagggaagaa gctgccaagt ggagccaggt ccggaaagat | 780 |
| ctgtgctctt tgaaggtctc tctgcagctg cggggggagg atggcagtgt ctggaactac | 840 |
| aaaccccag ccgacagtgg cgggaaagag atcttctccc tgctgcccca catggctgac | 900 |
| atgtcaacct acatgttcaa aggcatcatc agctttgcca aagtcatctc ctacttcagg | 960 |
| gacttgccca tcgaggacca gatctccctg ctgaagggg ccgcttcga gctgtgtcaa | 1020 |
| ctgagattca acacagtgtt caacgcggag actggaacct gggagtgtgg ccggctgtcc | 1080 |
| tactgcttgg aagacactgc aggtggcttc agcaacttc tactggagcc catgctgaaa | 1140 |
| ttccactaca tgctgaagaa gctgcagctg catgaggagg agtatgtgct gatgcaggcc | 1200 |
| atctccctct tctccccaga ccgcccaggt gtgctgcagc accgcgtggt ggaccagctg | 1260 |
| caggagcaat tcgccattac tctgaagtcc tacattgaat gcaatcggcc ccagcctgct | 1320 |
| cataggttct tgttcctgaa gatcatggct atgctcaccg agctccgcag catcaatgct | 1380 |
| cagcacaccc agcggctgct gcgcatccag gacatacacc cctttgctac gcccctcatg | 1440 |
| caggagttgt tcggcatcac aggtagctga gcggctgccc ttgggtgaca cctccgagag | 1500 |
| gcagccagac ccagagccct ctgagccgcc actcccgggc caagacagat ggacactgcc | 1560 |
| aagagccgac aatgccctgc tggcctgtct ccctaggaa ttcctgctat gacagctggc | 1620 |
| tagcattcct caggaaggac atgggtgccc ccacccca gttcagtctg tagggagtga | 1680 |
| agccacagac tcttacgtgg agagtgcact gacctgtagg tcaggaccat cagagaggca | 1740 |
| aggttgccct ttccttttaa aaggccctgt ggtctgggga gaaatccctc agatcccact | 1800 |
| aaagtgtcaa ggtgtggaag ggaccaagcg accaaggatg ggccatctgg ggtctatgcc | 1860 |
| cacatacccca cgtttgttcg cttcctgagt ctttttcattg ctacctctaa tagtcctgtc | 1920 |
| tcccacttcc cactcgttcc cctcctcttc cgagctgctt tgtgggctcc aggcctgtac | 1980 |
| tcatcggcag gcgcatgagt atctgtggga gtcctctaga gagatgagaa gccaggaggc | 2040 |
| ctgcaccaaa tgtcagaagc ttggcatgac ctcattccgg ccacatcatt ctgtgtctct | 2100 |
| gcatccattt gaacacatta ttaagcaccg ataataggta gcctgctgtg gggtatacag | 2160 |
| cattgactca gatatagatc ctgagctcac agagtttata gttaaaaaaa caaacagaaa | 2220 |
| cacaaacaat ttggatcaaa aggagaaatg ataagtgaca aaagcagcac aaggaatttc | 2280 |
| cctgtgtgga tgctgagctg tgatggcggg cactgggtac ccaagtgaag gttcccgagg | 2340 |
| acatgagtct gtaggagcaa gggcacaaac tgcagctgtg agtgcgtgtg tgtgatttgg | 2400 |
| tgtaggtagg tctgtttgcc acttgatggg gcctgggttt gttcctgggg ctggaatgct | 2460 |
| gggtatgctc tgtgacaagg ctacgctgac aatcagttaa acacaccgga gaagaaccat | 2520 |

-continued

| | |
|---|---|
| ttacatgcac cttatatttc tgtgtacaca tctattctca aagctaaagg gtatgaaagt | 2580 |
| gcctgccttg tttatagcca cttgtgagta aaaatttttt tgcattttca caaattatac | 2640 |
| tttatataag gcattccaca cctaagaact agttttggga aatgtagccc tgggtttaat | 2700 |
| gtcaaatcaa ggcaaaagga attaaataat gtacttttgg ctaaaaaaaa aaaaaaaaa | 2760 |
| aaaaaaaaaa aa | 2772 |

<210> SEQ ID NO 34
<211> LENGTH: 2213
<212> TYPE: DNA
<213> ORGANISM: Homo sapiens

<400> SEQUENCE: 34

| | |
|---|---|
| actctctcct cctcctcacc tcattgtctc cccgacttat cctaatgcga aattggattc | 60 |
| tgagcatttg tagcaaaatc gctgggatct ggagaggaag actcagtcca gaatcctccc | 120 |
| agggccttga aagtccatct ctgacccaaa acaatccaag gaggtagaag acatcgtaga | 180 |
| aggagtgaaa gaagaaaaga agacttagaa acatagctca aagtgaacac tgcttctctt | 240 |
| agtttcctgg atttcttctg gacatttcct caagatgaaa cttcagacac tttggagttt | 300 |
| tttttgaaga ccaccataaa gaaagtgcat ttcaattgaa aaatttggat gggatcaaaa | 360 |
| atgaatctca ttgaacattc ccatttacct accacagatg aattttcttt ttctgaaaat | 420 |
| ttatttggtg ttttaacaga acaagtggca ggtcctctgg gacagaacct ggaagtggaa | 480 |
| ccatactcgc aatacagcaa tgttcagttt ccccaagttc aaccacagat ttcctcgtca | 540 |
| tcctattatt ccaacctggg tttctacccc cagcagcctg aagagtggta ctctcctgga | 600 |
| atatatgaac tcaggcgtat gccagctgag actctctacc agggagaaac tgaggtagca | 660 |
| gagatgcctg taacaaagaa gccccgcatg ggcgcgtcag cagggaggat caaggggat | 720 |
| gagctgtgtg ttgtttgtgg agacagagcc tctggatacc actataatgc actgacctgt | 780 |
| gagggggtgta aaggtttctt caggagaagc attaccaaaa acgctgtgta caagtgtaaa | 840 |
| aacgggggca actgtgtgat ggatatgtac atgcgaagaa agtgtcaaga gtgtcgacta | 900 |
| aggaaatgca aagagatggg aatgttggct gaatgcttgt taactgaaat tcagtgtaaa | 960 |
| tctaagcgac tgagaaaaaa tgtgaagcag catgcagatc agaccgtgaa tgaagacagt | 1020 |
| gaaggtcgtg acttgcgaca gtgacctcg acaacaaagt catgcaggga gaaaactgaa | 1080 |
| ctcaccccag atcaacagac tcttctacat tttattatgg attcatataa caaacagagg | 1140 |
| atgcctcagg aaataacaaa taaaatttta aagaagaat tcagtgcaga agaaaatttt | 1200 |
| ctcattttga cggaaatggc aaccaatcat gtacaggttc ttgtagaatt cacaaaaaag | 1260 |
| ctaccaggat ttcagacttt ggaccatgaa gaccagattg cttttgctgaa agggtctgcg | 1320 |
| gttgaagcta tgttccttcg ttcagctgag attttcaata gaaaacttcc gtctgggcat | 1380 |
| tctgacctat tggaagaaag aattcgaaat agtggtatct ctgatgaata tataacacct | 1440 |
| atgtttagtt tttataaaag tattggggaa ctgaaaatga ctcaagagga gtatgctctg | 1500 |
| cttacagcaa ttgttatcct gtctccagat agacaataca taaaggatag agaggcagta | 1560 |
| gagaagcttc aggagccact tcttgatgtg ctacaaaagt tgtgtaagat tcaccagcct | 1620 |
| gaaaatcctc aacactttgc ctgtctcctg ggtcgcctga ctgaattacg gacattcaat | 1680 |
| catcaccacg ctgagatgct gatgtcatgg agagtaaacg accacaagtt tacccccactt | 1740 |
| ctctgtgaaa tctgggacgt gcagtgatgg ggattacagg ggaggggtct agctcctttt | 1800 |
| tctctctcat attaatctga tgtataactt tcctttattt cacttgtacc cagtttcact | 1860 |

```
caagaaatct tgatgaatat ttatgttgta attacatgtg taacttccac aactgtaaat    1920
attgggctag atagaacaac tttctctaca ttgtgtttta aaaggctcca gggaatcctg    1980
cattctaatt ggcaagccct gtttgcctaa ttaaattgat tgttacttca attctatctg    2040
ttgaactagg gaaaatctca ttttgctcat cttaccatat tgcatatatt ttattaaaga    2100
gttgtattca atcttggcaa taaagcaaac ataatggcaa cagaaaaaaa aaaaaaaaa     2160 aaaaaaaaaa aaaaaaaaaa aaaaaaaaaa aaaaaaaaaa aaaaaaaaaa aaa           2213

<210> SEQ ID NO 35
<211> LENGTH: 2293
<212> TYPE: DNA
<213> ORGANISM: Homo sapiens

<400> SEQUENCE: 35
atttgggaga gtgctgtgac tcatgctgga ctctaaccca cgagggtttc tcagagtcag      60
cagctggggg atgaagaagt gaaaagtgac tggcaggaaa ttctgcaagc aaggaaaggg     120
aaagagaaat gaactggtgc aggtctgcgg gaagagaatg aggctggatc ctcaaaatca     180
caggaggaag caggcccaga cctcagaggc agaaagagaa agaaaccaga gcttagagtc     240
aggaggagga aaccagaccc cggagccaca aggagagggc tggatccccg gctcagaggg     300
aagagtgtcg ccgcctctgc ctgcgtagcc ccggccatgg ctctgtagcc tcgacccctt     360 tgtgccccg gcccgtctcc gcgctcacca cgcctgcgct ctccgctccc accttctttc     420
ttcagccgag gccgccgcg cctctccttg ctgcagccat ggagtcttcc actttcgcct     480
tggtgcctgt cttcgcccac ctgagcatcc tccagagcct cgtgccagct gctggtgcag     540
cctctcctgt tgccatcagt gcccagcacc tgtgctacag ccatgtcact cctggcgacc     600
ctggggctgg agctggacag ggccctgctc ccagctagtg ggctgggatg gctcgtagac     660
tatgggaaac tccccccggc ccctgccccc tggctccct atgaggtcct tgggggagcc     720
ctggagggcg ggcttccagt gggggggagag ccctggcag gtgatggctt ctctgactgg     780
atgactgagc gagttgattt cacagctctc ctccctctgg agcctccctt accccccggc     840
accctccccc aaccttcccc aaccccacct gacctggaag ctatggcctc cctcctcaag     900
aaggagctgg aacagatgga agacttcttc ctagatgccc cgcccctccc accaccctcc     960
ccgccgccac taccaccacc accactacca ccagccccct ccctcccct gtccctccc     1020 tcctttgacc tcccccagcc ccctgtcttg gatactctgg acttgctggc catctactgc     1080
cgcaacgagc ccgggcagga ggaagtgggg atgccgcctc tgcccccgcc acagcagccc     1140
cctcctcctt ctccacctca accttctcgc ctggcccct acccacatcc tgccaccacc     1200
cgaggggacc gcaagcaaaa gaagagagac cagaacaagt cggcggctct gaggtaccgc     1260
cagcggaagc gggcagaggg tgaggccctg gagggcgagt gccaggggct ggaggcacgg     1320
aatcgcgagc tgaaggaacg ggcagagtcc gtggagcgcg agatccagta cgtcaaggac     1380
ctgctcatcg aggtttacaa ggcccggagc cagaggaccc gtagctgcta aagggcagg     1440 ggtgtggctt ctggggctg gtcttcagct ctggcgcctt catccccctg cctctacctt     1500
cattccaaac ccctctcggc cgggtgcagt ggcttatgct tgtaatccca gcactttggg     1560
aggccaaggc aggaggatcg tttgaggcca ggaggtcaat accagcctgg gcaacatagt     1620
aagaccctgt ctctattaaa aaaaaaaaat caaccttct tccccaccaa accacccaac     1680
tcctctctac tcttatcctt ttatcctctg tctctgctta tcacctctct tgcgtatttc     1740
tggatctcct tccctccttt ctcgtccaaa tcatgaaatg tttggcctta gtcaatgtct     1800
```

```
atgcccgtca cataacagcc gaggcaccga ggcccacagg gaagcagctg ggagcttgga    1860
aacctggtct cttgaatttc aaacctggtt tcttacaggt ggttgtctgg ggtgggtgga    1920
gtggcgacag gatagagctg aaggactatg caaatgagga agtaagtcag ggcgggcttt    1980
gagaaggggga cccatatcct acaggcaaaa agcaggctag gtgaccttgg gacactacgc    2040
taagggaggg aggctaaagg cggccaggtt tgcagtgcgg gaagatgagc aggccagtgg    2100
gaggaggggc agggcagggc tgtagttggt gactgggtgt tcattttagc tctaagaaaa    2160
aaaatcagtg tttcgtgaag gtgttggaga ggggctgtgt ctgggtgagg gatggcgggg    2220
tactgatttt tttgggaggt tatgagcaaa aataaaacga aacatttcct ctggcaaaaa    2280
aaaaaaaaaa aaa                                                       2293

<210> SEQ ID NO 36
<211> LENGTH: 4916
<212> TYPE: DNA
<213> ORGANISM: Homo sapiens

<400> SEQUENCE: 36
aaaaagtaca gagtccaggg aaagacttgc ttgtaacttt atgaattctg gattttttt      60
tttcctttgc tttttcttaa cttcactaa gggttactgt agtctgatgt gtccttccca     120
aggccacgaa atttgacaag ctgcactttt cttttgctca atgatttctg ctttaagcca     180
aagaactgcc tataatttca ctaagaatgt cttctaattc agatactggg gatttacaag     240
agtctttaaa gcacggactt acacctattg tgtctcaatt taaatggtg aattactcct      300
atgatgaaga tctggaagag ctttgtcccg tgtgtggaga taaagtgtct gggtaccatt     360
atgggctcct cacctgtgaa agctgcaagg gattttttaa gcaacagtc caaataata      420
aaaggtacac atgtatagaa aaccagaact gccaaattga caaaacacag agaaagcgtt     480
gtccttactg tcgttttcaa aaatgtctaa gtgttggaat gaagctagaa gctgtaaggg     540
ccgaccgaat gcgtggagga aggaataagt ttgggccaat gtacaagaga gacagggccc     600
tgaagcaaca gaaaaaagcc ctcatccgag ccaatggact taagctagaa gccatgtctc     660
aggtgatcca agctatgccc tctgacctga ccatttcctc tgcaattcaa aacatccact     720
ctgcctccaa aggcctacct ctgaaccatg ctgccttgcc tcctacagac tatgacagaa     780
gtcccttttgt aacatccccc attagcatga caatgccccc tcacggcagc ctgcaaggtt     840
accaaacata tggccacttt cctagccggg ccatcaagtc tgagtaccca gacccctata     900
ccagctcacc cgagtccata atgggctatt catatatgga tagttaccag acgagctctc     960
cagcaagcat cccacatctg atactggaac ttttgaagtg tgagccagat gagcctcaag    1020
tccaggctaa aatcatggcc tatttgcagc aagagcaggc taaccgaagc aagcacgaaa    1080
agctgagcac ctttgggctt atgtgcaaaa tggcagatca aactctcttc tccattgtcg    1140
agtgggccag gagtagtatc ttcttcagag aacttaaggt tgatgaccaa atgaagctgc    1200
ttcagaactg ctggagtgag ctcttaatcc tcgaccacat ttaccgacaa gtggtacatg    1260
gaaaggaagg atccatcttc ctggttactg ggcaacaagt ggactattcc ataatagcat    1320
cacaagccgg agccaccctc aacaacctca tgagtcatgc acaggagtta gtggcaaaac    1380
ttcgttctct ccagtttgat caacgagagt tcgtatgtct gaaattcttg gtgctcttta    1440
gtttagatgt caaaaacctt gaaaacttcc agctggtaga aggtgtccag gaacaagtca    1500
atgccgccct gctggactac acaatgtgta actacccgca gcagacagag aaatttggac    1560
agctacttct tcgactaccc gaaatccggg ccatcagtat gcaggctgaa gaatacctct    1620
```

```
actacaagca cctgaacggg gatgtgccct ataataacct tctcattgaa atgttgcatg   1680
ccaaaagagc ataagttaca acccctagga gctctgcttt caaaacaaaa agagattggg   1740
ggagtgggga gggggaagaa gaacaggaag aaaaaaagta ctctgaactg ctccaagtaa   1800
cgctaattaa aaacttgctt taaagatatt gaatttaaaa aggcataata atcaaatact   1860
taatagcaaa taaatgatgt atcagggtat ttgtattgca aactgtgaat caaaggcttc   1920
acagccccag aggattccat ataaaagaca ttgtaatgga gtggattgaa ctcacagatg   1980
gataccaaca cggtcagaag aaaaacggac agaacggttc ttgtatattt aaactgatct   2040
ccactatgaa gaaatttagg aactaatctt attaattagg cttatacagc gggggatttg   2100
agcttacagg attcctccat ggtaaagctg aactgaaaca attctcaaga atgcatcagc   2160
tgtacctaca atagcccctc cctcttcctt gaaggcccc agcacctctg ccctgtggtc     2220
accgaatctg tactaaggac ctgtgttcag ccacacccag tggtagctcc accaaatcat   2280
gaacagccta atttgagtg tctgtgtctt agacctgcaa acagctaata ggaaattcta     2340
ttaatatgtt agcttgccat tttaaatatg ttctgagggt tgttttgtct cgtgttcatg   2400
atgttaagaa aatgcaggca gtatccctca tcttatgtaa gtgtgaatta atattaaggg   2460
aaatgactac aaactttcaa agcaaatgct ccatagctaa agcaacttag accttatttc   2520
tgctactgtt gctgaaatgt ggctttggca ttgttggatt tcataaaaaa tttctggcag   2580
gaagtcttgt tagtatacat cagtcttttt catcatccaa gtttgtagtt catttaaaaa   2640
tacaacatta aacacatttt gctaggatgt caaatagtca cagttctaag tagttggaaa   2700
caaaattgac gcatgttaat ctatgcaaag agaaggaaa ggatgaggtg atgtattgac    2760
tcaaggttca ttcttgctgc aattgaacat cctcaagagt tgggatggaa atggtgattt   2820
ttacatgtgt cctggaaaga tattaaagta attcaaatct tccccaaagg ggaaaggaag   2880
agagtgatac tgaccttttt aagtcataga ccaaagtctg ctgtagaaca aatatgggag   2940
gacaaagaat cgcaaattct tcaaatgact attatcagta ttattaacat gcgatgccac   3000
aggtatgaaa gtcttgcctt atttcacaat tttaaaggt agctgtgcag atgtggatca    3060
acatttgttt aaaataaagt attaatactt taaagtcaaa taagatatag tgtttacatt   3120
ctttaggtcc tgaggggcag ggggatctgt gatataacaa aatagcaaaa gcggtaattt   3180
ccttaatgtt attttctga ttggtaatta tttttaacag tacttaatta ttctatgtcg     3240
tgagacacta aaatcaaaaa cgggaatctc atttagactt taatttttt gagattatcg     3300 gcggcacaat cactttgtag aaactgtaaa aaataaaagt atctcctagt cccttaattt   3360
tttcataaat atttctggct tttgagtagt gtatttatat tgtatatcat actttcaact   3420
gtagacaatt atgatgctaa tttattgttt cttggtttca cctttgtata agatatagcc   3480
aagactgaag aaaccaaata tatgtgttta ctgtagcatg tcttcaaatt agtggaactt   3540
agttcaggga catagaagag tcttaatgaa ttaaaatcat tcacttgatt aaatgtctgt   3600
aaatcttcat cattcctact gtagtttatt taatatctat tgtaaattat gtgacttgta   3660
gcttcctctg gttttcaagt aaactcaaca aggtggagtc ttacctggtt ttcctttcca   3720
agcattgtaa attgtatacc aaagatatta gttattactt ctgtgtgtac aaagaggatt   3780
attttattat gtttattaat cacctctaat actcatccac atgaagggta cacattaggt   3840
aagctgggcg ttgactcatg cgcagtctca gtcacccgtg ttatcttcgt ggctcaaagg   3900
acaatgcaaa atcgccgatc agagctcata cccaaagcat tacagagaac agcagcatca   3960
ttgccctccc cagctgaaaa acaagttggc tagaagatac atggagagga atggtgtggt   4020
```

-continued

| | |
|---|---|
| caacagttaa tgaaacggtt ctatcatgca tgtgtaatgt ggatggagac aattataaga | 4080 |
| tttgactata actatttgga gggtctttaa cattgccaaa aaaacaaata tgttgatttt | 4140 |
| tattttattt tatttttat tttaagaggc gggatcttga tctcacatgt tgcccaggct | 4200 |
| ggccttgaac tcctgggctc aagcattcct cctgcctcag cctcccccat agctgggact | 4260 |
| aggggtgcat gccagcatac ctggctacgt tgactcttaa aatctatgtt ctcttatttt | 4320 |
| aaagatacag tgctccccac tgaaaattaa acctaaaaaa tgtcacatat tggtatgttg | 4380 |
| ttaacctggt agattaaatc atgagaatga ttagaaagac gggcaacaca gcgggttaca | 4440 |
| tccacactgc tgatcacacc aacgacagga gctgataagc aagaaagcgt cacagccagc | 4500 |
| gtctgttcac ccaaggttga caagtgaagt ttctctaatg ttgattgtta gccgatttgt | 4560 |
| aacctggcat ttacttagca actgccttat caattacagg atttgccggt aaaagcagac | 4620 |
| tcaaatataa aggttttttgg cttaacttgg tttattatag ttgctctatg tttgtaaaca | 4680 |
| gacaatctct aatgtctgat tatttgtatc acagatctgc agctgccttg gacttgaatc | 4740 |
| catgcaatgt ttagagtgtg aagtcagtta cttgttgatg ttttcttact gtatcaatga | 4800 |
| aatacatatt gtcatgtcag ttcttgccag gaacttctca acaaaatgga attttttttt | 4860 |
| tcagtatttc aataaatatt gatatgccca gcctgataat ttttaaaaaa aaaaaa | 4916 |

<210> SEQ ID NO 37
<211> LENGTH: 1720
<212> TYPE: DNA
<213> ORGANISM: Homo sapiens

<400> SEQUENCE: 37

| | |
|---|---|
| agtccctccc ctcagccttt ccccaaattg ctacttctct ggggctccag gtcctgcttg | 60 |
| tgctcagctc cagctcactg gctggccacc gagacttctg gacaggaaac tgcaccatcc | 120 |
| tcttctccca gcaagggggc tccagagact gcccacccag gaagtctggt ggcctgggga | 180 |
| tttggacagt gccttggtaa tgaccagggc tccaggaaga gatgtccttg tggctggggg | 240 |
| cccctgtgcc tgacattcct cctgactctg cggtggagct gtggaagcca ggcgcacagg | 300 |
| atgcaagcag ccaggcccag ggaggcagca gctgcatcct cagagaggaa gccaggatgc | 360 |
| cccactctgc tgggggtact gcaggggtgg ggctggaggc tgcagagccc acagccctgc | 420 |
| tcaccagggc agagcccctt tcagaaccca cagagatccg tccacaaaag cggaaaaagg | 480 |
| ggccagcccc caaaatgctg gggaacgagc tatgcagcgt gtgtgggggac aaggcctcgg | 540 |
| gcttccacta caatgttctg agctgcgagg gctgcaaggg attcttccgc cgcagcgtca | 600 |
| tcaagggagc gcactacatc tgccacagtg gcggccactg ccccatggac acctacatgc | 660 |
| gtcgcaagtg ccaggagtgt cggcttcgca aatgccgtca ggctggcatg cgggaggagt | 720 |
| gtgtcctgtc agaagaacag atccgcctga agaaactgaa gcggcaagag gaggaacagg | 780 |
| ctcatgccac atccttgccc cccagggctt cctcaccccc caaatcctg ccccagctca | 840 |
| gcccggaaca actgggcatg atcgagaagc tcgtcgctgc ccagcaacag tgtaaccggc | 900 |
| gctcctttc tgaccggctt cgagtcacgc cttggcccat gcaccagat ccccatagcc | 960 |
| gggaggcccg tcagcagcgc tttgcccact tcactgagct ggccatcgtc tctgtgcagg | 1020 |
| agatagttga ctttgctaaa cagctacccg gcttcctgca gctcagccgg gaggaccaga | 1080 |
| ttgccctgct gaagacctct gcgatcgagg tgatgcttct ggagacatct cggaggtaca | 1140 |
| accctgggag tgagagtatc accttcctca aggatttcag ttataaccgg gaagactttg | 1200 |
| ccaaagcagg gctgcaagtg gaattcatca accccatctt cgagttctcc agggccatga | 1260 |

```
atgagctgca actcaatgat gccgagtttg ccttgctcat tgctatcagc atcttctctg    1320
cagaccggcc caacgtgcag gaccagctcc aggtagagag gctgcagcac acatatgtgg    1380
aagccctgca tgcctacgtc tccatccacc atccccatga ccgactgatg ttcccacgga    1440
tgctaatgaa actggtgagc ctccggaccc tgagcagcgt ccactcagag caagtgtttg    1500
cactgcgtct gcaggacaaa aagctcccac cgctgctctc tgagatctgg gatgtgcacg    1560
aatgactgtt ctgtccccat attttctgtt ttcttggccg gatggctgag gcctggtggc    1620
tgcctcctag aagtggaaca gactgagaag ggcaaacatt cctgggagct gggcaaggag    1680
atcctcccgt ggcattaaaa gagagtcaaa gggttgcgaa                         1720

<210> SEQ ID NO 38
<211> LENGTH: 2586
<212> TYPE: DNA
<213> ORGANISM: Homo sapiens

<400> SEQUENCE: 38
acagagccac agagggctgt gagcttgccc agccccaggt aacgctggcg gtgggtgggc      60
ctccagcttg gagcagagac cccccgaggc atctgcagac agaactggat ggacccatga     120
atacggattt agctgctgga agatggcttc tgctgcctg ctccatggac cccatcgaca      180
gctttgagct cctggatctc ctgttttgacc ggcaggacgg catcctgaga cacgtggagc     240
tgggcgaggg ctggggtcac gtcaaggacc agcaggtcct gccaaacccc gactctgacg     300
acttcctcag ctccatcctg ggctctggag actcactgcc cagctcccca ctctggtccc     360
ccgaaggcag tgatagtggc atctccgaag acctcccctc cgaccccag gacaccctc       420 cacgcagcgg accagccacc tcccccgccg gctgccatcc tgcccagcct ggcaaggggc     480
cctgcctctc ctatcatcct ggcaactctt gctccaccac aaccccaggg ccagtgatcc     540
aagtacctga agcctctgtg accatagacc tggaaatgtg gagcccagga ggaaggatct     600
gtgctgagaa gccggctgat ccggtggacc tgtccccacg atgcaatctc accgtgaaag     660
acctcctcct ttcgggcagc agtggggacc tgcaacagca tcacctgggg gcctcctacc     720
tcctgcgacc tggggctggg cactgtcagg agctggtgct caccgaggat gagaagaagc     780
tgctggctaa agaaggcatc accctgccca ctcagctgcc cctcactaag tacgaggagc     840
gagtgctgaa aaaaatccgc cggaaaatcc ggaacaagca gtcggcgcaa aaagcagga     900 agaagaagaa ggaatatatc gatggcctgg agactcggat gtcagcttgc actgctcaga     960
atcaggagtt acagaggaaa gtcttgcatc tcgagaagca aaaacctgtcc ctcttggagc    1020 aactgaagaa actccaggcc attgtggtgc agtccaccag caagtcagcc cagacaggca    1080
cctgtgtcgc agtcctgttg ctgtcctttg ccctcatcat cctcccctcc atcagccctt    1140 ttggcccaa caaaaccgag agcctgggg actttgcgcc tgtacgagtg ttctccagaa      1200
ctttgcacaa cgatgctgcc tcccgcgtgg ctgctgatgc tgtgccaggc tccgaggccc    1260
caggaccccg acccgaggct gacacaaccc gagaagagtc tccaggaagc ccggggcag    1320 actgggcttt ccaggacacc gcgaacctga ccaattcgac ggaggagctg acaacgcca    1380 ccctggtcct gaggaatgca acagaggggc tgggccaggt cgccctgctg gactgggtgg    1440
cgcctgggcc gagcactggc tcaggacgtg cagggctgga ggcggcggga gacgagctgt    1500
gagccccgcc aggactatgc tcccaggccc ctctgcccag gggtgccttg gggatgctgc    1560
actgggcagc tacccacctg gggatggac gtgaggccaa gacccagca gagatgccag     1620 aatggggag gcacagctca tagccacaca cccagggcct gactgaggcc cacgcaggaa    1680
```

```
ccgacactca gacacaaggc aaagagggcc acaggacccg ggaaatacac acagagccag   1740
gagcagaagc aaagagcaga cacacataca gcctgaaaca gacctggaca gacagacaca   1800
gcctgaaaca gacccggaca gacagacaca gcctgaaaca gacccagaca aacagacaga   1860
cagacacagc ctgaaacaga cccagacaga cagacagaca gcctgaaaca gacccagaca   1920
cagcctgaaa cagatccgga cagacagaca gaaacagcct gaaacagacc cagacagaca   1980
gacagacaca gcctgaaaca gacccggaca gacagacaga cacagcctga acagacccg    2040 gacagacaga cagacacagc tgaaacagac ccggacagac agacagacaga cagcctgaaa  2100 cagacctaga cagacagaca cagattgaaa cagacccaga caaacagaca gacacagcct   2160
gaaacagacc cagacacagc ctgaaacaga cccggacaga cagacagaca cagcctgaaa   2220
cagacccaga cagacagaca gacacagcct gaaacagacc cagacagaca gaccgacgca   2280
gcctgaaaga gacccagaca gagagacagg cagacacagc ctaaaacaga cctggacaga   2340
caggcagacg tagtctgaaa cagacctgaa cagacagaca gacgcacaca cacaacagat   2400
gcgcagcaac tccccgccca gggacccctc ccggcctccc tcgcacactg ggaggaggaa   2460
gccgccgaga ctgcagggag cctggccccg gagccccggg tgcgccctgg tctttggagc   2520
agccacggcc cacaatcacc cccttttcct aagactgcct gatccgaaat aaagtatttt   2580
gacaaa                                                              2586

<210> SEQ ID NO 39
<211> LENGTH: 1857
<212> TYPE: DNA
<213> ORGANISM: Homo sapiens

<400> SEQUENCE: 39
ccggacctcg gctttcaaag cggcctgggt gggaagagct gtttatataa acagagattc     60
cgctgtaaat gcgctaatat cccggctgcc agcgcatggc gagcgcctcc cacgcccatc    120
cgtaggagcg gcgtcccggc cgcccctccg ttcccagcct gccctgcccc cgcctccttc    180
ccctcctcgg ccatggccac ctctggacgc ctgagcttca ccgtgcgcag ccttctagat    240
ttacccgagc aggacgcgca acacctgccg aggcgggagc cagaaccacg cgcccccag     300 cccgaccct gcgccgcctg gctggattcg gagcgcggcc actacccttc ctcggacgag    360
agcagcctgg agaccagccc gccagactcg tcgcagcggc cgtccgctag cccgcgtct    420 ccgggctcgg acgccgagaa aaggaagaag cggcgggtgc tattctccaa ggcgcagacg    480
ctggagttgg agcggcgctt ccggcagcag cggtacctgt ctgcgcccga gcgcgagcag    540
ctggcgagcc tgcttcgcct cacgcccacg caggtcaaga tctggttcca gaatcatcgc    600
tacaagctga gcgcgctcg cgctccaggg gcggcggagt cgcctgacct ggcagcatcc    660
gccgagctgc acgccgcgcc cggcctgctg cgtcgcgtgg tggtgccggt gcttgttcgc    720
gacgggcagc cgtgcggcgg cggcggcggt ggcgaggtgg gaaccgccgc ggcccaggag    780
aagtgcggcg cccctccagc cgccgcctgc cctctgccgg gctaccctgc cttcggtccc    840
ggctcggcgc ttggcctctt cccgcctac cagcacttag catccccgc cctggtctcc    900 tggaactggt gaggccgcag ggcggcacct ggggctaccc tcgactttgg agcgcgctct    960
gcgattggag cagggccgga gccgaacgcc tggaacgctc tccgtccgcc tcctgcagc   1020 cccatctcct tgggcgccag ggtccctggc gcgccctcat cagccgtcgc gcaagcacac   1080
acgagggacg tgtgccagag ccccctcct caccttccct ccaccgccag cccagagtt    1140 agattttatg cttgggcctt atttgtatat ttttaaatag cgatttgtat aggaagcaag  1200
```

```
ttatttttt  aaaaaataga  gtatttttcc  tcgtagttcg  agaataaaat  gtgtggggtt    1260
gggtcccctg  cgcgcctgcg  gggaacgtag  gcgggagtcg  tgccccccag  accggtgttc    1320
gcatcgctgg  ctcgcccctt  gactggctaa  gtggggcccg  gccccagctg  atcgaaggg     1380
cgggttgcag  tcccgacacg  gctttaggaa  gatacctggg  ggatggaggg  gtggtgatgt    1440
cagggttggg  cgcgggaaga  aaaggagagg  aggaagctga  ggcaactttg  ggattcttgt    1500
cagcgggagg  cgtcactggc  cccagagtga  ctccgactct  ccgctgggct  cccagagctg    1560
ctggcgtttc  gaataccgaa  aagtcaaccc  tgtggaccac  gacagggcag  aaggagtttc    1620
tccggagatg  agccggcgag  gccaggtgcg  ggcgcgctg   caccggagca  gcccaggccg    1680
ggccgcaagc  tgtttccaga  gtgcaggagc  caagtgctcg  ggaccctttt  gaaaagtgcc    1740
tggggacctg  aagagcaccg  ggaatttgt   aaccctatt   taagcctgca  agtgcctaag    1800
ttaaaaaaaa  aaaaaaaaaa  aaaaaaaaaa  aaaaaaaaaa  aaaaaaaaaa  aaaaaaa       1857

<210> SEQ ID NO 40
<211> LENGTH: 1269
<212> TYPE: DNA
<213> ORGANISM: Homo sapiens

<400> SEQUENCE: 40
aggtgacagc  ctcgcttgga  cgcagagccc  ggcccgacgc  cgccatgagc  gccgcgctct      60
tcagcctgga  cggcccggcg  cgcggcgcgc  cctggcctgc  ggagcctgcg  cccttctacg     120
aaccgggccg  ggcgggcaag  ccgggccgcg  gggccgagcc  aggggcccta  ggcgagccag     180
gcgccgccgc  ccccgccatg  tacgacgacg  agagcgccat  cgacttcagc  gcctacatcg     240
actccatggc  cgccgtgccc  acctggagc   tgtgccacga  cgagctcttc  gccgacctct     300
tcaacagcaa  tcacaaggcg  ggcggcgcgg  ggcccctgga  gcttcttccc  ggcggccccg     360
cgcgcccctt  gggccggc    cctgccgctc  cccgcctgct  caagcgcgag  cccgactggg     420
gcgacggcga  cgcgcccggc  tcgctgttgc  ccgcgcaggt  ggccgcgtgc  gcacagaccg     480
tggtgagctt  ggcggccgca  gggcagccca  ccccgcccac  gtcgccggag  ccgccgcgca     540
gcagccccag  gcagaccccc  gcgcccgcc   ccgcccggga  gaagagcgcc  ggcaagaggg     600
gcccggaccg  cggcagcccc  gagtaccggc  agcggcgcga  gcgcaacaac  atcgccgtgc     660
gcaagagccg  cgacaaggcc  aagcggcgca  accaggagat  gcagcagaag  ttggtggagc     720
tgtcggctga  gaacgagaag  ctgcaccagc  gcgtggagca  gctcacgcgg  gacctggccg     780
gcctccggca  gttcttcaag  cagctgccca  gcccgccctt  cctgccggcc  gcgggacag     840
cagactgccg  gtaacgcgcg  gccggggcgg  gagagactca  gcaacgaccc  atacctcaga     900
cccgacggcc  cggagcggag  cgcgccctgc  cctggcgcag  ccagagccgc  cgggtgcccg     960
ctgcagtttc  ttgggacata  ggagcgcaaa  gaagctacag  cctggactta  ccaccactaa    1020
actgcgagag  aagctaaacg  tgtttatttt  cccttaaatt  attttttgtaa  tggtagcttt    1080
ttctacatct  tactcctgtt  gatgcagcta  aggtacattt  gtaaaagaa   aaaaaaccag    1140
actttttcaga  caaaccctttt  gtattgtaga  taagaggaaa  agactgagca  tgctcacttt    1200
tttatattaa  ttttttacagt  atttgtaaga  ataaagcagc  atttgaaatc  gaaaaaaaaa    1260
aaaaaaaaa                                                                  1269

<210> SEQ ID NO 41
<211> LENGTH: 5607
<212> TYPE: DNA
<213> ORGANISM: Homo sapiens
```

```
<400> SEQUENCE: 41
actcttgtca gggccgcggc acatgggcgg ccggatgcgc tgagcccggc gctgcggggc    60
cgcggagcgc tggggagcag cggccgccgg cgcggggagg ggggtggggt gggacggcgc   120
accgcctccg gtgctggcac taggggctgg ggtcggcgcg gtgtcttctg cccttctgca   180
gccgtcgaca tttttttttc tttctttttt tcaatttttga acattttgca aaacgagggg   240
ttcgaggcag gtgagagcat cctgcacgtc gccggggagc ccgcgggcac ttggcgcgct   300
ctcctgggac cgtctgcact ggaaacccga aagttttttt ttaatatata tttttatgca   360
gatgtattta taaagatata agtaattttt ttcttcccct ttctccaccg ccttgagagc   420
gagtactttt ggcaaaggac ggaggaaaag ctcagcaaca ttttaggggg cggttgtttc   480
tttcttattt cttttttttaa ggggaaaaaa tttgagtgca tcgcgatgga gaaaatgtcc   540
cgaccgctcc ccctgaatcc caccttattc ccgcctccct acggcgtgct caggtccctg   600
ctggagaacc cgctgaagct cccccttcac cacgaagacg catttagtaa agataaagac   660
aaggaaaaga agctggatga tgagagtaac agcccgacgg tcccccagtc ggcattcctg   720
gggcctacct tatgggacaa aacccttccc tatgacggag atactttcca gttggaatac   780
atggacctgg aggagttttt gtcagaaaat ggcattcccc ccagcccatc tcagcatgac   840
cacagccctc accctcctgg gctgcagcca gcttcctcgg ctgcccccctc ggtcatggac   900 ctcagcagcc gggcctctgc acccctttcac cctggcatcc catctccgaa ctgtatgcag   960
agccccatca gaccaggtca gctgttgcca gcaaaccgca atacaccaag tcccattgat  1020
cctgacacca tccaggtccc agtgggttat gagccagacc cagcagatct tgccctttcc  1080
agcatccctg gccaggaaat gtttgaccct cgcaaacgca agttctctga ggaagaactg  1140
aagccacagc ccatgatcaa gaaagctcgc aaagtcttca tccctgatga cctgaaggat  1200
gacaagtact gggcaaggcg cagaaagaac aacatggcag ccaagcgctc ccgcgacgcc  1260
cggaggctga aagagaacca gatcgccatc cgggcctcgt tcctggagaa ggagaactcg  1320
gccctccgcc aggaggtggc tgacttgagg aaggagctgg gcaaatgcaa gaacatactt  1380
gccaagtatg aggccaggca cgggcccctg taggatggca ttttttgcagg ctggctttgg  1440 aatagatgga cagtttgttt cctgtctgat agcaccacac gcaaaccaac ctttctgaca  1500 tcagcactttt accagaggca taaacacaac tgactcccat tttggtgtgc atctgtgtgt  1560
gtgtgcgtgt atatgtgctt gtgctcatgt gtgtggtcag cggtatgtgc gtgtgcgtgt  1620
tcctttgctc ttgccatttt aaggtagccc tctcatcgtc ttttagttcc aacaaagaaa  1680
ggtgccatgt ctttactaga ctgaggagcc ctctcgcggg tctcccatcc cctccctcct  1740
tcactcctgc ctcctcagct ttgcttcatg ttcgagctta cctactcttc caggactctc  1800
tgcttggatt cactaaaaag ggccctggta aaatagtgga tctcagtttt taagagtaca  1860
agctcttgtt tctgtttagt ccgtaagtta ccatgctaat gaggtgcaca caataactta  1920
gcactactcc gcagctctag tcctttataa gttgctttcc tcttactttc agttttggtg  1980
ataatcgtct tcaaattaaa gtgctgttta gatttattag atcccatatt tacttactgc  2040
tatctactaa gtttcctttt aattctacca accccagata agtaagagta ctattaatag  2100
aacacagagt gtgttttgc actgtctgta cctaaagcaa taatcctatt gtacgctaga  2160
gcatgctgcc tgagtattac tagtggacgt aggatatttt ccctacctaa gaatttcact  2220
gtcttttaaa aaacaaaaag taaagtaatg catttgagca tggccagact attccctagg  2280
acaaggaagc agagggaaat gggaggtcta aggatgaggg gttaatttat cagtacatga  2340
```

-continued

```
gccaaaaact gcgtcttgga ttagcctttg acattgatgt gttcggtttt gttgttcccc    2400
ttccctcaca ccctgcctcg cccccacttt tctagttaac ttttttccata tccctcttga    2460 cattcaaaac agttacttaa gattcagttt tcccactttt tggtaatata tatattttg     2520 tgaattatac tttgttgttt ttaaaaagaa aatcagttga ttaagttaat aagttgatgt    2580
tttctaaggc ccttttttcct agtggtgtca tttttgaatg cctcataaat taatgattct   2640
gaagcttatg tttcttattc tctgtttgct tttgaacgta tgtgctctta taaagtggac    2700
ttctgaaaaa tgaatgtaaa agacactggt gtatctcaga aggggatggt gttgtcacaa    2760
actgtggtta atccaatcaa tttaaatgtt tactatagac caaaggaga gattattaaa     2820 tcgtttaatg tttatacaga gtaattatag gaagttcttt tttgtacagt attttttcaga   2880 tataaatact gacaatgtat tttggaagac atatattata tatagaaaag aggagaggaa    2940
aactattcca tgttttaaaa ttatatagca aagatatata ttcaccaatg ttgtacagag    3000
aagaagtgct tgggggtttt tgaagtcttt aatattttaa gccctatcac tgacacatca    3060
gcatgttttc tgctttaaat taaaattta tgacagtatc gaggcttgtg atgacgaatc     3120
ctgctctaaa atacacaagg agcttttcttg tttcttatta ggcctcagaa agaagtcagt   3180
taacgtcacc caaaagcaca aaatggattt tagtcaaata tttattggat gatacagtgt    3240
tttttaggaa aagcatctgc cacaaaaatg ttcacttcga aattctgagt tcctggaatg    3300
gcacgttgct gccagtgccc cagacagttc ttttctaccc tgcgggcccg cacgttttat    3360
gaggttgata tcggtgctat gtgtttggtt tataatttga tagatgtttg acttaaaga    3420 tgattgttct tttgtttcat taagttgtaa aatgtcaaga aattctgctg ttacgacaaa    3480
gaaacatttt acgctagatt aaaatatcct ttcatcaatg ggattttcta gtttcctgcc    3540
ttcagagtat ctaatccttt aatgatctgg tggtctcctc gtcaatccat cagcaatgct    3600
tctctcatag tgtcatagac ttgggaaacc caaccagtag gatatttcta caaggtgttc    3660
attttgtcac aagctgtaga taacagcaag agatgggggt gtattggaat tgcaatacat    3720
tgttcaggtg aataataaaa tcaaaaactt ttgcaatctt aagcagagat aaataaaaga    3780
tagcaatatg agacacaggt ggacgtagag ttggcctttt tacaggcaaa gaggcgaatt    3840
gtagaattgt tagatggcaa tagtcattaa aaacatagaa aaatgatgtc tttaagtgga    3900
gaattgtgga aggattgtaa catggaccat ccaaatttat ggccgtatca aatggtagct    3960
gaaaaaacta tatttgagca ctggtctctc ttggaattag atgtttatat caaatgagca    4020
tctcaaatgt tttctgcaga aaaaaataaa aagattctaa taaaatgtat tctcttgtgt    4080
gccaggagag gtttcagaaa cctacctcgt cttacaaatt taaacacttt ggagtctgta    4140
caggtgcctt atatgtaggt cattgtcacg atacacacac acgaacactc cctctggact    4200
ggctgcctct ccatccaggg cagttaacta gcaaacaagg cagatctgct tcatggagcg    4260
ggaggccatg gcttgactct gagtgatttg ggtcaaccgg agtcagacgc atgtctgcac    4320
gctgcagcta ttatgagagt cccttttgtca ttttttcacct tttcatccta agcatctttc    4380
agagattaat tatttggcca ttaacaatga atccaaatca tatcatactg acatcatcta    4440
gacatgattt ggaaggaaca gcttaggacc tcctgatgag gtcacattgt tgtttctttt    4500
aactagactt ggcaaagaaa ggcaaaaatt gaccagccta tctttctgct ggtgctgcct    4560
taaggaggta gtttgttgag gggagggctg tagatcatta cttctttctc ttcaggaagt    4620
ggccactttg aaccattcaa ataccacatt aggcaagact gtgataggcc ttttgtcttc    4680
aaatacaaca ggcctccact gacccatccc tcaaagcaga aggaccctttt gaggagagta    4740
```

```
cagatgggat tccacagtgg ggtgggtgga atggaaacct gtactagacc acccagaggt    4800
tccttctaac ccactggttt ggtggggaac tcacagtaat tccaaatgta caatcagatg    4860
tctagggtct gttttcggaa gaagcaagaa ttatcagtgg caccctcccc actgccccca    4920
gtgtaaaaca atagacattc tgtgaaatgc aaagctattc tttggttttt ctagtagttt    4980
atctcatttt accctattct tcctttaagg aaaactcaat ctttatcaca gtcaattaga    5040
gcgatcccaa ggcatgggac caggcctgct tgcctatgtg tgatggcaat tggagatctg    5100
gatttagcac tggggtctca gcaccctgca ggtgtctgag actaagtgat ctgccctcca    5160
ggtggcgatc accttctgct cctaggtacc cccactggca aggccaaggt ctcctccacg    5220 tttttttctgc aattaataat gtcatttaaa aaatgagcaa agccttatcc gaatcggata    5280
tagcaactaa agtcaataca ttttgcagga ggctaagtgt aagagtgtgt gtgtgtgtgt    5340
gtgcgtgcat gtgtgtgtgt gtgtatgtgt gtgaataagt cgacataaag tctttaattt    5400
tgagcacctt accaaacata acaataatcc attatccttt tggcaacacc acaaagatcg    5460
catctgttaa acaggtacaa gttgacatga ggttagttta attgtacacc atgatattgg    5520
tggtatttat gctgttaagt ccaaacctttt atctgtctgt tattcttaat gttgaataaa    5580
ctttgaattt tttcctttca aaaaaaa                                        5607

<210> SEQ ID NO 42
<211> LENGTH: 1277
<212> TYPE: DNA
<213> ORGANISM: Homo sapiens

<400> SEQUENCE: 42 ttttttttcaa tgaacatgac ttctggagtc aaggttgttg ggccattccc cccgttccac      60
tcactgggaa tataaatagc acccacagcg cagaacacag agccagagag ctggaagtga    120
gagcagatcc ctaaccatga gcaccagcca accaggggcc tgcccatgcc agggagctgc    180
aagccgcccc gccattctct acgcacttct gagctccagc ctcaaggctg tcccccgacc    240
ccgtagccgc tgcctatgta ggcagcaccg gcccgtccag ctatgtgcac ctcatcgcac    300
ctgccgggag gccttggatg ttctggccaa gacagtggcc ttcctcagga acctgccatc    360
cttctggcag ctgcctcccc aggaccagcg gcggctgctg cagggttgct ggggcccct     420 cttcctgctt gggttggccc aagatgctgt gacctttgag gtggctgagg cccggtgcc     480 cagcatactc aagaagattc tgctggagga gcccagcagc agtggaggca gtggccaact    540
gccagacaga cccagccct ccctggctgc ggtgcagtgg cttcaatgct gtctggagtc     600
cttctggagc ctggagctta gccccaagga atatgcctgc ctgaaaggga ccatcctctt    660
caaccccgat gtgccaggcc tccaagccgc ctcccacatt gggcacctgc agcaggaggc    720
tcactgggtg ctgtgtgaag tcctggaacc ctggtgccca gcagcccaag gccgcctgac    780
ccgtgtcctc ctcacggcct ccaccctcaa gtccattccg accagcctgc ttggggacct    840
cttctttcgc cctatcattg gagatgttga catcgctggc cttcttgggg acatgctttt    900
gctcaggtga cctgttccag cccaggcaga gatcaggtgg gcagaggctg gcagtgctga    960
ttcagcctgg ccatccccag aggtgaccca atgctcctgg aggggcaag cctgtataga    1020 cagcacttgg ctccttagga acagctcttc actcagccac accccacatt ggacttcctt    1080
ggtttggaca cagtgttcca gctgcctggg aggcttttgg tggtccccac agcctctggg    1140
ccaagactcc tgtcccttct tgggatgaga atgaaagctt aggctgctta ttggaccaga    1200
agtcctatcg actttataca gaactgaatt aagttattga ttttttgtaat aaaaggtatg    1260
```

```
aaacacttgg aaaaaaa                                                  1277

<210> SEQ ID NO 43
<211> LENGTH: 4335
<212> TYPE: DNA
<213> ORGANISM: Homo sapiens

<400> SEQUENCE: 43 gcgcccctg cgctgccaac ccgcgagccc gcatcatgga tgtcgagctc ccctatttcg    60
cattgctagc cctggaattc gagaccccag acgaggacca ggattcatga aatcagtcgc   120
aggggccggg gcaggggcct ctggctcccg acactggccg agaggtgatg agtgaggttc   180
gaagaacgga agatttaaaa agcagccggg gcctccgtat tgaatgaaag acccagtgca   240
aagacatcac catgaacact agcattcctt atcagcagaa tccttacaat ccacggggca   300
gctccaatgt catccagtgc taccgctgtg agacacctg caaaggggaa gtggtccgcg    360
tgcacaacaa ccacttccac atcagatgct tcacctgtca agtatgtggc tgtggcctgg   420
cccagtcagg cttcttcttc aagaaccagg agtacatctg cacccaggac taccagcaac   480
tctatggcac ccgctgtgac agctgccggg acttcatcac aggcgaagtc atctcggccc   540
tgggccgcac ttaccacccc aagtgcttcg tgtgcagctt gtgcaggaag cctttcccca   600
ttggagacaa ggtgaccttc agcggtaaag aatgtgtgtg ccaaacgtgc tcccagtcca   660
tggccagcag taagcccatc aagattcgtg accaagcca ctgtgccggg tgcaaggagg    720
agatcaagca cggccagtca ctcctggctc tggacaagca gtggcacgtc agctgcttca   780
agtgccagac ctgcagcgtc atcctcaccg ggagtatat cagcaaggat ggtgttccat    840
actgtgagtc cgactaccat gcccagtttg gcattaaatg tgagacttgt gaccgataca   900
tcagtggcag agtcttggag gcaggaggga agcactacca cccaacctgt gccaggtgtg   960
tacgctgcca ccagatgttc accgaaggag aggaaatgta cctcacaggt tccgaggttt  1020
ggcaccccat ctgcaaacag gcagcccggg cagagaagaa gttaaagcat agacggacat  1080
ctgaaacctc catctcaccc cctggatcca gcattgggtc acccaaccga gtcatctgcg  1140
ctaaagtgga taatgagatc cttaattaca agacctggc ggctctcccc aaggttaagt    1200
ctatctacga ggtacaacgc cccgacctca tttcctatga gcctcattcc agatacatgt  1260
ccgacgagat gctggagaga tgtggctatg agagtcgct gggaacatta tctccctact   1320
cccaggacat ctacgagaac ctggacctcc ggcagagacg ggcctccagc ccggggtaca  1380
tagactcccc cacctacagc cggcaggca tgtcccccac cttctcccgc tcacctcacc    1440
actactaccg ctctgggccc gagagtggcc ggagctctcc ataccatagc cagttagatg   1500
tgaggtcctc cactccaacc tcttaccagg ctcccaagca ctttcacatc ccagctggag   1560
acagtaacat ctaccggaaa cccccgatct acaaacggca tggtgatttg tctacagcaa   1620
ccaagagcaa aacaagtgaa gacatcagcc agacctccaa gtacagtccc atctactcgc   1680
cagaccccta ctatgcttcg gagtctgagt actggaccta ccatgggtcc cccaaagtgc   1740
cccgagccaa aaggttctcg tctgaggag aggaggatga ttttgaccgc agcatgcaca   1800
agctccaaag tggaattggc cggctgattc tgaaggaaga aatgaaggcc cggtcgagct   1860
cctatgcaga tcctggacc cctccccgga gctccaccag cagccgggaa gccctgcaca    1920
cagctggcta tgagatgtcc ctcaatggct cccctcggtc gcactacctg ctgacagtg    1980 atcctctcat ctccaaatct gcctcccctgc ctgcctaccg aagaaatggg ctgcacagga  2040
cacccagcgc agacctcttc cactacgaca gcatgaacgc agtcaactgg ggcatgcgag   2100
```

```
agtacaagat ctacccttat gaactgctgc tggtgactac aagaggaaga aaccgactgc    2160
ccaaggatgt agacaggacc cgtttagagc gccacctgtc ccaggaagag ttctaccaag    2220
tctttggcat gaccatctct gagtttgacc ggctggccct ctggaagagg aatgaactga    2280
agaagcaagc ccggctgttc taggcagagg ctctataaat atatatgcat ttatataaag    2340
atatatgtaa aatctctcta ctgaagctcg gtataatcct ctcttgtgta atgggacaca    2400
ctgcctgcca tgagacttgc ttttctgtac tgtcaggcaa gcccacgtca tcgagatatt    2460
tttatgctcc ttactttctc ttttctaagt gctgtgggat ctgggaaggg atttgagggg    2520
actctgtcct tttattgggg atccttttta tactgaaaca tctgtcctaa cttgagtgcc    2580
ccaaggtcca actctctttc ctaaagaagg tgcctgaaga agtctctctt ctctctgctt    2640
cgtggcccct ttcttaaatt tctagggctg atgctgacca tgtggtttcc acaccttatt    2700
ggccccagag gggccctccc atgggaagat ctgcagcagt ctccccaaat cagtgagcac    2760
ctttgagcgc ccacgaagaa cttctcaac accccccaatt aggagctcag tgctctcttg    2820
gggcaatgca gttaaaaggg tgagcctcaa atctagtcat tacaccagtc aacagaagtg    2880
gacagggcct aggcctctcc tcagctcctt aaccctcctc cttctgccct ggattgtaac    2940
ctctcccttg tccaaatcta ggattcctgg taggaaaagg aaaaggccct tcccttccct    3000
ccaccacttc caactggccc cttttgcctga cctggacttg gagaaccaga ggaaaagaga    3060
gggagcggaa gtgggagatg gagcagggca cctgttagaa tcagagctgc aggatttctt    3120
gggaccctcc tctctccctc actgctccca gcacctcctg accccttccct ctttcaagga    3180 gaagcccatg attgcagctt gtattcttta gccttattac aatctatgtg cctgacaact    3240
caacacaccg cagggctaat gttcccacca gagctccaac tgaacaacca gacagacaac    3300
tctcatcatc ctccagagag aaaataggcc gtgtctcaaa gaaaggttct tggtctatgc    3360
ctctggtctg tgggctggca gggcaaccat accatacccc cgccagtcct cggctcctgc    3420
tgcaaagttg gccatgtttc acagggaaac ttttggaaga gtggctgctt atgagattcc    3480
aaaatgaagt gttggccaac accgctcatg gccatcctgg attttcccag tggcttccct    3540
tcctgctcgc ctccctgaac aggggagaaa gcttaacctc tcttctcctc tccaaaccttt    3600 tcaccttgaa tgggtaatgt ttggtggggg ctgttccttc ttggagaagc cttgagtcgg    3660
accattttga gatcatggag gaaggatgaa gaagtgaaaa tgacaataat gactctcaag    3720
aggctggcga tgtgacatgg caaatgtaga actgacttaa attgaacaaa ccctcactga    3780
gcacctctga tgttgagcac ctgctgaata ctgagcactg aatgggggag ggggagggga    3840
gcacggggtg agtcaacctg ggactcggtc tcagggatat gcctaccaat agcgggtatc    3900
gtaaggcatg tacccaaaca taacggatgt aaggcagaaa gtgatcggag aaggaatgag    3960
aaagtgtgcg tgatgttaat gaaaagtcat atgcagctag agcagaccca ggaaagcttt    4020
ctggaagaga ttgcatctga ggaaattcag gaaggatctt tgtagattgg ggggagattc    4080
taaattgaag gggtgatggg gtgaggggcc agagggaagt ctgctgtgtt ctcatgtagg    4140
atgtcagccc tccctgcaac ttctcttttt ggccaatgtc ttttcacttt cctgaccctt    4200
tagaatcatc cccagccaga cgcaatcatg gaagttgcct tattgtcact ggttaagaac    4260
ttggcgagat tgaagggctt ttgttattgt tgttggatat ttttgtttcc cataaaagca    4320
catcatttca accct                                                     4335
```

<210> SEQ ID NO 44
<211> LENGTH: 5873
<212> TYPE: DNA

<213> ORGANISM: Homo sapiens

<400> SEQUENCE: 44

```
gaaaaatgct tcctgtttct ttaaaggcgc tcgcggctcg ggcggcccgg gctggggagg      60
cggtggcggc gggagctgcc tcctctccgg gcggcggcgc tgactgatct cgcgaactgg     120
gcttctgtgt aaactgaggc taaacaaaca cagatggagc gcagcgggcg ttctccagaa     180
atgctggcaa ggaggcagcg acttcagatg acactctgag cgctccggga acggacagcc     240
cggcggcttc ccgaagccgg cggcgcagct gcccggggcg aggggagaa agggagagag      300
ggaggggag ggcgggcgaa gcgggagagc cagagactcc tcggcgctga gcgcggcggc      360
ggcccgggca gccccacgcc cctgcctcgc gcgccgcccg cgccatgaag cacatcccgg     420
tcctcgagga cgggccgtgg aagaccgtgt gcgtgaagga gctgaacggc ttaagaagc      480
tcaagcggaa aggcaaggag ccggcgcggc gcgcgaacgg ctataaaact ttccgactgg     540
acttggaagc gcccgagccc cgcgccgtag ccaccaacgg gctgcgggac aggacccatc     600
ggctgcagcc ggtcccggta ccggtgccgg tgccagtccc agtggcgccg gccgttcccc     660
caagagggg cacggacaca gccggggagc gcggggctc tcgggcgccc gaggtctccg       720
acgcgcggaa acgctgcttc gccctaggcg cagtggggcc aggactcccc acgccgccgc     780
cgccgccgcc tcctgcgccc cagagccagg cacctgggg cccagaggca cagccttttcc    840
gggagccggg tctgcgtcct cgcatcttgc tgtgcgcacc gcccgcgcgc ccgcgccgt      900
cagcaccccc agcaccgcca gcgccccgg agtccactgt gcgccctgcg ccccgacgc      960
gcccggga aagttcctac tcgtcaattt cacacgtaat ttacaataac caccaggatt     1020
cctccgcgtc gcctaggaaa cgaccgggcg aagcgactgc cgcctcctcc gagatcaaag    1080
ccctgcagca gacccggagg ctcctggcga acgcagggga gcggacgcgg gtgcacacca    1140
tcagcgcagc cttcgaggcg ctcaggaagc aggtgccgtg ctactcatat gggcagaagc    1200
tgtccaaact ggccatcctg aggatcgcct gtaactacat cctgtccctg gcgcggctgg    1260
ctgaccttga ctacagtgcc gaccacagca acctcagctt ctccgagtgt gtgcagcgct    1320
gcaccccgcac cctgcaggcc gagggacgtg ccaagaagcg caaggagtga ctggctgcag    1380
gcaagaccaa ggccaccact gtgggccctc cttccagtca ggcctgagga caaggtgagc    1440
tcgctgagtc cagcctcgtg gtcttctcca agatgccgcc agatgcccag cctacagcct    1500
ctcagggtcg gatcggagca cgcctgcctc cctctcccct ccgccctcac ccagccaatc    1560
cgaggctgct tcgcactttg ccctctgcct ggtggggagg ggagagctca gcccccgact    1620
cactcagacc ccaaggccca ctgtccagct gcagaaattc gttgccaaag attggacaga    1680
gacaccgaag gaaatgggt ggtgaaaccc cacagcgaaa agccacaccg ttgctctgtg     1740
acttttgctc ctcctgttgc ctgagcccca tctcaagcca aagatgagtc agtggttctg    1800
ctaggaactc atggaatgga tgggcatttg atgaccctg ggggtcatct tggccctctg     1860
acctggtgct ctctctccac tgggccttgt gctggctgag tgcaagacaa gccttagggg    1920
ctgtgagagg gaggctgggg tgcctggcg gggctgggag tggacctga gatccctgcc      1980
cactctctcc ccttcattgg ctgcccaggc cactggcccc agttctcagt gtcccttggg    2040
tccaggctcc ttgggcccta agcatcacca gaagggagta agcagggaga gaagcaatat    2100
tactccctcc cctacaccag ggacttgccc cagggcagct acctatgggt ctttgcttcc    2160
ccagccagcc tctcctcact gtgacccacc ccatgggcc ccgtcccag gcagccagca     2220
ccatgggcag gccctgccat ggacagaaaa agagttttc tcttgttcag cctgcacgtg    2280
```

```
gcctgaggaa ggagtagagg ctgggttggc tggagccgtc ctactgggca agatggcgcc   2340
ccacttggag ggcggtggtc tgttacaggg tgtgcagggg cagagaagga agggaccagg   2400
ggactgggcc agtatgtgga ggatggggcc tgcgtgttca aagccaaggc ccgccccttc   2460
cttgtgctca aatggccaaa gctgttcacg tctgtgctca accatctgct tcaaattgaa   2520
gtaaaagccc caaatgtca agaaaatact tgtgttgagt ggactctgtg ggtgaccagg    2580
actttggccg gtcatcagct ggggagtgtg agggaggggg ttggtttcta cctacaggtt   2640
gagagccctt caggatcagg cgctgtccga gtgagagtgt gtgtgtctgt gtgtggaagg   2700
gggtggaggg cggttcccac agtagtctca gcctggacta gtgaccagga ggcctggtca   2760
ggaacacatg aggagccctc tctgtccgca ctgcactcaa tctgtaccat ggatttatga   2820
gataggggcc cctattatta accccgtttc acagatgggg taactgaggc ctcaagtaga   2880
cagggtcagt cggtgacaga gccagtcatc gaatcaggat gggctcactt caaatcctgt   2940
gctctcaaac cttttccagc cccatcacca gtcccagccc aaagtctctt gtgtggcctt   3000
gtcacattgc ttcacctcag cgggcctaag gtagggacaa taaaggccca ttgggactgg   3060
gggaaggggt gataagataa aaaataggag agcactgtca aggcagaagg gacagggctg   3120
gccaaggaaa gggggatagg aggggaccgg aggctgcagc catacaggac acagtttgtc   3180
ccttggtttc accagtgtca ctttctcgtc tctgctgctc agactcctgg gctgggctgg   3240
ggctggctgc agggagcccc ccttgcagta gcgtttctca ggctggccct ttaccaagga   3300
ccacagtgtc catgctgtct tggatcccta ggctggcaca gaaacagggg acccaggtgg   3360
ccctgagcac tcctcagagc aaaggtgctc tggaagcaga ctggacagag tgggcatgga   3420
atggggccag gagggtctgt taggaaggtt cagccaccct gtgaagctgg cacagataac   3480
agcactgctc tgttgtccct cggagcctct gagtaaccct gatggcactt cctaaggcag   3540
caggacatgt ggactgacca gcatcaaact gttgacatag aagaccattt ctattaccaa   3600
agggagtgta cccattctg ctgccaaggg agcaaaccca tggccttacc acccagaaag   3660
agcccatcct ccacctccca tcccctcct gcatacatac ttcattacat gtttcccttt   3720
cattctgaag catcattgat gaccagctgc ctgtcagaca ctaagatagg cagtgggaat   3780
gaagagatgg atcttgtgtc atgcatggca tcacggagct ctgggttctg tacggagggt   3840
gggacagaca ggtagacaag caaataatta tgattatagc agatgactaa ggtgttgtcg   3900
ggagcttcag gaaaggaaga actaactctt ggggaggttc tcaggaagga tttccctgga   3960
aagtagccat gggacttgcg tcttaaatgg tgagtaaaag ctttctgagc aggggagtag   4020
gaaaagggct ttctatgcag aggagcactc agcgctggca ggaaattgga atcacccaag   4080
gagattatta aatattaaat attgatatga agtattgatg cccaatttca tctccagaaa   4140
ttctgatgta ttggtctagg gtgttgcctg gtcattggga tttttacaag ctcctcaagt   4200
gatcttaatg tgcaggcaag gttgaagccg ctggtctaag tggggtctgg tctacgataa   4260
gaaagtgact ttgagccatc gatttgggag acaggctctg ggtggatgtg tgtgtgtgca   4320
cacatatgta tgtatgtgga tgactaaaag tgcatgctct cctctccttt cccagcttcc   4380
tctccagcac agcaacttgt gttcgtatgc acacacatgc atactctctc tcatgggcac   4440
atgcataccc acacacacac tcgtgtacat ttccagaaaa tggaattaca tttcagatag   4500
attcagattc caacggcagt cttctaaaca ctttttatgca agcagccatt caaggagacc   4560
ctcagcaaaa tataaatgac gaggagctgc cctcatgggg ccctgtgaaa gcactttgca   4620
gtccagcctt gggtttgtgg tcacagagtc acctgtggat gtttgtagca cactctcctt   4680
```

```
gtcttgtctg ctctgggtca ccaggcacag gccataaagg gatgaggggg ccctctccag      4740
ggacccgcaa gatcttcctg ggtatgtctg catgaagccc cacgtgtgca cacccatctt      4800
catgtgtgtg tgtgccagcc tcctgctctc tgcagaacaa aaccagaagg aatggctctg      4860
ggagttggag atctcagctc acaggccaag ctttgcaaga ctctccaaag actgccaca       4920 gactgtgctg cttcctgggt ctggcctgag actatcccag aagagagggt taaattctgg      4980
aggtgaggtt ttgagcaagt gttcatcccc ccacactatg ctccttcctg tctccatggc      5040
cacatccttc aaggctctgt gctgttctct tttttctgg atttctccac ctccaccaag       5100 ttccccttc tcacagctag tggaggcatg agtaggcagg tcccaggggc tgggaactgg       5160
gtagcattgc catgtgcagg gactgtgttg ggagctgcag gtacagagct cctctgtgct      5220
caagagcttg ccggtgagcc tggacggagg cataggtgca gctaattagg ataagacagg      5280
ggccgcgctg tggtcagccg tgggaagccg gcgagggac tggagttggg gctacacttg        5340
cctccctcct atgctgcttc ctgagccacg aagtggtcat tgccagcatc ccaggcaaca      5400
aacagcaaga ctcagacatc tccaaggaaa ccctttgagt ggatctgtac cgttgttctc      5460
gtcttgctct cttgctgccc tgccaccttc acagctgctt tctgtttcct ggttccagga     5520
agacagcggg gcacagggtc cctgctttgt gaggagcagc tggcttctcc ctttgcccc       5580 aggttttgcc ctcccacatg tctccttct ggtgacccgg accccagaca aactatgcct       5640
gcctccctga agccaggcat cctgaggaac ttgatagaca aacaatgaca gtgttttcca     5700
gaactgtggg tacgtgtcta atctcagatg gtactatgaa ttcctggaga tcaaagtttg      5760
gatctaattc aaccctgat cctcgaaacg gctttcttgc aaagtgtata tattggtttc       5820
tttgctgaat gaatgaataa aacatggaaa atgtggtaat tcaaaaaaaa aaa              5873

<210> SEQ ID NO 45
<211> LENGTH: 2779
<212> TYPE: DNA
<213> ORGANISM: Homo sapiens

<400> SEQUENCE: 45
ccggggaccg tttgtagtta ggatccgctg tggcgtcctg agtggagttt gggacccag         60 ggagggaggg tgtgggcgtt cgggtccaga ggagctgttt agtatccaag atgaatgaca       120
gcctgtttgt cagtttggac agacttttgc tagaatttgt cttccagtat gagcaagaca       180
taagtactaa agaagagatg attcaaagaa ttaataaatg ctgtgaagat attaaggaaa       240
acaaagtaac tatttgtagg atacacgaaa ctataaatgc aacagatgag gaaattgatc       300
attactgtaa acatagtgag gagattaaag acaactgtag aaactggaag ccaacatgtg       360 atgttttcg taaacatgaa gattatatgc aggaccaatt tactgtttat caaggaactg       420
ttgaaaaaga caaagaaatg tatcatgatt atatatgtca gtataaagaa gttttgaagc       480
agtaccaact aaaatactca gaaacaccct tttcacgtga atattatgag aagaaaagag       540
aacatgaaga aattcaaagc agagtgttgg catgtactga acaattaaaa atgaatgaaa       600
caatttttat gaaatttcga gtgcctgctc cctttccatc acttactaaa tggactttaa       660
acattgttaa tttgagatgt gaaacacaag atattcttaa acatgccagc aatcttacca      720
aaagttcatc cgaattgaag aaagaagtag atgaaatgga aatagaaatt aattatttaa       780
accagcagat atctaggcat aatgaaacta aggctctttc agaaactctg gaagaaaaga      840
acaaaaatac agaaaacaga aaagaactga agaaagaat ttttggaaaa gatgagcatg         900
tacttacatt gaataaaact caaagcagtc aattatttct tccttatgaa tctcagaaat        960
```

-continued

```
tagtaagacc aataaagatg cattcttcag aaccaagagt tgcagatata aagaagaaa      1020 gttctgcgaa gcagtcaaag cttgccaata ttgactttag acaaaaagaa aatgatacac     1080
agatatttaa tgactctgct gtggataacc attcaaaatg ttcacatatt acgactatca     1140
caagttcaca aaagtttatg caagtcagat tgttaacccc acagaaacaa tcaaattcca     1200
atcagtggtc ggaaaaaggg gataaagatg ctgagtatgg agataaaggg acagtaagac     1260
aagtaagaga atcaaaatgt acttcacaag ctatatatac tgaacatttt gggaagtcaa     1320
tagaaaatga tagtgatgaa gtagaagaga gagctgagaa ttttccacga acgtctgaaa     1380
ttcctatatt tttaggaact cccaaagctg tgaaagcacc tgagtcattg gagaaaataa     1440
aattccctaa aaccccccg ttcgaaatta acagaaatag aaatgcagta cctgaagttc       1500
aaacagaaaa ggaatcccct ggactttctt ttcttatgag ttatacttct agatcacctg     1560
gattgaattt atttgattct tctgtatttg atacagaaat ctcatcagat cagtttaatg     1620
aacattattc tgcaagaaat ctaaatcctc tgtcatcaga gcaagagatt ggaaacttac     1680
ttgagaagcc agaaggagaa gatggcttta cattttcttt tccatcagac acttcaactc     1740
atacatttgg agctggaaaa gatgattta gttttccatt ttcatttgga cagggtcaaa      1800
attcaatacc ttcttcttct ttaaaaggtt tttcatcttc ctcacaaaat acaacacagt     1860 ttacttttt ttgagctagt cattaattcc ttaaattatt ttactgttct gtgttcatga      1920
gggcataaat ttacattatt gcttaaaaca tgaagactgc tttcttttat tgattaaagc     1980
agtaatgttt acattatttg attatattta ttgaaatatt gaaatactga atattttggg     2040
ttttgtgtgt gctattaact aatcattatt tattttggtt ttgattttgc gagccgtggt     2100
caggtagaac ttttattaat cttaatagaa tttgatgctt ttttcattac tctttattta    2160
aatattaagc ctgcttctcc ttggaaccta aggttttttt ctggaagtat tgttgggtact   2220 ttgataagaa caagaactgc agtagtaact ccagagttag tgctgaagcg tactttagct    2280
actaaaaatt tctattaaaa ttattgggtt tcacttctgc ttcactatgt agtatacaga    2340
gtggtactgt aataataatt tcaaataatt tatgttaata acaaaatctg tgttattttc    2400
ttctaatata acacatggta caattctaat tttatgagtt atgctaatgc tttcaatggc    2460
taaaaattaa atgtaaaggg caagagtaat ttctgaaaat tggattgttg tatcagtggt   2520
gatcctgtta atattctttt ttgcttaaat atttttgaa gaacatttac aattttgtct     2580
ccttcaataa caaaaatttc ttctttatgt tttgtgttca gtatttgtca attaattata    2640
tagcttaagt gaagatattt aagatttgat gaacttctgt aaacattttg ctcaatatca    2700
ttgtattttg tgctttgtaa attagctgta ctgagttacc aagtaataaa gggtttgact    2760
ccaaaaaaaa aaaaaaaa                                                  2779
```

<210> SEQ ID NO 46
<211> LENGTH: 2923
<212> TYPE: DNA
<213> ORGANISM: Homo sapiens

<400> SEQUENCE: 46

```
gtcgcgggag ctctctgatc cactcagggg tcagggcatc actggtctcg cgtgcgcgtg       60
accaggcccg gttccggtg ccaggacctt tccgaagcgt cgagtggcct aacggtcaca       120
gctgtcgccc atcggagagg caggactact gcgagcagtt ttaccgcgac ctccggaggc     180
cggcgtgaca ggtctgtca ctaaaatagg agtagaggtt taccactctt aggtgactaa      240
gcagtatcac aaataaaccc tccagcaagt ttaaaaataa ttaggtccaa ctcagaggaa     300
```

-continued

```
gtggagtttc tcctgttgca caaaaatgat gtctaacagc tccagtgaaa tcgatgtgat      360
aaaaacaaga atacctactt acgatgaaga tgacaacact attctttatg cgtatgaaac      420
aaaacctgaa tttgtcaata aagaaccgaa tattgtatct gacgcatcct gtaatactga      480
agagcaactg aagacagttg atgatgtcct tattcattgc caggttatat atgatgctct      540
gcaaaacctg ataagaaga ttgatgtgat tcgtagaaag gtttcaaaaa tccaacgttt       600
ccatgcgaga tccctgtgga caaatcataa gcgatatgga tataaaaagc attcttaccg      660
gcttgttaaa aagcttaaac tccagaaaat gaagaaaaat gaggtttacg agacattctc      720
ctaccctgaa agttacagcc ccactttacc agtgtcaagg cgtgagaata attccccgag      780
caaccttcca aggccatcct tttgcatgga agaataccag cgagctgagc tggaggagga      840
cccgatcctc agccgcactc cgagtccagt gcatccctca gatttctctg agcataattg      900
tcagccgtat tatgcatctg atggtgcaac gtatggttct tcttcagggc tctgccttgg      960
caaccctcgg gctgacagca tccacaacac ttactcaact gaccatgctt ctgcagcacc     1020
accttcagtt acaaggtcac cagttgaaaa tgacggttac atagaggaag gaagcatcac     1080
taagcaccct tcaacctggt cggtggaagc agtggtccta tttctaaaac aaacagatcc     1140
tcttgcatta tgccctcttg tcgacctctt cagaagccat gaaattgacg ggaaggctct     1200
gctcctactc acgagtgacg tgttgctgaa gcacttgggg gtgaagctgg gaacggctgt     1260
gaagctatgc tactacattg accgacttaa acaaggaaaa tgctttgaaa attgaaaaaa     1320
tccttgtgca aatttagatt gggccaactt ctagaggcac caatgccttc ttagtgtgga     1380 atcattttc tgccctttag tcgttttgt tttgtagaaa gtatctctca aaatatatta       1440
tagctagaat tgtagaacta tgttatagtc cagtctactt cttttaaaaac catttaaact    1500 gctagatagt attagaatag tccaatagaa aattcattct ttataggtct ttaaaaatta    1560
cttttattat attgtttaca aatatatttc atgcaagaaa cagaaaaaaa aaaaaaccct    1620
ttgattctgg ttcatctcga tacagagaac caaaacagct aagagaggta ttatcagggt    1680
tgacaactcc tatgattgaa tctatgggaa ttattcctca gaagagaatt taaaggtgta    1740
cccatatata tctcttctg gagtatttta tctgtctgat gttgcagtat tctacaagtt     1800
tccagaaaga gaatagccat ataaattatt ttcctttctg ctattatttc tctatatgtt    1860
ttatttattc agatttagag taaaaaataa gcatataaac ttttattatg tgctcttaac    1920
agttttaaga taaactatag gatagataga atggttattt tatgcaagaa atattgtacc    1980
gcaagggtgg tttggatgaa gtctgactac tttttttcaa acaaactatt atattaaaac    2040 tgtcatatt tggctaagtt tggacctata actacacttt cattgtttgc atctctctat     2100 gaagatacg ctgtccaaac ttttaaaagg cataactgta ttttatgtgt ttattcttta     2160
tatagatagt attttatatt ttattctcac ccgaagtatt cacacaatct ttttaaaaaa    2220
aatttgaaat ggcattttgt attgccacag aggtaggatg agccatatat tagtgaaatg    2280
ttttattttg taaaatataa atggattatt tgccatcatt agtacctctc aacttacttt    2340
ttagaggaca agaaacaatc tgtagattgg tttccataca gggaagttct ccgtcctatg    2400
caatgtttct aattaatttg cttaattctg agccattaat cctgctacac tttgaatgat    2460
acattaattc agactaatct tgggggcctt tattttgtaa gttagaactt tcaagggaaa    2520
catgttcaac actattattt tgttataaat ttataacttt gttattacat tgtgtaacaa    2580
atataaggtt tacgagctat gagaattggt gctatcacca ttagctattt gctgtaatgt    2640
caagaaaatg ttcaccagat gcaagaatgt acctttctt tttagaaagc caaatgtact    2700
```

| | | |
|---|---|---|
| ttagacatga atgcaactat ttaaagaata gcttcatcaa tgttattcct tacatgtcat | 2760 |
| aagattctta cttaaacttg gtcttctttc aaattgtttg tatgaagatg ctgtacccac | 2820 |
| ttgaacagtc ctcaggtgtt tacataaata ctatgtttta cagttttcat attttaaaat | 2880 |
| attaataaag ttaaatcaca atagttcaaa aaaaaaaaa aaa | 2923 |

<210> SEQ ID NO 47
<211> LENGTH: 2842
<212> TYPE: DNA
<213> ORGANISM: Homo sapiens

<400> SEQUENCE: 47

| | |
|---|---|
| gtcgcgggag ctctctgatc cactcagggg tcagggcatc actggtctcg cgtgcgcgtg | 60 |
| accaggcccg gtttccggtg ccaggacctt tccgaagcgt cgagtggcct aacggtcaca | 120 |
| gctgtcgccc atcggagagg caggactact gcgagcagtt ttaccgcgac ctccggaggc | 180 |
| cggcgtgaca ggctctgtca ctaaaatagg agtagaggtt taccactctt aggtgactaa | 240 |
| gcagtatcac aaataaaccc tccagcaagt ttaaaaataa ttaggtccaa ctcagaggaa | 300 |
| gtggagtttc tcctgttgca caaaaatgat gtctaacagc tccagtgaaa tcgatgtgca | 360 |
| ggaaccgaat attgtatctg acgcatcctg taatactgaa gagcaactga agacagttga | 420 |
| tgatgtcctt attcattgcc aggttatata tgatgctctg caaaacctgg ataagaagat | 480 |
| tgatgtgatt cgtagaaagg tttcaaaaat ccaacgtttc catgcgagat ccctgtggac | 540 |
| aaatcataag cgatatggat ataaaaagca ttcttaccgg cttgttaaaa agcttaaact | 600 |
| ccagaaaatg aagaaaaatg aggtttacga gacattctcc taccctgaaa gttacagccc | 660 |
| cactttacca gtgtcaaggc gtgagaataa ttcccccgagc aaccttccaa ggccatcctt | 720 |
| ttgcatggaa gaataccagc gagctgagct ggaggaggac ccgatcctca gccgcactcc | 780 |
| gagtccagtg catccctcag atttctctga gcataattgt cagccgtatt atgcatctga | 840 |
| tggtgcaacg tatggttctt cttcagggct ctgccttggc aaccctcggg ctgacagcat | 900 |
| ccacaacact tactcaactg accatgcttc tgcagcacca ccttcagtta caaggtcacc | 960 |
| agttgaaaat gacggttaca tagaggaagg aagcatcact aagcacccctt caacctggtc | 1020 |
| ggtggaagca gtggtcctat ttctaaaaca aacagatcct cttgcattat gccctcttgt | 1080 |
| cgacctcttc agaagccatg aaattgacgg gaaggctctg ctcctactca cgagtgacgt | 1140 |
| gttgctgaag cacttggggg tgaagctggg aacggctgtg aagctatgct actacattga | 1200 |
| ccgacttaaa caaggaaaat gctttgaaaa ttgaaaaaat ccttgtgcaa atttagattg | 1260 |
| ggccaacttc tagaggcacc aatgccttct tagtgtggaa tcatttttct gcccctttagt | 1320 |
| cgttttttgtt ttgtagaaag tatctctcaa aatatattat agctagaatt gtagaactat | 1380 |
| gttatagtcc agtctacttc tttaaaaacc atttaaactg ctagatagta ttagaatagt | 1440 |
| ccaatagaaa attcattctt tataggtctt taaaaattac ttttattata ttgtttacaa | 1500 |
| atatatttca tgcaagaaac agaaaaaaaa aaaacccctt tgattctggt tcatctcgat | 1560 |
| acagagaacc aaaacagcta agagaggtat tatcagggtt gacaactcct atgattgaat | 1620 |
| ctatgggaat tattcctcag aagagaattt aaaggtgtac ccatatatat ctctttctgg | 1680 |
| agtattttat ctgtctgatg ttgcagtatt ctacaagttt ccagaaagag aatagccata | 1740 |
| taaattattt tcctttctgc tattatttct ctatatgttt tatttattca gatttagagt | 1800 |
| aaaaaataag catataaact tttattatgt gctcttaaca gttttaagat aaactatagg | 1860 |
| atagatagaa tggttatttt atgcaagaaa tattgtaccg caagggtggt ttggatgaag | 1920 |

```
tctgactact ttttttcaaa caaactatta tattaaaact gtcatatttt ggctaagttt    1980
ggacctataa ctacacttc attgtttgca tctctctatg aagatacgtc tgtccaaact    2040
tttaaaaggc ataactgtat tttatgtgtt tattctttat atagatagta ttttatattt    2100
tattctcacc cgaagtattc acacaatctt tttaaaaaaa atttgaaatg gcattttgta    2160
ttgccacaga ggtaggatga gccatatatt agtgaaatgt tttattttgt aaaatataaa    2220
tggattattt gccatcatta gtacctctca acttactttt tagaggacaa gaaacaatct    2280
gtagattggt ttccatacag ggaagttctc cgtcctatgc aatgtttcta attaatttgc    2340
ttaattctga gccattaatc ctgctacact ttgaatgata cattaattca gactaatctt    2400
tgggggcttt attttgtaag ttagaacttt caagggaaac atgttcaaca ctattatttt    2460
gttataaatt tataactttg ttattacatt gtgtaacaaa tataaggttt acgagctatg    2520
agaattggtg ctatcaccat tagctatttg ctgtaatgtc aagaaaatgt tcaccagatg    2580
caagaatgta ccttttcttt ttagaaagcc aaatgtactt tagacatgaa tgcaactatt    2640
taaagaatag cttcatcaat gttattcctt acatgtcata agattcttac ttaaacttgg    2700
tcttctttca aattgtttgt atgaagatgc tgtacccact tgaacagtcc tcaggtgttt    2760
acataaatac tatgttttac agttttcata tttaaaata ttaataaagt aaatcacaa    2820 tagttcaaaa aaaaaaaaaa aa    2842

<210> SEQ ID NO 48
<211> LENGTH: 825
<212> TYPE: DNA
<213> ORGANISM: Homo sapiens

<400> SEQUENCE: 48
gcatggcacc ccgcccctcc ttggccaaga aacaaaggtt taggcatcgc aaccgcaaag     60
gctaccgttc acaacgaggc cacagccgtg gccgcaacca gaactcccgc cggccatccc    120
gcgccacgtg gctgtccttg ttctccagtg aggagagcaa cttgggagcc aacaactatg    180
atgactacag gatggactgg cttgtgcctg ccacctgtga acccatccag agtgtcttct    240
tcttctctgg agacaagtac taccgagtca atcttcgcac acgacggtgg cagcgggttg    300
ggttcccacc ggagaaagcg gaccaccttc agcaaagggc agctactgga gctggagagg    360
gcgtttgcag catggcccta ccccaacatc agcacccatg agcacctggc ctgggtcact    420
tgccttcctg aggccaaggt acaggtgtgg ttccagaagc gctgggccaa aataatcaag    480
aacaggaagt caggaattct aagccctggg tctgagtgcc cccagagctc ctgttctctt    540
ccagacaccc tccagcagcc ctgggatccc caaatgccag gccaacctcc accctccagc    600
ggcacacctc agcgcacctc agtgtgtcga catagctcct gtccagctcc tggcttgagt    660
ccacggcagg gctgggaagg ggctaaagct gtagcccat ggggatcagc tggggcttca    720
gaggtccacc cttcttttaga gcagctact ccccagactt cactaggcag cctgtctgac    780
ctcatctatg ccttggccat tgtcgtcaat gtggaccact cctag    825

<210> SEQ ID NO 49
<211> LENGTH: 2028
<212> TYPE: DNA
<213> ORGANISM: Homo sapiens

<400> SEQUENCE: 49
gcgcgccaag cacttccgga agcggcggcg ctcgggagga agtgccgatc ggctgctggg     60
gcgaaaaggg ggcgccgggc cgctctagcc ggtgaggccg gcgggctctc tgtggctgcg    120
```

| | |
|---|---|
| gctgggaaac cgcgcggagg aggtgcccgg ccggggacca gccctggtcc agcgcctccc | 180 |
| tctctcagca tggacgagga gagcctggag tcggccttgc agacctaccg tgcgcagctg | 240 |
| cagcaggtgg agctggcctt gggcgccggc ctggattcgt ctgagcaggc tgacctgcgc | 300 |
| cagctgcagg gggacctgaa ggagctcatc gagctcaccg aggccagcct ggtgtctgtc | 360 |
| aggaagagca gcttgttggc cgcgctggac gaagagcgcc cgggccgcca ggaagatgct | 420 |
| gagtaccagg ctttccggga ggccatcact gaggcggtgg aggcaccagc agcggcccgt | 480 |
| gggtccggat cagagaccgt tcctaaagca gaggcgggc cagaatctgc ggcaggtggg | 540 |
| caggaggagg aagagggaga ggacgaggaa gagctgagtg ggacaaaggt gagcgcgccc | 600 |
| tactacagct cctggggcac tctggagtat cacaacgcca tggtggtggg aacggaagag | 660 |
| gcggaggatg gctcggcggg tgtccgtgtg ctttacctgt accccactca caagtctctg | 720 |
| aagccgtgcc cgttcttcct ggagggaaag tgccgcttta aggagaactg caggttctcc | 780 |
| catgggcagg tggtctctct ggatgagctg cgccccttcc aggacccaga cctgagctcc | 840 |
| ctgcaggccg gctctgcgtg tctggccaag caccaggatg gcctctggca cgcagcacgc | 900 |
| atcaccgatg tggacaacgg ctactacaca gtcaagtttg actcgctgct gctgagggag | 960 |
| gccgtggtgg aggggacgg catcctgccc ccactgcgca cagaggccac agagtccgac | 1020 |
| tcagacagcg acgtacgggg tgactccagc tatgccagag tggtggggtc ggacgccgtg | 1080 |
| gactctgcac agtcctctgc cctctgtccg tctcttgcag tggtggggtc agatgctgtg | 1140 |
| gactctggga cctgcagctc tgcctttgct ggctgggagg tgcacacgcg aggtataggc | 1200 |
| tccagactcc tcaccaagat gggctatgag tttggcaagg gtttgggccg acacgcggaa | 1260 |
| ggccgggtgg agcccatcca tgctgtggtg ttgcctcgag ggaagtcgct ggaccagtgt | 1320 |
| gtggagaccc tgcagaagca gaccagggtt ggcaaggctg gcaccaacaa gccccccagg | 1380 |
| tgccggggaa gaggggccag gcctggggc cgcccagctc ctcggaatgt gtttgacttc | 1440 |
| ctcaatgaaa agctgcaagg tcaggctcct ggggccctag aagccggggc ggccccagcg | 1500 |
| gggaggagga gcaaggacat gtaccatgcc agcaagagtg ccaagcgggc cctgagcctg | 1560 |
| cggctcttcc agactgagga gaagatcgag cgaacccagc gggacatcag gagcatccag | 1620 |
| gaggctctcg cccgcaacgc tggccggcat agcgtggcgt cagcccagct gcaggagaag | 1680 |
| ctggcaggag cccagcgcca gctggggcag ctccgggctc aggaagccgg cctgcagcag | 1740 |
| gagcagagga aggcagacac ccacaagaag atgactgagt tctagagacc ccacaagcac | 1800 |
| tatgacgaa gcgtgggacc ccagcacggg ctgccctcag gaagaccagt gttgcccgag | 1860 |
| gaggggccgg cctgctggcc tggggcgtgc agacactgct gagtggagac agagctgcgg | 1920 |
| ggtcccatct ggacacttac ttgcccacct gccagtgtct gggcatttc cttggcaagg | 1980 |
| acattaaagt gatttcatca cagtgtcaaa aaaaaaaaa aaaaaaaa | 2028 |

```
<210> SEQ ID NO 50
<211> LENGTH: 1898
<212> TYPE: DNA
<213> ORGANISM: Homo sapiens

<400> SEQUENCE: 50
```

| | |
|---|---|
| gcgcgccaag cacttccgga agcggcggcg ctcgggagga agtgccgatc ggctgctggg | 60 |
| gcgaaaaggg ggcgccgggc cgctctagcc gccctggtcc agcgcctccc tctctcagca | 120 |
| tggacgagga gagcctggag tcggccttgc agacctaccg tgcgcagctg cagcaggtgg | 180 |
| agctggcctt gggcgccggc ctggattcgt ctgagcaggc tgacctgcgc cagctgcagg | 240 |

```
gggacctgaa ggagctcatc gagctcaccg aggccagcct ggtgtctgtc aggaagagca    300
gcttgttggc cgcgctggac gaagagcgcc cgggccgcca ggaagatgct gagtaccagg    360
ctttccggga ggccatcact gaggcggtgg aggcaccagc agcggcccgt gggtccggat    420
cagagaccgt tcctaaagca gaggcggggc cagaatctgc ggcaggtggg caggaggagg    480
aagagggaga ggacgaggaa gagctgagtg ggacaaaggt gagcgcgccc tactacagct    540
cctggggcac tctggagtat cacaacgcca tggtggtggg aacggaagag gcggaggatg    600
gctcggcggg tgtccgtgtg ctttacctgt accccactca caagtctctg aagccgtgcc    660
cgttcttcct ggagggaaag tgccgcttta aggagaactg caggttctcc catgggcagg    720
tggtctctct ggatgagctg cgccccttcc aggacccaga cctgagctcc ctgcaggccg    780
gctctgcgtg tctggccaag caccaggatg gcctctggca cgcagcacgc atcaccgatg    840
tggacaacgg ctactacaca gtcaagtttg actcgctgct gctgagggag gccgtggtgg    900 aggggacgg catcctgccc ccactgcgca cagaggccac agagtccgac tcagacagcg    960
acggtacggg tgactccagc tatgccagag tggtggggtc agatgctgtg gactctggga   1020
cctgcagctc tgcctttgct ggctgggagg tgcacgcgcg aggtataggc tccagactcc   1080
tcaccaagat gggctatgag tttggcaagg gtttgggccg acacgcggaa ggccgggtgg   1140
agcccatcca tgctgtggtg ttgcctcgag ggaagtcgct ggaccagtgt gtggagaccc   1200
tgcagaagca gaccagggtt ggcaaggctg gcaccaacaa gccccccagg tgccggggaa   1260
gaggggccag gctggggggc cgcccagctc ctcggaatgt gtttgacttc ctcaatgaaa   1320
agctgcaagg tcaggctcct ggggccctag aagccggggc ggcccagcg gggaggagga   1380 gcaaggacat gtaccatgcc agcaagagtg ccaagcgggc cctgagcctg cggctcttcc   1440
agactgagga gaagatcgag cgaacccagc gggacatcag gagcatccag gaggctctcg   1500
cccgcaacgc tggccggcat agcgtggcgt cagcccagct gcaggagaag ctggcaggag   1560
cccagcgcca gctggggcag ctccgggctc aggaagccgg cctgcagcag gagcaggga   1620 aggcagacac ccacaagaag atgactgagt tctagagacc ccacaagcac tatggacgaa   1680
gcgtgggacc ccagcacggg ctgccctcag gaagaccagt gttgcccgag gaggggccgg   1740
cctgctggcc tggggcgtgc agacactgct gagtggagac agagctgcgg ggtcccatct   1800
ggacacttac ttgcccacct gccagtgtct tgggcatttc cttggcaagg acattaaagt   1860
gatttcatca cagtgtcaaa aaaaaaaaa aaaaaaaa                            1898

<210> SEQ ID NO 51
<211> LENGTH: 1596
<212> TYPE: DNA
<213> ORGANISM: Homo sapiens

<400> SEQUENCE: 51
cgttgctcag tctcagtgtg gtctctgttt tgcaactggt cgtccgcgtc aggagactta     60
ggtccaggcg actgcccaga caatgactgg tcccgcatac cgagcagagc atgatcagca    120
gcagtctgag tggaagagtg cctgtgatct tagggaacct gatgggcgtt ggagcagcgg    180
ttcgacgcat gggtttctct ttaatccttc cgacttcccc aagcccagcg cactcaggtt    240
ccgctccaag tgcgggaccc gccggggtg tgtcgggggt actcggccgg aggcggccgg    300
tgagtgaggc ttacagggcc ccgggaccaa ggaacccag catgttaatt gaacttgatc    360
acccagttga aggaagaata atagtagatg ttggatcttc aggaagctga agagggcagt    420
gcccagaaat acctgtcttg ataggggat ttgagctgaa ccaaagcatc aacaccaatc    480
```

-continued

| | |
|---|---|
| agactgtttc cgaagaacta gagttttctg ggtcagcaat ggaaagcctc agagggaata | 540 |
| ctgctcaggg tcctacaaat gaagaagact ataaaaacga aggccaatta tcaaggcaaa | 600 |
| caaaatgtcc tgcacagaag aaatcctctt ttgagaacac agtggtcaga aaagtgtcag | 660 |
| tgacactcaa agaaattttc acaggggagg aaggccctga atccagtgaa tttagtctaa | 720 |
| gcccaaacct tgacgcacaa cagaaaattc aaagggaca tggatcccca atatctagga | 780 |
| aaaactccaa agataattca gacttaatta acaccaaag acttttctca caagaaaac | 840 |
| cttgtaaatg caatgaatgt gaaaaagcct ttagttacca atcagacctt cttgtacaca | 900 |
| gtagaattca tggtggagaa aagccttttg aatgcaacaa atgtgggaaa tctttcagcc | 960 |
| gaagtacaca ccttattgaa catcaaagaa ctcacactgg agagaaacct tatgaatgca | 1020 |
| atgaatgtgg aaaagctttt agccggagca cacatcttag tctacatcag agaatccata | 1080 |
| ctggagaaaa accatatgaa tgtagtgaat gtggaaaagc ctttagccga agcactaacc | 1140 |
| ttagtcagca tcagcgaact catactcaag aaaggcctta caaatgtaat gaatgtggga | 1200 |
| aagccttcgg tgaccgttca accataattc agcatcaacg aatacacact ggagagaatc | 1260 |
| cctatgaatg cagtaaatgt ggaaaagctt tcagttggat ctcatcgctt actgaacatc | 1320 |
| agagaacaca cactggggag aaccoctatg agtgcagtga atgtgggaaa gtgttcagtc | 1380 |
| gaagctcgtc tcttacagaa catcagagaa tccacagtgg agaaaagcct cacgagtgta | 1440 |
| gagtgtgtgg aaagggcttc agtcgaagct catcccttat tattcatcag agaactcata | 1500 |
| ccggggagaa gccgtacaaa tgtaatgact gtggaaaagc cttctgtcag agttcaactc | 1560 |
| tgatcagaca tcagcacctt catactaaag agtaat | 1596 |

<210> SEQ ID NO 52
<211> LENGTH: 2320
<212> TYPE: DNA
<213> ORGANISM: Homo sapiens

<400> SEQUENCE: 52

| | |
|---|---|
| gtgagcgcct gagagtcttt ttgcctttca gagttaaggc ctcactggcc tgggaaaata | 60 |
| attgctgcct tttgcatccg cgttggctcc gtccccagga tcttcccggt tcagggacct | 120 |
| ggcgatttct gagtgttccg gaatcccaat aaccctgttt aaagaggaat ggagattgcc | 180 |
| actgtccatt tagattaatg aggtgtcctg aagtgatggt gacatcaatg aaaggagggt | 240 |
| tctgacacgt tctccacctcg cgggatggca gctgctgatt tgtcccatgg acattatctt | 300 |
| tctggggacc cagtttgcct tcatgaagaa agacaccag caggaagaat agtggctgac | 360 |
| tgcctaacag attgttatca ggattcagtg acctttgacg atgtggctgt ggacttcacc | 420 |
| caggaggagt ggacttttact ggactcaact cagagaagcc tctacagtga cgtgatgctg | 480 |
| gagaactaca gaacctggc cacagtagga ggtcagatca tcaaacccag tctaatctct | 540 |
| tggttggaac aagaagagtc aaggacagtt caggaggag ttctccaagg atgggaaatg | 600 |
| cgacttgaaa cccagtggtc tatacttcag caggactttt tgagggtca gacatccatt | 660 |
| gggatacaat tggaaggaaa acacaatgga agggaactct gtgactgtga gcaatgtgga | 720 |
| gaagtcttca gtgaacactc atgccttaag acgcacgtga gaactcaaag tacagggaac | 780 |
| actcatgact gtaatcagta tggaaaagat ttccttaccc tgtgtgagaa acctctact | 840 |
| ggtgagaaac tttctgagtt taatcagagt gaaaaaatct tcagcctgac accaaatatt | 900 |
| gtataccaga gaactagcac acaagaaaag tcatttgaat gtagtcactg tggaaaatcc | 960 |
| ttcattaatg agtcatacct tcaggcacat atgagaactc acaatggaga aaaactctac | 1020 |

```
gaatggagga attatgggcc aggttttatt gactctacaa gcctttctgt gcttatagaa    1080
accctcaatg caaaaaagcc ctacaaatgt aaggaatgtg aaaaggcta tagatacccca    1140 gcctacctca gtattcacat gcgaacccac actggggaga aaccatatga atgtaaggaa    1200
tgtgggaaag ccttcaatta ttccaactca tttcagatac atggaagaac tcacactgga    1260
gagaaacccc atgtatgtaa ggaatgtggg aaagccttca ctcagtactc gggccttagt    1320
atgcatgtac gatctcacag tggagacaag ccctatgaat gtaaggaatg tgggaaatcc    1380
ttccttacat cctcacgcct tattcaacat ataagaactc acactggaga aagcctttt    1440 gtatgtgttg aatgtgggaa agcctttgca gtttcctcaa atcttagtgg acatttgaga    1500
actcacactg aagagaaggc ctgtgagtgt aagatatgtg gaaagtatt tgggtatccc    1560 tcatgtctta ataatcacat gcgaacgcac agtgcccaga aaccatacac ctgtaaggaa    1620
tgtgggaagg cttttaacta ttccacccac cttaaaattc acatgcgaat ccacactgga    1680 gaaaaccct atgagtgtaa acaatgtgga aaggccttca gtcattccag ttcatttcaa    1740
atacatgaaa ggactcacac tggagagaaa ccctatgaat gcaaggagtg tgggaaagcc    1800
ttcacgtgtt ccagttcctt tagaattcat gaaaaaactc acacagaaga gaaaccctat    1860
aaatgtcagc aatgcgggaa agcttacagt catccccgtt cacttcgaag acatgaacaa    1920
attcactagt gagaaactgt ccatgtaata aatgtgggaa agctctcatt tgttccagtt    1980
cactttaaag acatgaatga actcactctg gagagaagaa gctgcatgaa aattacttaa    2040
ttcctgtaat cccagcattt tgagaggctg aggtgggtgg atcacttgag gtcaggagtt    2100
tgagaccacc ctggccaaca tggtgaaacc ttgtctctac tgaaaataca aaaaatttag    2160
ccaggtgtgg tggcacctg taatcccagc tacttgggag gctgaggcaa gtgaatcact    2220
tgaacccagg aagcagaggt tgcagtgagc agagatcatg ccactgcact ccagcctggg    2280
cgatggagtg agactccatc tcaaaaaaaa aaaaaaaaa                          2320
```

<210> SEQ ID NO 53
<211> LENGTH: 2335
<212> TYPE: DNA
<213> ORGANISM: Homo sapiens

<400> SEQUENCE: 53

```
ggaaccggag cctgagagcc gggcgccgtg cgctcctccc cgcgctgtct cggcggccca      60
ggaattcact gtctgtagca tctgctcctc cacagaggga ccctggaatg gcgatggcac     120
tcccgatgcc tggacctcag gaggcggttg tgttcgagga tgtggctgtg tacttcacaa     180
ggatagagtg gagttgcctg gcccccgacc agcaggcact ctacagggac gtgatgctgg     240
agaactatgg gaacctggcc tcactaggct ttccttgttgc caaaccagca ctgatctccc     300
tattggagca aggagaggag ccgggggcct tgattctgca ggtggctgaa cagagcgtgg     360
ccaaagccag cctgtgcaca gattccagga tggaggctgg gatcatggag tctcctctgc     420
agagaaagct ctccaggcag gcaggactgc cgggcaccgt gtgggggtgc ctcccctggg     480
ggcaccctgt ggggggggcac cctgcaccac cccaccccgca tggcggtcct gaggacgggt    540
cagataaacc caccccacccc cgggctcggg agcacagcgc ctccccaagg gttctgcagg     600 aagcctggg ccggcctgtg gggagctcag cccccgcta caggtgcgtg tgcggcaagg      660
cgttcagata caactcgctg cttctcaggc accagatcat ccacaccggc gccaagccct     720
tccagtgcac agagtcgggg aaggccttca gcaaagctc catcctgctg cggcaccagc     780
tgatccacac tgaggagaag ccgttccagt gcggcgagtg cggaaaggcc ttccggcaga     840
```

-continued

```
gcacgcagct ggctgcccac caccgcgtcc acacccgcga gcggccctac gcatgcggcg    900
agtgcggcaa ggccttcagc cgcagctccc ggctgctgca gcaccagaag ttccacaccg    960
gggagaagcc cttcgcgtgc acagagtgcg gcaaggcgtt ctgccgcagg ttcaccctca   1020
acgagcacgg ccgcatccac agcggggagc ggccctaccg gtgcctgcgg tgtgggcagc   1080
gcttcatccg agggtcctcg ctcctgaagc accaccggct gcacgcgcag gagggtgccc   1140
aggacggcgg cgtggggcag ggcgccctgc tcggagctgc gcagaggccc caggcggggg   1200
acccgcccca cgagtgcccg gtgtgcggga ggccgttccg acacaactcc ctgctgctgc   1260
tgcacctgcg cctacacacg ggcgagaagc cgttcgagtg cgcggagtgc ggcaaggcct   1320
tcggtcgcaa gtccaacctc actctgcacc agaagatcca caccaaggag aagcccttcg   1380
cgtgcaccga gtgcggcaag gcgttccgca ggagctacac gctgaacgag cactaccggc   1440
tccacagcgg cgagaggcca taccggtgcc gcgcctgcgg gagggcctgc agccggctgt   1500
ccaccctcat ccagcaccag aaggtgcacg gccgcgagcc cggggaggac acagagggca   1560
ggcgggcgcc ctgttgggct tcctgatgac ggggacgaca ggccgaggat tcacgctgga   1620
agcccaccca agccggcggg gccctagcgc agaaattcag aacccctgt cctgaaggtg    1680
aagcaaagtc taaagaaagg gccagctccc atcaggagct cggcttcttg ctccagccgg   1740
gcactgggga gggaaagggc accaggcagc ccgtggtgtg gcctcaggaa ccactatcag   1800
ccaccatttc ctggggcctt ccggaaatgt ccaggagcgg gcagaaggga gagagggagg   1860
ggcagctatg ctcagtcccc aaagagcagg gcacaggggg cgccacagac gcatatgcag   1920
ctgagctccc cacaggccgg cccgggtctt cgtgcagaac cattgggcac agccaggcct   1980
tagcgccagg ctccgtgtgg cggtcaattc caggtgctgt aaagccgact aacagggtac   2040
agggagcctt agctggctgc catgtctcct gcctgtaatc ccatcacttt gggaggctga   2100
ggtgggaggt ttgcttaagc ccaggagttt gagaccagct tggcaacat ggtgaaactt    2160
ctctacaaaa aatttaaaaa taagtcaggt atcgtggtct gtgcctgtac gctgtagtcc   2220
cagctactca ggaggctgag gtgggaggat gggttgagcc tgggaagtca aggctgcagt   2280
gagctatgat agcaccacgg cactccaacc tggttgacag agtgacaccc tgttt        2335
```